(12) United States Patent
Xue et al.

(10) Patent No.: US 10,882,841 B2
(45) Date of Patent: Jan. 5, 2021

(54) WNT SIGNALING PATHWAY INHIBITORS FOR TREATMENTS OF DISEASE

(71) Applicant: UNIVERSITY OF MARYLAND, BALTIMORE, Baltimore, MD (US)

(72) Inventors: Fengtian Xue, Potomac, MD (US); Yan Shu, Clarksville, MD (US)

(73) Assignee: UNIVERSITY OF MARYLAND, BALTIMORE, Baltimore, MD (US)

(*) Notice: Subject to any disclaimer, the term of this patent is extended or adjusted under 35 U.S.C. 154(b) by 0 days.

(21) Appl. No.: 16/081,657

(22) PCT Filed: Mar. 1, 2017

(86) PCT No.: PCT/US2017/020224
§ 371 (c)(1),
(2) Date: Aug. 31, 2018

(87) PCT Pub. No.: WO2017/151786
PCT Pub. Date: Sep. 8, 2017

(65) Prior Publication Data
US 2019/0071424 A1    Mar. 7, 2019

Related U.S. Application Data

(60) Provisional application No. 62/352,634, filed on Jun. 21, 2016, provisional application No. 62/301,863,
(Continued)

(51) Int. Cl.
| | |
|---|---|
| *C07D 401/12* | (2006.01) |
| *C07D 413/14* | (2006.01) |
| *C07D 231/14* | (2006.01) |
| *C07D 207/416* | (2006.01) |
| *C07D 207/34* | (2006.01) |
| *C07D 249/06* | (2006.01) |
| *C07D 401/14* | (2006.01) |
| *C07D 403/12* | (2006.01) |
| *C07D 405/12* | (2006.01) |
| *C07D 413/12* | (2006.01) |
| *C07D 417/12* | (2006.01) |
| *C07D 417/14* | (2006.01) |
| *A61K 31/4439* | (2006.01) |
| *A61K 31/5377* | (2006.01) |
| *A61K 31/427* | (2006.01) |
| *A61K 31/4245* | (2006.01) |
| *A61K 31/4725* | (2006.01) |
| *A61K 31/353* | (2006.01) |
| *A61K 31/541* | (2006.01) |
| *A61K 31/422* | (2006.01) |
| *A61K 31/497* | (2006.01) |
| *A61K 31/4184* | (2006.01) |
| *A61P 1/16* | (2006.01) |

(Continued)

(52) U.S. Cl.
CPC ........ *C07D 401/12* (2013.01); *A61K 31/353* (2013.01); *A61K 31/4184* (2013.01); *A61K 31/422* (2013.01); *A61K 31/427* (2013.01); *A61K 31/4245* (2013.01); *A61K 31/4439* (2013.01); *A61K 31/4725* (2013.01); *A61K 31/497* (2013.01); *A61K 31/5377* (2013.01); *A61K 31/541* (2013.01); *A61P 1/16* (2018.01); *A61P 3/10* (2018.01); *A61P 35/00* (2018.01); *C07D 207/34* (2013.01); *C07D 207/416* (2013.01); *C07D 231/14* (2013.01); *C07D 249/06* (2013.01); *C07D 401/14* (2013.01); *C07D 403/12* (2013.01); *C07D 405/12* (2013.01); *C07D 413/12* (2013.01); *C07D 413/14* (2013.01); *C07D 417/12* (2013.01); *C07D 417/14* (2013.01)

(58) Field of Classification Search
CPC .............. A61K 31/353; A61K 31/4184; A61K 31/422; A61K 31/4245; A61K 31/427; A61K 31/4439; A61K 31/4725; A61K 31/497; A61K 31/5377; A61K 31/541; A61P 1/16; A61P 35/00; A61P 3/10; C07D 207/34; C07D 207/416; C07D 231/14; C07D 249/06; C07D 401/12; C07D 401/14; C07D 403/12; C07D 405/12; C07D 413/12; C07D 413/14; C07D 417/12; C07D 417/14
See application file for complete search history.

(56) References Cited

U.S. PATENT DOCUMENTS

| | | | |
|---|---|---|---|
| 2008/0234270 A1 | 9/2008 | Canne Bannen et al. | |
| 2011/0034441 A1* | 2/2011 | Hood ................... | A61K 31/416 514/218 |

(Continued)

FOREIGN PATENT DOCUMENTS

| | | |
|---|---|---|
| CN | 103 664 876 A | 3/2014 |
| EP | 2423208 A1 | 2/2012 |

(Continued)

OTHER PUBLICATIONS

Bailey et al., Evidence of non-pancreatic beta cell-dependent roles of Tcf7l2 in the regulation of glucose metabolism in mice, Hum Mol Genet, 2015, vol. 24, pp. 1646-1654.

Boj et al., Diabetes risk gene and Wnt effector Tcf7l2/TCF4 controls hepatic response to perinatal and adult metabolic demand, Cell, 2012, vol. 151, pp. 1595-1607.

Bordonaro, Role of Wnt signaling in the development of type 2 diabetes, Vitam Horm, 2009, vol. 80, pp. 563-581.

(Continued)

*Primary Examiner* — Erich A Leeser
(74) *Attorney, Agent, or Firm* — Morgan, Lewis & Bockius LLP

(57) ABSTRACT

Compounds and compositions are provided as inhibitors of the Wnt/β-catenin pathway for the treatment of diseases that implicate the same.

28 Claims, 40 Drawing Sheets

Specification includes a Sequence Listing.

Related U.S. Application Data filed on Mar. 1, 2016, provisional application No. 62/301,882, filed on Mar. 1, 2016.

(51) Int. Cl.
*A61P 3/10* (2006.01)
*A61P 35/00* (2006.01)

(56) References Cited

U.S. PATENT DOCUMENTS

| | | | |
|---|---|---|---|
| 2011/0065725 A1 | 3/2011 | Garzya et al. | |
| 2012/0318262 A1* | 12/2012 | Lee ..................... | A61K 45/06 128/202.17 |
| 2013/0079329 A1 | 3/2013 | Hood et al. | |
| 2014/0031374 A1 | 1/2014 | Holsworth et al. | |

FOREIGN PATENT DOCUMENTS

| | | |
|---|---|---|
| EP | 2842938 A1 | 4/2015 |
| WO | 2002068417 A2 | 9/2002 |
| WO | 2005086836 A2 | 9/2005 |
| WO | 2005086902 A2 | 9/2005 |
| WO | 2013134079 A1 | 1/2013 |
| WO | 2015017545 A1 | 2/2015 |
| WO | 2016166250 A1 | 10/2016 |
| WO | 2016170009 A1 | 10/2016 |
| WO | 2017151786 A1 | 9/2017 |

OTHER PUBLICATIONS

Caricasole et al., The Wnt pathway, cell-cycle activation and beta-amyloid: novel therapeutic strategies in Alzheimer's disease?, Trends Pharmacol Sci, 2003, vol. 24, pp. 233-238.
Cauchi et al., TCF7L2 is reproducibly associated with type 2 diabetes in various ethnic groups: a global meta-analysis, J Mol Med (Berl), 2007, 85, 777-782.
Clevers, Wnt/beta-catenin signaling in development and disease. Cell, 2006, 127, 469-480.
Cselenyi et al., LRP6 transduces a canonical Wnt signal independently of Axin degradation by inhibiting GSK3's phosphorylation of beta-catenin, Proceedings of the National Academy of Sciences of the United States of America, 2008, vol. 105, pp. 8032-8037.
Elbein, S.C., Chu, W.S., Das, S.K., Yao-Borengasser, A., Hasstedt, S.J., Wang, H., Rasouli, N., and Kern, P. A. (2007). Transcription factor 7-like 2 polymorphisms and type 2 diabetes, glucose homeostasis traits and gene expression in US participants of European and African descent. Diabetologia 50, 1621-1630.
Gwak et al., Small molecule-based disruption of the Axin/beta-catenin protein complex regulates mesenchymal stem cell differentiation, Cell Res, 2012, vol. 22, pp. 237-247.
Hao et al., Selective small molecule targeting beta-catenin function discovered by in vivo chemical genetic screen, Cell Rep., 2013, vol. 4, pp. 898-904.
Henderson et al., Inhibition of Wnt/beta-catenin/CREB binding protein (CBP) signaling reverses pulmonary fibrosis, Proc Natl Acad Sci U S A, 2010, vol. 107, pp. 14309-14314.
Huang et al., Tankyrase inhibition stabilizes axin and antagonizes Wnt signaling, Nature, 2009, 461, pp. 614-620.
Jin, The Wnt signalling pathway and diabetes mellitus, Diabetologia, 2008, 51, pp. 1771-1780.
Jones, H.M., and Houston, J.B. (2004). Substrate depletion approach for determining in vitro metabolic clearance: time dependencies in hepatocyte and microsomal incubations. Drug Metab Dispos 32, 973-982.
Kimelman et al., beta-catenin destruction complex: insights and questions from a structural perspective, Oncogene, 2006, 25, 7482-7491.
Lepourcelet et al., Small-molecule antagonists of the oncogenic Tcf/beta-catenin protein complex, Cancer Cell, 2004, vol. 5, pp. 91-102.
Liang et al., Wnt5a inhibits B cell proliferation and functions as a tumor suppressor in hematopoietic tissue, Cancer Cell, 2003, 4, 349-360.
Liu et al., Wnt signaling regulates hepatic metabolism, Sci. Signal, 2011, vol. 4, ra6.
Lu et al., Salinomycin inhibits Wnt signaling and selectively induces apoptosis in chronic lymphocytic leukemia cells, Proc. Natl. Acad. Sci. USA, 2011, vol. 108, pp. 13253-13257.
Luo et al., Wnt signaling and human diseases: what are the therapeutic implications? Lab Invest, 2007, vol. 87, pp. 97-103.
Oh et al., Medicine. Wnt fans the flames in obesity, Science, 2010, 329, pp. 397-398.
Ohishi et al., 9-Hydroxycanthin-6-one, a beta-Carboline Alkaloid from Eurycoma longifolia, Is the First Wnt Signal Inhibitor through Activation of Glycogen Synthase Kinase 3beta without Depending on Casein Kinase 1 alpha, J. Nat. Prod., 2015, vol. 22, pp. 1139-1146.
Park, et al., Calotropin: A Cardenolide from Calotropis gigantea that Inhibits Wnt Signaling by Increasing Casein Kinase 1 alpha in Colon Cancer Cells, Chembiochem, 2014, vol. 15, pp. 872-878.
Pokhodylo et al., Synthesis of 1-(R-Phenyl)-5-(R-Methyl)-IH-1,2,3-triazole-4-carboxylic Acids by One-Pot Tandem Reaction, Synthetic Communications, 2010, vol. 40, pp. 1932-1938.
Schinner, S. (2009). Wnt-signalling and the metabolic syndrome. Horm Metab Res 41, 159-163.
Smith, T.C., Kinkel, A.W., Gryczko, CM., and Goulet, J.R. (1976). Absorption of pyrvinium pamoate. Clin Pharmacol Ther 19, 802-806.
Thorne, et al. Small-molecule inhibition of Wnt signaling through activation of casein kinase 1 alpha, Nature Chemical Biology, 2010, 6, 829-836.
Toume et al., Xylogranin B: a potent Wnt signal inhibitory limonoid from Xylocarpus granatum, Org Lett, 2016, vol. 15, pp. 6106-6109.
Wu et al., Inhibition of GSK3 phosphorylation of beta-catenin via phosphorylated PPPSPXS motifs of Wnt coreceptor LRP6, PloS one, 2009, 4, e4926.
Yang, H., Li, Q., Lee, J.H. and Shu, Y. (2012). Reduction in Tcf7l2 expression decreases diabetic susceptibility in mice. Int J Biol Sci 8, 791-801.
Advanced Drug Delivery Reviews, 1996, 19, 115. (Fleisher).
Huang, CK et al. 'Restoration of Wnt/beta-catenin signaling attenuates alcoholic liver disease progression in a rat model'; Feb. 24, 2015, Journal of Hepatology; vol. 63, Issue 1, pp. 191-198; p. 191, first and second columns.
ISR_PCTUS170224; dated May 10, 2017; 3 pages.
WO_PCTUS170224; dated May 10, 2017; 9 pages.
Extended European Search Report for Application No. 17760727.2-1109 / 3423452 PCT/US2017/020224; dated Sep. 27, 2019; 11 pages.
Exelixis, Reaxys database search notes, dated Sep. 3, 2019; 5 pages.
European Examination Report for Application No. 17760727.2-1109 / 3423452 PCT/US2017/020224; dated Jul. 1, 2020; 6 pages.

* cited by examiner

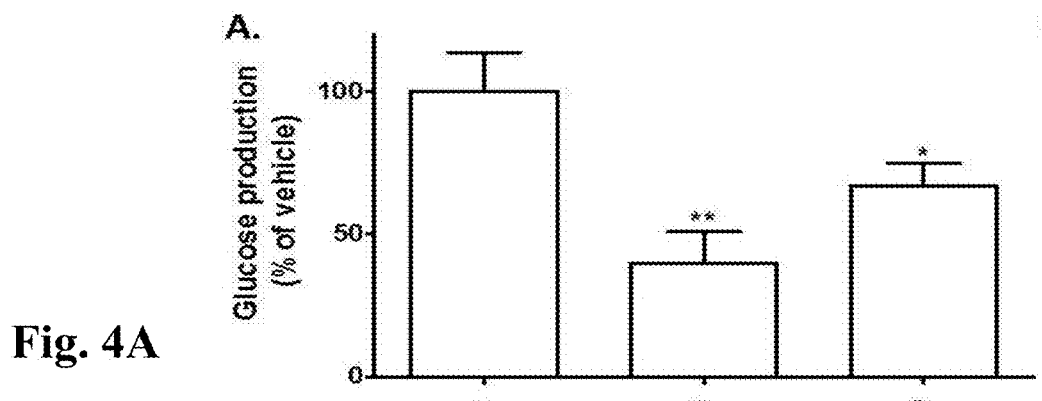
Fig. 4A
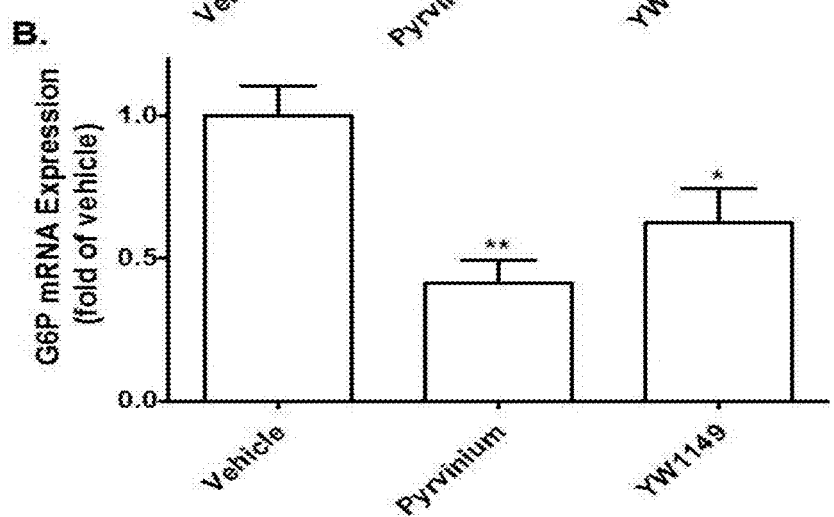
Fig. 4B
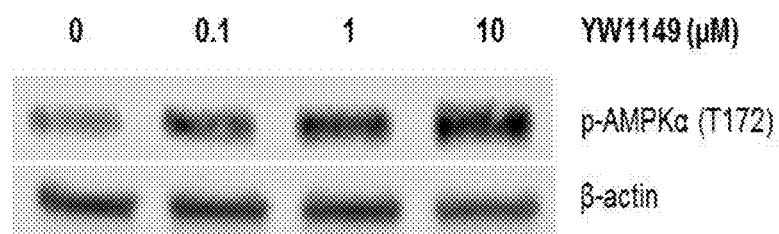
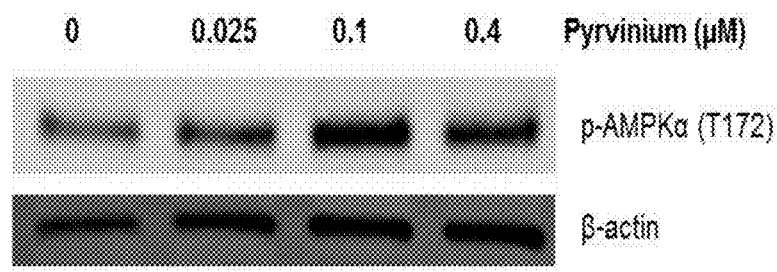
Fig. 4C

| compd | IC$_{50}$(μM) |
|---|---|
| YW 2125 | 17.29 |
| YW 2142 | 11 |
| YW 21172 | 35.23 |
| YW 2123 | 0.4953 |
| YW 2144 | 5 |
| YW 2120 | 22.77 |
| YW 2038 | 13 |
| YW 2076 | 3.9 |
| YW 2065 | 2.5 |
| YW 2013 | 14.3 |
| | |
| YW 2049 | >20 |
| | |
| YW 1128 | >20 |
| YW 2068 | 8.976 |
| YW 2046 | 24.61 |
| YW 2035 | 91.74 |
| YW 2048 | 7.195 |
| YW 2044 | 13.8 |

Fig. 9

| cell line | source | p53 | CTNNB1 (b-catenin) | APC | other |
|---|---|---|---|---|---|
| SW480 | primary carcinoma | p.P309S p.R273H | wt | p.Q1338* | |
| SW620 | lymph node metastatic adenocarcinoma | p.P309S p.R273H | wt | p.Q1338* | Ras G12V |
| HCT116 | primary carcinoma | wt | p.S45del | wild-type | Ras G13D |
| HT29 | primary adenocarcinoma | p.R273H | wt | truncated p.1555 | Braf V600E |
| WiDr | Unclear (metastatic) | p.R273H c.818G>A | wt | Truncated p.1,556 | |
| T84 | lung metastatic adenocarcinoma | ? mutated | wt | p.L1488fs*19 | Ras p.G13D |
| A549 | Lung Carcinoma | wt | wt | wt | CDKN2A RAS G12S |
| Hela | Cervix adenocarcinoma | wt | wt | wt | |
| MCF-7 | pleural effusion metastatic breast adenocarcinoma | wt | wt | wt | CDKN2A PI3KCA |
| HepG2 | hepatocellular carcinoma | wt | mutation | wt | |

| | WiDr | SW620 | HT29 | HEK_LTV | T84 |
|---|---|---|---|---|---|
| YW1059 | 1.592 | 4.764 | 2.118 | | |
| YW1061 | 26.66 | NI | NI | | |
| YW2013 | 5.364<br>2.347<br>23.62 | 17.72<br>26.93<br>32.71<br>8.028 | 9.435 | 4.9 | |
| YW1128 | | | | | >50 |
| YW2035 | 25.66 | | | NI | >50 |
| YW2044 | 9.233<br>4.718<br>128.5 | 31.39<br>27.98<br>20.36<br>24.81 | 19.17 | 6.736 | |
| YW2049 | 5.565<br>1.511 | | 13.36 | 17.91 | 43.59 |
| pyrvinium | 0.0283 | | | | |

WNT SIGNALING PATHWAY INHIBITORS FOR TREATMENTS OF DISEASE

CROSS-REFERENCE TO RELATED APPLICATIONS

This application is a U.S. National Phase Application under 35 U.S.C. § 371 of International Application PCT/US17/20224, filed Mar. 1, 2017 which claims the benefit of priority to U.S. Provisional Application No. 62/352,634, filed Jun. 21, 2016, U.S. Provisional Application No. 62/301,882, filed Mar. 1, 2016, and U.S. Provisional Application No. 62/301,863, filed Mar. 1, 2016, the entireties of which are incorporated herein by reference.

FIELD OF THE INVENTION

The present invention relates generally to compounds that inhibit the Wnt signaling pathway and more particularly, but not exclusively, to compounds that inhibit the Wnt/β-catenin pathway for the treatment of diseases that implicate the Wnt/β-catenin pathway.

BACKGROUND OF THE INVENTION

A number of individuals are affected each year by diseases that implicate aberrant activity in Wnt signalling, which may result in abnormal levels of β-catenin. These diseases include metabolic diseases and cancer, for example.

There is a need in the field for new and potent therapeutics that inhibit the Wnt/β-catenin pathway as treatments for disease. The present invention meets those needs.

SUMMARY OF THE INVENTION

The present invention meets the needs in the field by providing compounds and methods for the treatment of diseases that implicate the Wnt/β-catenin signaling pathway.

In one aspect the compounds of the invention may include a compound of formula I:

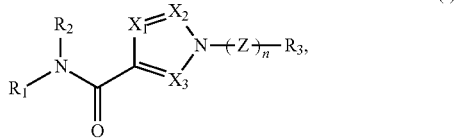

(I)

wherein $R_1$ and $R_2$ each may independently represent a substituent selected from the group consisting of H and substituted or unsubstituted alkyl, alkenyl, alkynyl, cycloalkyl, aryl, heterocycle, heteroaryl, alkoxy, carboxy, carbalkoxy, and carboxamido;

$R_3$ may represent a substituent selected from the group consisting of substituted or unsubstituted alkyl, alkenyl, alkynyl, cycloalkyl, aryl, heterocycle, and heteroaryl;

n may represent an integer of 0 to 2, Z represents one or more substituted or unsubstituted alkyl substituents when n is 1 or 2;

$X_1$ may represent N or $CR_4$;
$X_2$ may represent N or $CR_5$;
$X_3$ may represent N or $CR_6$; $R_4$, $R_5$, and $R_6$ each may independently represent a substituent selected from the group consisting of H, OH, $NO_2$, CN, halo, and substituted or unsubstituted alkyl, alkylcarbonyl, alkenyl, alkynyl, cycloalkyl, aryl, heterocycle, heteroaryl, amino, alkoxy, carboxy, carbalkoxy, carboxamido, sulfonyl, sulfonamido, sulfinyl, monoalkylaminosulfinyl, dialkylaminosulfinyl, monoalkylaminosulfonyl, dialkylaminosulfonyl, alkylsulfonylamino, hydroxysulfonyloxy, alkoxysulfonyloxy, alkylsulfonyloxy, hydroxysulfonyl, alkoxysulfonyl, alkylsulfonylalkyl, monoalkylaminosulfonylalkyl, dialkylaminosulfonylalkyl, monoalkylaminosulfinylalkyl, and dialkylaminosulfinylalkyl; where if $X_1$ and $X_2$ represent $CR_4$ and $CR_5$, respectively, then $R_4$ and $R_5$ may be taken together to form a substituted or unsubstituted m-membered cycloalkyl or heterocycle, wherein m may represent an integer of 5 to 7; or the pharmaceutically acceptable salts of said compounds.

In some embodiments, the compounds of formula I may include a compound of Table 1 or a pharmaceutically acceptable salt thereof.

In some embodiments, the compounds of the invention may include a compound of formula II:

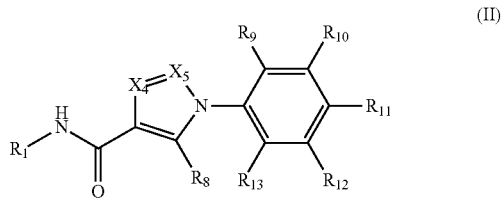

(II)

wherein $R_7$ may represent a substituent selected from the group consisting of H and substituted or unsubstituted alkyl, alkenyl, alkynyl, cycloalkyl, aryl, heterocycle, heteroaryl, alkoxy, carboxy, carbalkoxy, and carboxamido;

$R_8$ may represent a substituent selected from the group consisting of H, OH, $NO_2$, CN, halo, and substituted or unsubstituted alkyl, alkenyl, alkynyl, aryl, amino, and alkoxy;

$R_9$, $R_{10}$, $R_{11}$, $R_{12}$, and $R_{13}$ each may independently represent a substituent selected from the group consisting of H, OH, $NO_2$, CN, halo, and substituted or unsubstituted alkyl, alkylcarbonyl, alkenyl, alkynyl, cycloalkyl, aryl, heterocycle, heteroaryl, amino, alkoxy, carboxy, carbalkoxy, carboxamido, sulfonyl, sulfonamido, sulfinyl, monoalkylaminosulfinyl, dialkylaminosulfinyl, monoalkylaminosulfonyl, dialkylaminosulfonyl, alkylsulfonylamino, hydroxysulfonyloxy, alkoxysulfonyloxy, alkylsulfonyloxy, hydroxysulfonyl, alkoxysulfonyl, alkylsulfonylalkyl, monoalkylaminosulfonylalkyl, dialkylaminosulfonylalkyl, monoalkylaminosulfinylalkyl, and dialkylaminosulfinylalkyl;

$X_4$ may represent N or $CR_{14}$;
$X_5$ may represent N or $CR_{15}$; $R_{14}$ and $R_{15}$ each may independently represent a substitutent selected from the group consisting of H, OH, $NO_2$, CN, halo, and substituted or unsubstituted alkyl, alkylcarbonyl, alkenyl, alkynyl, cycloalkyl, aryl, heterocycle, heteroaryl, amino, alkoxy, carboxy, carbalkoxy, carboxamido, sulfonyl, sulfonamido, sulfinyl, monoalkylaminosulfinyl, dialkylaminosulfinyl, monoalkylaminosulfonyl, dialkylaminosulfonyl, alkylsulfonylamino, hydroxysulfonyloxy, alkoxysulfonyloxy, alkylsulfonyloxy, hydroxysulfonyl, alkoxysulfonyl, alkylsulfonylalkyl, monoalkylaminosulfonylalkyl, dialkylaminosulfonylalkyl, monoalkylaminosulfinylalkyl, and dialkylaminosulfinylalkyl; and where if $X_4$ and $X_5$ are $CR_{14}$ and $CR_{15}$, respectively, then $R_{14}$ and $R_{15}$ may be taken together to form a substituted or unsubstituted m-membered cycloalkyl or heterocycle, wherein m may be an integer of 5 to 7; or the pharmaceutically acceptable salts of said compound.

In some embodiments, the compounds of formula II may include a compound of Table 2 or a pharmaceutically acceptable salt thereof.

In some embodiments, the compounds of the invention may include a compound of Table 3 or a pharmaceutically acceptable salt thereof. In some embodiments, the compounds of the invention may include a compound selected from the group consisting of YW1132, YW1114, YW1130, YW1134, YW1128, YW1159, YW1169, YW1149, YW1173, YW1170, YW1157, YW1181, YW1179, YW2013, YW2018, YW2020, YW1132, YW2035, YW2038, YW2044, YW2049, YW2065, and YW2052, and a pharmaceutically acceptable salt thereof. In some embodiments, the compound of the invention may include YW1149, YW2013, YW2065, or YW2044, or a pharmaceutically acceptable salt thereof. In some embodiments, the compound of the invention may include YW1149, YW1128, or a pharmaceutically acceptable salt thereof.

In another aspect, the invention may include a method of treating a disease alleviated by inhibiting Wnt/β-catenin signaling in a patient in need of said treatment.

In some embodiments, the disease may be a metabolic disease or cancer.

In some embodiments, the metabolic disease may be selected from the group consisting of type 2 diabetes, obesity, hyperlipidemia, and fatty liver disease. In some embodiments, the metabolic disease is type 2 diabetes. In some embodiments, fatty liver disease may include alcoholic fatty liver disease (ALD) or non-alcoholic fatty liver disease (NAFLD). In some embodiments, NAFLD may include one or more of simple fatty liver disease (steatosis), non-alcoholic steatohepatitis (NASH), and liver cirrhosis. In certain embodiments, the metabolic disease may be NASH.

In some embodiments, the disease implicating the disease may be cancer. In some embodiments, the cancer may be selected from the group consisting of adrenocortical cancer, hepatocellular cancer, hepatoblastoma, malignant melanoma, ovarian cancer, Wilm's tumor, Barrett's esophageal cancer, prostate cancer, pancreatic cancer, bladder cancer, breast cancer, gastric cancer, head & neck cancer, lung cancer, mesothelioma, cervical cancer, uterine cancer, myeloid leukemia cancer, lymphoid leukemia cancer, pilometricoma cancer, medulloblastoma cancer, glioblastoma, and familial adenomatous polyposis. In some embodiments, the cancer may include colon cancer.

In some embodiments, the method may include administering a therapeutically effective amount of one or more compounds having the formula of formula I or the pharmaceutically acceptable salts of said one or more compounds. In some embodiments, the method may include administering a therapeutically effective amount of one or more compounds provided in Table 1 or a pharmaceutically acceptable salt of said one or more compounds. In some embodiments, the methods may include administering a therapeutically effective amount of one or more compounds having the formula of formula II or a pharmaceutically acceptable salt of said one or more compounds. In some embodiments, the methods may include administering a therapeutically effective amount of one or more compounds provided in Table 2 or a pharmaceutically acceptable salt of said one or more compounds. In some embodiments, the methods of the invention may include administering a therapeutically effective amount of one or more compounds provided in Table 3 or a pharmaceutically acceptable salt of said one or more compounds. In some embodiments, the methods of the invention may include administering a therapeutically effective amount of one or more compounds selected from the group consisting of YW1132, YW1114, YW1130, YW1134, YW1128, YW1159, YW1169, YW1149, YW1173, YW1170, YW1157, YW1181, YW1179, YW2013, YW2018, YW2020, YW1132, YW2035, YW2038, YW2044, YW2049, YW2065, and YW2052, and the pharmaceutically acceptable salts of said one or more compounds. In some embodiments, the methods of the invention may include administering a therapeutically effective amount of YW1149, YW2013, YW2065, or YW2044, or a pharmaceutically acceptable salt thereof. In some embodiments, the methods of the invention may include administering a therapeutically effective amount of YW1149, YW1128, or a pharmaceutically acceptable salt thereof.

In some embodiments, the compounds of the invention may include inhibitors of Wnt signaling. In some embodiments, the compounds of the invention may downregulate β-catenin by inhibiting Wnt signaling. In some embodiments, the compounds of the invention may upregulate Axin protein expression. In some embodiments, the compounds of the invention may downregulate c-Myc. In some embodiments, the compounds of the invention may modulate the activity of one or more of casein kinase 1 alpha (CK1α), protein kinase B (Akt/PKB), and glycogen synthase kinase 3 (GSK3). In some embodiments, the compounds of the invention may upregulate the activity of CK1α. In some embodiments, the compounds of the invention may inhibit one or more of Akt/PKB and GSK3.

In some embodiments, the compounds of the invention may suppress glucose production. The compounds of the invention may suppress the expression of glucose 6-phosphatase (G6P). In some embodiments, the compounds of the invention may, increase phosphorylation of 5' adenosine monophosphate-activated protein kinase (AMP kinase or AMPK).

In some embodiments of the invention, the compounds of the invention may treat or alleviate symptoms of a metabolic disease, such as type 2 diabetes. In some embodiments, the compounds of the invention may improve glucose tolerance in a patient in need thereof. In some embodiments, the compounds of the invention may reduce fasting glucose levels in a patient in need thereof. In some embodiments, the compounds of the invention may suppress gluconeogenesis in a patient in need thereof. In some embodiments, the compounds of the invention may reverse obesity and/or decrease weight gain in a patient in need thereof. In some embodiments, the compounds of the invention may increase insulin sensitivity in a patient in need thereof.

In some embodiments, the methods of the invention may include administering (1) a therapeutically effective amount of one or more of a compound of formula I, II, Table 1, Table 2, Table 3, and the pharmaceutically acceptable salts thereof; and (2) a therapeutically effective amount of an additional therapeutic agent. In some embodiments, the additional therapeutic agent may include one or more of a RAF inhibitor, an MEK inhibitor, an ERK inhibitor, a VEGFR inhibitor, and an EGFR inhibitor. In some embodiments, the VEGFR inhibitor may include one or more of Bevacizumab (AVASTIN), Aflibercept (ZALTRAP), and Regorafenib (STIVARGA). In some embodiments, the EGFR inhibitor may include one or more of Cetuximab (ERBITUX), Panitumumab (VECTIBIX), and Gefitinib. In some embodiments, the additional therapeutic agent may include pyrvinium.

In some embodiments of the invention, the compounds of the invention may treat or alleviate symptoms of a disease implicating the Wnt/β-catenin pathway, which may include metabolic disease or cancer.

In some embodiments, the disease implicating the Wnt/β-catenin pathway may be a metabolic disease, such as type 2 diabetes. In some embodiments, the compounds of the invention may improve glucose tolerance in a patient in need thereof. In some embodiments, the compounds of the invention may reduce fasting glucose levels in a patient in need thereof. In some embodiments, the compounds of the invention may suppress gluconeogenesis in a patient in need thereof. In some embodiments, the compounds of the invention may reverse obesity and/or decrease weight gain in a patient in need thereof. In some embodiments, the compounds of the invention may increase insulin sensitivity in a patient in need thereof.

In some embodiments, the disease implicating the Wnt/β-catenin pathway may be cancer or a hyperoliferative disease. In some embodiments, the cancer or hyperproliferative disease may be one or more of adrenocortical cancer, hepatocellular cancer, hepatoblastoma, malignant melanoma, ovarian cancer, Wilm's tumor, Barrett's esophageal cancer, prostate cancer, pancreatic cancer, bladder cancer, breast cancer, gastric cancer, head & neck cancer, lung cancer, mesothelioma, cervical cancer, uterine cancer, myeloid leukemia cancer, lymphoid leukemia cancer, pilometricoma cancer, medulloblastoma cancer, glioblastoma, and familial adenomatous polyposis. In some embodiments, the cancer or hyperproliferative disease may include colon cancer.

In another aspect, the invention includes a pharmaceutical composition that may include one or more compounds of formula I, or a pharmaceutically acceptable salt thereof, and a physiologically compatible carrier medium. In some embodiments, the invention includes a pharmaceutical composition that may include one or more compounds described in Table 1, or a pharmaceutically acceptable salt thereof, and a physiologically compatible carrier medium. In some embodiments, the invention includes a pharmaceutical composition that may include one or more compounds of formula II, or a pharmaceutically acceptable salt thereof, and a physiologically compatible carrier medium. In some embodiments, the invention includes a pharmaceutical composition that may include one or more compounds described in Table 2, or a pharmaceutically acceptable salt thereof, and a physiologically compatible carrier medium. In some embodiments, the invention includes a pharmaceutical composition that may include one or more compounds described in Table 3, or a pharmaceutically acceptable salt thereof, and a physiologically compatible carrier medium. In some embodiments, the invention includes a pharmaceutical composition that may include one or more of YW1132, YW1114, YW1130, YW1134, YW1128, YW1159, YW1169, YW1149, YW1173, YW1170, YW1157, YW1181, YW1179, YW2013, YW2018, YW2020, YW1132, YW2035, YW2038, YW2044, YW2049, YW2065, and YW2052, or a pharmaceutically acceptable salt thereof, and a physiologically compatible carrier medium. In some embodiments, the invention includes a pharmaceutical composition that may include YW1149, YW2013, YW2065, or YW2044, or a pharmaceutically acceptable salt thereof, and a physiologically compatible carrier medium. In some embodiments, the invention includes a pharmaceutical composition that may include YW1149, YW1128, or a pharmaceutically acceptable salt thereof, and a physiologically compatible carrier medium.

In some embodiments, the compositions of the invention may include (1) one or more of a compound of formula I, II, Table 1, Table 2, Table 3, and the pharmaceutically acceptable salts thereof; (2) an additional therapeutic agent; and a physiologically compatible carrier medium. In some embodiments, the additional therapeutic agent may include one or more of a RAF inhibitor, an MEK inhibitor, an ERK inhibitor, a VEGFR inhibitor, and an EGFR inhibitor. In some embodiments, the VEGFR inhibitor may include one or more of Bevacizumab (AVASTIN), Aflibercept (ZALTRAP), and Regorafenib (STIVARGA). In some embodiments, the EGFR inhibitor may include one or more of Cetuximab (ERBITUX), Panitumumab (VECTIBIX), and Gefitinib. In some embodiments, the additional therapeutic agent may include pyrvinium.

BRIEF DESCRIPTION OF THE DRAWINGS

The foregoing summary and the following detailed description of the exemplary embodiments of the present invention may be further understood when read in conjunction with the appended drawings, in which:

FIGS. 4A to 4C illustrate the effects of YW1149 and pyrvinium on glucose production (FIG. 4A), G6P expression (FIG. 4B), and AMPK phosphorylation (FIG. 4C) in HepG2 cells. In FIGS. 4A and 4B: 0.1 μM pyrvinium and 10 μM YW1149. *$P<0.05$; **$P<0.01$ compared to vehicle treatment.

In FIG. 7A, the cytotoxicity of YW1149 and pyrvinium was assessed using a colorimetric assay, CCK-8, in HEK293 cells. In FIG. 7B, a Kaplan-Meier survival analysis of the mice was performed where the mice received single intravenous (IV, tail vein) dosages of YW1149 (10 mg/kg) or pyrvinium pamoate (2 mg/kg). 12-week old C57BL/6 mice were used (n=5 or 6 mice/group).

FIG. 9 illustrates the inhibitory effect of certain compounds of the invention on cell proliferation and growth in SW480 cells.

FIG. 10 describes the relationships between various cells lines and their sources.

FIG. 11 illustrates the cytoxic activity of certain compounds of the invention in various cancer cells lines.

FIGS. 33A and 33B illustrate liver histology (H&E staining) for those mice euthanized at 11 weeks, which were given vehicle.

FIGS. 33C and 33D illustrate liver histology (H&E staining) for those mice euthanized at 11 weeks, which were given YW1128.

FIG. 34A illustrates the glucose level for mice over 120 minutes post-injection at week 0 of the study. FIG. 34B illustrates the glucose level for mice over 120 minutes post-injection at week 11 of the study. *P<0.05, **P<0.01 compared to the YW1128 group.

FIG. 36A illustrates representative liver histology by H&E staining. FIG. 36B illustrates an intraperitoneal glucose tolerance test (IPGTT) performed at the end of a study.

FIG. 36C illustrates body weight monitoring performed during the treatment. FIG. 36D illustrates increased phosphorylation of AMPKα1 at threonine 172 (T172) (p-AMPKα) in YW1128-treated livers as compared to vehicle-treated livers. CK1a did not show any significant change. *P<0.05, compared with the corresponding YW1128 group.

FIG. 37A illustrates tumor growth measured during the study every other day. FIG. 37B illustrates tumor weight that was measured after mouse euthanization. FIG. 37C illustrates the change in mouse body weight during the study.

FIG. 38A illustrates that YW2065 reduced oxygen consumption rate (OCR). FIG. 38B illustrates ATP production estimated from the OCR measurement. FIG. 38C illustrates how YW2065 (10 µM) caused short and punctuated mitochondria in SW480 cells after 4 hours of treatment. FIG. 38D illustrates how YW2065 increased ROS generation in SW480 cells as evaluated by staining the cells with DHE. DHE fluorescence intensity was measured by using ImageJ. ~300 cells were counted in each treatment.

DETAILED DESCRIPTION OF THE INVENTION

Figure 1:
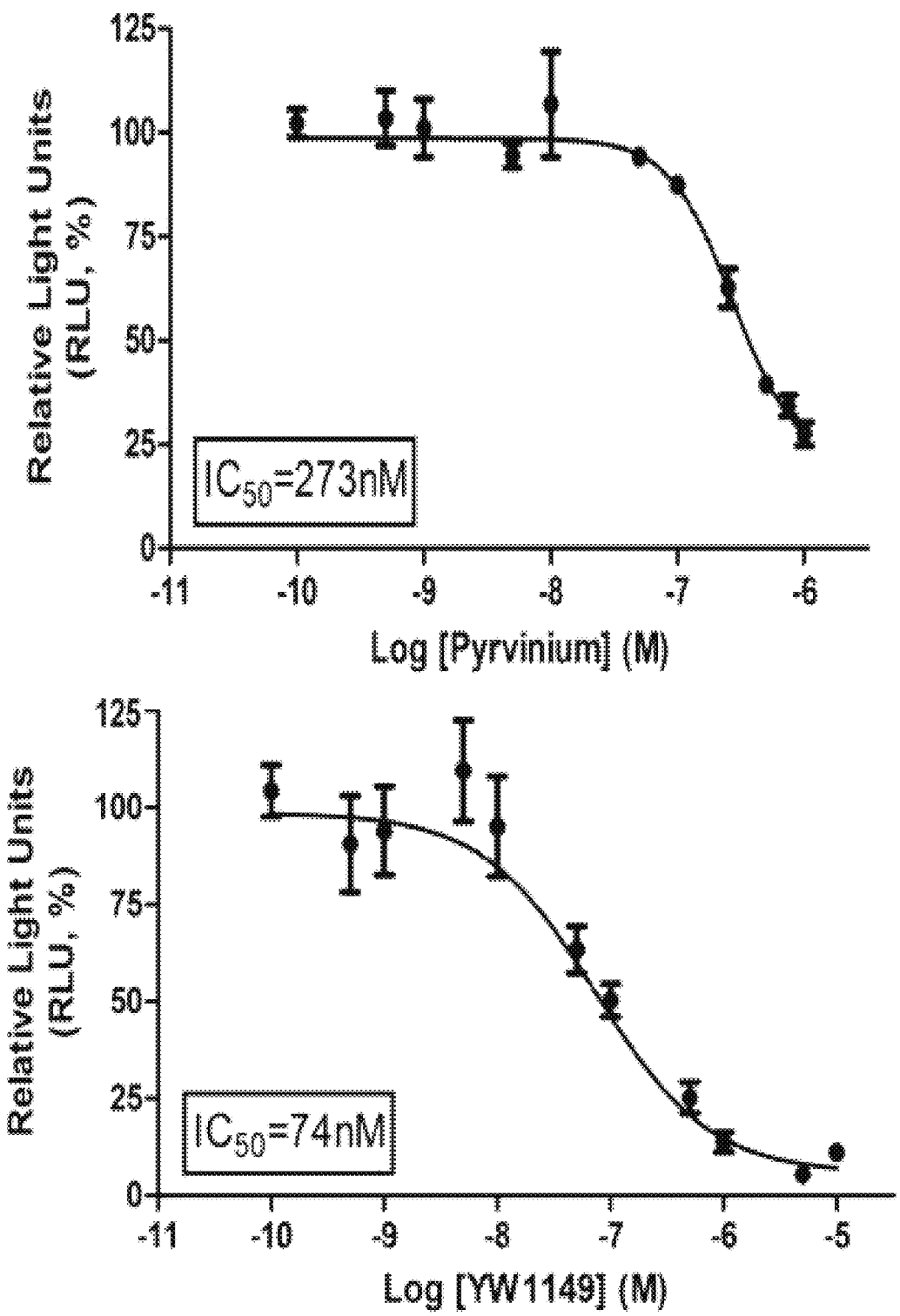
FIG. 1 illustrates the results of a dual luciferase gene reporter assay for Wnt/β-catenin signaling inhibition that compares the inhibitory activity of pyrvinium to YW1149.

The present invention relates generally to compounds, and methods of using such compounds, that may inhibit the Wnt/β-catenin signaling pathway. More specifically, the compounds of the invention are represented in formulas I and II, which may be used in treating diseases that implicate the Wnt/β-catenin signaling pathway.

The Wnt/β-catenin signaling pathway plays a pivotal role in cell proliferation and differentiation. Moreover, it regulates the transcription of its target genes through the transcriptional factor β-catenin. In the "off state" without Wnt ligands, β-catenin forms a cytoplasmic "destruction complex" with adenomatous polyposis coli (APC) and Axin, which facilitiates the phosphorylation of β-catenin by glycogen synthase kinase 3 (GSK3) and casein kinase 1 (CK1) at the N-terminal residues Ser45, Thr41, Ser37, and Ser33. Phosphorylated β-catenin is recognized and ubiquitinated by the F-box β-transducin repeat-containing protein (β-TrCP), and then degraded by the proteasome. On the other hand, the "on-state" of the pathway involves increased post-translational stability and thus accumulation of β-catenin, through Wnt-dependent degradation of Axin and inhibition of GSK3 by various mechanisms. As the β-catenin level increases, it translocates to the nucleus where it binds to LEF/TCF such as TCF7L2 and activates expression of downstream genes.

Increased expression of β-catenin and malfunction of the Wnt-signaling pathway are implicated in a variety of diseases.

In one embodiment, the compounds of the invention may be used as treatments for metabolic disease in a patient in need thereof. As used herein, the term "metabolic disease" may refer to diseases that involve a disruption to a patient's metabolic homeostasis, including, but not limited to, type 2 diabetes, obesity, hyperlipidemia, and fatty liver disease. In some embodiments, the metabolic disease described in the invention may be type 2 diabetes. In some embodiments, fatty liver disease may include alcoholic fatty liver disease (ALD) or non-alcoholic fatty liver disease (NAFLD). In some embodiments, NAFLD may include one or more of simple fatty liver disease (steatosis), non-alcoholic steatohepatitis (NASH), and liver cirrhosis. In certain embodiments, the metabolic disease may be NASH.

Research in different groups has identified an association between type 2 diabetes risk and single nucleotide polymorphisms (SNPs) in TCF7L2, an effector of the Wnt/β-catenin pathway. Similar genetic evidence has been obtained for additional modulators of the Wnt signaling pathway, including WNT5B, WNT10B, and LRP6. Therefore, the Wnt/β-catenin pathway has emerged as a novel therapeutic target for treating disease, including metabolic disorders.

With respect to cancer, the Wnt pathway may be activated in a variety of cancers including, for example, colon cancer, hepatocellular carcinoma, lung cancer, ovarian cancer, prostate cancer, pancreatic cancer, and leukemias such as CML, CLL and T-ALL. The activation is due to constitutively active β-catenin, perhaps, without being limited to any one theory, due to its stabilization by interacting factors or inhibition of the degradation pathway. Accordingly, the compounds and compositions described herein may be used to treat these cancers in which the Wnt pathway is constitutively activated.

In some embodiments, the disease implicating the Wnt/β-catenin pathway may be cancer or a hyperoliferative disease. In some embodiments, the cancer or hyperproliferative disease may be one or more of adrenocortical cancer, hepatocellular cancer, hepatoblastoma, malignant melanoma, ovarian cancer, Wilm's tumor, Barrett's esophageal cancer, prostate cancer, pancreatic cancer, bladder cancer, breast cancer, gastric cancer, head & neck cancer, lung cancer, mesothelioma, cervical cancer, uterine cancer, myeloid leukemia cancer, lymphoid leukemia cancer, pilometricoma cancer, medulloblastoma cancer, glioblastoma, and familial adenomatous polyposis. In some embodiments, the cancer or hyperproliferative disease may include colon cancer.

In some embodiments, cancers that may be treated by the compounds, compositions and methods described herein include, but are not limited to, the following:

1) Breast cancers, including, for example ER+ breast cancer, ER− breast cancer, her2− breast cancer, her2+ breast cancer, stromal tumors such as fibroadenomas, phyllodes tumors, and sarcomas, and epithelial tumors such as large duct papillomas; carcinomas of the breast including in situ (noninvasive) carcinoma that includes ductal carcinoma in situ (including Paget's disease) and lobular carcinoma in situ, and invasive (infiltrating) carcinoma including, but not limited to, invasive ductal carcinoma, invasive lobular carcinoma, medullary carcinoma, colloid (mucinous) carcinoma, tubular carcinoma, and invasive papillary carcinoma; and miscellaneous malignant neoplasms. Further examples of breast cancers can include luminal A, lumina B, basal A, basal B, and triple negative breast cancer, which is estrogen receptor negative (ER−), progesterone receptor negative, and her2 negative (her2−). In some embodiments, the breast cancer may have a high risk Oncotype score;
2) Cardiac cancers, including, for example sarcoma, e.g., angiosarcoma, fibrosarcoma, rhabdomyosarcoma, and liposarcoma; myxoma; rhabdomyoma; fibroma; lipoma and teratoma;
3) Lung cancers, including, for example, bronchogenic carcinoma, e.g., squamous cell, undifferentiated small cell, undifferentiated large cell, and adenocarcinoma; alveolar and bronchiolar carcinoma; bronchial adenoma; sarcoma; lymphoma; chondromatous hamartoma; and mesothelioma;
4) Gastrointestinal cancer, including, for example, cancers of the esophagus, e.g., squamous cell carcinoma, adenocarcinoma, leiomyosarcoma, and lymphoma; cancers of the stomach, e.g., carcinoma, lymphoma, and leiomyosarcoma; cancers of the pancreas, e.g., ductal adenocarcinoma, insulinoma, glucagonoma, gastrinoma, carcinoid tumors, and vipoma; cancers of the small bowel, e.g., adenocarcinoma, lymphoma, carcinoid tumors, Kaposi's sarcoma, leiomyoma, hemangioma, lipoma, neurofibroma, and fibroma; cancers of the large bowel, e.g., adenocarcinoma, tubular adenoma, villous adenoma, hamartoma, and leiomyoma;
5) Genitourinary tract cancers, including, for example, cancers of the kidney, e.g., adenocarcinoma, Wilm's tumor (nephroblastoma), lymphoma, and leukemia; cancers of the bladder and urethra, e.g., squamous cell carcinoma, transitional cell carcinoma, and adenocarcinoma; cancers of the prostate, e.g., adenocarcinoma, and sarcoma; cancer of the testis, e.g., seminoma, teratoma, embryonal carcinoma, teratocarcinoma, choriocarcinoma, sarcoma, interstitial cell carcinoma, fibroma, fibroadenoma, adenomatoid tumors, and lipoma;
6) Liver cancers, including, for example, hepatoma, e.g., hepatocellular carcinoma; cholangiocarcinoma; hepatoblastoma; angiosarcoma; hepatocellular adenoma; and hemangioma;
7) Bone cancers, including, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochrondroma (osteocartilaginous exostoses), benign chondroma, chondroblastoma, chondromyxofibroma, osteoid osteoma and giant cell tumors;
8) Nervous system cancers, including, for example, cancers of the skull, e.g., osteoma, hemangioma, granuloma, xanthoma, and osteitis deformans; cancers of the meninges, e.g., meningioma, meningiosarcoma, and gliomatosis; cancers of the brain, e.g., astrocytoma, medulloblastoma, glioma, ependymoma, germinoma (pinealoma), glioblastoma multiform, oligodendroglioma, schwannoma, retinoblastoma, and congenital tumors; and cancers of the spinal cord, e.g., neurofibroma, meningioma, glioma, and sarcoma;
9) Gynecological cancers, including, for example, cancers of the uterus, e.g., endometrial carcinoma; cancers of the cervix, e.g., cervical carcinoma, and pre tumor cervical dysplasia; cancers of the ovaries, e.g., ovarian carcinoma, including serous cystadenocarcinoma, mucinous cystadenocarcinoma, unclassified carcinoma, granulosa theca cell tumors, Sertoli Leydig cell tumors, dysgerminoma, and malignant teratoma; cancers of the vulva, e.g., squamous cell carcinoma, intraepithelial carcinoma, adenocarcinoma, fibrosarcoma, and melanoma; cancers of the vagina, e.g., clear cell carcinoma, squamous cell carcinoma, botryoid sarcoma, and embryonal rhabdomyosarcoma; and cancers of the fallopian tubes, e.g., carcinoma;

10) Hematologic cancers, including, for example, cancers of the blood, e.g., acute myeloid leukemia, chronic myeloid leukemia, acute lymphoblastic leukemia, chronic lymphocytic leukemia, myeloproliferative diseases, multiple myeloma, and myelodysplastic syndrome, Hodgkin's lymphoma, non Hodgkin's lymphoma (malignant lymphoma) and Waldenström's macroglobulinemia;

11) Skin cancers and skin disorders, including, for example, malignant melanoma, basal cell carcinoma, squamous cell carcinoma, Kaposi's sarcoma, moles dysplastic nevi, lipoma, angioma, dermatofibroma, keloids, and psoriasis;

12) Adrenal gland cancers, including, for example, neuroblastoma; and

13) Pancreatic cancer.

Cancers may be solid tumors that may or may not be metastatic. Cancers may also occur, as in leukemia, as a diffuse tissue. Thus, the term "tumor cell," as provided herein, includes a cell afflicted by any one of the above identified disorders.

A method of treating cancer using a compound or composition as described herein may be combined with existing methods of treating cancers, for example by chemotherapy, irradiation, or surgery (e.g., oophorectomy). In some embodiments, a compound or composition can be administered before, during, or after another anticancer agent, additional therapeutic agent, or treatment.

The compounds of the invention may include those described by formula I:

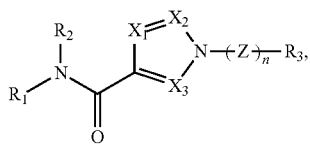

(I)

wherein $R_1$ and $R_2$ each may independently represent a substituent selected from the group consisting of H and substituted or unsubstituted alkyl, alkenyl, alkynyl, cycloalkyl, aryl, heterocycle, heteroaryl, alkoxy, carboxy, carbalkoxy, and carboxamido;

$R_3$ may represent a substituent selected from the group consisting of substituted or unsubstituted alkyl, alkenyl, alkynyl, cycloalkyl, aryl, heterocycle, and heteroaryl;

n may represent an integer of 0 to 2, Z represents one or more substituted or unsubstituted alkyl substituents when n is 1 or 2;

$X_1$ may represent N or $CR_4$;

$X_2$ may represent N or $CR_5$;

$X_3$ may represent N or $CR_6$; $R_4$, $R_5$, and $R_6$ each may independently represent a substituent selected from the group consisting of H, OH, $NO_2$, CN, halo, and substituted or unsubstituted alkyl, alkylcarbonyl, alkenyl, alkynyl, cycloalkyl, aryl, heterocycle, heteroaryl, amino, alkoxy, carboxy, carbalkoxy, carboxamido, sulfonyl, sulfonamido, sulfinyl, monoalkylaminosulfinyl, dialkylaminosulfinyl, monoalkylaminosulfonyl, dialkylaminosulfonyl, alkylsulfonylamino, hydroxysulfonyloxy, alkoxysulfonyloxy, alkylsulfonyloxy, hydroxysulfonyl, alkoxysulfonyl, alkylsulfonylalkyl, monoalkylaminosulfonylalkyl, dialkylaminosulfonylalkyl, monoalkylaminosulfinylalkyl, and dialkylaminosulfinylalkyl; and where if $X_1$ and $X_2$ represent $CR_4$ and $CR_5$, respectively, then $R_4$ and $R_5$ may be taken together to form a substituted or unsubstituted m-membered cycloalkyl or heterocycle, wherein m may represent an integer of 5 to 7.

In some embodiments of formula I, n may represent 0 or 1. In other embodiments, n represents 0.

In some embodiments of formula I, $X_3$ may represent $CR_6$, where $R_6$ may be alkyl (e.g., methyl, ethyl, n-propyl, i-propyl), halo (e.g., chloro, bromo), or substituted or unsubstituted amino (e.g., $NMe_2$).

In some embodiments of formula I, $R_1$ may represent substituted or unsubstituted aryl (e.g., phenyl, naphthyl) or heteroaryl (e.g., quinolinyl, thiazolyl, isooxazolyl, benzithiazolyl, benzimidizolyl, isoquinolinyl, pyridinyl, pyrimidinyl, benzopyronyl).

In some embodiments of formula I, $X_1$ and $X_2$ may be N. In some embodiments, $X_2$ is N and $X_3$ is $CR_6$. In some embodiments, $X_1$ is $CR_4$ and $X_2$ is N.

In some embodiments of formula I, $R_2$ may be H.

In some embodiments of formula I, $R_3$ may be substituted or unsubstituted phenyl.

In some embodiments of formula I, m may be an integer of 5 or 6.

In some embodiments, the compounds of the invention may include those described by formula II:

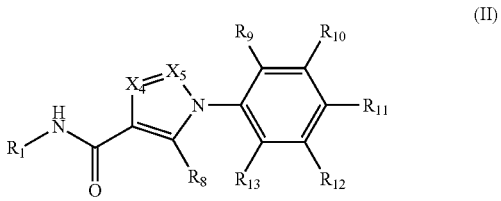

(II)

wherein $R_7$ may represent a substituent selected from the group consisting of H and substituted or unsubstituted alkyl, alkenyl, alkynyl, cycloalkyl, aryl, heterocycle, heteroaryl, alkoxy, carboxy, carbalkoxy, and carboxamido;

$R_8$ may represent a substituent selected from the group consisting of H, OH, $NO_2$, CN, halo, and substituted or unsubstituted alkyl, alkenyl, alkynyl, aryl, amino, and alkoxy;

$R_9$, $R_{10}$, $R_{11}$, $R_{12}$, and $R_{13}$ each may independently represent a substituent selected from the group consisting of H, OH, $NO_2$, CN, halo, and substituted or unsubstituted alkyl, alkylcarbonyl, alkenyl, alkynyl, cycloalkyl, aryl, heterocycle, heteroaryl, amino, alkoxy, carboxy, carbalkoxy, carboxamido, sulfonyl, sulfonamido, sulfinyl, monoalkylaminosulfinyl, dialkylaminosulfinyl, monoalkylaminosulfonyl, dialkylaminosulfonyl, alkylsulfonylamino, hydroxysulfonyloxy, alkoxysulfonyloxy, alkylsulfonyloxy, hydroxysulfonyl, alkoxysulfonyl, alkylsulfonylalkyl, monoalkylaminosulfonylalkyl, dialkylaminosulfonylalkyl, monoalkylaminosulfinylalkyl, and dialkylaminosulfinylalkyl;

$X_4$ may represent N or $CR_{14}$;

$X_5$ may represent N or $CR_{15}$; $R_{14}$ and $R_{15}$ each may independently represent a substituent selected from the group consisting of H, OH, $NO_2$, CN, halo, and substituted or unsubstituted alkyl, alkylcarbonyl, alkenyl, alkynyl, cycloalkyl, aryl, heterocycle, heteroaryl, amino, alkoxy, carboxy, carbalkoxy, carboxamido, sulfonyl, sulfonamido, sulfinyl, monoalkylaminosulfinyl, dialkylaminosulfinyl, monoalkylaminosulfonyl, dialkylaminosulfonyl, alkylsulfonylamino, hydroxysulfonyloxy, alkoxysulfonyloxy, alkylsulfonyloxy, hydroxysulfonyl, alkoxysulfonyl, alkylsulfonylalkyl, monoalkylaminosulfonylalkyl, dialkylaminosulfonylalkyl, monoalkylaminosulfinylalkyl, and dialkylaminosulfinylalkyl; and where if $X_4$ and $X_5$ are $CR_{14}$ and $CR_{15}$, respectively, then $R_{14}$ and $R_{15}$ may be taken together to form a substituted or unsubstituted m-membered cycloalkyl or heterocycle, wherein m may be an integer of 5 to 7.

In some embodiments of formula II, $R_7$ may be substituted or unsubstituted aryl (e.g., phenyl, naphthyl) or heteroaryl (e.g., quinolinyl, thiazolyl, isooxazolyl, benzithiazolyl, benzimidizolyl, isoquinolinyl, pyridinyl, pyrimidinyl, benzopyronyl).

In some embodiments of formula II, m may be an integer of 5 or 6.

In some embodiments of formula II, $X_4$ and $X_5$ may both be N.

In some embodiments of formula II, $R_8$ may be alkyl (e.g., methyl, ethyl, n-propyl, i-propyl), halo (e.g., chloro, bromo), or substituted or unsubstituted amino (e.g., $NMe_2$).

Regarding the compounds of the invention, which are encompassed within formulas I and II, as used herein, the term "alkyl" denotes branched or unbranched hydrocarbon chains, having about 1 to 10 carbons, such as, methyl, ethyl, n-propyl, iso-propyl, n-butyl, sec-butyl, iso-butyl, tert-butyl, 2-methylpentyl, pentyl, hexyl, isohexyl, heptyl, 4,4-dimethyl pentyl, octyl, 2,2,4-trimethylpentyl, and the like. "Substituted alkyl" includes an alkyl group optionally substituted with one or more functional groups which are attached commonly to such chains, such as, hydroxy, halogen, mercapto or thio, cyano, alkylthio, carboxy, nitro, alkoxy, or optionally substituted, alkyl, amino, alkenyl, carboxamido, carbalkoxy, alkynyl, heterocyclyl, aryl, heteroaryl, and the like to form alkyl groups such as trifluoromethyl, 3-hydroxyhexyl, 2-carboxypropyl, 2-fluoroethyl, carboxymethyl, cyanobutyl, phenethyl, benzyl, and the like.

The term "halogen" or "halo" as used herein alone or as part of another group refers to chloro, bromo, fluoro, or iodo.

The term "alkoxy" refers to alkyl-O—, in which alkyl is as defined above.

The term "alkylthio" refers to alkyl-S—, in which alkyl is as defined above.

The term "alkylamino" refers to —NR'R", in which R' and R" each may independently represent H, alkyl, or aryl, all as defined herein.

The term "alkylcarbonyl" refers to —C(=O)-alkyl, in which alkyl is as defined above.

The term "carboxy" refers to the moiety —C(=O)OH.

The term "carbalkoxy" refers to the moiety —C(=O)—O-alkyl, in which alkyl is as defined above.

The term "carboxamido" refers to the moiety —C(=O)—NR'R", in which R' and R", each may independently represent H, alkyl, or aryl, all as defined herein.

The term "alkylsulfonyl" refers to the moiety —S(=O)$_2$-alkyl, in which alkyl is as defined above.

The term "arylsulfonyl" refers to the moiety —S(=O)$_2$-aryl, in which aryl is as defined herein. For example, arylsulfonyl may be —S(=O)$_2$-phenyl.

The term "arylsulfonyloxy" refers to the moiety —OS(=O)$_2$-alkyl, wherein alkyl is as defined above.

The term "amino(monoalkylamino-, dialkylamino-)sulfinyl" refers to the moiety —S(=O)NR'R", in which R' and R" each may independently represent H, alkyl, or aryl, all as defined herein.

The term "amino(monoalkylamino-, dialkylamino-)sulfonyl" refers to the moiety —S(=O)$_2$NR'R", in which R' and R" each may independently represent H, alkyl, or aryl, all as defined herein.

The term "alkylsulfonylamino" refers to the moiety —NHS(=O)$_2$-alkyl, in which alkyl is as previously defined.

The term "hydroxysulfonyloxy" refers to the moiety —OS(=O)$_2$OH.

The term "alkoxysulfonyloxy" refers to the moiety —OS(=O)$_2$O-alkyl, in which alkyl is as defined above.

The term "alkylsulfonyloxy" refers to the moiety —OS(=O)$_2$-alkyl, in which alkyl is as previously defined.

The term "hydroxysulfonyl" refers to the moiety —S(=O)$_2$OH.

The term "alkoxysulfonyl" refers to the moiety —S(=O)$_2$O-alkyl, wherein alkyl is as previously defined.

The term "alkylsulfonylalkyl" refers to the moiety -alkyl-S(=O)$_2$-alkyl, wherein each alkyl may be as previously defined.

The term "amino(monoalkylamino-, dialkylamino-)sulfonylalkyl" refers to the moiety -alkyl-S(=O)$_2$—NR'R", wherein alkyl is as previously defined, and R' and R" each may independently represent H, alkyl, or aryl, all as defined herein.

The term "amino(monoalkylamino-, dialkylamino-)sulfinylalkyl" refer to the moieties -alkyl-S(=O)—NR'R", wherein alkyl is as previously defined, and R' and R" each may independently represent H, alkyl, or aryl, all as defined herein.

Unless otherwise indicated, the term "cycloalkyl" as employed herein alone or as part of another group includes saturated or partially unsaturated (containing 1 or more double bonds) cyclic hydrocarbon groups containing 1 to 3 rings, including monocyclicalkyl, bicyclicalkyl and tricyclicalkyl, containing a total of 3 to 20 carbons forming the rings, preferably 3 to 10 carbons, forming the ring and which may be fused to 1 or 2 aromatic rings as described for aryl, which include cyclopropyl, cyclobutyl, cyclopentyl, cyclohexyl, cycloheptyl, cyclooctyl, cyclodecyl, cyclododecyl, and cyclohexenyl. "Substituted cycloalkyl" includes a cycloalkyl group optionally substituted with 1 or more substituents such as halogen, alkyl, substituted alkyl, alkoxy, hydroxy, aryl, substituted aryl, aryloxy, cycloalkyl, alkylamido, alkanoylamino, oxo, acyl, arylcarbonylamino, amino, nitro, cyano, thiol and/or alkylthio and/or any of the substituents included in the definition of "substituted alkyl."

Unless otherwise indicated, the term "alkenyl" as used herein by itself or as part of another group refers to straight or branched chain of 2 to 20 carbons, preferably 2 to 12 carbons, and more preferably 2 to 8 carbons in the normal chain, which include one or more double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8, 12-tetradecatrienyl, and the like. "Substituted alkenyl" includes an alkenyl group optionally substituted with one or more substituents, such as the substituents included above in the definition of "substituted alkyl" and "substituted cycloalkyl."

Unless otherwise indicated, the term "alkynyl" as used herein by itself or as part of another group refers to straight or branched chain of 2 to 20 carbons, preferably 2 to 12 carbons and more preferably 2 to 8 carbons in the normal chain, which include one or more triple bonds in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like. "Substituted alkynyl" includes an alkynyl group optionally substituted with one or more substituents, such as the substituents included above in the definition of "substituted alkyl" and "substituted cycloalkyl."

Unless otherwise indicated, the term "aryl" or "Ar" as employed herein alone or as part of another group refers to monocyclic, bicyclic, and/or polycyclic aromatic groups containing 6 to 10 carbons in the ring portion (such as phenyl or naphthyl including 1-naphthyl and 2-naphthyl) and may optionally include one to three additional rings fused to a carbocyclic ring or a heterocyclic ring, such as aryl, cycloalkyl, heteroaryl, or cycloheteroalkyl rings or substituted forms thereof.

"Substituted aryl" includes an aryl group optionally substituted with one or more functional groups, such as halo, alkyl, haloalkyl (e.g., trifluoromethyl), alkoxy, haloalkoxy (e.g., difluoromethoxy), alkenyl, alkynyl, cycloalkyl-alkyl, cycloheteroalkyl, cycloheteroalkylalkyl, aryl, heteroaryl, arylalkyl, aryloxy, aryloxyalkyl, arylalkoxy, alkoxycarbonyl, alkylcarbonyl, arylcarbonyl, arylalkenyl, aminocarbonylaryl, arylthio, arylsulfinyl, arylazo, heteroarylalkyl, heteroarylalkenyl, heteroarylheteroaryl, heteroaryloxy, hydroxy, nitro, cyano, amino, substituted amino wherein the amino includes 1 or 2 substituents (which are optionally substituted alkyl, aryl or any of the other substituents recited herein), thiol, alkylthio, arylthio, heteroarylthio, arylthioalkyl, alkoxyarylthio, alkylaminocarbonyl, arylaminocarbonyl, aminocarbonyl, alkylcarbonyloxy, arylcarbonyloxy, alkylcarbonylamino, arylcarbonylamino, arylsulfinyl, arylsulfinylalkyl, arylsulfonylamino, or arylsulfonaminocarbonyl and/or any of the alkyl substituents recited herein.

Unless otherwise indicated, the term "heteroaryl" as used herein alone or as part of another group refers to a 5- to 7-membered aromatic ring which includes 1, 2, 3 or 4 hetero atoms such as nitrogen, oxygen or sulfur and such rings fused to an aryl, cycloalkyl, heteroaryl or heterocycloalkyl ring (e.g. benzothiophene, indole, quinoline, thiazole, isooxazole, benzothiazole, benzimidizole, isoquinoline, pyridine, pyrimidine, benzopyrone, oxazole, thiazole, pyrazine), and includes possible N-oxides. "Substituted heteroaryl" includes a heteroaryl group optionally substituted with 1 to 4 substituents, such as the substituents included above in the definition of "substituted alkyl" and "substituted cycloalkyl." Substituted heteroaryl also includes fused heteroaryl groups which include, for example, quinoline, isoquinoline, indole, isoindole, carbazole, acridine, benzopyrene, benzopyrone, benzimidazole, benzofuran, isobenzofuran, phenanthroline, purine, and the like.

Moreover, the terms "heterocyclo," "heterocycle," or "heterocyclic ring," as used herein, refer to an unsubstituted or substituted stable 5- to 7-membered monocyclic ring system which may be saturated or unsaturated, and which consists of carbon atoms and from one to four heteroatoms selected from N, O or S, and wherein the nitrogen and sulfur heteroatoms may optionally be oxidized, and the nitrogen heteroatom may optionally be quaternized. The heterocyclic ring may be attached at any heteroatom or carbon atom which results in the creation of a stable structure. Examples of such heterocyclic groups include, but are not limited to, piperidinyl, piperazinyl, oxopiperazinyl, oxopiperidinyl, oxopyrrolidinyl, oxoazepinyl, azepinyl, pyrrolyl, pyrrolidinyl, benzothiophene, chromone, benzopyrene, benzopyrone, furanyl, thienyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isooxazolyl, isoxazolidinyl, morpholinyl, thiazolyl, thiazolidinyl, isothiazolyl, thiadiazolyl, tetrahydropyranyl, thiamorpholinyl, thiamorpholinylsulfoxide, thiamorpholinylsulfone, and oxadiazolyl.

As used herein, the terms "optionally substituted" or "substituted" may indicate that a chemical moiety referred to, for example, alkyl, aryl, and heteroaryl, may be unsubstituted or substituted with one or more groups including, without limitation, alkyl, substituted alkyl, alkenyl, substituted alkenyl, alkynyl, substituted alkynyl, cycloalkyl, substituted cycloalkyl, arylalkyl, substituted arylalkyl, aryl, substituted aryl, heterocycle, substituted heterocycle, heteroaryl, substituted heteroaryl, hydroxyl, amino, substituted amino, alkoxy, substituted alkoxy, halogen, carboxy, nitro, carbalkoxy, substituted carbalkoxy, carboxamido, substituted carboxamido, alkylamino, substituted alkyl amino, monoalkylaminosulfinyl, substituted, monoalkylaminosulfinyl, dialkylaminosulfinyl, substituted dialkylaminosulfinyl, monoalkylaminosulfonyl, substituted monoalkylaminosulfonyl, dialkylaminosulfonyl, substituted dialkylaminosulfonyl, alkylsulfonylamino, substituted alkylsulfonylamino, hydroxysulfonyloxy, alkoxysulfonyloxy, substituted alkoxysulfonyloxy, alkylsulfonyloxy, substituted alkylsulfonyloxy, hydroxysulfonyl, alkoxysulfonyl, substituted alkoxysulfonyl, alkylsulfonylalkyl, substituted alkylsulfonylalkyl, monoalkylaminosulfonylalkyl, substituted monoalkylaminosulfonylalkyl, dialkylaminosulfonylalkyl, substituted dialkylaminosulfonylalkyl, monoalkylaminosulfinylalkyl, substituted monoalkylaminosulfinylalkyl, dialkylaminosulfinylalkyl, substituted dialkylaminosulfinylalkyl, and the like. The chemical moieties of formulas I and II, above, that may be optionally substituted include alkyl, alkenyl, alkynyl, cycloalkyl, arylalkyl, aryl, heterocycle, and heteroaryl, as described herein. For example, optionally substituted alkyl may include both propyl and 2-chloro-propyl. Additionally, "optionally substituted" is also inclusive of embodiments where the named substituent or substituents have multiple substituents rather than simply a single substituent. For example, optionally substituted aryl may include both phenyl and 3-ethyl-5-methyl-6-bromo-phenyl.

The compounds of the invention may be administered as salts, which are also within the scope of this invention. Pharmaceutically acceptable (i.e., non-toxic, physiologically compatible) salts are preferred. If the compounds of the invention have, for example, at least one basic center, they can form acid addition salts. These are formed, for example, with strong inorganic acids, such as mineral acids, for example sulfuric acid, phosphoric acid or a hydrohalic acid, with strong organic carboxylic acids, such as alkane carboxylic acids of 1 to 4 carbon atoms which are unsubstituted or substituted, for example, by halogen, for example acetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, (for example aspartic or glutamic acid or lysine or arginine), or benzoic acid, or with organic sulfonic acids, such as ($C_1$-$C_4$) alkyl or arylsulfonic acids which are unsubstituted or substituted, for example by halogen, for example methyl- or paratoluene-sulfonic acid. Corresponding acid addition salts can also be formed having plural basic centers, if desired.

The compounds of the invention having at least one acid group (e.g., carboxylic acid) can also form salts with suitable bases. Representative examples of such salts include metal salts, such as alkali metal or alkaline earth metal salts, for example sodium, potassium or magnesium salts, or salts with ammonia or an organic amine, such as morpholine, thiomorpholine, piperidine, pyrrolidine, a mono, di or trihydroxy lower alkylamine, for example ethyl, tert-butyl, diethyl, diisopropyl, triethyl, tributyl or dimethyl-propylamine, or a mono, di or trihydroxy lower alkylamine, for example mono, di or triethanolamine. Corresponding internal salts may also be formed.

For example, certain salts of the compounds described herein which contain a basic group include monohydrochloride, hydrogensulfate, methanesulfonate, phosphate or nitrate. Moreover, certain salts of the compounds described herein which contain an acid group include sodium, potassium and magnesium salts and pharmaceutically acceptable organic amines.

All stereoisomers of the compounds of the invention, either in a mixture or in pure or substantially pure form, are considered to be within the scope of this invention. The compounds of the invention may have asymmetric centers at any of the carbon atoms including any one of the substituents. Consequently, compounds of the invention may exist in enantiomeric or diastereomeric forms or in mixtures thereof. Furthermore, where a stereocenter existing in a compound of the invention is represented as a racemate, it is understood that the stereocenter may encompass the racemic mixture of R and S isomers, the S isomers, and the R isomers. The processes for preparation of such compounds can utilize racemates, enantiomers, or diastereomers as starting materials. When diastereomeric or enantiomeric products are prepared, they can be separated by conventional methods including, chromatographic, chiral HPLC, fractional crystallization, or distillation. Some compounds of the present invention have groups including alkenyls, iminyls, and the like, which may exist as entgegen (E) or zusammen (Z) conformations, in which case all geometric forms thereof, both E and Z, cis and trans, and mixtures thereof, are within the scope of the present invention. Accordingly, when such geometric isomeric products are prepared, they can be separated by conventional methods for example, chromatographic, HPLC, distillation or crystallization In some embodiments, the compounds of the invention may include those compounds of formula I that are set forth in Table 1, below:

TABLE 1

Compounds of Formula I

| Compound Identifiers | Compound Name | Compound Structure |
|---|---|---|
| YW1109 (14) | 2,5-Dimethyl-N-(pyridin-2-yl)-1-(p-tolyl)-1H-pyrrole-3-carboxamide | 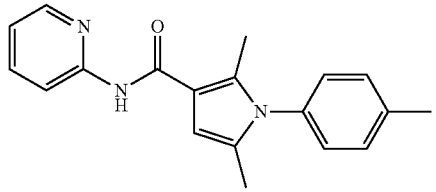 [SMILES: Cc1ccc(-n2c(C)cc(C(=O)Nc3ccccn3)c2C)cc1] |
| YW1117-2 (15) | 2,5-Dimethyl-N-(pyrazin-2-yl)-1-(p-tolyl)-1H-pyrrole-3-carboxamide | 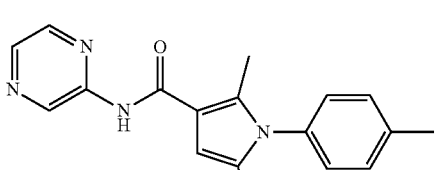 |
| YW1114 (16) | 2,5-Dimethyl-N-(4-phenylthiazol-2-yl)-1-(p-tolyl)-1H-pyrrole-3-carboxamide | 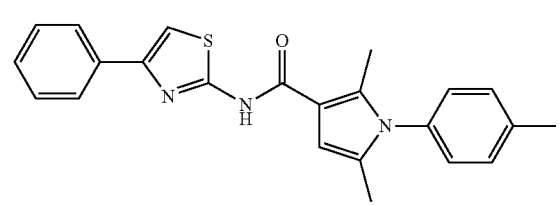 [SMILES: Cc1ccc(-n2c(C)cc(C(=O)Nc3nc(-c4ccccc4)cs3)c2C)cc1] |
| YW1104 (17) | N-Benzyl-2,5-dimethyl-1-(p-tolyl)-1H-pyrrole-3-carboxamide | 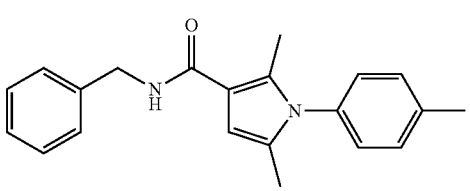 [SMILES: Cc1ccc(-n2c(C)cc(C(=O)NCc3ccccc3)c2C)cc1] |
| YW1119 (20) | 5-Methyl-N-(pyridin-2-yl)-1-(p-tolyl)-1H-1,2,3-triazole-4-carboxamide | 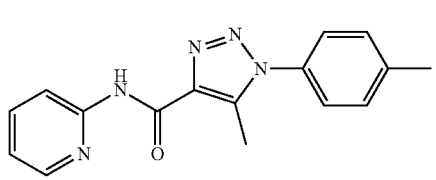 [SMILES: Cc1ccc(-n2nnc(C(=O)Nc3ccccn3)c2C)cc1] |

TABLE 1-continued

Compounds of Formula I

| Compound Identifiers | Compound Name | Compound Structure |
|---|---|---|
| YW1134 (21) | 5-Methyl-N-(6-methylpyridin-2-yl)-1-(p-tolyl)-1H-1,2,3-triazole-4-carboxamide | 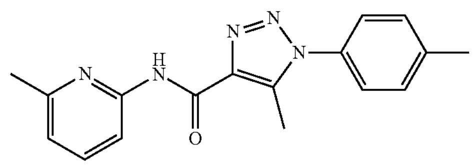 |
| YW1121 (25) | 5-Methyl-N-(pyridin-2-ylmethyl)-1-(p-tolyl)-1H-1,2,3-triazole-4-carboxamide | 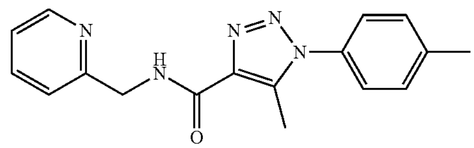 [SMILES: Cc1ccc(-n2nnc(C(=O)NCc3ccccn3)c2C)cc1] |
| YW1123 (26) | 5-Methyl-N-(2-methyl-4-oxo-4H-chromen-7-yl)-1-(p-tolyl)-1H-1,2,3-triazole-4-carboxamide | 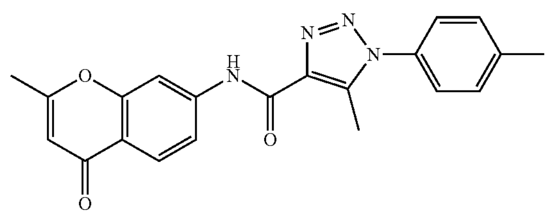 |
| YW1124 (24) | 5-Methyl-N-(3-methylisoxazol-5-yl)-1-(p-tolyl)-1H-1,2,3-triazole-4-carboxamide | 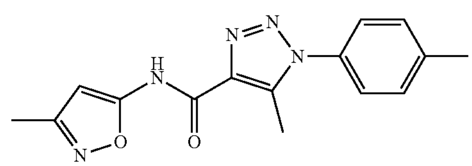 |
| YW1125 (22) | N-(4,5-diphenylthiazol-2-yl)-5-methyl-1-(p-tolyl)-1H-1,2,3-triazole-4-carboxamide | 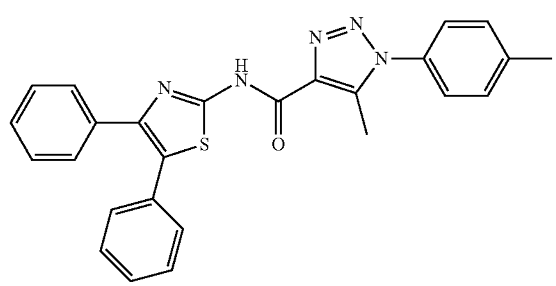 [SMILES: Cc1ccc(-n2nnc(C(=O)Nc3nc(-c4ccccc4)c(-c4ccccc4)s3)c2C)cc1] |
| YW1126 (23) | 5-Methyl-N-(1-methyl-1H-benzo[d]imidazol-2-yl)-1-(p-tolyl)-1H-1,2,3-triazole-4-carboxamide | 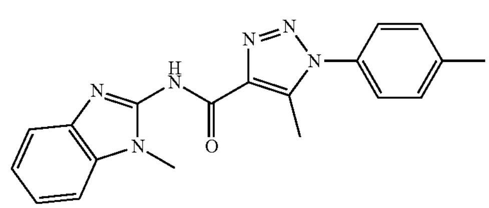 [SMILES: Cc1ccc(-n2nnc(C(=O)Nc3nc4ccccc4n3C)c2C)cc1] |
| YW1127 (27) | 5-Methyl-N-(quinolin-2-yl)-1-(p-tolyl)-1H-i,2,3-triazole-4-carboxamide | 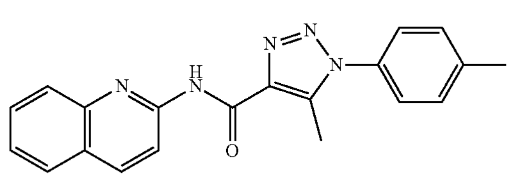 [SMILES: Cc1ccc(-n2nnc(C(=O)Nc3ccc4ccccc4n3)c2C)cc1] |

TABLE 1-continued

Compounds of Formula I

| Compound Identifiers | Compound Name | Compound Structure |
|---|---|---|
| YW1128 (28) | 5-Methyl-N-(quinolin-2-yl)-1-(o-tolyl)-1H-1,2,3-triazole-4-carboxamide | 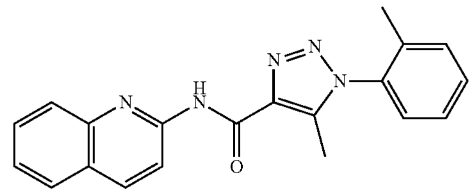 |
| YW1130 (31) | 5-Methyl-N-(naphthalen-2-yl)-1-(o-tolyl)-1H-1,2,3-triazole-4-carboxamide | 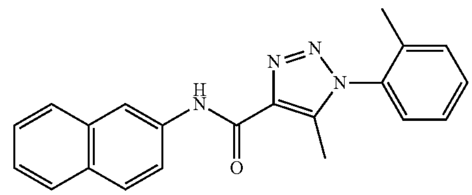 [SMILES: Cc1ccccc1-n1nnc(C(=O)Nc2ccc3ccccc3c2)c1C] |
| YW1132 (29) | N-(benzo[d]thiazol-2-yl)-5-methyl-1-(o-tolyl)-1H-1,2,3-triazole-4-carboxamide | 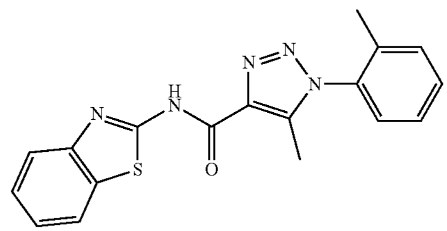 [SMILES: Cc1ccccc1-n1nnc(C(=O)Nc2nc3ccccc3s2)c1C] |
| YW1183 (30) | 5-Methyl-N-(4-phenylthiazol-2-yl)-1-(o-tolyl)-1H-1,2,3-triazole-4-carboxamide | 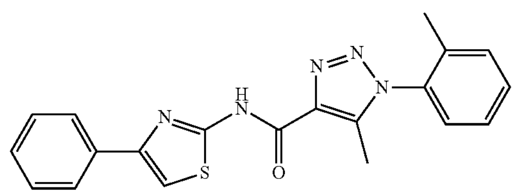 [SMILES: Cc1ccccc1-n1nnc(C(=O)Nc2nc(-c3ccccc3)cs2)c1C] |
| YW1170 (42) | 1-(2,3-Dimethylphenyl)-5-methyl-N-(quinolin-2-yl)-1H-1,2,3-triazole-4-carboxamide | 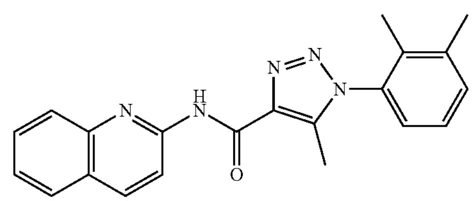 [SMILES: Cc1cccc(-n2nnc(C(=O)Nc3ccc4ccccc4n3)c2C)c1C] |
| YW1179 (32) | 1-(2,4-Dimethylphenyl)-5-methyl-N-(quinolin-2-yl)-1H-1,2,3-triazole-4-carboxamide | 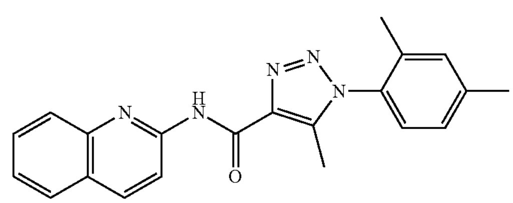 [SMILES: Cc1ccc(-n2nnc(C(=O)Nc3ccc4ccccc4n3)c2C)c(C)c1] |
| YW1173 (44) | 1-(3-Chlorophenyl)-5-methyl-N-(quinolin-2-yl)-1H-1,2,3-triazole-4-carboxamide | 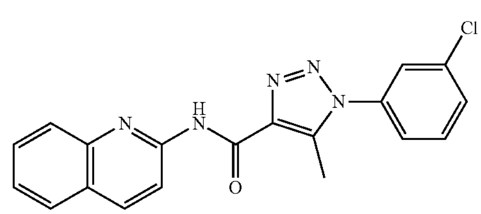 [SMILES: Cc1c(C(=O)Nc2ccc3ccccc3n2)nnn1-c1cccc(Cl)c1] |

TABLE 1-continued

Compounds of Formula I

| Compound Identifiers | Compound Name | Compound Structure |
|---|---|---|
| YW1159 (33) | 1-(2-Fluorophenyl)-5-methyl-N-(quinolin-2-yl)-1H-1,2,3-triazole-4-carboxamide | 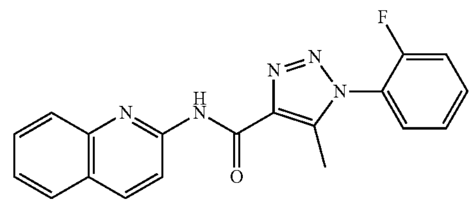 [SMILES: Cc1c(C(=O)Nc2ccc3ccccc3n2)nnn1-c1ccccc1F] |
| YW1169 (36) | 1-(2-Bromophenyl)-5-methyl-N-(quinolin-2-yl)-1H-1,2,3-triazole-4-carboxamide | 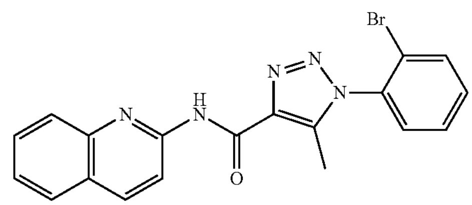 [SMILES: Cc1c(C(=O)Nc2ccc3ccccc3n2)nnn1-c1ccccc1Br] |
| YW1157 (34) | 1-(2-Cyanophenyl)-5-methyl-N-(quinolin-2-yl)-1H-1,2,3-triazole-4-carboxamide | 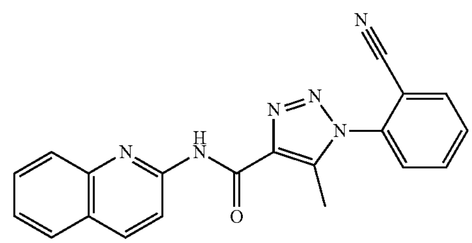 [SMILES: Cc1c(C(=O)Nc2ccc3ccccc3n2)nnn1-c1ccccc1C#N] |
| YW1149 (35) | 1-(2-Methoxyphenyl)-5-methyl-N-(quinolin-2-yl)-1H-1,2,3-triazole-4-carboxamide | 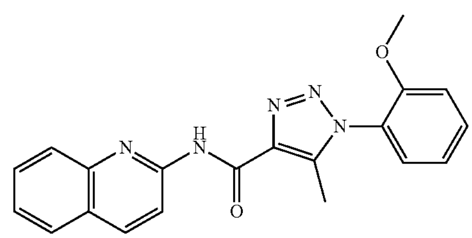 [SMILES: COc1ccccc1-n1nnc(C(=O)Nc2ccc3ccccc3n2)c1C] |
| YW1171 (41) | 1-(4-Fluoro-2-nitrophenyl)-5-methyl-N-(quinolin-2-yl)-1H-1,2,3-triazole-4-carboxamide | 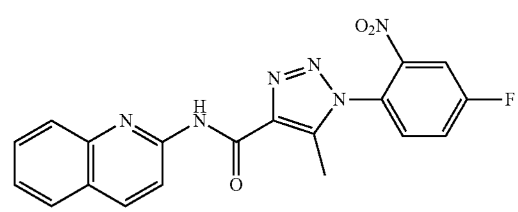 [SMILES: Cc1c(C(=O)Nc2ccc3ccccc3n2)nnn1-c1ccc(F)cc1[N+](=O)[O-]] |
| YW1181 (39) | 1-(2-Acetylphenyl)-5-methyl-N-(quinolin-2-yl)-1H-1,2,3-triazole-4-carboxamide | 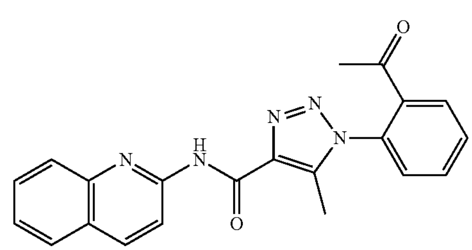 [SMILES: CC(=O)c1ccccc1-n1nnc(C(=O)Nc2ccc3ccccc3n2)c1C] |

TABLE 1-continued

Compounds of Formula I

| Compound Identifiers | Compound Name | Compound Structure |
|---|---|---|
| YW1182 (40) | 1-(2-Carbamoylphenyl)-5-methyl-N-(quinolin-2-yl)-1H-1,2,3-triazole-4-carboxamide | 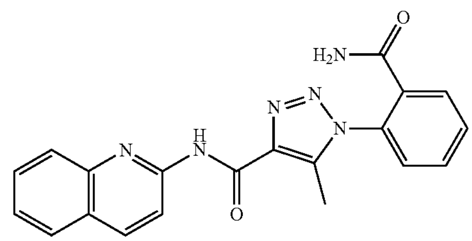 [SMILES: Cc1c(C(=O)Nc2ccc3ccccc3n2)nnn1-c1ccccc1C(N)=O] |
| YW1180 (38) | 1-([1,1'-biphenyl]-2-yl)-5-methyl-N-(quinolin-2-yl)-1H-1,2,3-triazole-4-carboxamide | 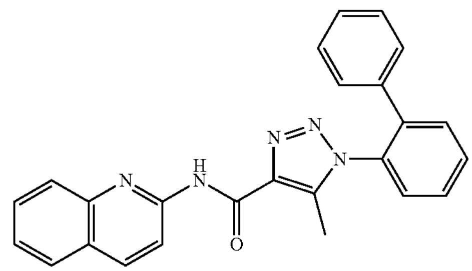 [SMILES: Cc1c(C(=O)Nc2ccc3ccccc3n2)nnn1-c1ccccc1-c1ccccc1] |
| YW1155 (37) | 5-Methyl-1-(2-morpholinophenyl)-N-(quinolin-2-yl)-1H-1,2,3-triazole-4-carboxamide | 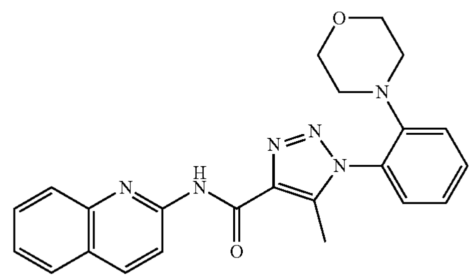 [SMILES: Cc1c(C(=O)Nc2ccc3ccccc3n2)nnn1-c1ccccc1N1CCOCC1] |
| YW1151 (43) | 5-Methyl-1-(naphthalen-1-yl)-N-(quinolin-2-yl)-1H-1,2,3-triazole-4-carboxamide | 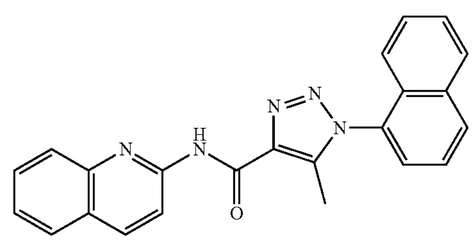 [SMILES: Cc1c(C(=O)Nc2ccc3ccccc3n2)nnn1-c1cccc2ccccc12] |
| YW2020 (46) | 1-(2-fluorophenyl)-5-isopropyl-N-(quinolin-2-yl)-1H-1,2,3-triazole-4-carboxamide | 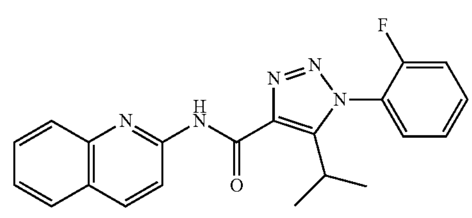 [SMILES: CC(C)c1c(C(=O)Nc2ccc3ccccc3n2)nnn1-c1ccccc1F] |
| YW2018 (45) | 5-Ethyl-1-(2-fluorophenyl)-N-(quinolin-2-yl)-1H-1,2,3-triazole-4-carboxamide | 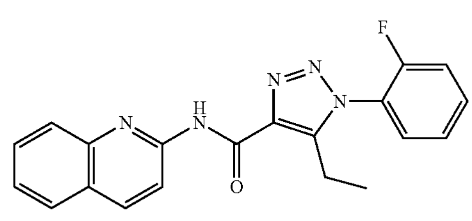 [SMILES: CCc1c(C(=O)Nc2ccc3ccccc3n2)nnn1-c1ccccc1F] |

TABLE 1-continued

Compounds of Formula I

| Compound Identifiers | Compound Name | Compound Structure |
|---|---|---|
| YW2013 (132) | 5-Methyl-N-(quinolin-2-yl)-1-(o-tolyl)-1H-pyrazole-4-carboxamide | 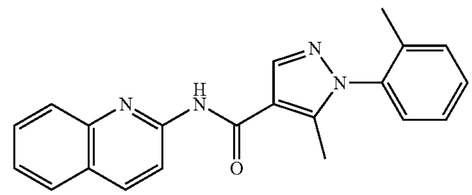 [SMILES: Cc1ccccc1-n1ncc(C(=O)Nc2ccc3ccccc3n2)c1C] |
| YW2035 (133) | 1-(2-Fluorophenyl)-5-methyl-N-(quinolin-2-yl)-1H-pyrazole-4-carboxamide | 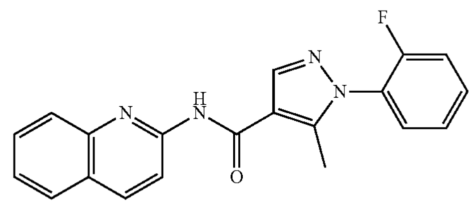 [SMILES: Cc1c(C(=O)Nc2ccc3ccccc3n2)cnn1-c1ccccc1F] |
| YW2065 (134) | 1-(2-Bromophenyl)-5-methyl-N-(quinolin-2-yl)-1H-pyrazole-4-carboxamide | 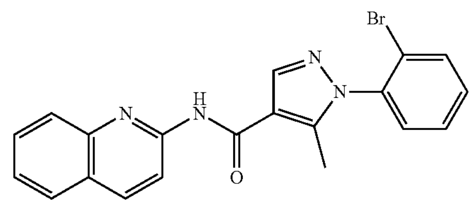 [SMILES: Cc1c(C(=O)Nc2ccc3ccccc3n2)cnn1-c1ccccc1Br] |
| YW6001 (166) | 2,5-Dimethyl-N-(quinolin-2-yl)-1-(o-tolyl)-1H-imidazole-4-carboxamide | 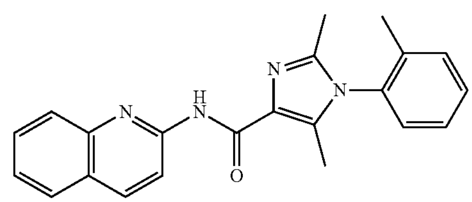 [SMILES: Cc1ccccc1-n1c(C)nc(C(=O)Nc2ccc3ccccc3n2)c1C] |
| YW6002 (167) | 1-(2-Fluorophenyl)-2,5-dimethyl-N-(quinolin-2-yl)-1H-imidazole-4-carboxamide | 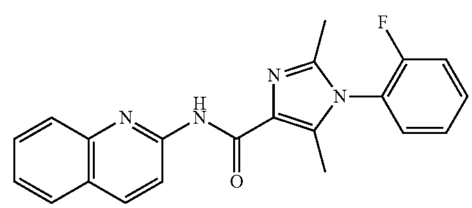 [SMILES: Cc1nc(C(=O)Nc2ccc3ccccc3n2)c(C)n1-c1ccccc1F] |
| YW6003 (168) | 1-(2-Bromophenyl)-2,5-dimethyl-N-(quinolin-2-yl)-1H-imidazole-4-carboxamide | 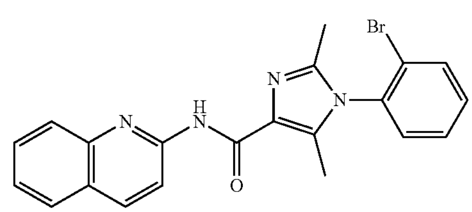 [SMILES: Cc1nc(C(=O)Nc2ccc3ccccc3n2)c(C)n1-c1ccccc1Br] |
| YW6004 (169) | 2,5-Dimethyl-1-phenyl-N-(quinolin-2-yl)-1H-imidazole-4-carboxamide | 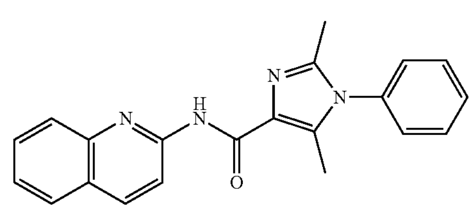 [SMILES: Cc1nc(C(=O)Nc2ccc3ccccc3n2)c(C)n1-c1ccccc1] |

TABLE 1-continued

Compounds of Formula I

| Compound Identifiers | Compound Name | Compound Structure |
|---|---|---|
| YW2038 (135) | 1-(2-Chlorophenyl)-5-methyl-N-(quinolin-2-yl)-1H-pyrazole-4-carboxamide | 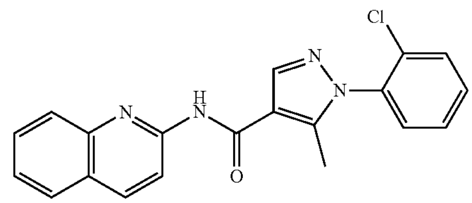 |
| YW2044 (136) | 1-(2-Ethylphenyl)-5-methyl-N-(quinolin-2-yl)-1H-pyrazole-4-carboxamide | 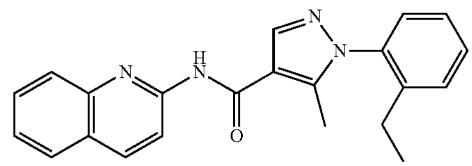 [SMILES: CCc1ccccc1-n1ncc(C(=O)Nc2ccc3ccccc3n2)c1C] |
| YW2048 (137) | 1-(2,6-dimethylphenyl)-5-methyl-N-(quinolin-2-yl)-1H-pyrazole-4-carboxamide | 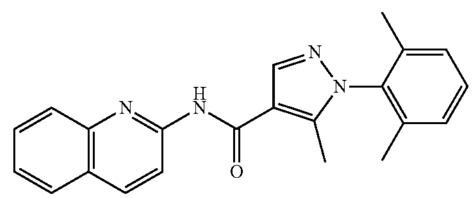 [SMILES: Cc1cccc(C)c1-n1ncc(C(=O)Nc2ccc3ccccc3n2)c1C] |
| YW2049 (138) | 1-(Tert-butyl)-5-methyl-N-(quinolin-2-yl)-1H-pyrazole-4-carboxamide | 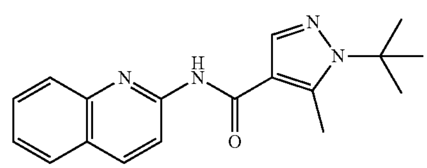 [SMILES: Cc1c(C(=O)Nc2ccc3ccccc3n2)cnn1C(C)(C)C] |
| YW2046 (139) | 1-(2,5-dimethylphenyl)-5-methyl-N-(quinolin-2-yl)-1H-pyrazole-4-carboxamide | 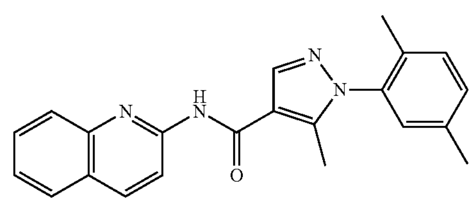 [SMILES: Cc1ccc(C)c(-n2ncc(C(=O)Nc3ccc4ccccc4n3)c2C)c1] |
| YW2039 (140) | 1-(2,4-difluorophenyl)-5-methyl-N-(quinolin-2-yl)-1H-pyrazole-4-carboxamide | 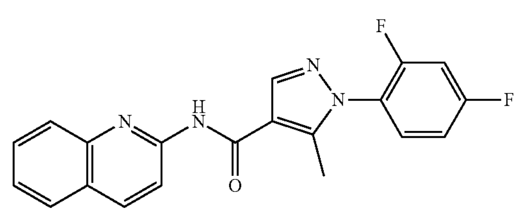 [SMILES: Cc1c(C(=O)Nc2ccc3ccccc3n2)cnn1-c1ccc(F)cc1F] |
| YW2036 (141) | 5-methyl-1-phenyl-N-(quinolin-2-yl)-1H-pyrazole-4-carboxamide | 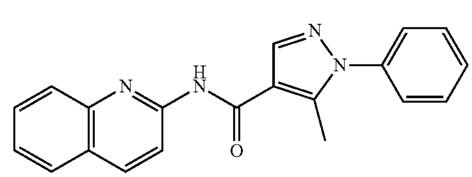 [SMILES: Cc1c(C(=O)Nc2ccc3ccccc3n2)cnn1-c1ccccc1] |
| YW2070 (142) | 1-cyclohexyl-5-methyl-N-(quinolin-2-yl)-1H-pyrazole-4-carboxamide | 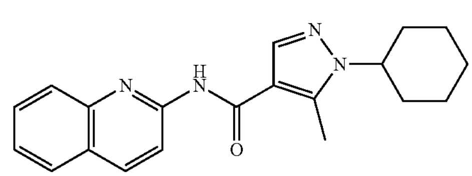 [SMILES: Cc1c(C(=O)Nc2ccc3ccccc3n2)cnn1C1CCCCC1] |

TABLE 1-continued

Compounds of Formula I

| Compound Identifiers | Compound Name | Compound Structure |
|---|---|---|
| YW2052 (143) | 5-methyl-1-(1-phenylethyl)-N-(quinolin-2-yl)-1H-pyrazole-4-carboxamide | 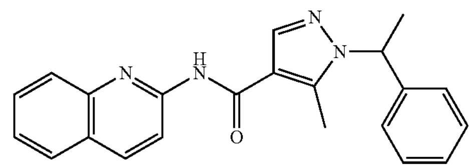 [SMILES: Cc1c(C(=O)Nc2ccc3ccccc3n2)cnn1C(C)c1ccccc1] |
| YW2056 (144) | 5-methyl-N-(quinolin-2-yl)-1-(2,2,2-trifluoroethyl)-1H-pyrazole-4-carboxamide | 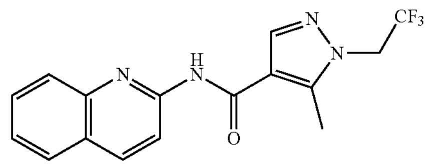 [SMILES: Cc1c(C(=O)Nc2ccc3ccccc3n2)cnn1CC(F)(F)F] |
| YW2055 (145) | 5-methyl-1-(3-methylpyridin-2-yl)-N-(quinolin-2-yl)-1H-pyrazole-4-carboxamide | 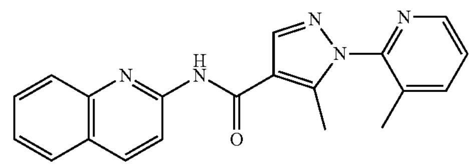 [SMILES: Cc1cccnc1-n1ncc(C(=O)Nc2ccc3ccccc3n2)c1C] |
| YW2068 (146) | 1-(3-chloro-2-fluorophenyl)-5-methyl-N-(quinolin-2-yl)-1H-pyrazole-4-carboxamide | 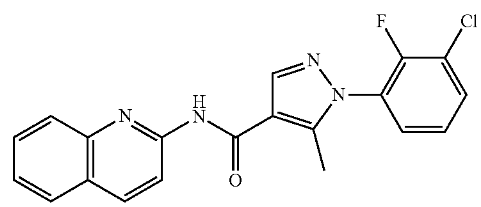 [SMILES: Cc1c(C(=O)Nc2ccc3ccccc3n2)cnn1-c1cccc(Cl)c1F] |
| YW2074 (147) | 1-(2,6-difluorophenyl)-5-methyl-N-(quinolin-2-yl)-1H-pyrazole-4-carboxamide | 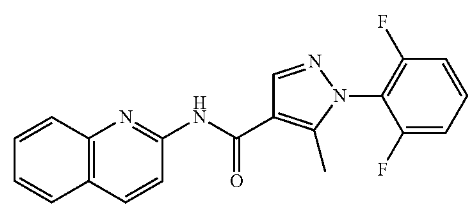 [SMILES: Cc1c(C(=O)Nc2ccc3ccccc3n2)cnn1-c1c(F)cccc1F] |
| YW2076 (148) | 1-(2-bromo-6-fluorophenyl)-5-methyl-N-(quinolin-2-yl)-1H-pyrazole-4-carboxamide | 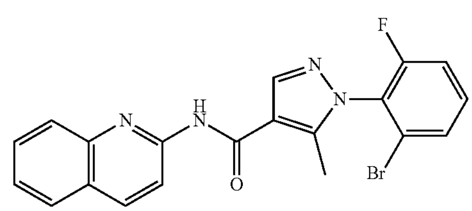 [SMILES: Cc1c(C(=O)Nc2ccc3ccccc3n2)cnn1-c1c(F)cccc1Br] |
| YW2106 (149) | 5-methyl-1-phenyl-N-(quinolin-2-yl)-1H-pyrazole-3-carboxamide | 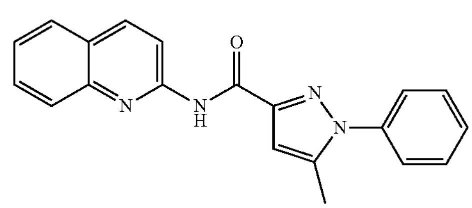 [SMILES: Cc1cc(C(=O)Nc2ccc3ccccc3n2)nn1-c1ccccc1] |
| YW2107 (150) | 5-methyl-N-(quinolin-2-yl)-1-(o-tolyl)-1H-pyrazole-3-carboxamide | 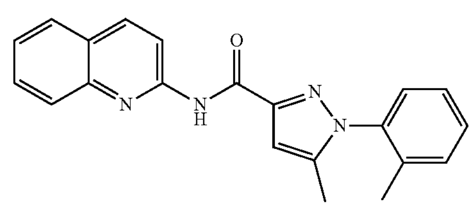 [SMILES: Cc1ccccc1-n1nc(C(=O)Nc2ccc3ccccc3n2)cc1C] |

TABLE 1-continued

Compounds of Formula I

| Compound Identifiers | Compound Name | Compound Structure |
|---|---|---|
| YW2108 (151) | 1-(2-ethylphenyl)-5-methyl-N-(quinolin-2-yl)-1H-pyrazole-3-carboxamide | 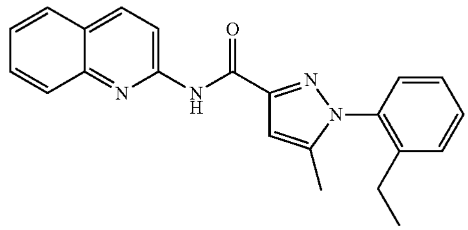 [SMILES: CCc1ccccc1-n1nc(C(=O)Nc2ccc3ccccc3n2)cc1C] |
| YW2111 (152) | 1-phenyl-N-(quinolin-2-yl)-1,4,5,6-tetrahydrocyclopenta[c]pyrazole-3-carboxamide | 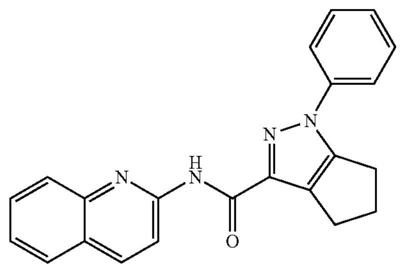 [SMILES: O=C(Nc1ccc2ccccc2n1)c1nn(-c2ccccc2)c2c1CCC2] |
| YW2122 (153) | 1-phenyl-N-(quinolin-2-yl)-4,5,6,7-tetrahydro-1H-indazole-3-carboxamide | 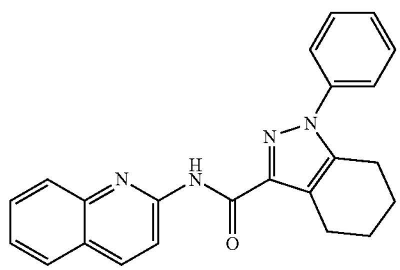 [SMILES: O=C(Nc1ccc2ccccc2n1)c1nn(-c2ccccc2)c2c1CCCC2] |
| YW21172 (154) | 3,5-dimethyl-1-phenyl-N-(quinolin-2-yl)-1H-pyrazole-4-carboxamide | 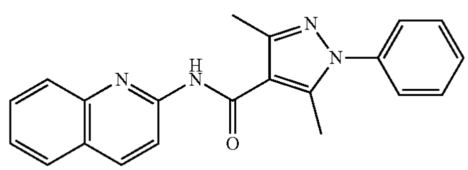 [SMILES: Cc1nn(-c2ccccc2)c(C)c1C(=O)Nc1ccc2ccccc2n1] |
| YW2120 (155) | 1-(2,5-dimethylphenyl)-3,5-dimethyl-N-(quinolin-2-yl)-1H-pyrazole-4-carboxamide | 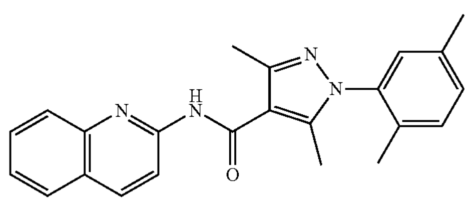 [SMILES: Cc1ccc(C)c(-n2nc(C)c(C(=O)Nc3ccc4ccccc4n3)c2C)c1] |
| YW2123 (156) | 1-(2-bromophenyl)-3,5-dimethyl-N-(quinolin-2-yl)-1H-pyrazole-4-carboxamide | 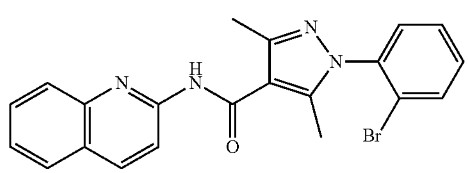 [SMILES: Cc1nn(-c2ccccc2Br)c(C)c1C(=O)Nc1ccc2ccccc2n1] |
| YW2126 (157) | 5-ethyl-1-phenyl-N-(quinolin-2-yl)-1H-pyrazole-4-carboxamide | 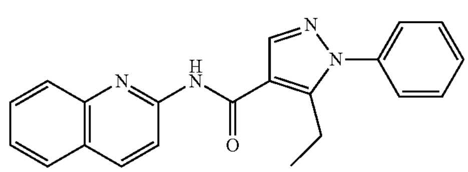 [SMILES: CCc1c(C(=O)Nc2ccc3ccccc3n2)cnn1-c1ccccc1] |

TABLE 1-continued

Compounds of Formula I

| Compound Identifiers | Compound Name | Compound Structure |
|---|---|---|
| YW2125 (158) | 5-isopropyl-1-phenyl-N-(quinolin-2-yl)-1H-pyrazole-4-carboxamide | 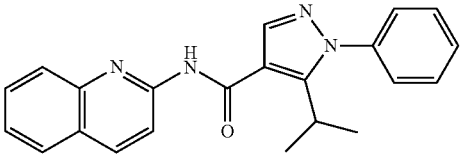 |
| YW2137 (159) | 5-chloro-1-phenyl-N-(quinolin-2-yl)-1H-pyrazole-4-carboxamide | 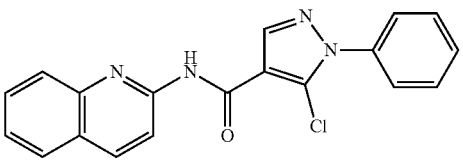 |
| YW2136 (160) | 5-bromo-1-phenyl-N-(quinolin-2-yl)-1H-pyrazole-4-carboxamide | 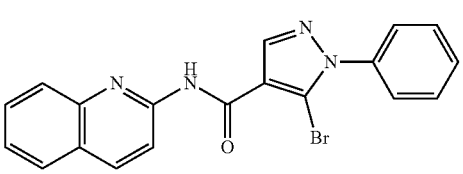 [SMILES: O=C(Nc1ccc2ccccc2n1)c1cnn(-c2ccccc2)c1Br] |
| YW2147 (161) | 5-(dimethylamino)-1-phenyl-N-(quinolin-2-yl)-1H-pyrazole-4-carboxamide | 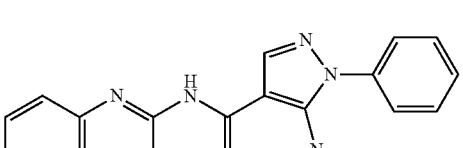 |
| YW2142 (162) | 1-(2-ethylphenyl)-5-methyl-N-(naphthalen-2-yl)-1H-pyrazole-4-carboxamide | 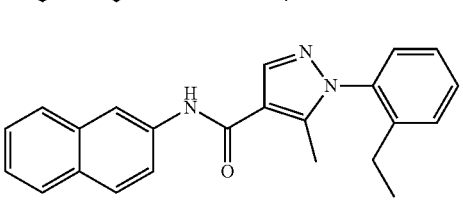 |
| YW2144 (163) | 1-(2-ethylphenyl)-N-(isoquinolin-3-yl)-5-methyl-1H-pyrazole-4-carboxamide | 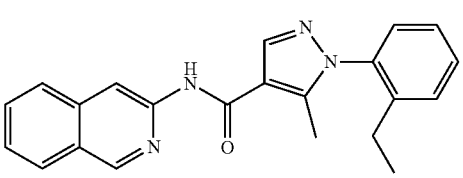 [SMILES: CCc1ccccc1-n1ncc(C(=O)Nc2cc3ccccc3cn2)c1C] |
| YW2143 (164) | 1-(2-ethylphenyl)-5-methyl-N-(quinolin-3-yl)-1H-pyrazole-4-carboxamide | 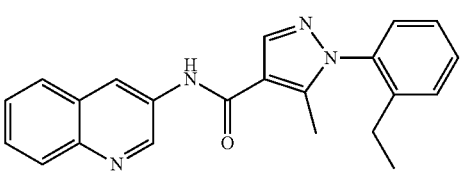 [SMILES: CCc1ccccc1-n1ncc(C(=O)Nc2cnc3ccccc3c2)c1C] |
| YW2146 (165) | 1-(2-ethylphenyl)-5-methyl-N-(6-methylpyridin-2-yl)-1H-pyrazole-4-carboxamide | 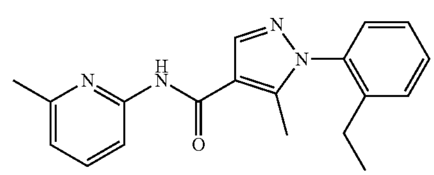 [SMILES: CCc1ccccc1-n1ncc(C(=O)Nc2cccc(C)n2)c1C] |

TABLE 1-continued

Compounds of Formula I

| Compound Identifiers | Compound Name | Compound Structure |
|---|---|---|
| YA1061 | N-(6-bromoquinolin-2-yl)-5-methyl-1-(o-tolyl)-1H-1,2,3-triazole-4-carboxamide | 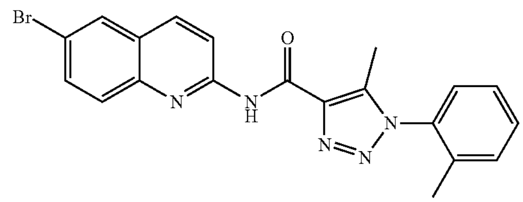 [SMILES: Cc1ccccc1-n1nnc(C(=O)Nc2ccc3cc(Br)ccc3n2)c1C] |
| YA1065 | 5-methyl-N-(6-(morpholinomethyl)quinolin-2-yl)-1-(o-tolyl)-1H-1,2,3-triazole-4-carboxamide | 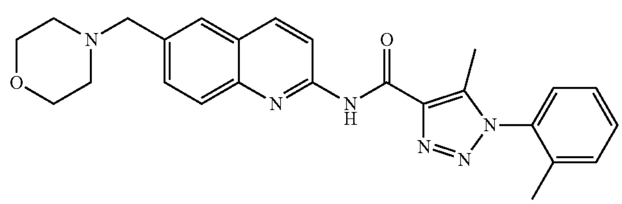 [SMILES: Cc1ccccc1-n1nnc(C(=O)Nc2ccc3cc(CN4CCOCC4)ccc3n2)c1C] |
| YA1073 | 5-methyl-N-(6-((4-methylpiperazin-1-yl)methyl)quinolin-2-yl)-1-(o-tolyl)-1H-1,2,3-triazole-4-carboxamide | 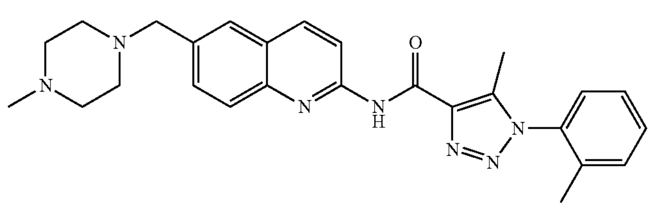 [SMILES: Cc1ccccc1-n1nnc(C(=O)Nc2ccc3cc(CN4CCN(C)CC4)ccc3n2)c1C] |
| YA1081 | 5-methyl-N-(6-(pyrrolidin-1-ylmethyl)quinolin-2-yl)-1-(o-tolyl)-1H-1,2,3-triazole-4-carboxamide | 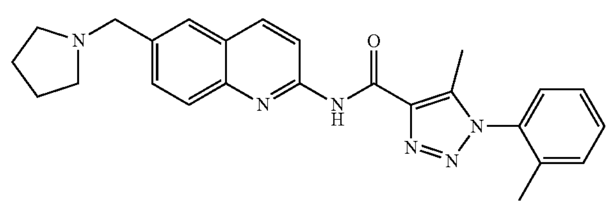 [SMILES: Cc1ccccc1-n1nnc(C(=O)Nc2ccc3cc(CN4CCCC4)ccc3n2)c1C] |
| YA1083 | N-(6-((diethylamino)methyl)quinolin-2-yl)-5-methyl-1-(o-tolyl)-1H-1,2,3-triazole-4-carboxamide | 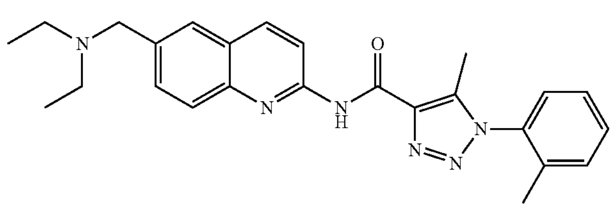 [SMILES: CCN(CC)Cc1ccc2nc(NC(=O)c3nnn(-c4ccccc4C)c3C)ccc2c1] |
| YA1093 | 5-methyl-N-(6-(piperidin-1-ylmethyl)quinolin-2-yl)-1-(o-tolyl)-1H-1,2,3-triazole-4-carboxamide | 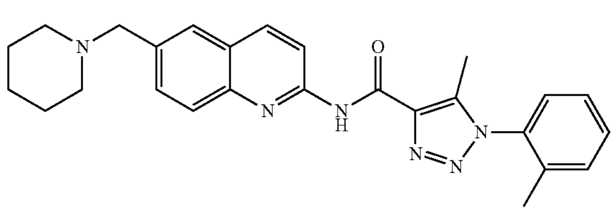 [SMILES: Cc1ccccc1-n1nnc(C(=O)Nc2ccc3cc(CN4CCCCC4)ccc3n2)c1C] |
| YA1095 | tert-butyl 4-((2-(5-methyl-1-(o-tolyl)-1H-1,2,3-triazole-4-carboxamido)quinolin-6-yl)methyl)piperazine-1-carboxylate | 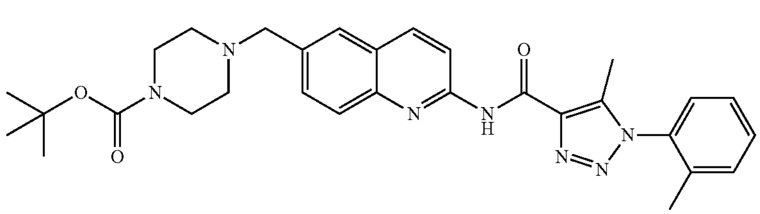 [SMILES: Cc1ccccc1-n1nnc(C(=O)Nc2ccc3cc(CN4CCN(C(=O)OC(C)(C)C)CC4)ccc3n2)c1C] |

TABLE 1-continued

Compounds of Formula I

| Compound Identifiers | Compound Name | Compound Structure |
|---|---|---|
| YA1097 | N-(6-((dimethylamino)methyl)quinolin-2-yl)-5-methyl-1-(o-tolyl)-1H-1,2,3-triazole-4-carboxamide | 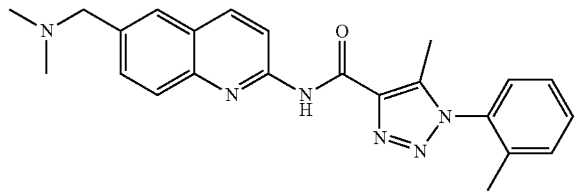 [SMILES: Cc1ccccc1-n1nnc(C(=O)Nc2ccc3cc(CN(C)C)ccc3n2)c1C] |
| YA1099 | 5-methyl-N-(6-(thiomorpholinomethyl)quinolin-2-yl)-1-(o-tolyl)-1H-1,2,3-triazole-4-carboxamide | 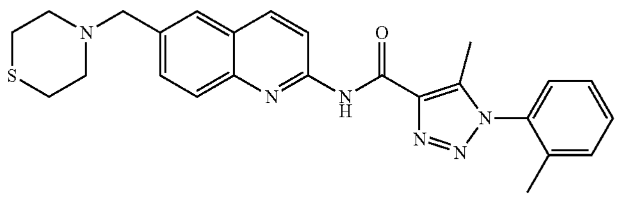 [SMILES: Cc1ccccc1-n1nnc(C(=O)Nc2ccc3cc(CN4CCSCC4)ccc3n2)c1C] |
| YA1105 | 5-methyl-N-(6-((4-morpholinopiperidin-1-yl)methyl)quinolin-2-yl)-1-(o-tolyl)-1H-1,2,3-triazole-4-carboxamide | 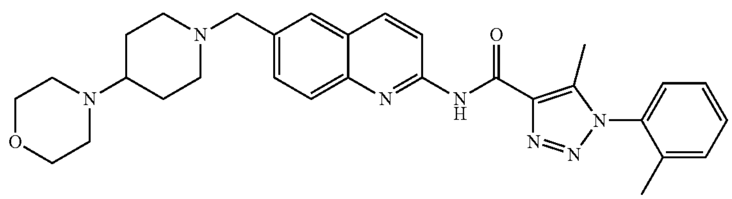 [SMILES: Cc1ccccc1-n1nnc(C(=O)Nc2ccc3cc(CN4CCC(N5CCOCC5)CC4)ccc3n2)c1C] |
| YA1109 | 5-methyl-N-(6-((4-(4-methylpiperazin-1-yl)piperidin-1-yl)methyl)quinolin-2-yl)-1-(o-tolyl)-1H-1,2,3-triazole-4-carboxamide | 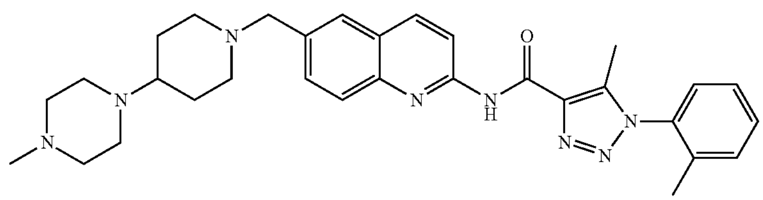 [SMILES: Cc1ccccc1-n1nnc(C(=O)Nc2ccc3cc(CN4CCC(N5CCN(C)CC5)CC4)ccc3n2)c1C] |

In some embodiments, the compounds of the invention may include those compounds of formula II set forth in Table 2, below:

TABLE 2

Compounds of Formula II

| Compound Identifiers | Compound Name | Compound Structure |
|---|---|---|
| YW1109 (14) | 2,5-Dimethyl-N-(pyridin-2-yl)-1-(p-tolyl)-1H-pyrrole-3-carboxamide | 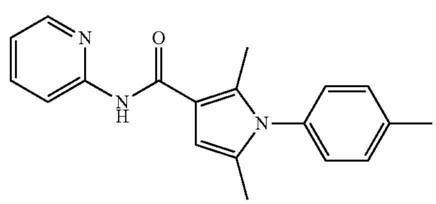 [SMILES: Cc1ccc(-n2c(C)cc(C(=O)Nc3ccccn3)c2C)cc1] |
| YW1117-2 (15) | 2,5-Dimethyl-N-(pyrazin-2-yl)-1-(p-tolyl)-1H-pyrrole-3-carboxamide | 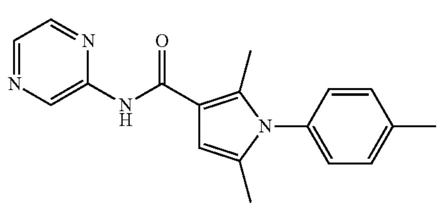 [SMILES: Cc1ccc(-n2c(C)cc(C(=O)Nc3cnccn3)c2C)cc1] |

TABLE 2-continued

Compounds of Formula II

| Compound Identifiers | Compound Name | Compound Structure |
|---|---|---|
| YW1114 (16) | 2,5-Dimethyl-N-(4-phenylthiazol-2-yl)-1-(p-tolyl)-1H-pyrrole-3-carboxamide | 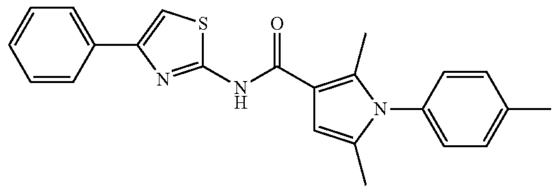 [SMILES: Cc1ccc(-n2c(C)cc(C(=O)Nc3nc(-c4ccccc4)cs3)c2C)cc1] |
| YW1104 (17) | N-Benzyl-2,5-dimethyl-1-(p-tolyl)-1H-pyrrole-3-carboxamide | 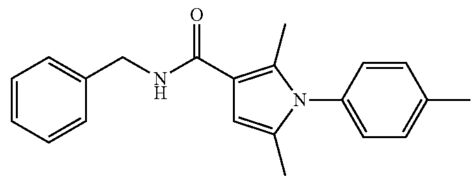 [SMILES: Cc1ccc(-n2c(C)cc(C(=O)NCc3ccccc3)c2C)cc1] |
| YW1119 (20) | 5-Methyl-N-(pyridin-2-yl)-1-(p-tolyl)-1H-1,2,3-triazole-4-carboxamide | 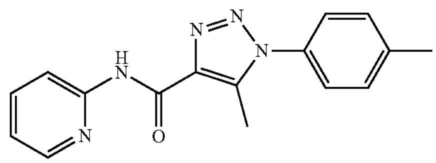 [SMILES: Cc1ccc(-n2nnc(C(=O)Nc3ccccn3)c2C)cc1] |
| YW1134 (21) | 5-Methyl-N-(6-methylpyridin-2-yl)-1-(p-tolyl)-1H-1,2,3-triazole-4-carboxamide | 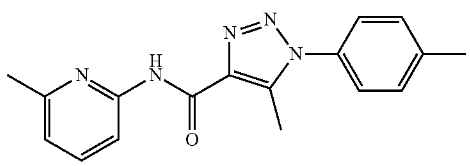 |
| YW1121 (25) | 5-Methyl-N-(pyridin-2-ylmethyl)-1-(p-tolyl)-1H-1,2,3-triazole-4-carboxamide | 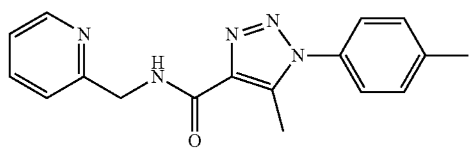 [SMILES: Cc1ccc(-n2nnc(C(=O)NCc3ccccn3)c2C)cc1] |
| YW1123 (26) | 5-Methyl-N-(2-methyl-4-oxo-4H-chromen-7-yl)-1-(p-tolyl)-1H-1,2,3-triazole-4-carboxamide | 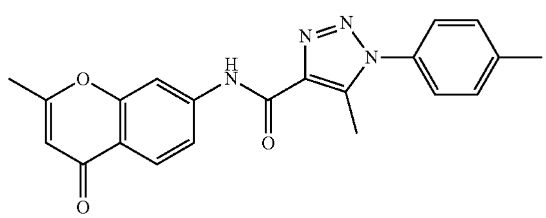 |
| YW1124 (24) | 5-Methyl-N-(3-methylisoxazol-5-yl)-1-(p-tolyl)-1H-1,2,3-triazole-4-carboxamide | 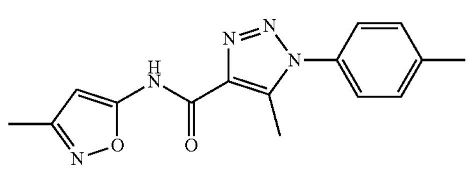 |
| YW1125 (22) | N-(4,5-diphenylthiazol-2-yl)-5-methyl-1-(p-tolyl)-1H-1,2,3-triazole-4-carboxamide | 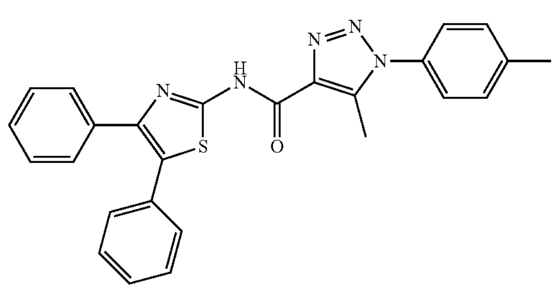 [SMILES: Cc1ccc(-n2nnc(C(=O)Nc3nc(-c4ccccc4)c(-c4ccccc4)s3)c2C)cc1] |

TABLE 2-continued

Compounds of Formula II

| Compound Identifiers | Compound Name | Compound Structure |
|---|---|---|
| YW1126 (23) | 5-Methyl-N-(1-methyl-1H-benzo[d]imidazol-2-yl)-1-(p-tolyl)-1H-1,2,3-triazole-4-carboxamide | 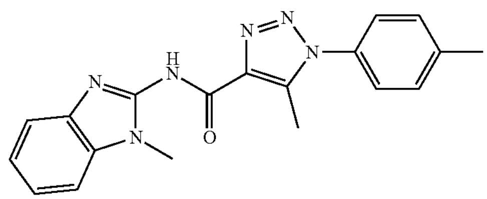 [SMILES: Cc1ccc(-n2nnc(C(=O)Nc3nc4ccccc4n3C)c2C)cc1] |
| YW1127 (27) | 5-Methyl-N-(quinolin-2-yl)-1-(p-tolyl)-1H-1,2,3-triazole-4-carboxamide | 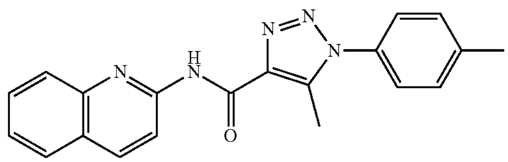 [SMILES: Cc1ccc(-n2nnc(C(=O)Nc3ccc4ccccc4n3)c2C)cc1] |
| YW1128 (28) | 5-Methyl-N-(quinolin-2-yl)-1-(o-tolyl)-1H-1,2,3-triazole-4-carboxamide | 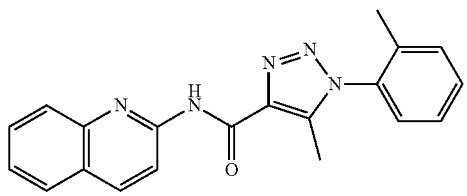 [SMILES: Cc1ccccc1-n1nnc(C(=O)Nc2ccc3ccccc3n2)c1C] |
| YW1130 (31) | 5-Methyl-N-(naphthalen-2-yl)-1-(o-tolyl)-1H-1,2,3-triazole-4-carboxamide | 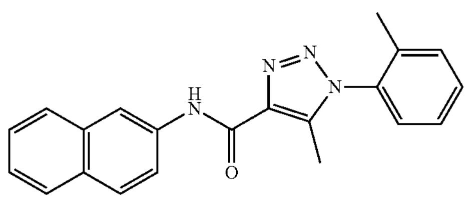 [SMILES: Cc1ccccc1-n1nnc(C(=O)Nc2ccc3ccccc3c2)c1C] |
| YW1132 (29) | N-(benzo[d]thiazol-2-yl)-5-methyl-1-(o-tolyl)-1H-1,2,3-triazole-4-carboxamide | 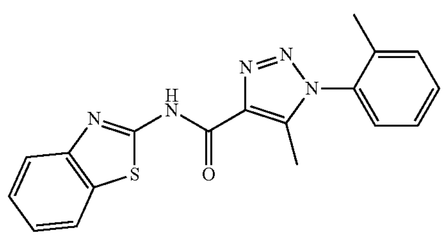 [SMILES: Cc1ccccc1-n1nnc(C(=O)Nc2nc3ccccc3s2)c1C] |
| YW1183 (30) | 5-Methyl-N-(4-phenylthiazol-2-yl)-1-(o-tolyl)-1H-1,2,3-triazole-4-carboxamide | 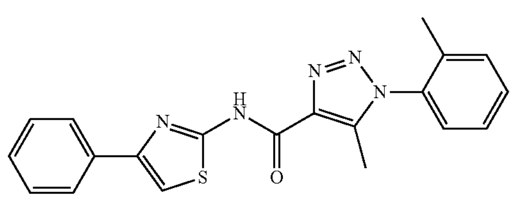 [SMILES: Cc1ccccc1-n1nnc(C(=O)Nc2nc(-c3ccccc3)cs2)c1C] |
| YW1170 (42) | 1-(2,3-Dimethylphenyl)-5-methyl-N-(quinolin-2-yl)-1H-1,2,3-triazole-4-carboxamide | 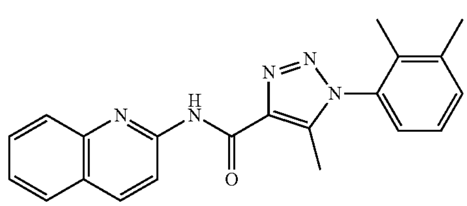 |

TABLE 2-continued

Compounds of Formula II

| Compound Identifiers | Compound Name | Compound Structure |
| --- | --- | --- |
| YW1179 (32) | 1-(2,4-Dimethylphenyl)-5-methyl-N-(quinolin-2-yl)-1H-1,2,3-triazole-4-carboxamide | 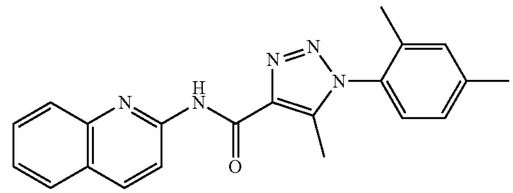 [SMILES: Cc1ccc(-n2nnc(C(=O)Nc3ccc4ccccc4n3)c2C)c(C)c1] |
| YW1173 (44) | 1-(3-Chlorophenyl)-5-methyl-N-(quinolin-2-yl)-1H-1,2,3-triazole-4-carboxamide | 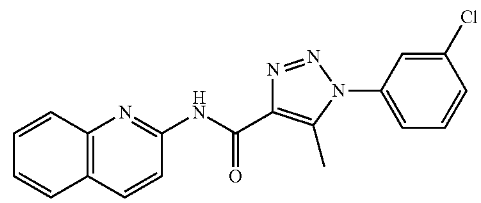 [SMILES: Cc1c(C(=O)Nc2ccc3ccccc3n2)nnn1-c1cccc(Cl)c1] |
| YW1159 (33) | 1-(2-Fluorophenyl)-5-methyl-N-(quinolin-2-yl)-1H-1,2,3-triazole-4-carboxamide | 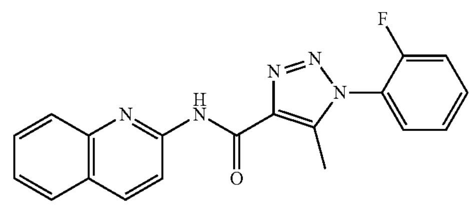 [SMILES: Cc1c(C(=O)Nc2ccc3ccccc3n2)nnn1-c1ccccc1F] |
| YW1169 (36) | 1-(2-Bromophenyl)-5-methyl-N-(quinolin-2-yl)-1H-1,2,3-triazole-4-carboxamide | 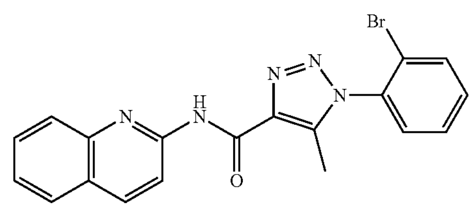 |
| YW1157 (34) | 1-(2-Cyanophenyl)-5-methyl-N-(quinolin-2-yl)-1H-1,2,3-triazole-4-carboxamide | 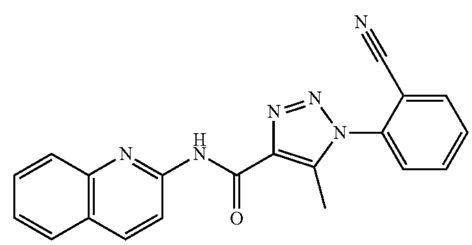 [SMILES: Cc1c(C(=O)Nc2ccc3ccccc3n2)nnn1-c1ccccc1C#N] |
| YW1149 (35) | 1-(2-Methoxyphenyl)-5-methyl-N-(quinolin-2-yl)-1H-1,2,3-triazole-4-carboxamide | 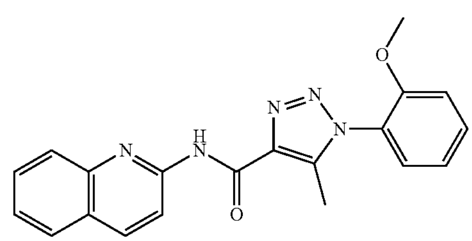 [SMILES: COc1ccccc1-n1nnc(C(=O)Nc2ccc3ccccc3n2)c1C] |
| YW1171 (41) | 1-(4-Fluoro-2-nitrophenyl)-5-methyl-N-(quinolin-2-yl)-1H-1,2,3-triazole-4-carboxamide | 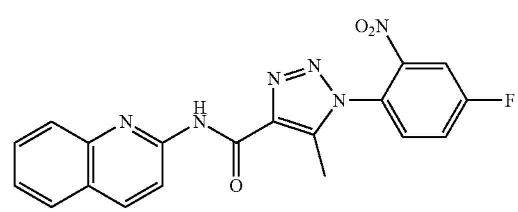 [SMILES: Cc1c(C(=O)Nc2ccc3ccccc3n2)nnn1-c1ccc(F)cc1[N+](=O)[O-]] |

TABLE 2-continued

Compounds of Formula II

| Compound Identifiers | Compound Name | Compound Structure |
|---|---|---|
| YW1181 (39) | 1-(2-Acetylphenyl)-5-methyl-N-(quinolin-2-yl)-1H-1,2,3-triazole-4-carboxamide | 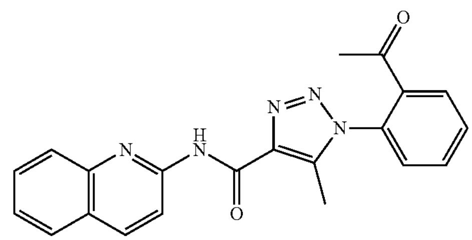 [SMILES: CC(=O)c1ccccc1-n1nnc(C(=O)Nc2ccc3ccccc3n2)c1C] |
| YW1182 (40) | 1-(2-Carbamoylphenyl)-5-methyl-N-(quinolin-2-yl)-1H-1,2,3-triazole-4-carboxamide | 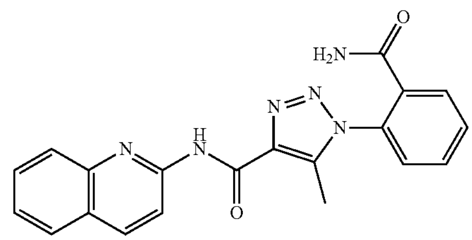 [SMILES: Cc1c(C(=O)Nc2ccc3ccccc3n2)nnn1-c1ccccc1C(N)=O] |
| YW1180 (38) | 1-([1,1'-biphenyl1-2-yl)-5-methyl-N-(quinolin-2-yl)-1H-1,2,3-triazole-4-carboxamide | 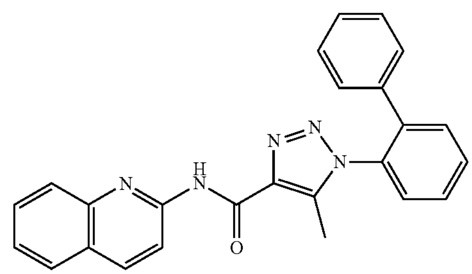 [SMILES: Cc1c(C(=O)Nc2ccc3ccccc3n2)nnn1-c1ccccc1-c1ccccc1] |
| YW1155 (37) | 5-Methyl-1-(2-morpholinophenyl)-N-(quinolin-2-yl)-1H-1,2,3-triazole-4-carboxamide | 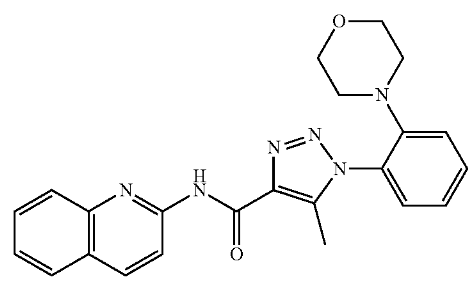 [SMILES: Cc1c(C(=O)Nc2ccc3ccccc3n2)nnn1-c1ccccc1N1CCOCC1] |
| YW1151 (43) | 5-Methyl-1-(naphthalen-1-yl)-N-(quinolin-2-yl)-1H-1,2,3-triazole-4-carboxamide | 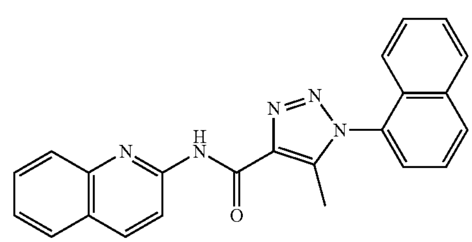 [SMILES: Cc1c(C(=O)Nc2ccc3ccccc3n2)nnn1-c1cccc2ccccc12] |
| YW2020 (46) | 1-(2-fluorophenyl)-5-isopropyl-N-(quinolin-2-yl)-1H-1,2,3-triazole-4-carboxamide | 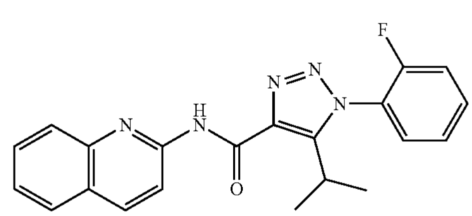 [SMILES: CC(C)c1c(C(=O)Nc2ccc3ccccc3n2)nnn1-c1ccccc1F] |

TABLE 2-continued

Compounds of Formula II

| Compound Identifiers | Compound Name | Compound Structure |
|---|---|---|
| YW2018 (45) | 5-Ethyl-1-(2-fluorophenyl)-N-(quinolin-2-yl)-1H-1,2,3-triazole-4-carboxamide | 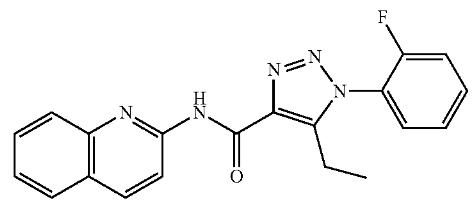 [SMILES: CCc1c(C(=O)Nc2ccc3ccccc3n2)nnn1-c1ccccc1F] |
| YW2013 (132) | 5-Methyl-N-(quinolin-2-yl)-1-(o-tolyl)-1H-pyrazole-4-carboxamide | 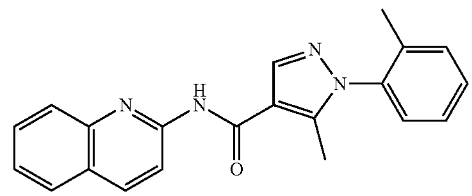 |
| YW2035 (133) | 1-(2-Fluorophenyl)-5-methyl-N-(quinolin-2-yl)-1H-pyrazole-4-carboxamide | 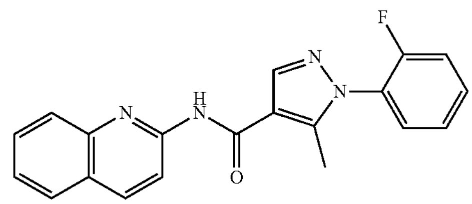 [SMILES: Cc1c(C(=O)Nc2ccc3ccccc3n2)cnn1-c1ccccc1F] |
| YW2065 (134) | 1-(2-Bromophenyl)-5-methyl-N-(quinolin-2-yl)-1H-pyrazole-4-carboxamide | 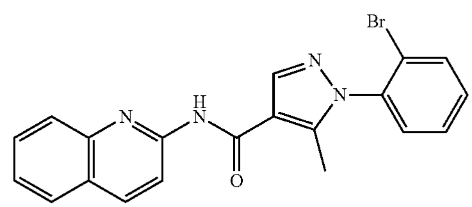 |
| YW6001 (166) | 2,5-Dimethyl-N-(quinolin-2-yl)-1-(o-tolyl)-1H-imidazole-4-carboxamide | 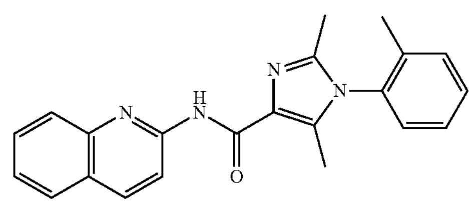 |
| YW6002 (167) | 1-(2-Fluorophenyl)-2,5-dimethyl-N-(quinolin-2-yl)-1H-imidazole-4-carboxamide | 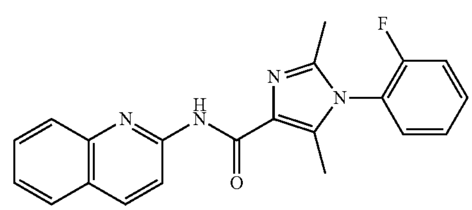 [SMILES: Cc1nc(C(=O)Nc2ccc3ccccc3n2)c(C)n1-c1ccccc1F] |
| YW6003 (168) | 1-(2-Bromophenyl)-2,5-dimethyl-N-(quinolin-2-yl)-1H-imidazole-4-carboxamide | 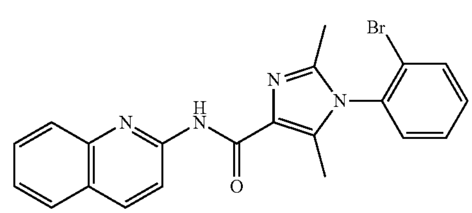 |

TABLE 2-continued

Compounds of Formula II

| Compound Identifiers | Compound Name | Compound Structure |
|---|---|---|
| YW6004 (169) | 2,5-Dimethyl-1-phenyl-N-(quinolin-2-yl)-1H-imidazole-4-carboxamide | 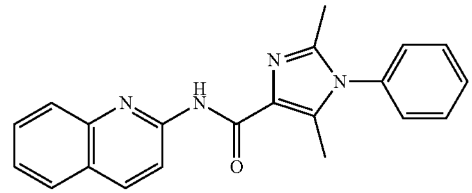 [SMILES: Cc1nc(C(=O)Nc2ccc3ccccc3n2)c(C)n1-c1ccccc1] |
| YW2038 (135) | 1-(2-Chlorophenyl)-5-methyl-N-(quinolin-2-yl)-1H-pyrazole-4-carboxamide | 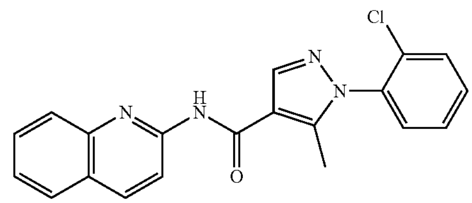 [SMILES: Cc1c(C(=O)Nc2ccc3ccccc3n2)cnn1-c1ccccc1Cl] |
| YW2044 (136) | 1-(2-Ethylphenyl)-5-methyl-N-(quinolin-2-yl)-1H-pyrazole-4-carboxamide | 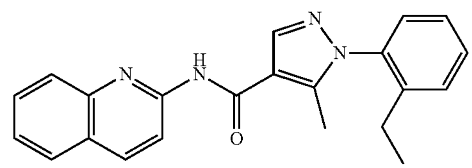 [SMILES: CCc1ccccc1-n1ncc(C(=O)Nc2ccc3ccccc3n2)c1C] |
| YW2048 (137) | 1-(2,6-dimethylphenyl)-5-methyl-N-(quinolin-2-yl)-1H-pyrazole-4-carboxamide | 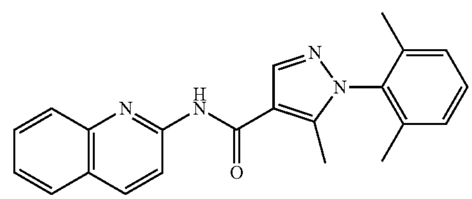 [SMILES: Cc1cccc(C)c1-n1ncc(C(=O)Nc2ccc3ccccc3n2)c1C] |
| YW2046 (139) | 1-(2,5-dimethylphenyl)-5-methyl-N-(quinolin-2-yl)-1H-pyrazole-4-carboxamide | 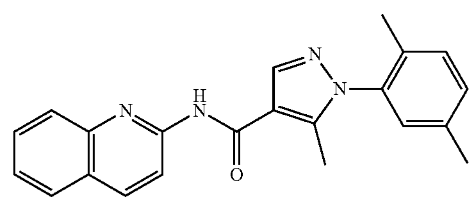 [SMILES: Cc1ccc(C)c(-n2ncc(C(=O)Nc3ccc4ccccc4n3)c2C)c1] |
| YW2039 (140) | 1-(2,4-difluorophenyl)-5-methyl-N-(quinolin-2-yl)-1H-pyrazole-4-carboxamide | 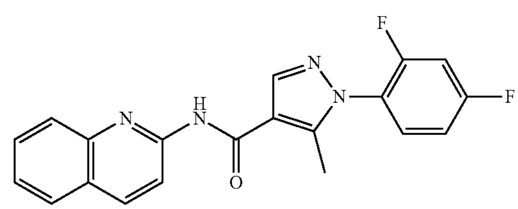 [SMILES: Cc1c(C(=O)Nc2ccc3ccccc3n2)cnn1-c1ccc(F)cc1F] |
| YW2036 (141) | 5-methyl-1-phenyl-N-(quinolin-2-yl)-1H-pyrazole-4-carboxamide | 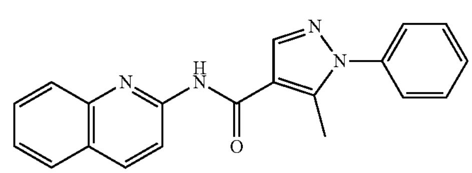 [SMILES: Cc1c(C(=O)Nc2ccc3ccccc3n2)cnn1-c1ccccc1] |
| YW2055 (145) | 5-methyl-1-(3-methylpyridin-2-yl)-N-(quinolin-2-yl)-1H-pyrazole-4-carboxamide | 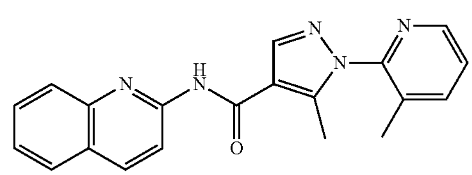 [SMILES: Cc1cccnc1-n1ncc(C(=O)Nc2ccc3ccccc3n2)c1C] |

TABLE 2-continued

Compounds of Formula II

| Compound Identifiers | Compound Name | Compound Structure |
|---|---|---|
| YW2068 (146) | 1-(3-chloro-2-fluorophenyl)-5-methyl-N-(quinolin-2-yl)-1H-pyrazole-4-carboxamide | 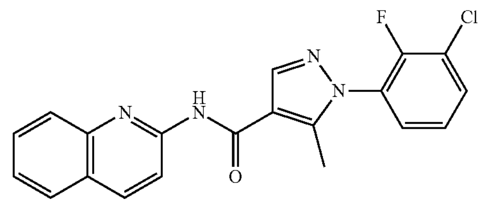 [SMILES: Cc1c(C(=O)Nc2ccc3ccccc3n2)cnn1-c1cccc(Cl)c1F] |
| YW2074 (147) | 1-(2,6-difluorophenyl)-5-methyl-N-(quinolin-2-yl)-1H-pyrazole-4-carboxamide | 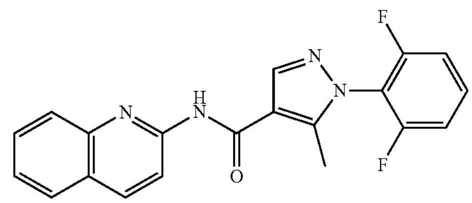 |
| YW2076 (148) | 1-(2-bromo-6-fluorophenyl)-5-methyl-N-(quinolin-2-yl)-1H-pyrazole-4-carboxamide | 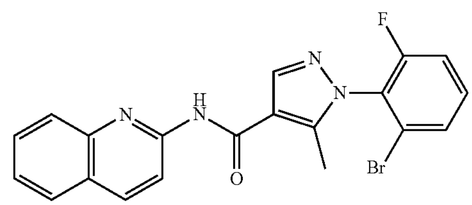 [SMILES: Cc1c(C(=O)Nc2ccc3ccccc3n2)cnn1-c1c(F)cccc1Br] |
| YW21172 (154) | 3,5-dimethyl-1-phenyl-N-(quinolin-2-yl)-1H-pyrazole-4-carboxamide | 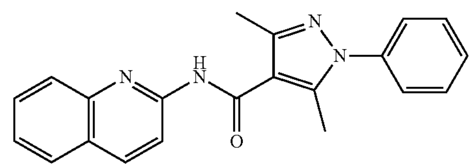 [SMILES: Cc1nn(-c2ccccc2)c(C)c1C(=O)Nc1ccc2ccccc2n1] |
| YW2120 (155) | 1-(2,5-dimethylphenyl)-3,5-dimethyl-N-(quinolin-2-yl)-1H-pyrazole-4-carboxamide | 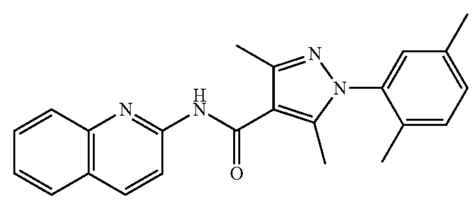 [SMILES: Cc1ccc(C)c(-n2nc(C)c(C(=O)Nc3ccc4ccccc4n3)c2C)c1] |
| YW2023 (156) | 1-(2-bromophenyl)-3,5-dimethyl-N-(quinolin-2-yl)-1H-pyrazole-4-carboxamide | 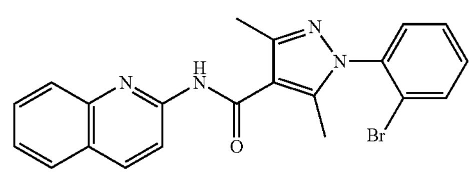 [SMILES: Cc1nn(-c2ccccc2Br)c(C)c1C(=O)Nc1ccc2ccccc2n1] |
| YW2126 (157) | 5-ethyl-1-phenyl-N-(quinolin-2-yl)-1H-pyrazole-4-carboxamide | 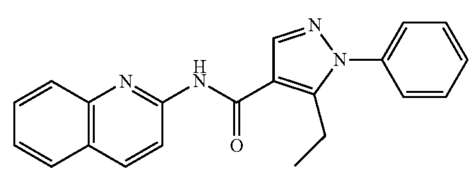 [SMILES: CCc1c(C(=O)Nc2ccc3ccccc3n2)cnn1-c1ccccc1] |
| YW2125 (158) | 5-isopropyl-1-phenyl-N-(quinolin-2-yl)-1H-pyrazole-4-carboxamide | 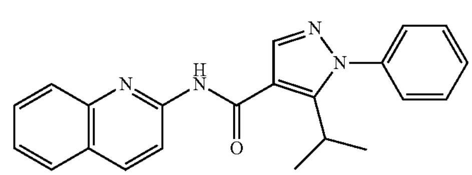 [SMILES: CC(C)c1c(C(=O)Nc2ccc3ccccc3n2)cnn1-c1ccccc1] |

TABLE 2-continued

Compounds of Formula II

| Compound Identifiers | Compound Name | Compound Structure |
|---|---|---|
| YW2137 (159) | 5-chloro-1-phenyl-N-(quinolin-2-yl)-1H-pyrazole-4-carboxamide | 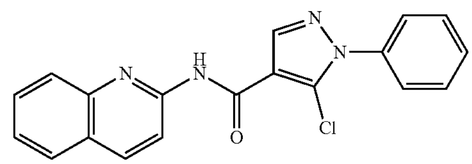 |
| YW2136 (160) | 5-bromo-1-phenyl-N-(quinolin-2-yl)-1H-pyrazole-4-carboxamide | 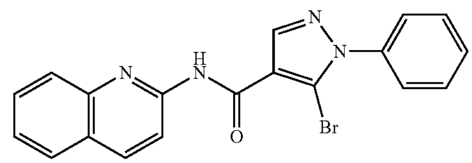 |
| YW2147 (161) | 5-(dimethylamino)-1-phenyl-N-(quinolin-2-yl)-1H-pyrazole-4-carboxamide | 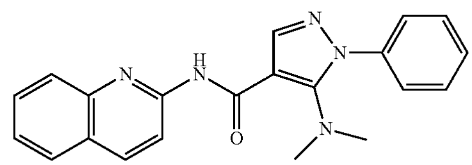 |
| YW2142 (162) | 1-(2-ethylphenyl)-5-methyl-N-(naphthalen-2-yl)-1H-pyrazole-4-carboxamide | 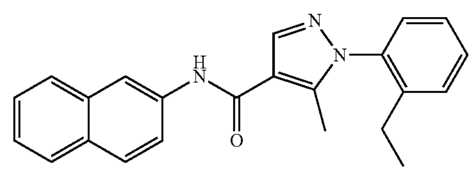 |
| YW2144 (163) | 1-(2-ethylphenyl)-N-(isoquinolin-3-yl)-5-methyl-1H-pyrazole-4-carboxamide | 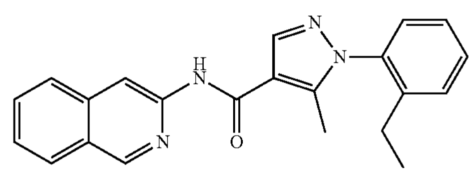 [SMILES: CCc1ccccc1-n1ncc(C(=O)Nc2cc3ccccc3cn2)c1C] |
| YW2143 (164) | 1-(2-ethylphenyl)-5-methyl-N-(quinolin-3-yl)-1H-pyrazole-4-carboxamide | 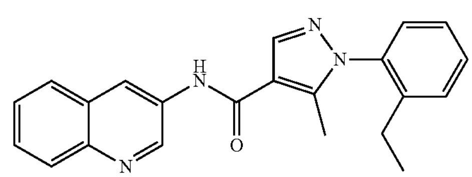 [SMILES: CCc1ccccc1-n1ncc(C(=O)Nc2cnc3ccccc3c2)c1C] |
| YW2146 (165) | 1-(2-ethylphenyl)-5-methyl-N-(6-methylpyridin-2-yl)-1H-pyrazole-4-carboxamide | 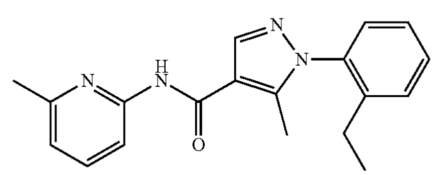 [SMILES: CCc1ccccc1-n1ncc(C(=O)Nc2cccc(C)n2)c1C] |
| YA1061 | N-(6-bromoquinolin-2-yl)-5-methyl-1-(o-tolyl)-1H-1,2,3-triazole-4-carboxamide | 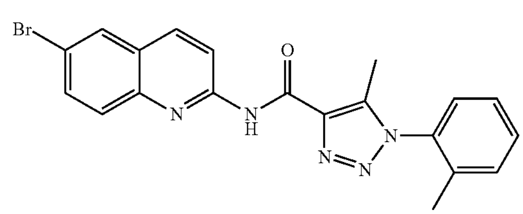 [SMILES: Cc1ccccc1-n1nnc(C(=O)Nc2ccc3cc(Br)ccc3n2)c1C] |

TABLE 2-continued

Compounds of Formula II

| Compound Identifiers | Compound Name | Compound Structure |
|---|---|---|
| YA1065 | 5-methyl-N-(6-(morpholinomethyl)quinolin-2-yl)-1-(o-tolyl)-1H-1,2,3-triazole-4-carboxamide | 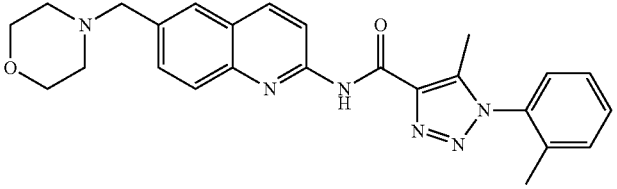 [SMILES: Cc1ccccc1-n1nnc(C(=O)Nc2ccc3cc(CN4CCOCC4)ccc3n2)c1C] |
| YA1073 | 5-methyl-N-(6-((4-methylpiperazin-1-yl)methyl)quinolin-2-yl)-1-(o-tolyl)-1H-1,2,3-triazole-4-carboxamide | 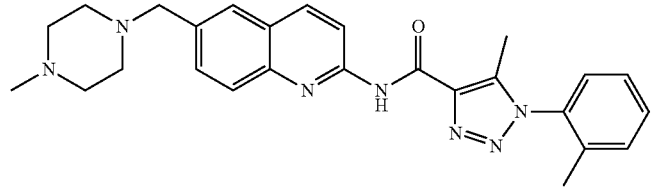 [SMILES: Cc1ccccc1-n1nnc(C(=O)Nc2ccc3cc(CN4CCN(C)CC4)ccc3n2)c1C] |
| YA1081 | 5-methyl-N-(6-(pyrrolidin-1-ylmethyl)quinolin-2-yl)-1-(o-tolyl)-1H-1,2,3-triazole-4-carboxamide | 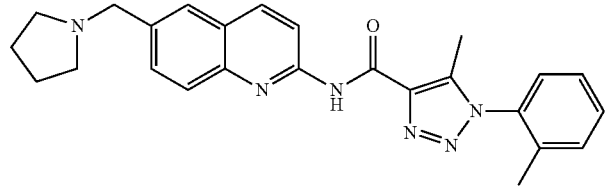 [SMILES: Cc1ccccc1-n1nnc(C(=O)Nc2ccc3cc(CN4CCCC4)ccc3n2)c1C] |
| YA1083 | N-(6-((diethylamino)methyl)quinolin-2-yl)-5-methyl-1-(o-tolyl)-1H-1,2,3-triazole-4-carboxamide | 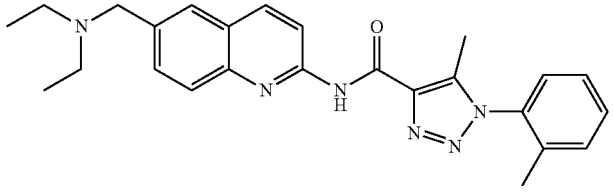 [SMILES: CCN(CC)Cc1ccc2nc(NC(=O)c3nnn(-c4ccccc4C)c3C)ccc2c1] |
| YA1093 | 5-methyl-N-(6-(piperidin-1-ylmethyl)quinolin-2-yl)-1-(o-tolyl)-1H-1,2,3-triazole-4-carboxamide | 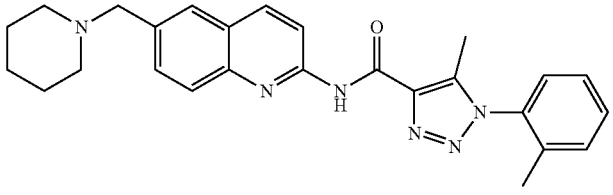 [SMILES: Cc1ccccc1-n1nnc(C(=O)Nc2ccc3cc(CN4CCCCC4)ccc3n2)c1C] |
| YA1095 | tert-butyl 4-((2-(5-methyl-1-(o-tolyl)-1H-1,2,3-triazole-4-carboxamido)quinolin-6-yl)methyl)piperazine-1-carboxylate | 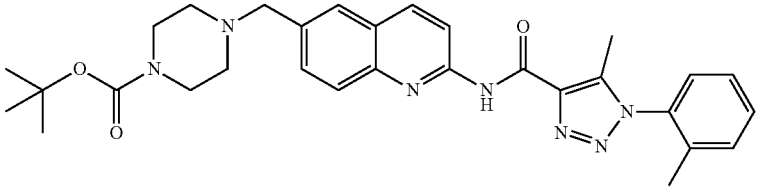 [SMILES: Cc1ccccc1-n1nnc(C(=O)Nc2ccc3cc(CN4CCN(C(=O)OC(C)(C)C)CC4)ccc3n2)c1C] |
| YA1097 | N-(6-((dimethylamino)methyl)quinolin-2-yl)-5-methyl-1-(o-tolyl)-1H-1,2,3-triazole-4-carboxamide | 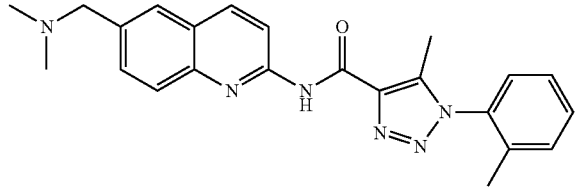 [SMILES: Cc1ccccc1-n1nnc(C(=O)Nc2ccc3cc(CN(C)C)ccc3n2)c1C] |

TABLE 2-continued

Compounds of Formula II

| Compound Identifiers | Compound Name | Compound Structure |
|---|---|---|
| YA1099 | 5-methyl-N-(6-(thiomorpholinomethyl)quinolin-2-yl)-1-(o-tolyl)-1H-1,2,3-triazole-4-carboxamide | 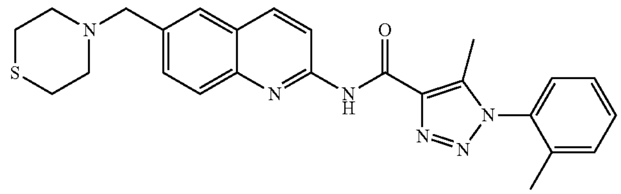 [SMILES: Cc1ccccc1-n1nnc(C(=O)Nc2ccc3cc(CN4CCSCC4)ccc3n2)c1C] |
| YA1105 | 5-methyl-N-(6-((4-morpholinopiperidin-1-yl)methyl)quinolin-2-yl)-1-(o-tolyl)-1H-1,2,3-triazole-4-carboxamide | 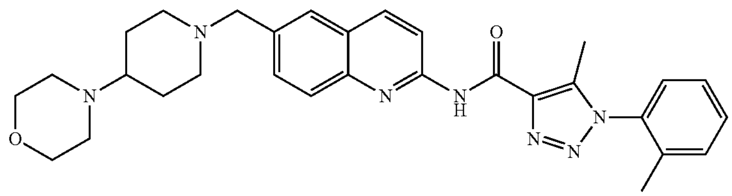 [SMILES: Cc1ccccc1-n1nnc(C(=O)Nc2ccc3cc(CN4CCC(N5CCOCC5)CC4)ccc3n2)c1C] |
| YA1109 | 5-methyl-N-(6-((4-(4-methylpiperazin-1-yl)piperidin-1-yl)methyl)quinolin-2-yl)-1-(o-tolyl)-1H-1,2,3-triazole-4-carboxamide | 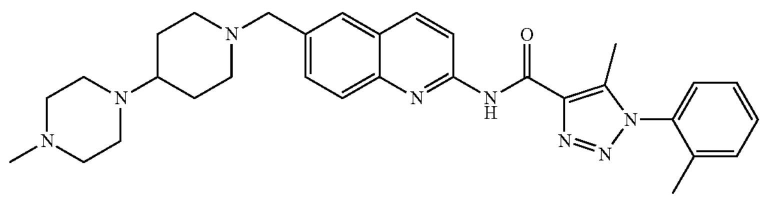 [SMILES: Cc1ccccc1-n1nnc(C(=O)Nc2ccc3cc(CN4CCC(N5CCN(C)CC5)CC4)ccc3n2)c1C] |

In some embodiments, the compounds of the invention may include the compounds of Table 3.

In some embodiments, the compounds of the invention may include those having the Wnt/β-catenin signaling inhibition activity set forth in Table 3, below:

TABLE 3

Compounds of Formula I with associated Wnt/β-catenin inhibitory activity (RLU % = Relative Light Units in reporter gene assays; SD = Standard Deviation).

| Compound | At 1 μM concentration | | $IC_{50}$ |
|---|---|---|---|
| | RLU % | SD | |
| YW1132 | 4.9 | 2 | 34 nM |
| YW1104 | 92.9 | 20.3 | 49 μM |
| YW1121 | 92.1 | 4 | ND |
| YW1125 | 55.1 | 9.9 | ND |
| YW1114 | 34.6 | 3.9 | 379 nM |
| YW1117-2 | 112.6 | 10 | ND |
| YW1123 | 87.6 | 9.7 | ND |
| YW1130 | 19.7 | 3.2 | 471 nM |
| YW1134 | 79.5 | 2 | 273 nM |
| YW1124 | 121.3 | 13.4 | 48 μM |
| YW1119 | 106.1 | 17.1 | ND |
| YW1127 | 56.4 | 2 | ND |
| YW1109 | 79.8 | 3.8 | ND |
| YW1128 | 3.7 | 0.8 | 7.7 nM |
| YW1155 | 99.8 | 4.8 | ND |
| YW1159 | 1.4 | 0.1 | 6.5 nM |
| YW1169 | 3.2 | 1.7 | 10 nM |
| YW1151 | 79.3 | 6.4 | 4 μM |
| YW1149 | 5 | 0.3 | 88 nM |
| YW1173 | 26.3 | 1.3 | 731 nM |
| YW1170 | 17.8 | 1.7 | 567 nM |
| YW1157 | 6.5 | 0.6 | 76 nM |
| YW1171 | 77.8 | 3.2 | 5 μM |
| YW1180 | 104.5 | 8.7 | 52 μM |
| YW1182 | 89.9 | 1.8 | >100 μM |

TABLE 3-continued

Compounds of Formula I with associated Wnt/β-catenin inhibitory activity (RLU % = Relative Light Units in reporter gene assays; SD = Standard Deviation).

| Compound | At 1 μM concentration | | $IC_{50}$ |
|---|---|---|---|
| | RLU % | SD | |
| YW1183 | 90.8 | 5.2 | 22 μM |
| YW1181 | 18.1 | 0.8 | 814 nM |
| YW1179 | 10.6 | 0.8 | 130 nM |
| YW2013 | 1.9 | 0.4 | 9.6 nM |
| YW2018 | 2.3 | 0.9 | 47 nM |
| YW2020 | 17.7 | 4.3 | 177 nM |

In some embodiments, the compounds of the invention may include one or more compounds selected from the group consisting of YW1132, YW1114, YW1130, YW1134, YW1128, YW1159, YW1169, YW1149, YW1173, YW1170, YW1157, YW1181, YW1179, YW2013, YW2018, YW2020, YW1132, YW2035, YW2038, YW2044, YW2049, YW2065, and YW2052. In some embodiments, the compound of the invention may be YW1149, YW2013, YW2065, and YW2044. In some embodiments, the compounds of the invention may include one or more compounds selected from the group consisting of YW1132, YW1114, YW1130, YW1134, YW1128, YW1159, YW1169, YW1149, YW1173, YW1170, YW1157, YW1181, YW1179, YW2013, YW2018, and YW2020. In some embodiments, the compound of the invention may be YW1149 or YW1128.

The compounds of the invention may be used as part of a therapy or methodology in treating a variety of diseases or conditions that implicate the Wnt/β-catenin pathway.

Specifically, the compounds of the invention may be used for treating or delaying the progression of a disorder or disease that may be alleviated by inhibiting the Wnt/β-catenin pathway, in a patient in need of such treatment, by administering a therapeutically effective amount of one or more compounds of formulas I or II, as set forth herein.

In some embodiments, the compounds and compositions provided herein may be used as inhibitors of one or more members of the Wnt pathway, including one or more Wnt proteins, and thus can be used to treat a variety of disorders and diseases in which aberrant Wnt signaling may be implicated, such as cancer and other diseases associated with abnormal angiogenesis, cellular proliferation, and cell cycling. Accordingly, the compounds and compositions provided herein can be used to treat cancer, to reduce or inhibit angiogenesis, to reduce or inhibit cellular proliferation and correct a genetic disorder due to mutations in Wnt signaling components.

In some embodiments, the cancer may be one or more of adrenocortical cancer, hepatocellular cancer, hepatoblastoma, malignant melanoma, ovarian cancer, Wilm's tumor, Barrett's esophageal cancer, prostate cancer, pancreatic cancer, bladder cancer, breast cancer, gastric cancer, head & neck cancer, lung cancer, mesothelioma, cervical cancer, uterine cancer, myeloid leukemia cancer, lymphoid leukemia cancer, pilometricoma cancer, medulloblastoma cancer, glioblastoma, and familial adenomatous polyposis. In some embodiments, the cancer or hyperproliferative disease may include colon cancer.

Non-limiting examples of diseases which may be treated with the compounds and compositions provided herein include a variety of cancers, diabetic retinopathy, neovascular glaucoma, rheumatoid arthritis, psoriasis, mycotic and viral infections, osteochondrodysplasia, Alzheimer's disease, osteoarthritis, polyposis coli, osteoporosis-pseudoglioma syndrome, familial exudative vitreoretinopathy, retinal angiogenesis, early coronary disease, tetra-amelia syndrome, Müllerian-duct regression and virilization, SERKAL syndrome, Fuhrmann syndrome, Al-Awadi/Raas-Rothschild/Schinzel phocomelia syndrome, odonto-onychodermal dysplasia, split-hand/foot malformation, caudal duplication syndrome, tooth agenesis, Wilms tumor, skeletal dysplasia, focal dermal hypoplasia, autosomal recessive anonychia, neural tube defects, alpha-thalassemia (ATRX) syndrome, fragile X syndrome, ICF syndrome, Angelman syndrome, Prader-Willi syndrome, Beckwith-Wiedemann Syndrome and Rett syndrome.

In some embodiments, the methods of the invention may be used in the treatment of metabolic disease, including, without limitation, type 2 diabetes, obesity, hyperlipidemia, or fatty liver disease. In certain embodiments, the methods of the invention may be used in the treatment of type 2 diabetes. In some embodiments, fatty liver disease may include alcoholic fatty liver disease (ALD) or non-alcoholic fatty liver disease (NAFLD). In some embodiments, NAFLD may include one or more of simple fatty liver disease (steatosis), non-alcoholic steatohepatitis (NASH), and liver cirrhosis. In certain embodiments, the methods of the invention may be used in the treatment of NASH.

As used herein, the terms "administer," "administration" or "administering" refer to (1) providing, giving, dosing, and/or prescribing by either a health practitioner or his authorized agent or under his or her direction according to the disclosure; and/or (2) putting into, taking or consuming by the mammal, according to the disclosure.

As used herein, the terms "treat," "treatment," and/or "treating" may refer to the management of a disease, disorder, or pathological condition (e.g., cancer or metabolic disease) with the intent to cure, ameliorate, stabilize, and/or control the disease, disorder, or pathological condition. Regarding control of the disease, disorder, or pathological condition more specifically, "control" may include the absence of disease progression, as assessed by the response to the methods recited herein, where such response may be complete (e.g., placing the disease in remission) or partial (e.g., lessening or ameliorating any symptoms associated with the disease). As used herein, the terms "prevent," "preventing," and/or "prevention" may refer to reducing the risk of developing a disease, disorder, or pathological condition (e.g., cancer or metabolic disorder).

In some embodiments, the methods of the invention may include the modulation of protein activity, regulation, and/or expression. As used herein, the terms "modulate" and "modulation" refer to a change in biological activity for a biological molecule (e.g., a protein, gene, peptide, antibody, and the like), where such change may relate to an increase in biological activity (e.g., increased activity, activation, expression, upregulation, and/or increased expression) or decrease in biological activity (e.g., decreased activity, suppression, deactivation, downregulation, and/or decreased expression) for the biological molecule.

As described herein, in some embodiments, the compounds used in the methods of the invention may inhibit Wnt signaling, which may result in a reduction of β-catenin. Indeed, in some embodiments, the compounds used in the methods of the invention may inhibit Wnt signaling by downregulating β-catenin levels. In some embodiments, the compounds of the invention may upregulate Axin protein expression. In some embodiments, the compounds of the invention may downregulate c-Myc. In some embodiments, the compounds of the invention may modulate the activity of one or more of casein kinase 1 alpha (CK1α), protein kinase B (Akt/PKB), and glycogen synthase kinase 3 (GSK3). In some embodiments, the compounds of the invention may upregulate the activity of casein kinase 1 alpha (CK1α). In some embodiments, the compounds of the invention may downregulate the activity of one or more of Akt/PKB and GSK3. In some embodiments, the compounds of the invention may suppress the expression of glucose 6-phosphatase (G6P). In some embodiments, the compounds of the invention may increase phosphorylation of 5' adenosine monophosphate-activated protein kinase (AMP kinase or AMPK).

In some embodiments of the invention, the methods described herein may include the treatment of certain symptoms of diseases that implicate the Wnt/β-catenin signaling pathway.

For example, the methods of the invention may include treatments for symptoms of cancer or metabolic diseases. In some embodiments, the methods of the invention may include treatments for symptoms of type 2 diabetes.

In some embodiments, the compounds of the invention may suppress glucose production. Furthermore, in some embodiments, the compounds of the invention may improve glucose tolerance in a patient in need thereof. In some embodiments, the compounds of the invention may reduce fasting glucose levels in a patient in need thereof. In some embodiments, the compounds of the invention may suppress gluconeogenesis in a patient in need thereof. In some embodiments, the compounds of the invention may reverse obesity and/or decrease weight gain in a patient in need thereof. In some embodiments, the compounds of the invention may increase insulin sensitivity in a patient in need thereof.

In some embodiments, the methods may include the co-administration of a compound of the invention with an additional therapeutic agent. The term "co-administering" as used herein means a process whereby the combination of a compound of the invention and at least one additional therapeutic agent is administered to the same patient. The compound of the invention and additional therapeutic may be administered simultaneously, at essentially the same time, or sequentially. If administration takes place sequentially, the compound of the invention may be administered before or after a given additional therapeutic agent or treatment. The compound of the invention and additional therapeutic agent or treatment need not be administered by means of the same vehicle or physiologically compatible carrier medium. The compound of the invention and the additional therapeutic agent may be administered one or more times and the number of administrations of each component of the combination may be the same or different. In addition, the compound of the invention and additional therapeutic agent or treatment need not be administered at the same site.

In some embodiments, the methods of the invention may include administering (1) a therapeutically effective amount of one or more of a compound of formula I, II, Table 1, Table 2, Table 3, and the pharmaceutically acceptable salts thereof; and (2) a therapeutically effective amount of an additional therapeutic agent. In some embodiments, the additional therapeutic agent may include one or more of a RAF inhibitor, an MEK inhibitor, an ERK inhibitor, a VEGFR inhibitor, and an EGFR inhibitor. In some embodiments, the VEGFR inhibitor may include one or more of Bevacizumab (AVASTIN), Aflibercept (ZALTRAP), and Regorafenib (STIVARGA). In some embodiments, the EGFR inhibitor may include one or more of Cetuximab (ERBITUX), Panitumumab (VECTIBIX), and Gefitinib. In some embodiments, the additional therapeutic agent may include pyrvinium.

Furthermore, the described methods of treatment may normally include medical follow-up to determine the therapeutic or prophylactic effect brought about in the subject undergoing treatment with the compound(s) and/or composition(s) described herein.

Molecular modeling and computer-based modeling may be used in accordance with the invention to both understand the protein targets of the therapeutic agents described herein or to direct drug design in the preparation of analogs. Data reflecting the effect of compounds of the invention on protein binding, for example, or other resulting in vitro or in vivo activity data, may be used to develop a pharmacophore and pharmacophore model. As used herein, the term "pharmacophore" refers to the ensemble of steric and electronic features that are necessary to ensure the optimal supramolecular interactions with a specific biological target structure and to trigger, activate, block, inhibit or modulate the biological target's biological activity, as the case may be. See, IUPAC, Pure and Applied Chemistry (1998) 70: 1129-1143.

As used herein, the term "pharmacophore model" refers to a representation of points in a defined coordinate system wherein a point corresponds to a position or other characteristic of an atom or chemical moiety in a bound conformation of a ligand and/or an interacting polypeptide, protein, or ordered water. An ordered water is an observable water in a model derived from structural determination of a polypeptide or protein. A pharmacophore model can include, for example, atoms of a bound conformation of a ligand, or portion thereof. A pharmacophore model can include both the bound conformations of a ligand, or portion thereof, and one or more atoms that interact with the ligand and are from a bound polypeptide or protein. Thus, in addition to geometric characteristics of a bound conformation of a ligand, a pharmacophore model can indicate other characteristics including, for example, charge or hydrophobicity of an atom or chemical moiety. A pharmacophore model can incorporate internal interactions within the bound conformation of a ligand or interactions between a bound conformation of a ligand and a polypeptide, protein, or other receptor including, for example, van der Waals interactions, hydrogen bonds ionic bonds, and hydrophobic interactions. A pharmacophore model can be derived from 2 or more bound conformations of a ligand.

Turning to the administration of therapeutics, the compounds of the invention may be administered as described herein, or in a form from which the active agent can be derived, such as a prodrug. A "prodrug" is a derivative of a compound described herein, the pharmacologic action of which results from the conversion by chemical or metabolic processes in vivo to the active compound. Prodrugs include compounds wherein an amino acid residue, or a polypeptide chain of two or more (e.g., two, three or four) amino acid residues is covalently joined through an amide or ester bond to a free amino, hydroxyl or carboxylic acid group of formulas I and II. The amino acid residues include but are not limited to the 20 naturally occurring amino acids commonly designated by one or three letter symbols but also include, for example, 4-hydroxyproline, hydroxylysine, desmosine, isodesmosine, 3-methylhistidine, beta-alanine, gamma-aminobutyric acid, citrulline, homocysteine, homoserine, omithine and methionine sulfone. Additional types of prodrugs are also encompassed. For instance, free carboxyl groups can be derivatized as amides or alkyl esters. Prodrug esters as employed herein includes esters and carbonates formed by reacting one or more hydroxyls of compounds of the method of the invention with alkyl, alkoxy, or aryl substituted acylating agents employing procedures known to those skilled in the art to generate acetates, pivalates, methylcarbonates, benzoates and the like. As further examples, free hydroxyl groups may be derivatized using groups including but not limited to hemisuccinates, phosphate esters, dimethylaminoacetates, and phosphoryloxymethyloxycarbonyls, as outlined in Advanced Drug Delivery Reviews, 1996, 19, 115. Carbamate prodrugs of hydroxyl and amino groups are also included, as are carbonate prodrugs, sulfonate prodrugs, sulfonate esters and sulfate esters of hydroxyl groups. Free amines can also be derivatized to amides, sulfonamides or phosphonamides. All of the stated prodrug moieties may incorporate groups including but not limited to ether, amine and carboxylic acid functionalities. Moreover, any compound that can be converted in vivo to provide the bioactive agent (e.g., a compound of formula I) is a prodrug within the scope of the invention. Various forms of prodrugs are well known in the art. A comprehensive description of pro drugs and prodrug derivatives are described in: (a) The Practice of Medicinal Chemistry, Camille G. Wermuth et al., (Academic Press, 1996); (b) Design of Prodrugs, edited by H. Bundgaard, (Elsevier, 1985); (c) A Textbook of Drug Design and Development, P. Krogsgaard-Larson and H. Bundgaard, eds., (Harwood Academic Publishers, 1991).

In general, prodrugs may be designed to improve the penetration of a drug across biological membranes in order to obtain improved drug absorption, to prolong duration of action of a drug (slow release of the parent drug from a prodrug, decreased first-pass metabolism of the drug), to target the drug action (e.g. organ or tumor-targeting, lymphocyte targeting), to modify or improve aqueous solubility of a drug (e.g., i.v. preparations and eyedrops), to improve topical drug delivery (e.g. dermal and ocular drug delivery), to improve the chemical/enzymatic stability of a drug, or to decrease off-target drug effects, and more generally in order to improve the therapeutic efficacy of the compounds utilized in the invention.

A compound used in practicing any method of the invention may be administered in an amount sufficient to induce the desired therapeutic effect in the recipient thereof. Thus the term "therapeutically effective amount" as used herein refers to an amount of a compound of the invention that is sufficient to treat a disease in accordance with the invention by administration of one or more of the compounds of formulas I and/or II or a prodrug thereof. Preferably, the therapeutically effective amount refers to the amount appropriate to inhibit the Wnt/β-catenin pathway. In addition, the term therapeutically effective amount may include the amount of a compound necessary, for example, to bring about a detectable therapeutic, preventative, or ameliorative effect in a patient having a disease as set forth herein. The effect may include, for example, the reduction, prevention, amelioration, or stabilization of symptoms or conditions associated with a disease as described herein.

The compound(s) described herein may also be administered at a dose in range from about 0.01 mg to about 200 mg/kg of body weight per day. A dose of from about 0.1 to 100 mg/kg, or from about 1 to 50 mg/kg per day in one or more applications per day may be effective to produce the desired result. By way of example, a suitable dose for oral administration may be in the range of 1-50 mg/kg of body weight per day, whereas a dose for intravenous administration may be in the range of 1-10 mg/kg of body weight per day.

Of course, as those skilled in the art will appreciate, the dosage actually administered will depend upon the condition being treated, the age, health and weight of the recipient, the type of concurrent treatment, if any, and the frequency of treatment. Moreover, the effective dosage amount may be determined by one skilled in the art on the basis of routine empirical activity testing to measure the bioactivity of the compound(s) in a bioassay, and thus establish the appropriate dosage to be administered.

The compounds used in certain methods of the invention may typically be administered from 1-4 times a day, so as to deliver the above-mentioned daily dosage. However, the exact regimen for administration of the compounds described herein will necessarily be dependent on the needs of the individual subject being treated, the type of treatment administered and the judgment of the attending medical specialist. As used herein, the term "subject" or "patient" includes both humans and animals.

In general, the compounds used in the methods of the invention can be administered in pure form or, as described herein, with physiologically compatible and/or acceptable carrier mediums, using any acceptable route known in the art, either alone or in combination with one or more other therapeutic agents. Thus, the compound(s) and/or composition(s) of the invention can be administered orally, parenterally, such as by intravenous or intraarterial infusion, intramuscular, intraperitoneal, intrathecal or subcutaneous injection, by liposome-mediated delivery, rectally, vaginally, by inhalation or insufflation, transdermally or by otic delivery.

The orally administered dosage unit may be in the form of tablets, caplets, dragees, pills, semisolids, soft or hard gelatin capsules, aqueous or oily solutions, emulsions, suspensions or syrups. Suitable dosage forms for parenteral administration include injectable solutions or suspensions, suppositories, powder formulations, such as microcrystals or aerosol spray. The active agents of the invention may also be incorporated into a conventional transdermal delivery system.

As used herein, the expression "physiologically compatible carrier medium" (or "physiologically acceptable carrier medium" and the like) includes any and all solvents, diluents, or other liquid vehicles, dispersions or suspension aids, surface agent agents, isotonic agents, thickening or emulsifying agents, preservatives, solid binders, lubricants, fillers and the like as suited for the particular dosage form desired. Remington: The Science and Practice of Pharmacy, 20th edition, A. R. Genaro et al., Part 5, Pharmaceutical Manufacturing, pp. 669-1015 (Lippincott Williams & Wilkins, Baltimore, Md./Philadelphia, Pa.) (2000) discloses various carriers used in formulating pharmaceutical compositions and known techniques for the preparation thereof. Except insofar as any conventional pharmaceutical carrier medium is incompatible with the compounds of the present invention, such as by producing an undesirable biological effect or otherwise interacting in an deleterious manner with any other component(s) of a formulation comprising such compounds or agents, its use is contemplated to be within the scope of this invention.

For the production of solid dosage forms, including hard and soft capsules, the agents of the invention may be mixed with pharmaceutically inert, inorganic or organic excipients, such as lactose, sucrose, glucose, gelatine, malt, silica gel, starch or derivatives thereof, talc, stearic acid or its salts, dried skim milk, vegetable, petroleum, animal or synthetic oils, wax, fat, polyols, and the like. For the production of liquid solutions, emulsions or suspensions or syrups one may use excipients such as water, alcohols, aqueous saline, aqueous dextrose, polyols, glycerine, lipids, phospholipids, cyclodextrins, vegetable, petroleum, animal or synthetic oils. For suppositories one may use excipients, such as vegetable, petroleum, animal or synthetic oils, wax, fat and polyols. For aerosol formulations, one may use compressed gases suitable for this purpose, such as oxygen, nitrogen and carbon dioxide. Pharmaceutical compositions or formulations may also contain one or more additives including, without limitation, preservatives, stabilizers, e.g., UV stabilizers, emulsifiers, sweeteners, salts to adjust the osmotic pressure, buffers, coating materials and antioxidants.

The invention further includes controlled-release, sustained release, or extended-release therapeutic dosage forms for administration of the compounds of the invention, which involves incorporation of the compounds into a suitable delivery system in the formation of certain compositions. This dosage form controls release of the compound(s) in such a manner that an effective concentration of the compound(s) in the bloodstream may be maintained over an extended period of time, with the concentration in the blood remaining relatively constant, to improve therapeutic results and/or minimize side effects. Additionally, a controlled-release system would provide minimum peak to trough fluctuations in blood plasma levels of the compound.

In pharmaceutical compositions used in practicing the methods of the invention more particularly, the specified compound(s) may be present in an amount of at least 0.5 and generally not more than 95% by weight, based on the total weight of the composition, including carrier medium and/or supplemental active agent(s), if any. In some embodiments, the proportion of compound(s) varies between about 30-90% by weight of the composition.

In some embodiments, the compositions of the invention may include (1) one or more of a compound of formula I, II, Table 1, Table 2, Table 3, and the pharmaceutically acceptable salts thereof; (2) an additional therapeutic agent; and a physiologically compatible carrier medium. In some embodiments, the additional therapeutic agent may include one or more of a RAF inhibitor, an MEK inhibitor, an ERK inhibitor, a VEGFR inhibitor, and an EGFR inhibitor. In some embodiments, the VEGFR inhibitor may include one or more of Bevacizumab (AVASTIN), Aflibercept (ZAL-TRAP), and Regorafenib (STIVARGA). In some embodiments, the EGFR inhibitor may include one or more of Cetuximab (ERBITUX), Panitumumab (VECTIBIX) Gefitinib. In some embodiments, the additional therapeutic agent may include pyrvinium.

The following examples describe the invention in further detail. These examples are provided for illustrative purposes only, and should in no way be considered as limiting the invention.

EXAMPLES

Example 1: Development of New Inhibitors for Wnt Signaling Pathway

Pyrvinium (Scheme 1) is an FDA approved anti-helminthic drug for the treatment of pinworm infection. Recently lines of experimental evidence have shown that pyrvinium is an inhibitor for the Wnt/β-catenin signaling pathway that works by direct binding and activating of CK1α. Although pyrvinium showed promising activity in regulating the Wnt signaling pathway, its further clinical application was prohibited due to major limitations of this compound. First, the inhibitory potency of pyrvinium for the Wnt signaling pathway is modest. In addition, pyrvinium adopts various salt forms that are permanently charged, which led to low bioavailability. Furthermore, the alkene linker of pyrvinium makes the dimethyl pyrrole fragment electron rich, which impairs the chemical stability of the pyrrole moiety.

In the on-going program in developing novel Wnt signaling inhibitors for various diseases such as cancer, diabetes, and other metabolic disorders, it is hypothesized that molecules that mimic the chemical structure of pyrvinium, while with improved potency and bioavailability, can be novel candidates as therapeutics to target the Wnt signaling pathway.

Scheme 1: Pyrvinium Structure

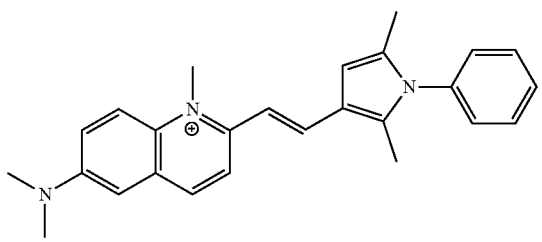

A variety of compounds were prepared as Wnt signaling inhibitors. These compounds, as shown below, were subsequently tested in a dual-luciferase assay to measure Wnt/β-catenin pathway inhibition using a TCF/LEF responsive reporter construct similar to that described in the field (see Thome et al, 2010).

In this assay, HEK293 cells were transiently transfected with firefly luciferase plasmid containing the latter construct and constitutively active *renilla* luciferase expression plasmids as control. Lithium chloride (LiCl), which has been previously established as an activator of the Wnt/β-catenin pathway through its direct and indirect effects on GSK3β was used for pathway activation. The inhibition of the Wnt/β-catenin pathway by a compound may be determined after its incubation with cells for 24 hours. As a point of comparison, when pyrvinium is tested in the foregoing assay at 1 μM, the remaining Wnt signaling activity (or RLU %) was 29.1% with a standard deviation (SD) of 3.5%. The 50% of inhibition ($IC_{50}$) was calculated with a series of pyrvinium concentrations to be at 294 μM of pyrvinium.

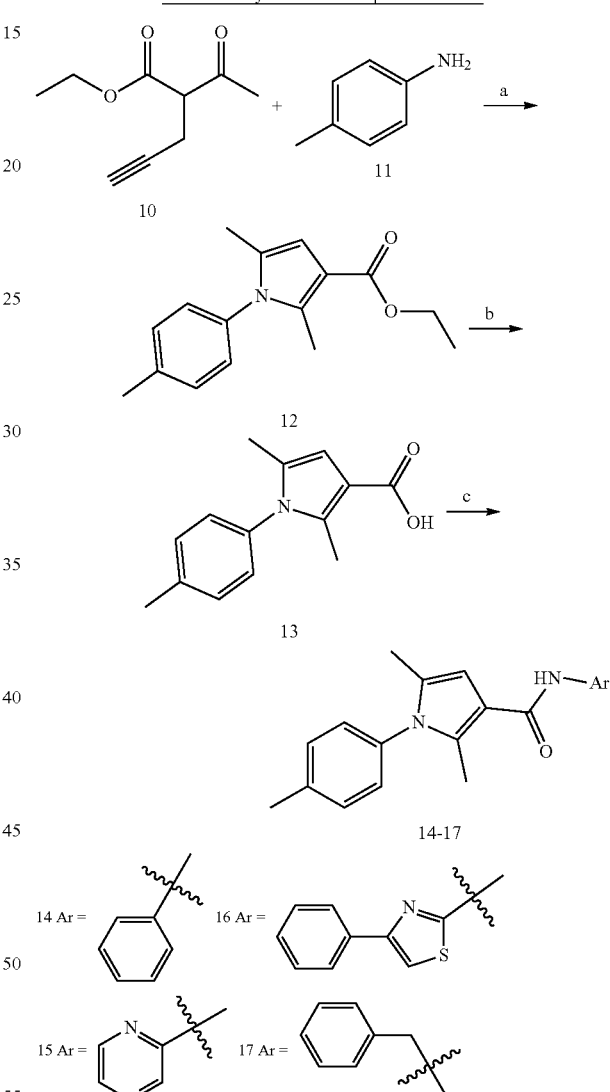

Scheme 2. Synthesis of compounds 14-17[a]

[a]Reagents and conditions: (a) FeCl₃, toluene, 80° C.; (b) KOH, methanol, reflux; (c) ArNH₂, PyCIU, DIPEA, DCE, 80° C.

Scheme 2 describes the preparation of pyrrole-based derivatives 14-17. The synthesis started from the FeCl₃-catalyzed reaction of 10 and 4-Toluidine 11 to generate the pyrrole-3-ester 12 followed by the hydrolysis of the ester to afford pyrrole-3-carboxylic acid 13. Coupling of the acid 13 with various amines yielded the final products 14-17 by the employment of PyCIU as coupling reagent in moderate to good yields.

Scheme 3. Synthesis of compounds 20-45[a]

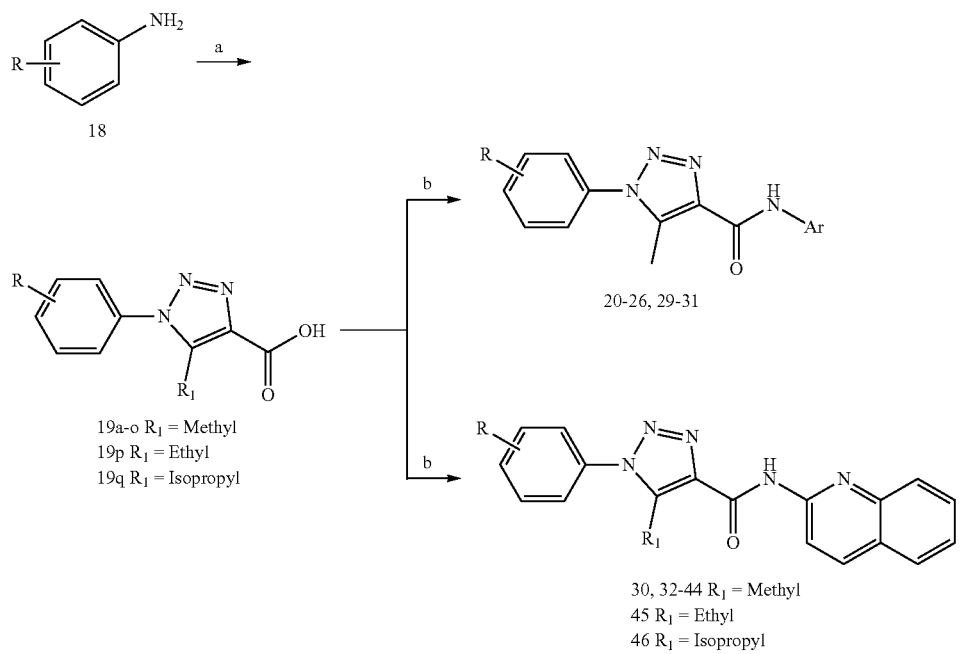

19a-o R₁ = Methyl
19p R₁ = Ethyl
19q R₁ = Isopropyl 20-26, 29-31

30, 32-44 R₁ = Methyl
45 R₁ = Ethyl
46 R₁ = Isopropyl

[a]Reagents and conditions: (a)(i) NaNO₂, HCl, NaN₃, H₂O, 0° C.: (ii) ethyl 3-oxobutanoate for 19a-o, ethyl 3-oxopentanoatein for 19p, ethyl 4-methyl-3-oxopentanoate for 19q, EtONa, EtOH, 80° C.; (b) ArNH₂, PyClU, DIPEA, DCE, 80° C.

The access to trizaole-based compounds 20-45 was described in Scheme 3. Starting with the diazotization of the appropriate aniline, followed by the addition of sodium azide and cyclization with β-ketone ester in the EtONa/EtOH medium gave the key intermediate trizaole-3-carboxylic acid 19. Finally, the PyClU-mediated coupling reaction of 19 with various aromatic amines in dichloroethane solvent allowed access to target compounds 20-45 in moderate to good yields.

TABLE 4

Effect of Quinoline Modifications in Pyrrole-based Scaffold on Inhibitory Activities against LiCl-mediated WNT Signaling Pathway.

| Compound | R | IC₅₀ (nM) or remaining activity at 1 μM |
|---|---|---|
| Pyrvinium | — | 293 |
| 14 | 2-pyridyl | 79.8% @ 1 μM |

TABLE 4-continued

Effect of Quinoline Modifications in Pyrrole-based Scaffold on Inhibitory Activities against LiCl-mediated WNT Signaling Pathway.

| Compound | R | IC₅₀ (nM) or remaining activity at 1 μM |
|---|---|---|
| 15 | pyrazinyl | 112% @ 1 μM |
| 16 | 4-phenylthiazol-2-yl | 379 |
| 17 | benzyl | 93% @ 1 μM |

TABLE 5

Optimization of the replacement of quinolone in the trizaole-based scaffold.

| Compound | Ar | IC$_{50}$ (nM) or remaining activity at 1 μM |
|---|---|---|
| 20 | pyridin-2-yl | 100% @ 1 μM |
| 21 | 6-methylpyridin-2-yl | 273 |
| 22 | 4,5-diphenylthiazol-2-yl | 1000 |
| 23 | 1-methylbenzimidazol-2-yl | ND |
| 24 | 3-methylisoxazol-5-yl | 48000 |
| 25 | (pyridin-2-yl)methyl | >1000 |
| 26 | 2-methyl-4-oxo-4H-chromen-7-yl | >1000 |

TABLE 6

Optimization of the phenyl substituents in the trizaole-based scaffold.

| Compound | R | IC$_{50}$ (nM) or remaining activity at 1 μM |
|---|---|---|
| 27 | 4-CH$_3$ | 56.4 ± 2.0 @ 1 μM |
| 28 | 2-CH$_3$ | 6.3 |
| 32 | 2-CH$_3$, 4-CH$_3$ | 130 |
| 33 | 2-F | 6.5 |
| 34 | 2-CN | 76 |
| 35 | 2-OCH$_3$ | 88 |
| 36 | 2-Br | 10 |
| 37 | 2-morpholine | >1000 |
| 38 | 2-Ph | 52000 |
| 39 | 2-COCH3 | 814 |
| 40 | 2-CONH2 | >100000 |
| 41 | 2-NO2, 4-F | 5000 |
| 42 | 2-CH3, 3-CH3 | 567 |
| 43 | 1-naphthyl | 4000 |
| 44 | 3-Cl | 731 |

TABLE 7

Optimization of the ortho-position on the phenyl substituent while varying the amide substituents on the triazole-based scaffold.

| Compound | Ar | R1 | R2 | IC$_{50}$ (nM) |
|---|---|---|---|---|
| 29 | benzothiazol-2-yl | CH$_3$ | CH$_3$ | 34 |
| 30 | 4-phenylthiazol-2-yl | CH$_3$ | CH$_3$ | 22000 |
| 31 | naphthalen-2-yl | CH$_3$ | CH$_3$ | 471 |
| 45 | quinolin-2-yl | CH$_2$CH$_3$ | F | 47 |

TABLE 7-continued

Optimization of the ortho-position on the phenyl substituent while varying the amide substituents on the triazole-based scaffold.

| Compound | Ar | R1 | R2 | IC$_{50}$ (nM) |
|---|---|---|---|---|
| 46 | 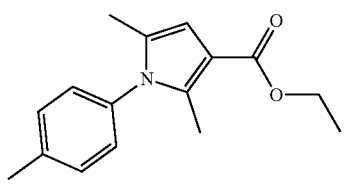 | CH(CH$_3$)$_2$ | F | 177 |

EXPERIMENTALS

Chemistry.

All chemicals were obtained from commercial suppliers and used without further purification. Analytical thin layer chromatography was visualized by ultraviolet light at 256 nM. $^1$H NMR spectra were recorded on a Varian (400 MHz) spectrometer. Data are presented as follows: chemical shift (in ppm on the δ scale relative to δ=0.00 ppm for the protons in tetramethylsilane (TMS)), integration, multiplicity (s=singlet, d=doublet, t=triplet, q=quartet, m=multiplet, br=broad), coupling constant (J/Hz). $^{13}$C NMR spectra were recorded at 100 MHz, and all chemical shifts values are reported in ppm on the δ scale with an internal reference of δ 77.0 or 39.0 for CDCl3 or DMSO-d$_6$, respectively. The purities of title compounds were determined by analytic HPLC, performed on an Agilent 1100 instrument and a reverse-phase column (Waters XTerrra RP18, 5 μM, 4.6× 250 mm). All compounds were eluted with 60% acetonitrile/ 40 water (containing 0.1% TFA) over 20 mins with a detection at 260 nM and a flow rate at 1.0 mL/min. All tested compounds were >95% pure.

Ethyl 2,5-dimethyl-1-(p-tolyl)-1H-pyrrole-3-carboxylate (12)

To a solution of ethyl 2-acetylpent-4-ynoate (1.68 g, 10 mmol), 4-methylaniline (1.07 g, 10 mmol) in toluene (20 mL) was added FeCl$_3$ (168 mg, 1 mmol). The mixture was stirred at 80° C. overnight. After cooling to room temperature, to the mixture was added ethyl acetate (50 mL). The resulting mixture was washed with water, dried over Na$_2$SO$_4$ and concentrated. The residue was purified by column chromatography (Hexane/AcOEt, v/v=4/1) to give the title compound as oil (2.18 g, 85%).

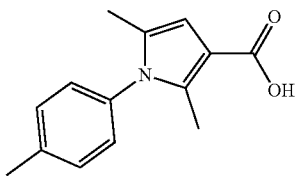

2,5-Dimethyl-1-(p-tolyl)-1H-pyrrole-3-carboxylic acid (13)

To a solution of 12 (2.57 g, 10 mmol) in MeOH (20 mL) was added KOH (2.8 g, 50 mmol). The mixture was stirred under reflux overnight. The solvent was removed under vacuum and the residue was dissolved in water, washed with diethyl ether. The aqueous layer was acidified to pH=1-2 using 1M HCl to give the title compound 13 as a white solid (1.6 g, 70%). $^1$H-NMR (400 MHz, DMSO-d$_6$) δ 11.58 (s, 1H), 7.32-7.30 (d, J=8 Hz, 2H), 7.14-7.12 (d, J=8 Hz, 2H), 6.17 (s, 1H), 2.35 (s, 3H), 2.14 (s, 3H), 1.87 (s, 3H); $^{13}$C-NMR (100 MHz, DMSO-d$_6$) δ 166.7, 138.5, 135.5, 134.9, 130.4, 128.2, 122.7, 111.7, 108.0, 21.1, 12.9, 12.5.

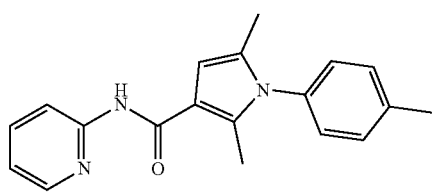

2,5-dimethyl-N-(pyridin-2-yl)-1-(p-tolyl)-1H-pyrrole-3-carboxamide (14)

To a solution of 13 (274 mg, 1.2 mmol), 2-aminopyridine (94 mg, 1.0 mmol) in dichloroethane (5 mL) was added 1-(chloro-1-pyrrolidinylmethylene)pyrrolidinium hexafluorophosphate (398 mg, 1.2 mmol) and DIPEA (516 mg, 4 mmol). The mixture was stirred at 80° C. overnight. The solvent was removed under vacuum and the residue was re-dissolved in ethyl acetate (15 mL). The resulting solution was washed with water and brine, dried over Na$_2$SO$_4$ and concentrated. The crude product was purified by column chromatography (Hexane/AcOEt, v/v=2/1) to give the targeted compound as a white solid (152 mg, 50%). $^1$H-NMR (400 MHz, CDCl$_3$) δ 8.37-8.35 (d, J=8 Hz, 1H), 8.27-8.24 (m, 2H), 7.71-7.69 (t, J=8 Hz, 1H), 7.30-7.28 (d, J=8 Hz, 2H), 7.08-7.06 (d, J=8 Hz, 2H), 7.00-6.97 (t, J=5.6 Hz, 1H), 6.24 (s, 1H), 2.43 (s, 3H), 2.36 (s, 3H), 2.00 (s, 3H); $^{13}$C-NMR (100 MHz, CDCl$_3$) δ 164.1, 152.2, 147.6, 138.6 138.2, 134.8, 130.2, 130.0, 129.2, 127.8, 127.7, 118.8, 113.8, 104.4, 21.2, 12.7, 12.4. HRMS (ESI): m/z [M+H]$^+$ calcd for C$_{19}$H$_{20}$N$_3$O 306.1606, found 306.1602. HPLC: t$_R$=7.02 min, 98.0%.

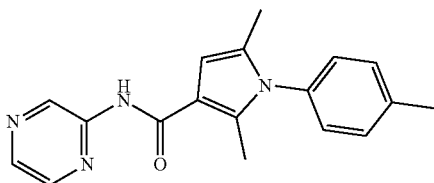

2,5-Dimethyl-N-(pyrazin-2-yl)-1-(p-tolyl)-1H-pyrrole-3-carboxamide (15)

Compound 15 was prepared from pyrazinamine (95 mg, 1.0 mmol) in a manner similar to that described for compound 14. (Purification: silica gel column chromatography (hexane/AcOEt, v/v=4/1 to 2/1)). White solid. Yield: 146 mg, 48%. $^1$H-NMR (400 MHz, CDCl$_3$) δ 9.72 (s, 1H), 8.31 (s, 1H), 8.23 (s, 1H), 8.16 (s, 1H) 7.32-7.30 (d, J=8.0 Hz, 2H), 7.09-7.07 (d, J=8.0 Hz, 2H), 6.26 (s, 1H), 2.45 (s, 3H), 2.37 (s, 3H), 2.01 (s, 3H); $^{13}$C-NMR (100 MHz, CDCl$_3$) δ 163.6, 149.0, 141.8, 139.2, 138.8, 137.1, 136.6, 134.7, 130.1, 129.5, 127.8, 112.9, 104.4, 21.2, 12.7, 12.5. HRMS (ESI): m/z [M+H]$^+$ calcd for C$_{18}$H$_{19}$N$_4$O 307.1559, found 307.1557. HPLC: t$_R$=6.42 min, 99.6%.

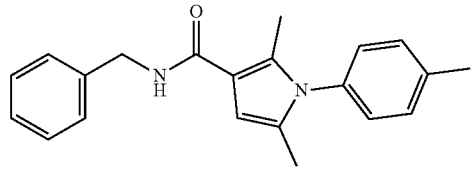

2,5-dimethyl-N-(4-phenylthiazol-2-yl)-1-(p-tolyl)-1H-pyrrole-3-carboxamide (16)

Compound 16 was prepared from 4-phenylthiazol-2-amine (176 mg, 1.0 mmol) in a manner similar to that described for compound 14. (Purification: silica gel column chromatography (hexane/AcOEt, v/v=4/1 to 2/1)). White solid. Yield: 263 mg, 68%. $^1$H-NMR (400 MHz, CDCl$_3$) δ 9.60 (s, 1H), 7.86-7.84 (d, J=8.0 Hz, 2H), 7.46-7.42 (t, J=8.0 Hz, 2H), 7.37-7.30 (m, 3H), 7.11 (s, 1H), 7.10-7.08 (d, J=8.0 Hz, 2H), 6.34 (s, 1H), 2.45 (s, 3H), 2.40 (s, 3H), 2.02 (s, 3H); $^{13}$C-NMR (100 MHz, CDCl$_3$) δ 162.7, 158.6, 149.6, 138.8, 137.0, 134.6, 134.6, 130.1, 129.6, 128.7, 127.8, 127.7, 126.0, 111.7, 107.2, 104.2, 21.2, 12.7, 12.5. HRMS (ESI): m/z [M+H]$^+$ calcd for C$_{23}$H$_{22}$N$_3$OS 388.1484, found 388.1557. HPLC: t$_R$=12.18 min, 99.0%.

N-benzyl-2,5-dimethyl-1-(p-tolyl)-1H-pyrrole-3-carboxamide (17)

Compound 17 was prepared from benzylamine (107 mg, 1.0 mmol) in a manner similar to that described for compound 14. (Purification: silica gel column chromatography (hexane/AcOEt, v/v=4/1 to 2/1)). White solid. Yield: 241 mg, 76%. $^1$H-NMR (400 MHz, DMSO-d$_6$) δ 8.19 (s, 1H), 7.36-7.28 (m, 6H), 7.22 (m, 1H), 7.17-7.15 (d, J=8.0 Hz, 2H), 6.41 (s, 1H), 2.39 (s, 3H), 2.20 (s, 3H), 1.93 (s, 3H); $^{13}$C-NMR (100 MHz, CDCl$_3$) δ 165.9, 139.2, 138.4, 135.0, 134.3, 129.9, 128.7, 128.6, 127.9, 127.7, 127.2, 113.6, 104.1, 43.2, 21.2, 12.7, 12.3. HRMS (ESI): m/z [M+H]$^+$ calcd for C$_{21}$H$_{23}$N$_2$O 319.1810, found 319.1807. HPLC: t$_R$=5.88 min, 96.0%.

5-Methyl-1-(p-tolyl)-1H-1,2,3-triazole-4-carboxylic acid (19a)

To a mixture of 4-methylaniline (2.14 g, 20 mmol) in concentrated HCl (8.0 mL) was added a solution of NaNO$_2$ (1.4 g, 21 mmol) in H$_2$O (6.0 mL) dropwise at 0° C. The mixture was stirred at 0° C. for 1 h followed by the addition of a solution of NaN$_3$ (1.3 g, 20 mmol) in H$_2$O (6.0 mL) at 0° C. The resulting mixture was stirred for another 1 h, extracted with diethyl ether for three times. The combined organic layers were washed with brine, dried over Na$_2$SO$_4$, and concentrated to give the residue. To the residue was added ethyl acetoacetate (2.86 g, 22 mmol) and a solution of NaOEt (2.04 g, 30 mmol) in EtOH (120 mL) at room temperature. The mixture was stirred at 80° C. overnight. After cooling to room temperature, the solvent was removed under vacuum, and 1M HCl (250 mL) was added to generate the precipitate. The solid was collected and washed with water to offer the crude product which was recrystallized from ethanol to give 19a (2.0 g, 46%). $^1$H-NMR (400 MHz, DMSO-d$_6$) δ 13.08 (s, 1H), 7.42-7.38 (m, 4H), 2.41 (s, 3H), 2.36 (s, 3H); $^{13}$C-NMR (100 MHz, DMSO-d$_6$) δ 163.1, 140.3, 136.8, 133.3, 130.5, 125.7, 123.2, 21.2, 10.1.

5-Methyl-1-(o-tolyl)-1H-1,2,3-triazole-4-carboxylic acid (19b)

Compound 19b was prepared from 2-Methylaniline (2.14 g, 20 mmol) in a similar manner to that described for compound 19a. Yield: 2.4 g, 55%. $^1$H-NMR (400 MHz, DMSO-d$_6$) δ 13.16 (s, 1H), 7.57-7.52 (m, 2H), 7.46-7.44 (m, 2H), 2.32 (s, 3H), 2.00 (s, 3H); $^{13}$C-NMR (100 MHz, DMSO-d$_6$) δ 163.0, 140.1, 136.5, 135.5, 134.6, 131.7, 131.2, 127.8, 127.6, 17.1, 9.6.

1-(2,4-Dimethylphenyl)-5-methyl-1H-1,2,3-triazole-4-carboxylic acid (19c)

Compound 19c was prepared from 2,4-Dimethylaniline (2.42 g, 20 mmol) in a similar manner to that described for compound 19a. Yield: 3.4 g, 73%. $^1$H-NMR (400 MHz, DMSO-d$_6$) δ 13.01 (s, 1H), 7.28-7.24 (m, 2H), 7.20-7.18 (m, 1H), 2.34 (s, 3H), 2.26 (s, 3H), 1.88 (s, 3H); $^{13}$C-NMR (100 MHz, DMSO-d$_6$) δ 163.0, 140.9, 140.1, 136.4, 135.1, 132.2, 132.1, 128.0, 127.5, 21.1, 17.0, 9.6.

1-(2-Fluorophenyl)-5-methyl-1H-1,2,3-triazole-4-carboxylic acid (19d)

Compound 19d was prepared from 2-Fluoroaniline (2.22 g, 20 mmol) in a similar manner to that described for compound 19a. Yield: 2.6 g, 60%. $^1$H-NMR (400 MHz, DMSO-d$_6$) δ 13.24 (s, 1H), 7.74-7.68 (m, 2H), 7.64-7.56 (m, 1H), 7.52-7.45 (m, 1H), 2.40 (s, 3H); $^{13}$C-NMR (100 MHz, DMSO-d$_6$) δ 162.8, 157.5, 155.0, 140.8, 136.7, 133.5, 133.5, 129.5, 126.1, 123.2, 123.0, 117.6, 117.4, 9.5.

1-(2-Cyanophenyl)-5-methyl-1H-1,2,3-triazole-4-carboxylic acid (19e)

Compound 19e was prepared from 2-Aminobenzonitrile (2.36 g, 20 mmol) in a similar manner to that described for compound 19a. Yield: 4.56 g, 71%. $^1$H-NMR (400 MHz, DMSO-d$_6$) δ 13.37 (s, 1H), 8.23-8.21 (d, J=6.8 Hz, 1H), 8.05-8.01 (t, J=7.2 Hz), 7.92-7.87 (m, 2H), 2.47 (s, 3H); $^{13}$C-NMR (100 MHz, DMSO-d$_6$) δ 162.7, 140.6, 136.9, 136.8, 135.3, 134.9, 132.0, 128.8, 115.6, 110.5, 9.8.

1-(2-Methoxyphenyl)-5-methyl-1H-1,2,3-triazole-4-carboxylic acid (19f)

Compound 19f was prepared from o-Anisidine (2.46 g, 20 mmol) in a similar manner to that described for compound 19a. Yield: 3.7 g, 80%. $^1$H-NMR (400 MHz, DMSO-d$_6$) δ 13.14 (s, 1H), 7.66-7.62 (t, J=8.0 Hz, 1H), 7.49-7.47 (d, J=8.0 Hz, 1H), 7.35-7.33 (d, J=8.0 Hz, 1H), 7.20-7.16 (t, J=8.0 Hz, 1H), 3.80 (s, 3H), 2.31 (s, 3H); $^{13}$C-NMR (100 MHz, DMSO-d$_6$) δ 163.0, 154.1, 140.8, 136.3, 132.7, 128.9, 123.9, 121.3, 113.3, 56.4, 9.5.

1-(2-Bromophenyl)-5-methyl-1H-1,2,3-triazole-4-carboxylic acid (19g)

Compound 19g was prepared from 2-Bromoaniline (3.4 g, 20 mmol) in a similar manner to that described for compound 19a. Yield: 4.5 g, 80%. $^1$H-NMR (400 MHz, DMSO-d$_6$) δ 13.26 (s, 1H), 7.98-7.96 (m, 1H), 7.73-7.62 (m, 3H), 2.34 (s, 3H); $^{13}$C-NMR (100 MHz, DMSO-d$_6$) δ 167.6, 145.3, 141.3, 139.3, 138.8, 138.1, 134.9, 134.4, 125.9, 14.4.

5-Methyl-1-(2-morpholinophenyl)-1H-1,2,3-triazole-4-carboxylic acid (19h)

Compound 19h was prepared from 2-Morpholinoanilinein (3.56 g, 20 mmol) in a similar manner to that described for compound 19a. Yield: 4.78 g, 83%. $^1$H-NMR (400 MHz, DMSO-d$_6$) δ 13.17 (s, 1H), 7.63-7.59 (t, J=8.0 Hz, 1H), 7.44-7.42 (d, J=8.0 Hz, 1H), 7.33-7.31 (d, J=8.0 Hz, 1H), 7.30-7.26 (t, J=8.0 Hz, 1H), 3.42 (br s, 4H), 2.63 (br s, 4H), 2.38 (s, 3H); $^{13}$C-NMR (100 MHz, DMSO-d$_6$) δ 162.9, 148.0, 140.5, 136.7, 132.3, 129.2, 129.1, 124.0, 120.9, 66.6, 51.4, 10.0.

1-([1,1'-biphenyl]-2-yl)-5-methyl-1H-1,2,3-triazole-4-carboxylic acid (19i)

Compound 19i was prepared from 2-Phenylaniline (3.38 g, 20 mmol) in a similar manner to that described for compound 19a. Yield: 3.6 g, 65%. $^1$H-NMR (400 MHz, DMSO-d$_6$) δ 7.72-7.68 (m, 1H), 7.63-7.61 (m, 2H), 7.53-7.51 (m, 1H), 7.26-7.21 (m, 3H), 7.02-6.96 (m, 2H), 1.97 (s, 3H); $^{13}$C-NMR (100 MHz, DMSO-d$_6$) δ 164.2, 140.1, 138.9, 137.9, 137.5, 133.5, 131.5, 131.4, 129.3, 129.0, 128.8, 128.4, 128.3, 9.5.

1-(2-Acetylphenyl)-5-methyl-1H-1,2,3-triazole-4-carboxylic acid (19j)

Compound 19j was prepared from 2-Acetylaniline (2.7 g, 20 mmol) in a similar manner to that described for compound 19a. Yield: 1.9 g, 40%. $^1$H-NMR (400 MHz, DMSO-d$_6$) δ 8.02-7.99 (m, 1H), 7.77-7.73 (m, 2H), 7.61-7.59 (m, 1H), 2.32 (s, 3H), 2.26 (s, 3H); $^{13}$C-NMR (100 MHz, DMSO-d$_6$) δ 199.0, 163.0, 140.7, 136.5, 136.3, 133.3, 132.6, 131.5, 130.4, 128.8, 29.3, 9.8.

1-(2-Carbamoylphenyl)-5-methyl-1H-1,2,3-triazole-4-carboxylic acid (19k)

Compound 19k was prepared from 2-Aminobenzamide (2.72 g, 20 mmol) in a similar manner to that described for compound 19a. Yield: 3.2 g, 65%. $^1$H-NMR (400 MHz, DMSO-d$_6$) δ 13.10 (s, 1H), 7.93 (s, 1H), 7.70-7.68 (m, 1H), 7.67-7.62 (m, 2H), 7.55-7.52 (m, 1H), 7.38 (s, 1H), 2.38 (s, 3H); $^{13}$C-NMR (100 MHz, DMSO-d$_6$) δ 167.6, 163.2, 140.8, 136.0, 135.9, 131.4, 131.0, 129.1, 128.5, 129.1, 128.5, 128.3, 9.9.

1-(4-Fluoro-2-nitrophenyl)-5-methyl 1H-1,2,3-triazole-4-carboxylic acid (19l). Compound 19l was prepared from 4-Fluoro-2-nitroaniline (3.12 g, 20 mmol) in a similar manner to that described for compound 19a. Yield: 1.6 g, 30%. $^1$H-NMR (400 MHz, DMSO-d$_6$) δ 13.29 (s, 1H), 7.86-7.83 (m, 2H), 7.55-7.54 (d, J=7.2 Hz, 1H), 2.43 (s, 3H); $^{13}$C-NMR (100 MHz, DMSO-d$_6$) δ 167.5, 165.5, 151.3, 146.0, 141.3, 135.9, 125.4, 125.0, 116.6, 14.4.

1-(2,3-Dimethylphenyl)-5-methyl-1H-1,2,3-triazole-4-carboxylic acid (19m)

Compound 19m was prepared from 2,3-Dimethylaniline (2.42 g, 20 mmol) in a similar manner to that described for compound 19a. Yield: 3.23 g, 70%. $^1$H-NMR (400 MHz, DMSO-d$_6$) δ 13.14 (s, 1H), 7.46-7.45 (m, 1H), 7.36-7.32 (m, 1H), 7.26-7.25 (m, 1H), 2.36 (s, 3H), 2.30 (s, 3H), 1.81 (s, 3H); $^{13}$C-NMR (100 MHz, DMSO-d$_6$) δ 167.8, 144.9, 143.9, 141.2, 139.3, 138.9, 137.0, 131.6, 130.1, 24.9, 18.7, 14.3.

5-Methyl-1-(naphthalen-1-yl)-1H-1,2,3-triazole-4-carboxylic acid (19n)

Compound 19n was prepared from 1-Aminonaphthalene (2.86 g, 20 mmol) in a similar manner to that described for compound 19a. Yield: 3.64 g, 72%. $^1$H-NMR (400 MHz, DMSO-d$_6$) δ 13.15 (s, 1H), 8.27-8.25 (d, J=8.0 Hz, 1H), 8.16-8.14 (d, J=8.0 Hz, 1H), 7.80-7.30 (m, 2H), 7.69-7.65 (t, J=8.0 Hz, 1H), 7.62-7.58 (t, J=8.0 Hz, 1H), 7.14-7.12 (d, J=8.0 Hz, 1H), 2.31 (s, 3H); $^{13}$C-NMR (100 MHz, DMSO-d$_6$) δ 163.0, 141.1, 136.7, 134.1, 131.5, 129.2, 128.9, 128.8, 127.9, 127.7, 126.2, 126.0, 122.0, 9.7.

1-(3-Chlorophenyl)-5-methyl-1H-1,2,3-triazole-4-carboxylic acid (19o)

Compound 19o was prepared from 3-Chloroaniline (2.54 g, 20 mmol) in a similar manner to that described for compound 19a. Yield: 3.2 g, 68%. $^1$H-NMR (400 MHz, DMSO-d$_6$) δ 13.15 (s, 1H), 7.78 (s, 1H), 7.67-7.63 (m, 2H), 7.61-7.59 (m, 1H), 2.48 (s, 3H); $^{13}$C-NMR (100 MHz, DMSO-d$_6$) δ 162.9, 139.7, 136.9, 136.8, 134.3, 131.8, 130.5, 125.9, 124.8, 10.1.

5-Ethyl-1-(2-fluorophenyl)-1H-1,2,3-triazole-4-carboxylic acid (19p)

Compound 19p was prepared from 2-Flouroaniline (2.22 g, 20 mmol) and ethyl 3-oxopentanoatein (3.16 g, 22 mmol)

in a similar manner to that described for compound 19a. Yield: 3.76 g, 80%. $^1$H-NMR (400 MHz, DMSO-d$_6$) δ 13.31 (s, 1H), 7.77-7.74 (m, 2H), 7.64-7.59 (t, J=8.8 Hz, 1H), 7.52-7.48 (t, J=8.0 Hz, 1H), 2.84-2.78 (q, J=7.2 Hz, 2H), 1.02-0.98 (t, J=7.2 Hz, 3H); $^{13}$C-NMR (100 MHz, DMSO-d$_6$) δ 167.4, 162.6, 160.1, 150.5, 140.9, 138.6, 138.5, 134.6, 130.9, 130.8, 122.3, 122.1, 21.6, 17.6.

1-(2-Fluorophenyl)-5-isopropyl-1H-1,2,3-triazole-4-carboxylic acid (19q)

Compound 19q was prepared from 2-Flouroaniline (2.22 g, 20 mmol) and ethyl 4-methyl-3-oxopentanoate (3.5 g, 22 mmol) in a similar manner to that described for compound 19a. Yield: 1.2 g, 25%. $^1$H-NMR (400 MHz, DMSO-d$_6$) δ 13.01 (s, 1H), 7.77-7.74 (m, 2H), 7.64-7.60 (t, J=8.0 Hz, 1H), 7.52-7.48 (t, J=8.0 Hz, 1H), 3.24-3.20 (m, 1H), 1.23-1.21 (d, J=6.8 Hz, 6H); $^{13}$C-NMR (100 MHz, DMSO-d$_6$) δ 167.6, 162.8, 160.3, 153.5, 140.6, 138.7, 138.6, 135.0, 130.8, 122.2, 122.0, 29.5, 24.6.

General procedure for the synthesis of compounds 20-46.

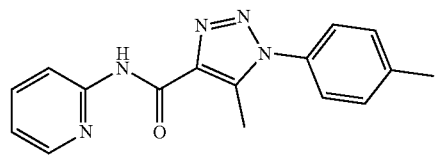

5-Methyl-N-(pyridin-2-yl)-1-(p-tolyl)-1H-1,2,3-triazole-4-carboxamide (20)

To a solution of 2-aminopyridine (94 mg, 1.0 mmol) and 19a (260 mg, 1.2 mmol) in DCE (5 mL) was added PyCIU (398 mg, 1.2 mmol) and DIPEA (516 mg, 4.0 mmol). The mixture was stirred at 80° C. overnight. After cooling to room temperature, the solvent was removed under vacuum. To the residue was added ethyl acetate (30 mL), and the resulting mixture was washed with brine, dried over Na$_2$SO$_4$ and concentrated. The crude material was purified by column chromatography (Hexane/AcOEt, v/v=2/1) to give the title product as a white solid (117 mg, 40%). $^1$H-NMR (400 MHz, DMSO-d$_6$) δ 9.89 (s, 1H), 8.41-8.40 (d, J=4.0 Hz, 1H), 8.21-8.19 (d, J=8.0 Hz, 1H), 7.91-7.87 (t, J=8.0 Hz, 1H), 7.57-7.55 (d, J=8.0 Hz, 2H), 7.49-7.47 (d, J=8.0 Hz, 2H), 7.23-7.20 (t, J=8.0 Hz, 1H), 2.59 (s, 3H), 2.45 (s, 3H); $^{13}$C-NMR (100 MHz, CDCl$_3$) δ 159.7, 151.1, 147.9, 140.4, 138.3, 137.7, 132.9, 130.2, 125.1, 119.7, 114.0, 21.3, 9.8. HRMS (ESI): m/z [M+H]$^+$ calcd for C$_{16}$H$_{16}$N$_5$O, 294.1355; found, 294.1353. HPLC: t$_R$=4.02 min, 99.2%.

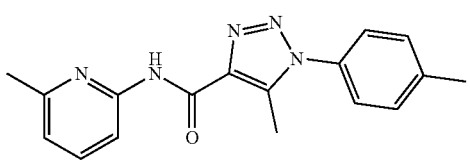

5-Methyl-N-(6-methylpyridin-2-yl)-1-(p-tolyl)-1H-1,2,3-triazole-4-carboxamide (21)

Compound 21 was synthesized from 6-Methyl-2-aminopyridine (108 mg, 1.0 mmol) and 19a in a similar manner to that described for compound 20. White solid. Yield: 154 mg, 50%. $^1$H-NMR (400 MHz, CDCl$_3$) δ 9.62 (s, 1H), 8.14-8.12 (d, J=8.0 Hz, 1H), 7.64-7.60 (t, J=8.0 Hz, 1H), 7.39-7.34 (m, 4H), 6.94-6.92 (d, J=8.0 Hz, 1H), 2.65 (s, 3H), 2.50 (s, 3H), 2.46 (s, 3H); $^{13}$C-NMR (100 MHz, CDCl$_3$) δ 159.7, 157.2, 150.4, 140.3, 138.4, 138.2, 137.6, 132.9, 130.2, 125.1, 119.2, 110.7, 24.1, 21.2, 9.8. HRMS (ESI): m/z [M+H]$^+$ calcd for C$_{17}$H$_{18}$N$_5$O, 308.1511; found, 308.1515. HPLC: t$_R$=70.15 min, 99.4%.

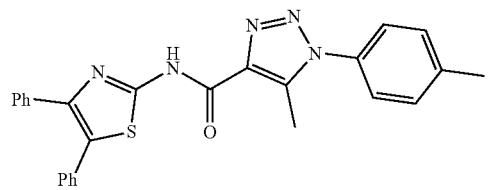

N-(4,5-diphenylthiazol-2-yl)-5-methyl-1-(p-tolyl)-1H-1,2,3-triazole-4-carboxamide (22)

Compound 22 was synthesized from 2-Amino-4,5-diphenylthiazole (252 mg, 1.0 mmol) and 19a in a similar manner to that described for compound 20. White solid. Yield: 252 mg, 56%. $^1$H-NMR (400 MHz, DMSO-d$_6$) δ 12.61 (s, 1H), 7.58-7.56 (d, J=8.0 Hz, 2H), 7.50 (m, 4H), 7.41-7.33 (m, 8H), 2.60 (s, 3H), 2.45 (s, 3H); $^{13}$C-NMR (100 MHz, DMSO-d$_6$) δ 160.0, 155.6, 144.6, 140.5, 139.3, 137.1, 135.1, 133.1, 132.2, 130.6, 129.7, 129.4, 129.0, 128.7, 128.5, 128.2, 126.4, 125.7, 21.2, 10.0. HRMS (ESI): m/z [M+H]$^+$ calcd for C$_{26}$H$_{22}$N$_5$OS, 452.1545; found, 452.1550. HPLC: t$_R$=5.00 min, 99.0%.

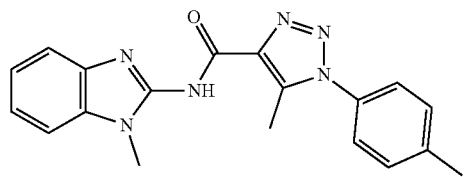

5-Methyl-N-(1-methyl-1H-benzo[d]imidazol-2-yl)-1-(p-tolyl)-1H-1,2,3-triazole-4-carboxamide (23)

Compound 23 was synthesized from 2-Amino-1-methyl-benzimidazole (147 mg, 1.0 mmol) and 19a in a similar manner to that described for compound 20. White solid. Yield: 253 mg, 73%. $^1$H-NMR (400 MHz, DMSO-d$_6$) δ 12.70 (s, 1H), 7.56-7.45 (m, 6H), 7.28-7.24 (m, 2H), 3.70 (s, 3H), 2.69 (s, 3H), 2.45 (s, 3H). HRMS (ESI): m/z [M+H]$^+$ calcd for C$_{19}$H$_{19}$N$_6$O, 347.1620; found, 347.1617. HPLC: t$_R$=2.32 min, 98.0%.

5-Methyl-N-(3-methylisoxazol-5-yl)-1-(p-tolyl)-1H-1,2,3-triazole-4-carboxamide (24)

Compound 24 was synthesized from 5-Amino-3-methylisoxazole (98 mg, 1.0 mmol) and 19a in a similar manner to that described for compound 20. White solid. Yield: 47 mg, 16%. $^1$H-NMR (400 MHz, DMSO-$d_6$) δ 9.78 (s, 1H), 7.40-7.38 (d, J=8.0 Hz, 2H), 7.35-7.33 (d, J=8.0 Hz, 2H), 6.33 (s, 1H), 2.64 (s, 3H), 2.47 (s, 3H), 2.31 (s, 3H); $^{13}$C-NMR (100 MHz, CDCl$_3$) δ 161.6, 159.6, 157.0, 140.7, 138.4, 137.0, 132.6, 130.3, 125.0, 89.4, 21.3, 11.9, 9.7. HRMS (ESI): m/z [M+H]$^+$ calcd for $C_{15}H_{16}N_5O_2$, 298.1304; found, 298.1300. HPLC: $t_R$=7.38 min, 97.6%.

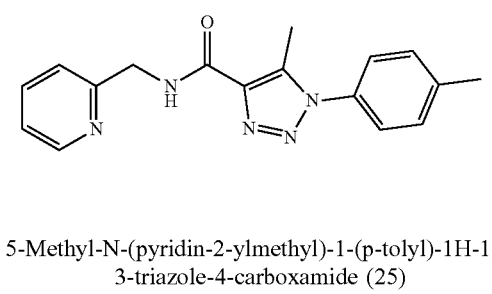

5-Methyl-N-(pyridin-2-ylmethyl)-1-(p-tolyl)-1H-1,2,3-triazole-4-carboxamide (25)

Compound 25 was synthesized from 2-Picolylamine (108 mg, 1.0 mmol) and 19a in a similar manner to that described for compound 20. Yield: 166 mg, 54%. $^1$H-NMR (400 MHz, CDCl$_3$) δ 8.55-8.54 (d, J=4.8 Hz 1H), 8.20 (s, 1H), 7.63-7.61 (t, J=8 Hz, 1H), 7.41-7.39 (m, 5H), 7.17-7.14 (t, J=4.8 Hz 1H), 4.82 (s, 2H), 2.60 (s, 3H), 2.41 (s, 3H); $^{13}$C-NMR (100 MHz, CDCl$_3$) δ 161.5, 161.4, 156.9, 149.2, 140.1, 138.3, 136.7, 133.1, 130.1, 125.0, 122.3, 121.7, 44.2, 21.2, 9.6. HRMS (ESI): m/z [M+H]$^+$ calcd for $C_{17}H_{18}N_5O$, 308.1511; found, 308.1513. HPLC: $t_R$=2.04 min, 99.9%.

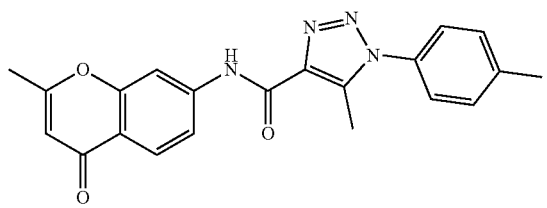

5-Methyl-N-(2-methyl-4-oxo-4H-chromen-7-yl)-1-(p-tolyl)-1H-1,2,3-triazole-4-carboxamide (26)

Compound 26 was synthesized from 7-Amino-2-methyl-4H-chromen-4-one (175 mg, 1.0 mmol) and 19a in a similar manner to that described for compound 20. Yellow solid. Yield: 86 mg, 23%. $^1$H-NMR (400 MHz, CDCl$_3$) δ 9.32 (s, 1H), 8.21 (s, 1H), 8.18-8.16 (d, J=8.4 Hz 1H), 7.44-7.35 (m, 5H), 6.17 (s, 1H), 2.68 (s, 3H), 2.48 (s, 3H), 2.39 (s, 3H); $^{13}$C-NMR (100 MHz, CDCl$_3$) δ 177.6, 166.2, 161.0, 159.5, 157.4, 142.2, 140.6, 138.0, 132.8, 130.3, 126.6, 119.6, 116.6, 110.4, 107.2, 21.3, 20.6, 9.8. HRMS (ESI): m/z [M+H]$^+$ calcd for $C_{21}H_{19}N_4O_3$ 375.1457, found 375.1458. HPLC: $t_R$=6.00 min, 98.4%.

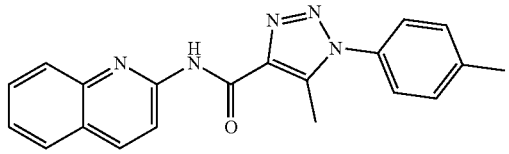

5-Methyl-N-(quinolin-2-yl)-1-(p-tolyl)-1H-1,2,3-triazole-4-carboxamide (27)

Compound 27 was synthesized from 2-Aminoquinoline (44 mg, 0.3 mmol) and 19a (78 mg, 0.36 mmol) in a similar manner to that described for compound 20. White solid. Yield: 50 mg, 49%. $^1$H-NMR (400 MHz, DMSO-$d_6$) δ 10.19 (s, 1H), 8.49-8.47 (d, J=8.8 Hz, 1H), 8.42-8.40 (d, J=8.8 Hz, 1H), 8.00-7.98 (d, J=8.0 Hz, 1H), 7.91-7.89 (d, J=8.0 Hz, 1H), 7.79-7.75 (t, J=8.0 Hz, 1H), 7.59-7.57 (d, J=8.0 Hz, 2H), 7.50-7.48 (d, J=8.0 Hz, 2H), 2.60 (s, 3H), 2.40 (s, 3H); $^{13}$C-NMR (100 MHz, DMSO-$d_6$) δ 160.0, 150.8, 146.8, 140.5, 139.2, 138.6, 137.9, 133.1, 130.6, 130.6, 128.3, 127.7, 126.4, 125.7, 125.7, 114.6, 21.2, 9.9. HRMS (ESI): m/z [M+H]$^+$ calcd for $C_{20}H_{18}N_5O$, 344.1511; found, 344.1511. HPLC: $t_R$=8.82 min, 99.6%.

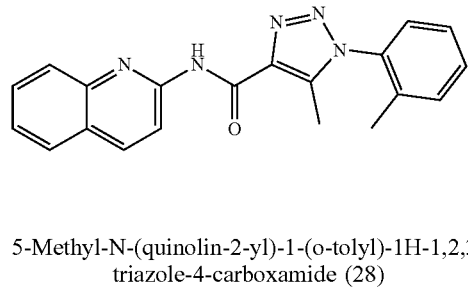

5-Methyl-N-(quinolin-2-yl)-1-(o-tolyl)-1H-1,2,3-triazole-4-carboxamide (28)

Compound 28 was synthesized from 2-Aminoquinoline (44 mg, 0.3 mmol) and 19b (78 mg, 0.36 mmol) in a similar manner to that described for compound 20. Colorless solid. Yield: 62 mg, 60%. $^1$H-NMR (400 MHz, DMSO-$d_6$) δ 10.22 (s, 1H), 8.49-8.47 (d, J=8.8 Hz, 1H), 8.42-8.40 (d, J=8.8 Hz, 1H), 8.00-7.98 (d, J=8.0 Hz, 1H), 7.91-7.89 (d, J=8.0 Hz, 1H), 7.69 (t, J=8.0 Hz, 1H), 7.61-7.56 (m, 3H), 7.51-7.50 (m, 2H), 2.45 (s, 3H), 2.04 (s, 3H); $^{13}$C-NMR (100 MHz, DMSO-$d_6$) δ 160.0, 150.8, 146.8, 139.5, 139.1, 137.6, 135.5, 134.4, 131.8, 131.4, 130.7, 128.3, 127.8, 127.7, 127.7, 126.4, 125.8, 114.7, 17.2, 9.4. HRMS (ESI): m/z [M+H]$^+$ calcd for $C_{20}H_{18}N_5O$, 344.1511, found, 344.1510. HPLC: $t_R$=8.75 min, 98.2%.

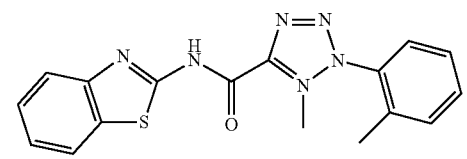

N-(benzo[d]thiazol-2-yl)-5-methyl-1-(o-tolyl)-1H-1,2,3-triazole-4-carboxamide (29)

Compound 29 was synthesized from 2-Aminobenzothiazole (45 mg, 0.3 mmol) and 19b (78 mg, 0.36 mmol) in a similar manner to that described for compound 20. White solid. Yield: 70 mg, 67%. $^1$H-NMR (400 MHz, DMSO-d$_6$) δ 12.83 (s, 1H), 8.18 (s, 1H), 7.96 (s, 1H), 7.73-7.63 (m, 5H), 7.51 (s, 1H), 2.58 (s, 3H), 2.18 (s, 3H); $^{13}$C-NMR (100 MHz, CDCl$_3$) δ 159.0, 156.8, 148.6, 139.6, 136.4, 135.4, 134.0, 132.2, 131.6, 131.0, 127.2, 127.1, 126.3, 124.0, 121.3, 121.2, 17.2, 9.2. HRMS (ESI): m/z [M+H]$^+$ calcd for C$_{18}$H$_{16}$N$_5$OS, 350.1076; found, 350.1063. HPLC: $t_R$=9.09 min, 99.4%.

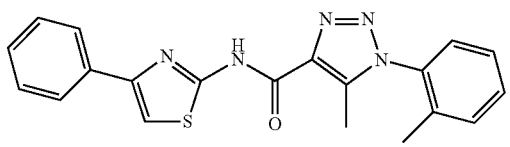

5-Methyl-N-(4-phenylthiazol-2-yl)-1-(o-tolyl)-1H-1,2,3-triazole-4-carboxamide (30)

Compound 30 was synthesized from 2-Amino-4-phenylthiazole (53 mg, 0.3 mmol) and 19b (78 mg, 0.36 mmol) in a similar manner to that described for compound 20. White solid. Yield: 73 mg, 70%. $^1$H-NMR (400 MHz, DMSO-d$_6$) δ 12.51 (s, 1H), 7.99-7.97 (m, 2H), 7.73 (s, 1H), 7.62-7.55 (m, 2H), 7.50-7.44 (m, 4H), 7.37-7.35 (m, 1H), 2.43 (s, 3H), 2.03 (s, 3H); $^{13}$C-NMR (100 MHz, DMSO-d$_6$) δ 164.7, 162.4, 154.3, 144.7, 141.6, 140.3, 139.4, 139.2, 136.6, 136.1, 133.9, 133.0, 132.6, 132.4, 131.0, 113.8, 21.9, 14.2. HRMS (ESI): m/z [M+H]$^+$ calcd for C$_{20}$H$_{18}$N$_5$OS, 370.1232; found, 350.1063. HPLC: $t_R$=12.08 min, 99.0%.

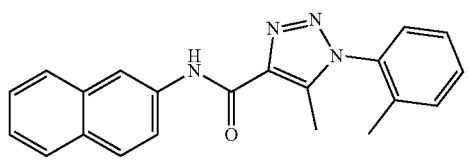

5-Methyl-N-(naphthalen-2-yl)-1-(o-tolyl)-1H-1,2,3-triazole-4-carboxamide (31)

Compound 31 was synthesized from 2-Aminonaphthalene (43 mg, 0.3 mmol) and 19b (78 mg, 0.36 mmol) in a similar manner to that described for compound 20. White solid. Yield: 58 mg, 57%. $^1$H-NMR (400 MHz, CDCl$_3$) δ 9.28 (s, 1H), 8.47 (s, 1H), 7.87-7.81 (m, 3H), 7.67-7.64 (dd, J$_1$=1.6 Hz, J$_2$=8.8 Hz, 1H), 7.53-7.39 (m, 5H), 7.26 (s, 1H), 2.53 (s, 3H), 2.09 (s, 3H); $^{13}$C-NMR (100 MHz, CDCl$_3$) δ 159.4, 138.4, 138.1, 135.5, 135.2, 134.3, 133.9, 131.5, 130.8, 130.7, 128.8, 127.7, 127.6, 127.2, 127.1, 126.5, 125.0, 119.8, 116.4, 17.2, 9.2. HRMS (ESI): m/z [M+H]$^+$ calcd for C$_{21}$H$_{19}$N$_4$O, 343.1559; found, 343.1561. HPLC: $t_R$=11.64 min, 98.6%.

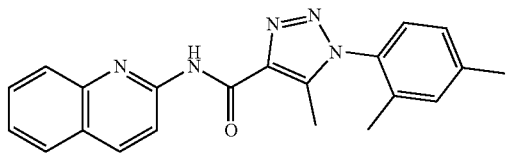

1-(2,4-Dimethylphenyl)-5-methyl-N-(quinolin-2-yl)-1H-1,2,3-triazole-4-carboxamide (32)

Compound 32 was synthesized from 2-Aminoquinoline (44 mg, 0.3 mmol) and 19c (83 mg, 0.36 mmol) in a similar manner to that described for compound 20. White solid. Yield: 74 mg, 69%. $^1$H-NMR (400 MHz, CDCl$_3$) δ 9.94 (s, 1H), 8.57-8.55 (d, J=8.8 Hz, 1H), 8.23-8.21 (d, J=8.8 Hz, 1H), 7.93-7.91 (d, J=8.0 Hz, 1H), 7.82-7.80 (d, J=8.0 Hz, 1H), 7.71-7.67 (t, J=8.0 Hz, 1H), 7.49-7.45 (t, J=8.0 Hz, 1H), 7.26-7.24 (d, J=8.0 Hz, 1H), 7.20-7.18 (d, J=8.0 Hz, 1H), 7.15-7.13 (d, J=8.0 Hz, 1H), 2.51 (s, 3H), 2.44 (s, 3H), 2.03 (s, 3H); $^{13}$C-NMR (100 MHz, CDCl$_3$) δ 160.1, 150.6, 141.1, 138.9, 138.4, 137.7, 135.1, 132.1, 131.7, 129.9, 127.8, 127.7, 127.5, 126.9, 126.4, 125.1, 114.2, 21.5, 17.1, 9.3. HRMS (ESI): m/z [M+H]$^+$ calcd for C$_{21}$H$_{20}$N$_5$O 358.1668, found 358.1661. HPLC: $t_R$=17.12 min, 99.9%.

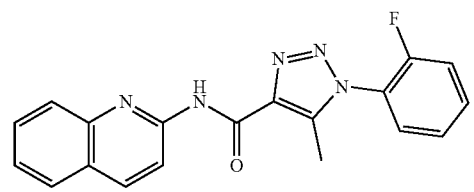

1-(2-Fluorophenyl)-5-methyl-N-(quinolin-2-yl)-1H-1,2,3-triazole-4-carboxamide (20)

Compound 33 was synthesized from 2-Aminoquinoline (44 mg, 0.3 mmol) and 19d (80 mg, 0.36 mmol) in a similar manner to that described for compound 20. White solid. Yield: 52 mg, 50%. $^1$H-NMR (400 MHz, DMSO-d$_6$) δ 10.25 (s, 1H), 8.46-8.44 (m, 2H), 7.97-7.54 (m, 9H), 2.52 (s, 3H); $^{13}$C-NMR (100 MHz, DMSO-d$_6$) δ 159.8, 157.5, 155.0, 150.8, 146.8, 140.2, 139.1, 137.7, 133.7, 130.6, 129.5, 128.2, 127.7, 126.4, 126.2, 125.8, 123.0, 117.7, 117.5, 114.7, 9.3. HRMS (ESI): m/z [M+H]$^+$ calcd for C$_{19}$H$_{15}$FN$_5$O, 348.1261; found, 348.1252. HPLC: $t_R$=9.53 min, 99.9%.

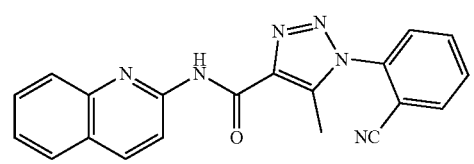

1-(2-Cyanophenyl)-5-methyl-N-(quinolin-2-yl)-1H-1,2,3-triazole-4-carboxamide (34)

Compound 34 was synthesized from 2-Aminoquinoline (44 mg, 0.3 mmol) and 19e (82 mg, 0.36 mmol) in a similar manner to that described for compound 20. White solid. Yield: 60 mg, 57%. $^1$H-NMR (400 MHz, DMSO-d$_6$) δ 10.35 (s, 1H), 8.49-8.46 (d, J=8.8 Hz, 1H), 8.40-8.38 (d, J=8.8 Hz, 1H), 8.27-8.25 (d, J=8.0 Hz, 1H), 8.08-8.04 (t, J=8.0 Hz, 1H), 7.99-7.96 (t, 2H), 7.94-7.90 (t, J=8.0 Hz, 2H), 7.79-7.75 (t, J=8.0 Hz, 1H), 7.57-7.53 (t, J=8.0 Hz, 1H), 2.60 (s, 3H); $^{13}$C-NMR (100 MHz, DMSO-d$_6$) δ 159.7, 150.8, 146.8, 140.1, 139.1, 138.0, 136.6, 135.4, 135.1, 132.1, 130.7, 128.8, 128.3, 127.8, 126.4, 125.8, 115.6, 114.9, 110.5, 9.6. HRMS (ESI): m/z [M+H]$^+$ calcd for C$_{20}$H$_{15}$N$_6$O, 355.1307; found 355.1304. HPLC: t$_R$=7.45 min, 99.8%.

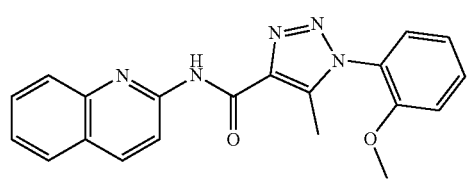

1-(2-Methoxyphenyl)-5-methyl-N-(quinolin-2-yl)-1H-1,2,3-triazole-4-carboxamide (35)

Compound 35 was synthesized from 2-Aminoquinoline (44 mg, 0.3 mmol) and 19f (84 mg, 0.36 mmol) in a similar manner to that described for compound 20. White solid. Yield: 52 mg, 48%. $^1$H-NMR (400 MHz, DMSO-d$_6$) δ 10.28 (s, 1H), 8.61-8.51 (m, 2H), 8.09 (m, 1H), 8.01 (m, 1H), 7.88 (m, 1H), 7.78 (m, 1H), 7.66 (m, 2H), 7.52-7.47 (m, 1H), 7.35-7.32 (m, 1H), 3.97-3.94 (q, J=4 Hz, 3H), 2.56-2.53 (q, J=4 Hz, 3H); $^{13}$C-NMR (100 MHz, DMSO-d$_6$) δ 160.0, 154.1, 150.9, 146.2, 140.2, 139.1, 137.3, 132.9, 130.6, 128.9, 128.2, 127.7, 126.4, 125.7, 123.7, 121.4, 114.7, 113.4, 56.5, 9.4. HRMS (ESI): m/z [M+H]$^+$ calcd for C$_{20}$H$_{18}$N$_5$O$_2$, 360.1460; found, 360.1460. HPLC: t$_R$=8.88 min, 99.8%.

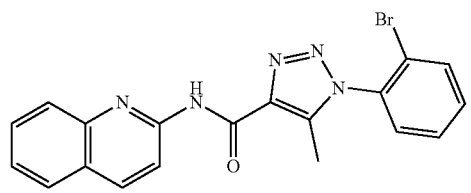

1-(2-Bromophenyl)-5-methyl-N-(quinolin-2-yl)-1H-1,2,3-triazole-4-carboxamide (21)

Compound 36 was synthesized from 2-Aminoquinoline (44 mg, 0.3 mmol) and 19g (100 mg, 0.36 mmol) in a similar manner to that described for compound 20. White solid. Yield: 83 mg, 68%. $^1$H-NMR (400 MHz, DMSO-d$_6$) δ 10.26 (s, 1H), 8.48-8.46 (d, J=8.0 Hz, 1H), 8.41-8.39 (d, J=8.0 Hz, 1H), 8.02-8.99 (t, J=8.8 Hz, 2H), 7.91-7.89 (d, J=8.0 Hz, 1H), 7.77-7.67 (m, 4H), 7.57-7.53 (d, J=8.0 Hz, 1H), 2.46 (s, 3H); $^{13}$C-NMR (100 MHz, DMSO-d$_6$) δ 164.6, 155.5, 151.6, 144.7, 143.9, 142.3, 139.2, 138.9, 138.3, 135.4, 135.0, 134.5, 133.0, 132.5, 131.2, 130.6, 125.9, 119.6, 14.2. HRMS (ESI): m/z [M+H]$^+$ calcd for C$_{19}$H$_{15}$BrN$_5$O$_2$, 408.0460; found, 408.0458. HPLC: t$_R$=8.21 min, 99.9%.

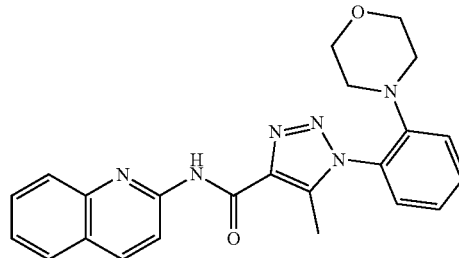

5-Methyl-1-(2-morpholinophenyl)-N-(quinolin-2-yl)-1H-1,2,3-triazole-4-carboxamide (28)

Compound 37 was synthesized from 2-Aminoquinoline (44 mg, 0.3 mmol) and 19h (104 mg, 0.36 mmol) in a similar manner to that described for compound 20. White solid. Yield: 60 mg, 48%. $^1$H-NMR (400 MHz, DMSO-d$_6$) δ 10.20 (s, 1H), 8.48-8.46 (d, J=8.8 Hz, 1H), 8.43-8.40 (d, J=8.8 Hz, 1H), 7.99-7.97 (d, J=8.4 Hz, 1H), 7.90-7.88 (d, J=8.4 Hz, 1H), 7.78-7.74 (t, J=8.0 Hz, 1H), 7.66-7.62 (t, J=8.0 Hz, 1H), 7.57-7.53 (t, J=8.0 Hz, 1H), 7.50-7.48 (d, J=8.0 Hz, 1H), 7.37-7.33 (t, J=8.0 Hz, 1H), 7.31-7.29 (d, J=8.0 Hz, 1H), 3.45 (br s, 4H), 2.67 (br s, 4H), 2.50 (s, 3H); $^{13}$C-NMR (100 MHz, DMSO-d$_6$) δ 159.9, 150.8, 146.8, 139.8, 139.1, 137.8, 132.4, 130.6, 129.3, 129.0, 128.3, 127.7, 126.4, 125.7, 124.1, 121.0, 114.7, 66.6, 51.4, 9.7. HRMS (ESI): m/z [M+H]$^+$ calcd for C$_{23}$H$_{23}$N$_6$O$_2$, 415.1882; found, 415.1873. HPLC: t$_R$=10.48 min, 99.6%.

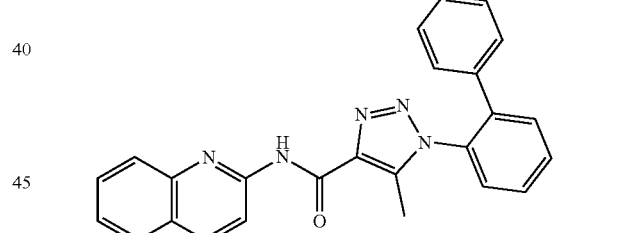

1-([1,1'-biphenyl]-2-yl)-5-methyl-N-(quinolin-2-yl)-1H-1,2,3-triazole-4-carboxamide (38)

Compound 38 was synthesized from 2-Aminoquinoline (44 mg, 0.3 mmol) and 19i (100 mg, 0.36 mmol) in a similar manner to that described for compound 20. White solid. Yield: 70 mg, 58%. $^1$H-NMR (400 MHz, DMSO-d$_6$) δ 10.11 (s, 1H), 8.45-8.43 (d, J=8.0 Hz, 1H), 8.33-8.31 (d, J=8.0 Hz, 1H), 7.98-7.96 (d, J=8.0 Hz, 1H), 7.89-7.87 (d, J=8.0 Hz, 1H), 7.81-7.69 (m, 5H), 7.56-7.52 (t, J=7.2 Hz, 1H), 7.34-7.32 (m, 3H), 7.09-7.07 (m, 2H), 2.16 (s, 3H); $^{13}$C-NMR (100 MHz, DMSO-d$_6$) δ 159.7, 150.7, 146.8, 139.6, 139.1, 137.4, 137.2, 132.8, 131.9, 131.5, 130.6, 129.5, 129.2, 128.7, 128.5, 128.2, 127.7, 126.4, 125.8, 114.7, 9.28. HRMS (ESI): m/z [M+H]$^+$ calcd for C$_{25}$H$_{20}$N$_5$O, 406.1668; found, 406.1665. HPLC: t$_R$=11.17 min, 99.9%.

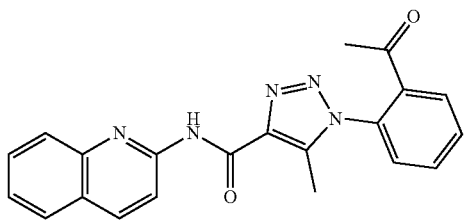

1-(2-Acetylphenyl)-5-methyl-N-(quinolin-2-yl)-1H-1,2,3-triazole-4-carboxamide (39)

Compound 39 was synthesized from 2-Aminoquinoline (44 mg, 0.3 mmol) and 19j (88 mg, 0.36 mmol) in a similar manner to that described for compound 20. Brown solid. Yield: 53 mg, 48%. $^1$H-NMR (400 MHz, DMSO-$d_6$) δ 10.37 (s, 1H), 8.65-8.63 (d, J, =8.8 Hz, 1H), 8.58-8.56 (d, J=8.8 Hz, 1H), 8.30-8.28 (d, J=7.2 Hz, 1H), 8.16-8.14 (d, J=8.0 Hz, 1H), 8.07-8.01 (m, 3H), 7.95-7.89 (m, 2H), 7.74-7.70 (t, J=7.2 Hz, 1H), 2.67 (s, 6H); $^{13}$C-NMR (100 MHz, DMSO-$d_6$) δ 203.7, 164.7, 155.6, 151.6, 144.9, 143.9, 142.3, 140.9, 138.2, 137.1, 136.4, 135.4, 133.6, 133.0, 132.5, 131.2, 130.5, 119.5, 34.1, 14.3. HRMS (ESI): m/z [M+H]$^+$ calcd for $C_{21}H_{18}N_5O_2$, 372.1460; found, 372.1455. HPLC: $t_R$=7.39 min, 99.2%.

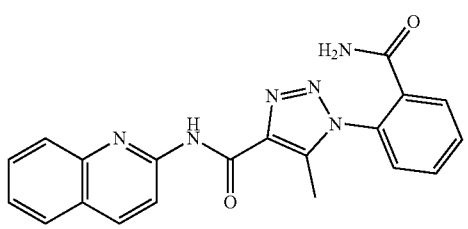

1-(2-Carbamoylphenyl)-5-methyl-N-(quinolin-2-yl)-1H-1,2,3-triazole-4-carboxamide (40)

Compound 40 was synthesized from 2-Aminoquinoline (44 mg, 0.3 mmol) and 19k (88 mg, 0.36 mmol) in a similar manner to that described for compound 20. Buff solid. Yield: 55 mg, 49%. $^1$H-NMR (400 MHz, DMSO-$d_6$) δ 10.13 (s, 1H), 8.48-8.46 (d, J=8.8 Hz, 1H), 8.42-8.39 (d, J=8.8 Hz, 1H), 8.06 (s, 1H), 7.99-7.97 (d, J=8.0 Hz, 1H), 7.90-7.88 (d, J=8.0 Hz, 1H), 7.80-7.74 (m, 4H), 7.68-7.66 (m, 1H), 7.57-7.53 (t, J=8.0 Hz, 1H), 7.49 (s, 1H), 2.50 (s, 3H); $^{13}$C-NMR (100 MHz, DMSO-$d_6$) δ 172.3, 164.8, 155.6, 151.6, 145.1, 143.9, 141.7, 139.7, 137.6, 136.2, 135.9, 135.4, 133.9, 133.3, 133.0, 132.5, 131.2, 130.5, 119.4, 14.4. HRMS (ESI): m/z [M+H]$^+$ calcd for $C_{20}H_{17}N_6O_2$, 373.1413; found, 373.1413. HPLC: $t_R$=2.72 min, 95.0%.

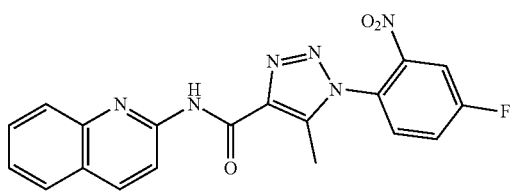

1-(4-Fluoro-2-nitrophenyl)-5-methyl-N-(quinolin-2-yl)-1H-1,2,3-triazole-4-carboxamide (41)

Compound 41 was synthesized from 2-Aminoquinoline (44 mg, 0.3 mmol) and 19l (96 mg, 0.36 mmol) in a similar manner to that described for compound 20. Yellow solid. Yield: 35 mg, 30%. $^1$H-NMR (400 MHz, DMSO-$d_6$) δ 10.26 (s, 1H), 8.49-8.47 (d, J=8.8 Hz, 1H), 8.40-8.38 (d, J=8.8 Hz, 1H), 8.00-7.98 (d, J=8.0 Hz, 1H), 7.92-7.87 (m, 3H), 7.78-7.75 (t, J=8.0 Hz, 1H), 7.59-7.54 (m, 2H), 2.55 (s, 3H); $^{13}$C-NMR (100 MHz, DMSO-$d_6$) δ 160.9, 159.8, 150.8, 146.8, 146.5, 140.8, 139.1, 137.6, 131.3, 130.6, 128.6, 127.8, 126.4, 125.8, 120.8, 120.0, 114.9, 111.9, 9.4. HRMS (ESI): m/z [M+H]$^+$ calcd for $C_{19}H_{14}FN_6O_3$, 393.1111; found, 393.1120. HPLC: $t_R$=8.26 min, 95.0%.

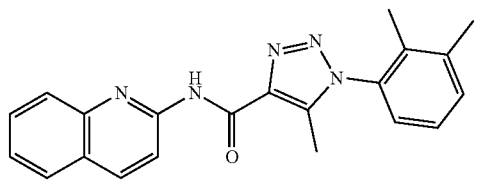

1-(2,3-Dimethylphenyl)-5-methyl-N-(quinolin-2-yl)-1H-1,2,3-triazole-4-carboxamide (42)

Compound 42 was synthesized from 2-Aminoquinoline (44 mg, 0.3 mmol) and 19m (85 mg, 0.36 mmol) in a similar manner to that described for compound 20. White solid. Yield: 72 mg, 67%. $^1$H-NMR (400 MHz, CDCl$_3$) δ 9.95 (s, 1H), 8.57-8.55 (d, J=8.4 Hz, 1H), 8.23-8.21 (d, J=8.4 Hz, 1H), 7.93-7.91 (d, J=8.8 Hz, 1H), 7.81-7.79 (d, J=8.4 Hz, 1H), 7.71-7.67 (t, J=8.0 Hz, 1H), 7.49-7.45 (t, J=7.2 Hz, 1H), 7.40-7.38 (d, J=7.2 Hz, 1H), 7.31-7.27 (t, J=8.0 Hz, 1H), 7.12-7.10 (d, J=8.0 Hz, 1H), 2.50 (s, 3H), 2.39 (s, 3H), 1.91 (s, 3H); $^{13}$C-NMR (100 MHz, CDCl$_3$) δ 160.1, 150.6, 146.9, 139.1, 139.0, 138.4, 137.7, 134.3, 134.0, 132.2, 129.9, 127.8, 127.5, 126.5, 126.4, 125.1, 124.8, 114.2, 20.3, 14.0, 9.3. HRMS (ESI): m/z [M+H]$^+$ calcd for $C_{21}H_{20}N_5O$, 358.1668; found, 358.1670. HPLC: $t_R$=11.23 min, 99.9%.

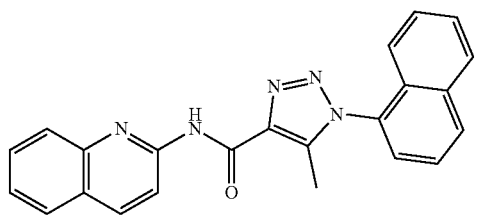

5-Methyl-1-(naphthalen-1-yl)-N-(quinolin-2-yl)-1H-1,2,3-triazole-4-carboxamide (43)

Compound 43 was synthesized from 2-Aminoquinoline (44 mg, 0.3 mmol) and 19n (91 mg, 0.36 mmol) in a similar manner to that described for compound 20. White solid. Yield: 54 mg, 47%. $^1$H-NMR (400 MHz, DMSO-$d_6$) δ 10.56 (s, 1H), 8.76-8.69 (m, 2H), 8.58-8.56 (d, J=8.0 Hz, 1H), 8.46-8.44 (d, J=8.0 Hz, 1H), 8.26-8.24 (d, J=8.0 Hz, 1H), 8.19-8.17 (d, J=8.0 Hz, 1H), 8.10 (s, 1H), 8.07-8.10 (m, 2H), 7.97-7.95 (m, 1H), 7.92-7.89 (t, J=6.4 Hz, 1H), 7.82 (t, J=6.4 Hz, 1H), 7.49-7.47 (d, J=8.0 Hz, 1H), 2.67 (s, 3H); $^{13}$C-NMR (100 MHz, DMSO-d$_6$) δ 160.0, 150.9, 146.8, 140.4, 139.2, 137.8, 134.1, 131.7, 131.4, 130.7, 129.2, 128.9, 128.8, 128.3, 127.8, 127.7, 126.4, 126.3, 126.0, 125.8, 122.1, 114.7, 9.5. HRMS (ESI): m/z [M+H]$^+$ calcd for C$_{23}$H$_{18}$N$_5$O, 380.1511; found, 380.1512. HPLC: t$_R$=9.54 min, 97.4%.

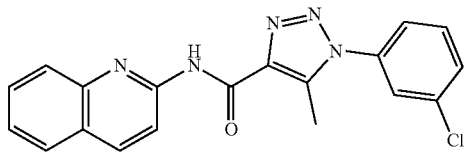

44

1-(3-Chlorophenyl)-5-methyl-N-(quinolin-2-yl)-1H-1,2,3-triazole-4-carboxamide (44)

Compound 44 was synthesized from 2-Aminoquinoline (44 mg, 0.3 mmol) and 19o (85 mg, 0.36 mmol) in a similar manner to that described for compound 20. White solid. Yield: 66 mg, 60%. $^1$H-NMR (400 MHz, DMSO-d$_6$) δ 10.22 (s, 1H), 8.48-8.46 (d, J=8.8 Hz, 1H), 8.42-8.40 (d, J=8.8 Hz, 1H), 7.99-7.97 (d, J=8.0 Hz, 1H), 7.91-7.88 (m, 2H), 7.78-7.71 (m, 4H), 7.57-7.53 (t, J=8.0 Hz, 1H), 2.65 (s, 3H); $^{13}$C-NMR (100 MHz, DMSO-d$_6$) δ 164.6, 155.6, 151.6, 143.9, 142.7, 141.5, 139.1, 136.6, 135.5, 135.4, 133.0, 132.5, 131.2, 130.6, 130.5, 129.6, 119.4, 14.6. HRMS (ESI): m/z [M+H]$^+$ calcd for C$_{19}$H$_{15}$ClN$_5$O, 364.0965; found, 364.0952. HPLC: t$_R$=16.54 min, 99.8%.

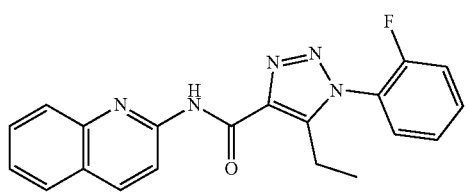

45

5-Ethyl-1-(2-fluorophenyl)-N-(quinolin-2-yl)-1H-1,2,3-triazole-4-carboxamide (45)

Compound 45 was synthesized from 2-Aminoquinoline (44 mg, 0.3 mmol) and 19p (85 mg, 0.36 mmol) in a similar manner to that described for compound 20. White solid. Yield: 65 mg, 60%. $^1$H-NMR (400 MHz, DMSO-d$_6$) δ 10.28 (s, 1H), 8.49-8.46 (d, J=8.8 Hz, 1H), 8.42-8.40 (d, J=8.8 Hz, 1H), 8.00-7.98 (d, J=8.8 Hz, 1H), 7.91-7.89 (d, J=8.8 Hz, 1H), 7.84-7.75 (m, 3H), 7.69-7.65 (t, J=8.0 Hz, 1H), 7.57-7.53 (m, 2H), 2.96-2.91 (q, J 7.2 Hz, 2H), 1.11-1.08 (t, J=7.2 Hz, 3H); $^{13}$C-NMR (100 MHz, DMSO-d$_6$) δ 164.4, 162.6, 160.1, 155.6, 151.6, 149.9, 143.9, 142.1, 138.8, 138.7, 135.4, 134.6, 133.0, 132.5, 131.2, 131.0, 130.9, 130.5, 122.4, 122.2, 119.5, 21.6, 17.5. HRMS (ESI): m/z [M+H]$^+$ calcd for C$_{20}$H$_{17}$FN$_5$O, 362.1417; found, 362.1415. HPLC: t$_R$=14.04 min, 99.7%.

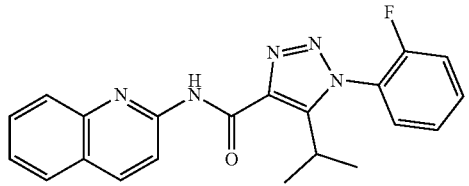

46

1-(2-Fluorophenyl)-5-isopropyl-N-(quinolin-2-yl)-1H-1,2,3-triazole-4-carboxamide (46)

Compound 46 was synthesized from 2-Aminoquinoline (44 mg, 0.3 mmol) and 19q (90 mg, 0.36 mmol) in a similar manner to that described for compound 20. White solid. Yield: 78 mg, 69%. $^1$H-NMR (400 MHz, DMSO-d$_6$) δ 10.34 (s, 1H), 8.49-8.47 (d, J=8.8 Hz, 1H), 8.43-8.41 (d, J=8.8 Hz, 1H), 8.00-7.98 (d, J=8.8 Hz, 1H), 7.91-7.89 (d, J=8.8 Hz, 1H), 7.84-7.75 (m, 3H), 7.69-7.65 (t, J=8.0 Hz, 1H), 7.57-7.53 (m, 2H), 3.24-3.20 (m, 1H), 1.34-1.32 (d, J=7.2 Hz, 6H); $^{13}$C-NMR (100 MHz, DMSO-d$_6$) δ 164.3, 162.8, 160.3, 155.6, 153.1, 151.6, 143.9, 142.1, 138.9, 138.8, 135.4, 134.9, 133.0, 132.5, 131.2, 131.0, 130.5, 128.4, 128.3, 122.3, 122.1, 119.5, 29.7, 24.8. HRMS (ESI): m/z [M+H]$^+$ calcd for C$_{21}$H$_{19}$FN$_5$O, 376.1574; found, 376.1581. HPLC: t$_R$=10.69 min, 99.0%.

TABLE 8

| HPLC analytic data | | | |
|---|---|---|---|
| Compounds | Method | Retention Time (min) | Area (%) |
| 14 (YW1109) | A | 7.02 | 99.0 |
| 15 (YW1117-2) | A | 6.42 | 99.8 |
| 16 (YW1114) | B | 12.18 | 99.5 |
| 17 (YW1104) | A | 5.88 | 98.0 |
| 20 | A | 4.02 | 99.6 |
| 21 | E | 7.15 | 99.7 |
| 22 | D | 5.00 | 99.5 |
| 23 | C | 2.32 | 99.0 |
| 24 | A | 7.38 | 98.8 |
| 25 | C | 2.04 | 100 |
| 26 | A | 6.00 | 99.2 |
| 27 | A | 8.82 | 99.8 |
| 28 | A | 8.75 | 99.1 |
| 29 | A | 9.09 | 99.7 |
| 30 | A | 12.08 | 99.5 |
| 31 | A | 11.64 | 99.3 |
| 32 | A | 17.12 | 100 |
| 33 | A | 9.53 | 100 |
| 34 | A | 7.45 | 99.9 |
| 35 | A | 8.88 | 99.9 |
| 36 | A | 8.21 | 100 |
| 37 | A | 10.48 | 99.8 |
| 38 | A | 11.17 | 100 |
| 39 | A | 7.39 | 99.6 |
| 40 | B | 2.72 | 97.5 |
| 41 | A | 8.26 | 97.5 |
| 42 | A | 11.23 | 100 |
| 43 | A | 9.54 | 98.7 |
| 44 | A | 16.54 | 99.9 |
| 45 | A | 14.04 | 99.9 |
| 46 | A | 10.69 | 99.5 |

Method A: 60% acetonitrile/40% H$_2$O (0.1% trifluoroacetic acid), 1 mL/min, 20 min.
Method B: 70% acetonitrile/30% H$_2$O (0.1% trifluoroacetic acid), 1 mL/min, 20 min.
Method C: 80% acetonitrile/20% H$_2$O (0.1% trifluoroacetic acid), 1 mL/min, 20 min.
Method D: 96% acetonitrile/4% H$_2$O (0.1% trifluoroacetic acid), 1 mL/min, 20 min.
Method E: 50% acetonitrile/50% H$_2$O (0.1% trifluoroacetic acid), 1 mL/min, 20 min.

Example 2: Synthesis of Pyrazole-Based Wnt/β-Catenin Signaling Inhibitors

A variety of pyrazole-based Wnt/β-catenin inhibitors were also prepared according to the schemes set forth herein.

Scheme 4. Synthesis of pyrazole-based Wnt/β-catenin inhibitiors.

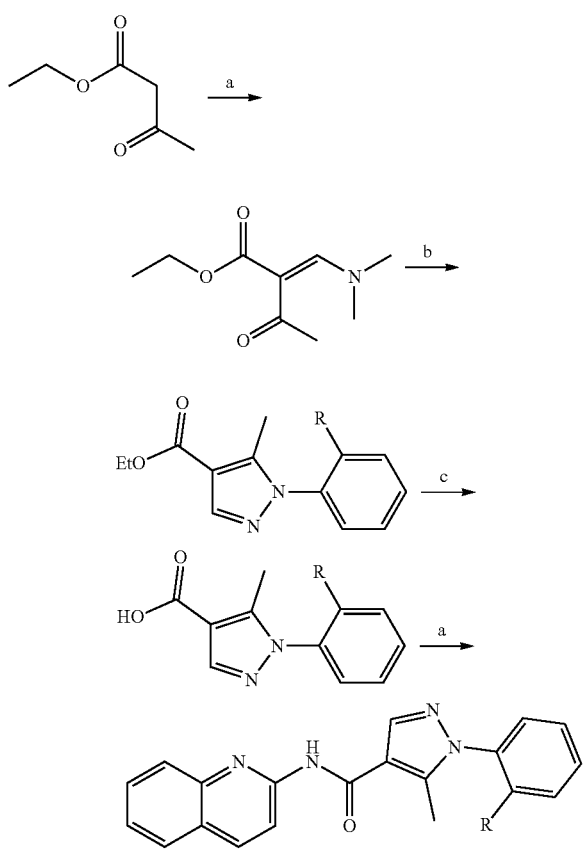

[a]Reagents and conditions: (a) N,N-Dimethylformamide dimethyl acetal, EtOH, 60° C.; (b) phenylhydrazine hydrochloride, DIPEA, EtOH, 60° C.; (c) NaOH, EtOH, 65° C.; (d) 2-aminoquinoline, PyClU, DIPEA, DCE, 70° C.

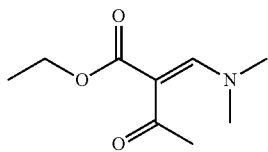

(E)-ethyl 2-((dimethylamino)methylene)-3-oxobutanoate (S110)

To a solution of ethyl acetoacetate (2.6 g, 20 mmol) in ethanol (10 mL) was added N,N-Dimethylformamide dimethyl acetal (2.5 g, 21 mmol). The mixture was allowed to stir at 60° C. for 3 h, then cooled to room temperature and concentrated to give a crude product (3.6 g, 97%), which was used without further purification.

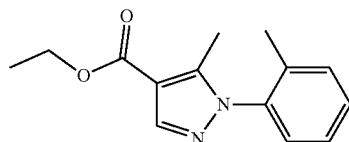

Ethyl 5-methyl-1-(o-tolyl)-1H-pyrazole-4-carboxylate (S111a)

To a solution of the above crude S110 (3.6 g, 19.5 mmol) in ethanol (20 mL) was added DIPEA (2.71 g, 21 mmol) and 2-metylphenyhdrazine.HCl (3.3 g, 21 mmol). The mixture was allowed to stir at 60° C. for 3 h. Then, the mixture was cooled to room temperature, concentrated to give the crude product as an oil (4.3 g, 90%).

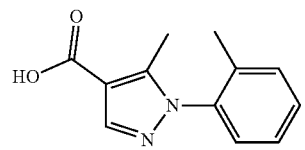 [SMILES: Cc1ccccc1-n1ncc(C(=O)O)c1C]

5-Methyl-1-(o-tolyl)-1H-pyrazole-4-carboxylic acid (S112a)

The above crude product of S111a was dissolved in ethanol. The reaction mixture was allowed to stir at 65° C. for 4 h and concentrated. The residue was dissolved in water, acidified to pH 1-2 using HCl to give S112a (96%), which was used for the next step without further purification.

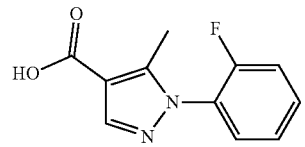 [SMILES: Cc1c(C(=O)O)cnn1-c1ccccc1F]

1-(2-Fluorophenyl)-5-methyl-1H-pyrazole-4-carboxylic acid (S112b)

The title compound was synthesized according to the same procedure described for the synthesis of compound S112a (94%). $^1$H-NMR (400 MHz, DMSO-$d_6$) δ 12.56 (s, 1H), 8.03 (s, 1H), 7.64-7.58 (m, 2H), 7.53-7.748 (t, J=8.8 Hz, 1H), 7.43-7.39 (t, J=8.8 Hz, 1H), 2.37 (s, 3H); $^{13}$C-NMR (100 MHz, DMSO-$d_6$) δ 169.5, 162.9, 160.2, 149.9, 147.3, 136.9, 136.8, 134.5, 130.5, 130.5, 122.0, 121.8, 117.9, 15.8.

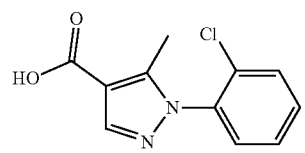 [SMILES: Cc1c(C(=O)O)cnn1-c1ccccc1Cl]

1-(2-Chlorophenyl)-5-methyl-1H-pyrazole-4-carboxylic acid (S112c)

The title compound was synthesized according to the same procedure described for the synthesis of compound S112a (90%). $^1$H-NMR (400 MHz, DMSO-d$_6$) δ 12.38 (s, 1H), 8.00 (s, 1H), 7.75-7.73 (d, J=8.0 Hz, 1H), 7.64-7.54 (m, 3H), 2.29 (s, 3H); $^{13}$C-NMR (100 MHz, DMSO-d$_6$) δ 169.6, 149.8, 147.0, 141.0, 136.8, 136.3, 135.4, 135.2, 133.6, 117.5, 15.9.

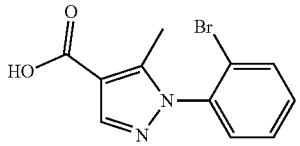 [SMILES: Cc1c(C(=O)O)cnn1-c1ccccc1Br]

1-(2-Bromophenyl)-5-methyl-1H-pyrazole-4-carboxylic acid (S112d)

The title compound was synthesized according to the same procedure described for the synthesis of compound S112a (98%).

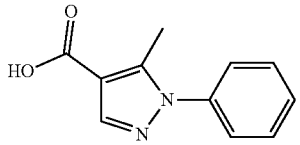

5-Methyl-1-phenyl-1H-pyrazole-4-carboxylic acid (S112e)

The title compound was synthesized according to the same procedure described for the synthesis of compound S112a (80%). $^1$H-NMR (400 MHz, DMSO-d$_6$) δ 12.45 (s, 1H), 7.98 (s, 1H), 7.59-7.49 (m, 5H), 2.51 (s, 3H); $^{13}$C-NMR (100 MHz, DMSO-d$_6$) δ 169.7, 148.4, 146.8, 143.8, 134.5, 133.7, 130.5, 118.2, 16.7.

1-(2,4-Difluorophenyl)-5-methyl-1H-pyrazole-4-carboxylic acid (S112f)

The title compound was synthesized according to the same procedure described for the synthesis of compound S112a (83%). $^1$H-NMR (400 MHz, DMSO-d$_6$) δ 12.49 (s, 1H), 8.01 (s, 1H), 7.72-7.66 (m, 1H), 7.62-7.56 (m, 1H), 7.33-7.29 (m, 1H), 2.36 (s, 3H); $^{13}$C-NMR (100 MHz, DMSO-d$_6$) δ 169.5, 168.9, 168.8, 166.4, 166.3, 163.3, 163.1, 160.7, 160.6, 150.2, 147.4, 136.0, 135.9, 117.9, 117.8, 117.6, 117.6, 110.8, 110.5, 110.3, 15.8.

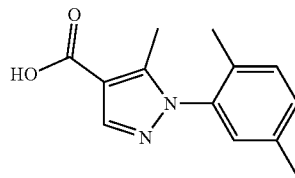

1-(2,5-Dimethylphenyl)-5-methyl-1H-pyrazole-4-carboxylic acid (S112g)

The title compound was synthesized according to the same procedure described for the synthesis of compound S112a (75%). $^1$H-NMR (400 MHz, DMSO-d$_6$) δ 12.11 (s, 1H), 7.96 (s, 1H), 7.31-7.29 (d, J=8.0 Hz, 1H), 7.26-7.24 (d, J=8.0 Hz, 1H), 7.13 (s, 1H), 2.32 (s, 3H), 2.26 (s, 3H), 1.90 (s, 3H); $^{13}$C-NMR (100 MHz, DMSO-d$_6$) δ 169.8, 148.9, 146.4, 142.5, 141.5, 137.3, 135.9, 135.5, 133.1, 117.1, 25.4, 21.4, 15.9.

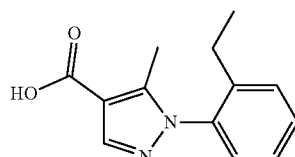

1-(2-Ethylphenyl)-5-methyl-1H-pyrazole-4-carboxylic acid (S112h)

The title compound was synthesized according to the same procedure described for the synthesis of compound S112a (78%). $^1$H-NMR (400 MHz, DMSO-d$_6$) δ 12.41 (s, 1H), 7.98 (s, 1H), 7.53-7.47 (m, 2H), 7.40-7.36 (t, J=8.0 Hz, 1H), 7.32-7.30 (d, J=8.0 Hz, 1H), 2.29-2.67 (m, 5H), 1.00-0.96 (t, J=8.0 Hz, 3H); $^{13}$C-NMR (100 MHz, DMSO-d$_6$) δ 169.7, 149.2, 146.4, 146.4, 142.0, 135.1, 134.8, 132.9, 131.9, 117.1, 28.6, 19.6, 16.2.

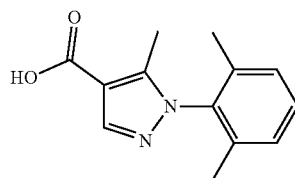

1-(2,6-Dimethylphenyl)-5-methyl-1H-pyrazole-4-carboxylic acid (S112j)

The title compound was synthesized according to the same procedure described for the synthesis of compound S112a (48%). $^1$H-NMR (400 MHz, DMSO-d$_6$) δ 12.44 (s, 1H), 8.01 (s, 1H), 7.39-7.35 (t, J=8.0 Hz, 1H), 7.27-7.25 (d, J=8.0 Hz, 1H), 2.20 (s, 3H), 1.88 (s, 6H); $^{13}$C-NMR (100 MHz, DMSO-d$_6$) δ 169.8, 148.9, 146.9, 141.8, 141.0, 134.8, 133.5, 117.0, 21.9, 15.4.

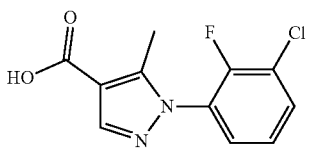 [SMILES: Cc1c(C(=O)O)cnn1-c1cccc(Cl)c1F]

1-(3-Chloro-2-fluorophenyl)-5-methyl-1H-pyrazole-4-carboxylic acid

The title compound was synthesized according to the same procedure described for the synthesis of compound S112a (86%). $^1$H-NMR (400 MHz, DMSO-$d_6$) δ 12.45 (s, 1H), 8.04 (s, 1H), 7.84-7.80 (t, J=7.2 Hz, 1H), 7.63-7.59 (t, J=7.2 Hz, 1H), 7.46-7.42 (t, J=7.2 Hz, 1H), 2.38 (s, 3H); $^{13}$C-NMR (100 MHz, DMSO-$d_6$) δ 169.4, 158.7, 156.1, 150.2, 147.6, 137.1, 133.5, 132.6, 132.5, 131.0, 130.9, 126.2, 126.0, 118.1, 15.9.

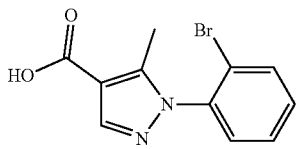 [SMILES: Cc1c(C(=O)O)cnn1-c1ccccc1Br]

1-(2-Bromophenyl)-5-methyl-1H-pyrazole-4-carboxylic acid

The title compound was synthesized according to the same procedure described for the synthesis of compound S112a (65%). $^1$H-NMR (400 MHz, DMSO-$d_6$) δ 12.45 (s, 1H), 7.99 (s, 1H), 7.89-7.87 (d, J=8.0 Hz, 1H), 7.61-7.54 (m, 3H), 2.28 (s, 3H); $^{13}$C-NMR (100 MHz, DMSO-$d_6$) δ 169.6, 149.5, 146.8, 142.7, 138.5, 137.0, 135.2, 134.1, 126.6, 117.5, 16.0.

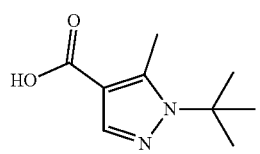

1-(Tert-butyl)-5-methyl-1H-pyrazole-4-carboxylic acid (S112i)

The title compound was synthesized according to the same procedure described for the synthesis of compound S12a (40%). $^1$H-NMR (400 MHz, DMSO-$d_6$) δ 12.16 (s, 1H), 7.68 (s, 1H), 2.69 (s, 3H), 1.59 (s, 9H); $^{13}$C-NMR (100 MHz, DMSO-$d_6$) δ 170.1, 147.5, 143.7, 118.1, 65.8, 34.8, 17.6.

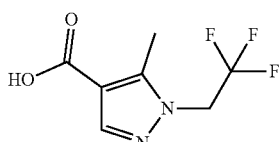

5-methyl-1-(2,2,2-trifluoroethyl)-1H-pyrazole-4-carboxylic acid

The title compound was synthesized according to the same procedure described for the synthesis of compound S112a (62%). $^1$H-NMR (400 MHz, DMSO-$d_6$) δ 12.42 (s, 1H), 7.86 (s, 1H), 5.21-5.16 (m, 2H), 2.54 (s, 3H); $^{13}$C-NMR (100 MHz, DMSO-$d_6$) δ 169.4, 150.1, 146.8, 145.7, 117.8, 54.1, 54.1, 15.1.

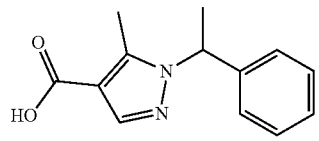 [SMILES: Cc1c(C(=O)O)cnn1C(C)c1ccccc1]

5-methyl-1-(1-phenylethyl)-1H-pyrazole-4-carboxylic acid

The title compound was synthesized according to the same procedure described for the synthesis of compound S112a (58%). $^1$H-NMR (400 MHz, DMSO-$d_6$) δ 12.26 (s, 1H), 7.84 (s, 1H), 7.34-7.30 (t, J=7.2 Hz, 2H), 7.27-7.23 (t, J=7.2 Hz, 1H), 7.20-7.18 (d, J=7.2 Hz, 1H), 5.70-5.64 (q, J=7.2 Hz, 1H), 2.44 (s, 3H), 1.80-1.78 (d, J=7.2 Hz, 3H); $^{13}$C-NMR (100 MHz, DMSO-$d_6$) δ 169.9, 147.7, 147.1, 145.3, 133.8, 132.6, 131.3, 117.0, 61.9, 26.7, 15.1.

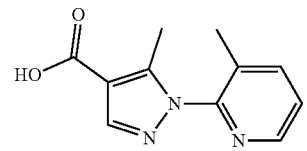 [SMILES: Cc1cccnc1-n1ncc(C(=O)O)c1C]

5-Methyl-1-(3-methylpyridin-2-yl)-1H-pyrazole-4-carboxylic acid

The title compound was synthesized according to the same procedure described for the synthesis of compound S112a (48%). $^1$H-NMR (400 MHz, DMSO-$d_6$) δ 12.27 (s, 1H), 8.47-8.46 (d, J=4.0 Hz, 1H), 7.99-7.96 (m, 2H), 7.56-7.53 (m, 1H), 2.37 (s, 3H), 2.11 (s, 3H); $^{13}$C-NMR (100 MHz, DMSO-$d_6$) δ 169.6, 154.9, 151.7, 149.1, 146.6, 146.1, 135.8, 130.3, 117.5, 21.8, 16.0.

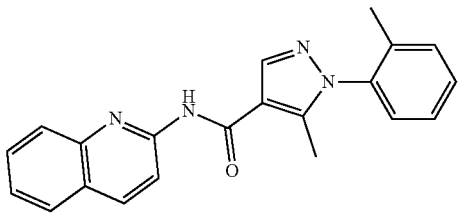 [SMILES: Cc1ccccc1-n1ncc(C(=O)Nc2ccc3ccccc3n2)c1C]

5-Methyl-N-(quinolin-2-yl)-1-(o-tolyl)-1H-pyrazole-4-carboxamide (132)

The title compound was synthesized according to the same procedure described for the synthesis of compound 5.

White solid. Yield: 58%, 60 mg. ¹H-NMR (400 MHz, DMSO-d₆) δ 10.86 (s, 1H), 8.62 (s, 1H), 8.40-8.36 (m, 2H), 7.95-7.93 (d, J=8.0 Hz, 1H), 7.90-7.88 (d, J=8.8 Hz, 1H), 7.75-7.71 (t, J=7.2 Hz, 1H), 7.53-7.34 (m, 5H), 2.36 (s, 3H), 2.00 (s, 3H); ¹³C-NMR (100 MHz, DMSO-d₆) δ 167.7, 157.3, 151.6, 149.2, 144.9, 143.1, 142.7, 140.7, 136.2, 135.1, 134.9, 132.9, 132.8, 132.1, 132.0, 130.8, 130.1, 120.6, 119.2, 21.9, 16.3. HRMS [M+H]⁺ (ESI-TOF) calcd for C₂₁H₁₉N₄O 343.1559, found 343.1588. HPLC: $t_R$=6.33 min, 99.8%.

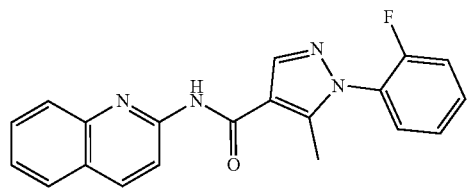 [SMILES: Cc1c(C(=O)Nc2ccc3ccccc3n2)cnn1-c1ccccc1F]

1-(2-Fluorophenyl)-5-methyl-N-(quinolin-2-yl)-1H-pyrazole-4-carboxamide (133)

The title compound was synthesized according to the same procedure described for the synthesis of compound 5. White solid. Yield: 82%, 85 mg. ¹H-NMR (400 MHz, DMSO-d₆) δ 10.93 (s, 1H), 8.64 (s, 1H), 8.39 (m, 2H), 7.96-7.94 (d, J=8.0 Hz, 1H), 7.90-7.88 (d, J=8.0 Hz, 1H), 7.55-7.71 (t, J=8.0 Hz, 1H), 7.65-7.61 (m, 2H), 7.57-7.50 (m, 2H), 7.46-7.42 (t, J=8.0 Hz, 1H), 2.46 (s, 3H); ¹³C-NMR (100 MHz, DMSO-d₆) δ 167.5, 162.7, 160.2, 157.2, 151.6, 150.1, 145.8, 145.6, 143.1, 136.9, 136.8, 135.1, 134.6, 132.9, 132.1, 130.9, 130.6, 130.1, 122.0, 121.9, 120.6, 119.8, 16.2. HRMS [M+H]⁺ (ESI-TOF) calcd for C₂₀H₁₆FN₄O 347.1308, found 347.1300. HPLC: $t_R$=5.83 min, 99.7%.

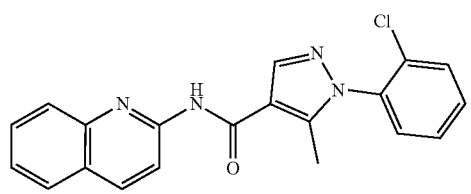 [SMILES: Cc1c(C(=O)Nc2ccc3ccccc3n2)cnn1-c1ccccc1Cl]

1-(2-Chlorophenyl)-5-methyl-N-(quinolin-2-yl)-1H-pyrazole-4-carboxamide (135)

The title compound was synthesized according to the same procedure described for the synthesis of compound 5. White solid. Yield: 64%, 70 mg. ¹H-NMR (400 MHz, DMSO-d₆) δ 10.91 (s, 1H), 8.65 (s, 1H), 8.39 (m, 2H), 7.96-7.94 (d, J=8.8 Hz, 1H), 7.90-7.88 (d, J=8.8 Hz, 1H), 7.78-7.74 (m, 2H), 7.64-7.59 (m, 3H), 7.54-7.50 (t, J=8.0 Hz, 1H), 2.39 (s, 3H); ¹³C-NMR (100 MHz, DMSO-d₆) δ 167.5, 157.2, 151.6, 150.0, 145.4, 143.1, 141.1, 136.8, 136.3, 135.5, 135.2, 135.1, 133.6, 132.9, 132.1, 130.9, 130.1, 120.6, 119.5, 16.2. HRMS [M+H]⁺ (ESI-TOF) calcd for C₂₀H₁₆ClN₄O 363.1013, found 363.1015. HPLC: $t_R$=6.96 min, 99.6%.

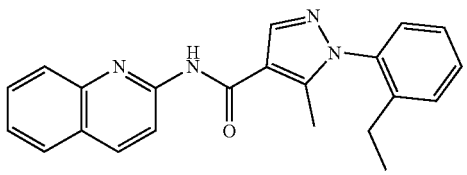 [SMILES: CCc1ccccc1-n1ncc(C(=O)Nc2ccc3ccccc3n2)c1C]

1-(2-Ethylphenyl)-5-methyl-N-(quinolin-2-yl)-1H-pyrazole-4-carboxamide (136)

The title compound was synthesized according to the same procedure described for the synthesis of compound 5. Brown solid. Yield: 84%, 90 mg. ¹H-NMR (400 MHz, DMSO-d₆) δ 10.85 (s, 1H), 8.62 (s, 1H), 8.39 (m, 2H), 7.96-7.94 (d, J=8.0 Hz, 1H), 7.90-7.88 (d, J=8.0 Hz, 1H), 7.55-7.71 (t, J=8.0 Hz, 1H), 7.53-7.50 (m, 3H), 7.42-7.38 (t, J=8.0 Hz, 1H), 7.34-7.32 (d, J=8.0 Hz, 1H), 2.36-2.31 (m, 5H), 1.03-1.0 (q, J=8.0 Hz, 3H); ¹³C-NMR (100 MHz, DMSO-d₆) δ 167.7, 157.2, 151.6, 149.4, 146.5, 144.7, 143.1, 142.1, 135.2, 135.1, 134.8, 133.0, 132.9, 132.1, 131.9, 130.8, 130.1, 120.6, 119.1, 28.6, 19.7, 16.5. HRMS [M+H]⁺ (ESI-TOF) calcd for C₂₂H₂₁N₄O 357.1715, found 357.1715. HPLC: $t_R$=9.03 min, 99.2%.

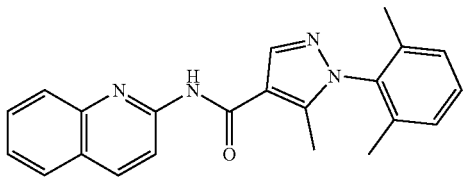 [SMILES: Cc1cccc(C)c1-n1ncc(C(=O)Nc2ccc3ccccc3n2)c1C]

1-(2,6-dimethylphenyl)-5-methyl-N-(quinolin-2-yl)-1H-pyrazole-4-carboxamide (137)

The title compound was synthesized according to the same procedure described for the synthesis of compound 5. Yellow foam. Yield: 74%, 80 mg. ¹H-NMR (400 MHz, DMSO-d₆) δ 10.85 (s, 1H), 8.67 (s, 1H), 8.39 (m, 2H), 7.96-7.94 (d, J=8.0 Hz, 1H), 7.90-7.88 (d, J=8.0 Hz, 1H), 7.76-7.72 (t, J=8.0 Hz, 1H), 7.54-7.50 (t, J=8.0 Hz, 1H), 7.40-7.36 (t, J=8.0 Hz, 1H), 7.29-7.27 (m, 2H), 2.29 (s, 3H), 1.91 (s, 6H); ¹³C-NMR (100 MHz, DMSO-d₆) δ 167.7, 157.2, 151.6, 149.1, 145.2, 143.1, 141.8, 141.1, 135.1, 134.8, 133.5, 132.9, 132.1, 130.8, 130.1, 120.6, 119.1, 21.9, 15.8. HRMS [M+H]⁺ (ESI-TOF) calcd for C₂₂H₂₁N₄O 357.1715, found 357.1714. HPLC: $t_R$=7.82 min, 99.6%.

1-(Tert-butyl)-5-methyl-N-(quinolin-2-yl)-1H-pyrazole-4-carboxamide (138)

The title compound was synthesized according to the same procedure described for the synthesis of compound 5.

White solid. Yield: 57%, 53 mg. $^1$H-NMR (400 MHz, DMSO-$d_6$) δ 10.73 (s, 1H), 8.43 (s, 2H), 8.34 (s, 1H), 8.02-8.00 (d, J=8.0 Hz, 1H), 7.95-7.93 (d, J=8.0 Hz, 1H), 7.82-7.78 (t, J=8.0 Hz, 1H), 7.60-7.56 (t, J=8.0 Hz, 1H), 2.86 (s, 3H), 1.71 (s, 9H); $^{13}$C-NMR (100 MHz, DMSO-$d_6$) 168.2, 157.3, 151.6, 147.4, 142.9, 142.1, 135.0, 132.9, 132.0, 130.8, 130.0, 120.6, 120.3, 65.8, 34.8, 18.0. HRMS [M+H]$^+$ (ESI-TOF) calcd for $C_{18}H_{21}N_4O$ 309.1715, found 309.1722. HPLC: $t_R$=5.08 min, 96.2%.

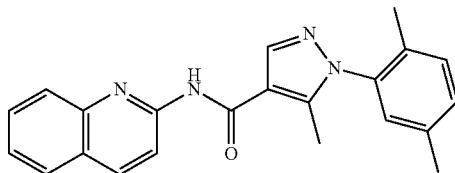

1-(2,5-dimethylphenyl)-5-methyl-N-(quinolin-2-yl)-1H-pyrazole-4-carboxamide (139)

Yellow oil. Yield: 56%, 60 mg. $^1$H-NMR (400 MHz, CDCl$_3$) δ 8.84 (s, 1H), 8.56-8.54 (d, J=8.8 Hz, 1H), 8.20-8.18 (d, J=8.8 Hz, 1H), 8.11 (s, 1H), 7.84-7.82 (d, J=8.8 Hz, 1H), 7.79-7.77 (d, J=8.8 Hz, 1H), 7.68-7.64 (t, J=8.0 Hz, 1H), 7.46-7.42 (t, J=8.0 Hz, 1H), 7.21-7.18 (m, 2H), 7.04 (s, 1H), 2.45 (s, 3H), 2.35 (s, 3H), 1.98 (s, 3H); $^{13}$C-NMR (100 MHz, CDCl$_3$) δ 162.4, 151.3, 146.4, 144.4, 138.6, 138.4, 137.3, 136.7, 132.5, 130.9, 130.6, 130.0, 127.6, 127.1, 126.2, 125.1, 114.6, 114.4, 20.7, 16.7, 11.3. HRMS [M+H]$^+$ (ESI-TOF) calcd for $C_{22}H_{21}N_4O$ 357.1715, found 357.1728. HPLC: $t_R$=8.39 min, 99.9%.

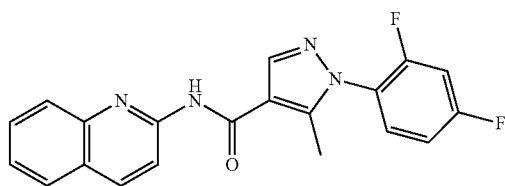 [SMILES: Cc1c(C(=O)Nc2ccc3ccccc3n2)cnn1-c1ccc(F)cc1F]

1-(2,4-difluorophenyl)-5-methyl-N-(quinolin-2-yl)-1H-pyrazole-4-carboxamide (140)

Brown solid. Yield: 82%, 89 mg. $^1$H-NMR (400 MHz, CDCl$_3$) δ 8.75 (s, 1H), 8.54-8.52 (d, J=8.8 Hz, 1H), 8.22-8.20 (d, J=8.8 Hz, 1H), 8.14 (s, 1H), 7.84-7.82 (d, J=8.8 Hz, 1H), 7.81-7.79 (d, J=8.8 Hz, 1H), 7.69-7.65 (t, J=8.8 Hz, 1H), 7.50-7.44 (m, 2H), 7.06-7.02 (m, 2H), 2.55 (s, 3H); $^{13}$C-NMR (100 MHz, CDCl$_3$) δ 164.4, 164.3, 161.9, 158.4, 155.7, 151.1, 146.4, 145.6, 139.4, 138.7, 130.1, 130.0, 127.6, 127.0, 126.3, 125.2, 115.2, 114.5, 112.4, 112.2, 105.4, 105.2, 104.9, 11.2. HRMS [M+H]$^+$ (ESI-TOF) calcd for $C_{20}H_{15}F_2N_4O$ 365.1214, found 365.1202. HPLC: $t_R$=6.07 min, 99.8%.

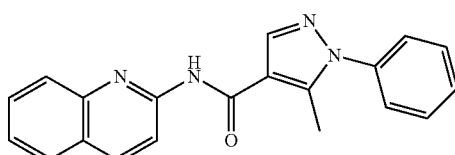

5-methyl-1-phenyl-N-(quinolin-2-yl)-1H-pyrazole-4-carboxamide (141)

Yellow solid. Yield: 81%, 80 mg. $^1$H-NMR (400 MHz, CDCl$_3$) δ 8.74 (s, 1H), 8.55-8.53 (d, J=9.6 Hz, 1H), 8.20-8.18 (d, J=9.6 Hz, 1H), 8.09 (s, 1H), 7.84-7.82 (d, J=8.8 Hz, 1H), 7.79-0.77 (d, J=8.0 Hz, 1H), 7.68-7.64 (t, J=8.0 Hz, 1H), 7.53-7.49 (m, 2H), 7.47-7.43 (m, 4H), 2.66 (s, 3H); $^{13}$C-NMR (100 MHz, CDCl$_3$) δ 162.2, 151.2, 146.4, 143.6, 138.6, 138.4, 130.1, 129.3, 128.8, 127.6, 127.0, 126.3, 125.5, 125.1, 115.4, 114.5, 12.1. HRMS [M+H]$^+$ (ESI-TOF) calcd for $C_{20}H_{17}N_4O$ 329.1402, found 329.1409. HPLC: $t_R$=5.45 min, 99.9%.

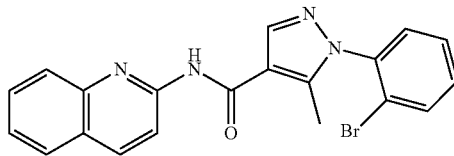

1-(2-bromophenyl)-5-methyl-N-(quinolin-2-yl)-1H-pyrazole-4-carboxamide (134)

Yellow solid. Yield: 65%, 80 mg. $^1$H-NMR (400 MHz, CDCl$_3$) δ 8.74 (s, 1H), 8.55-8.53 (d, J=8.0 Hz, 1H), 8.20-8.18 (d, J=8.8 Hz, 1H), 8.11 (s, 1H), 7.84-7.82 (d, J=8.8 Hz, 1H), 7.79-7.77 (d, J=8.8 Hz, 1H), 7.74-7.72 (d, J=8.8 Hz, 1H), 7.68-7.64 (t, J=8.0 Hz, 1H), 7.49-7.44 (m, 2H), 7.42-7.37 (m, 2H), 2.50 (s, 3H); $^{13}$C-NMR (100 MHz, CDCl$_3$) δ 162.1, 151.2, 146.6, 145.2, 138.8, 138.5, 137.8, 133.6, 131.4, 130.0, 129.6, 128.4, 127.6, 127.2, 126.3, 125.1, 122.3, 114.8, 114.5, 11.4. HRMS [M+H]$^+$ (ESI-TOF) calcd for $C_{20}H_{15}BrN_4O$ 407.0507, found 407.0513. HPLC: $t_R$=7.11 min, 97.6%.

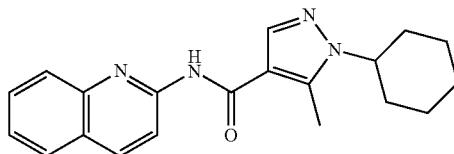

1-cyclohexyl-5-methyl-N-(quinolin-2-yl)-1H-pyrazole-4-carboxamide (142)

Light yellow solid. Yield: 60%, 60 mg. $^1$H-NMR (400 MHz, CDCl$_3$) δ 8.71 (s, 1H), 8.51-8.49 (d, J=8.4 Hz, 1H), 8.16-8.14 (d, J=9.6 Hz, 1H), 7.93 (s, 1H), 7.80-7.78 (d, J=8.8 Hz, 1H), 7.76-7.74 (d, J=8.0 Hz, 1H), 7.65-7.61 (t, J=8.0 Hz, 1H), 7.43-7.39 (t, J=8.0 Hz, 1H), 4.06-4.01 (m, 1H), 2.64 (s, 3H), 1.96-1.74 (m, 6H), 1.44-1.21 (m, 4H); $^{13}$C-NMR (100 MHz, CDCl$_3$) δ 162.6, 151.4, 146.4, 141.8, 138.5, 137.2, 129.9, 127.5, 127.0, 126.2, 124.9, 114.5, 113.9, 57.7, 32.5, 25.6, 25.1, 10.4. HRMS [M+H]$^+$ (ESI-TOF) calcd for $C_{20}H_{22}N_4O$ 335.1872, found 335.1871. HPLC: $t_R$=5.73 min, 99.2%.

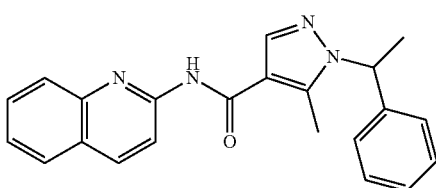

5-methyl-1-(1-phenylethyl)-N-(quinolin-2-yl)-1H-pyrazole-4-carboxamide (143)

Off-white solid. Yield: 70%, 75 mg. $^1$H-NMR (400 MHz, CDCl$_3$) δ 8.51 (s, 1H), 8.49 (s, 1H), 8.19-8.17 (d, J=8.4 Hz, 1H), 7.98 (s, 1H), 7.84-7.82 (d, J=8.8 Hz, 1H), 7.79-7.77 (d, J=8.0 Hz, 1H), 7.69-7.65 (t, J=8.0 Hz, 1H), 7.47-7.43 (t, J=8.0 Hz, 1H), 7.35-7.31 (t, J=7.2 Hz, 2H), 7.29-7.27 (d, J=7.2 Hz, 1H), 7.17-7.15 (d, J=7.2 Hz, 2H), 5.52-5.47 (q, J=6.8 Hz, 1H), 2.57 (s, 3H), 1.97-1.95 (d, J=6.8 Hz, 3H); $^{13}$C-NMR (100 MHz, CDCl$_3$) δ 162.4, 151.2, 146.6, 143.0, 141.4, 138.5, 137.1, 130.0, 128.8, 127.8, 127.6, 127.1, 126.3, 125.9, 125.0, 114.7, 114.5, 58.1, 21.6, 10.6. HRMS [M+H]$^+$ (ESI-TOF) calcd for C$_{22}$H$_{21}$N$_4$O 357.1715, found 357.1709. HPLC: t$_R$=7.72 min, 99.8%.

5-methyl-N-(quinolin-2-yl)-1-(2,2,2-trifluoroethyl)-1H-pyrazole-4-carboxamide (144)

White solid. Yield: 35%, 35 mg. $^1$H-NMR (400 MHz, CDCl$_3$) δ 8.80 (s, 1H), 8.50-8.48 (d, J=8.4 Hz, 1H), 8.21-8.18 (d, J=9.6 Hz, 1H), 8.02 (s, 1H), 7.83-7.81 (d, J=9.6 Hz, 1H), 7.80-7.78 (d, J=8.4 Hz, 1H), 7.69-7.65 (t, J=7.2 Hz, 1H), 7.48-7.44 (t, J=7.2 Hz, 1H), 4.75-4.69 (q, J=8.8 Hz, 2H), 2.69 (s, 3H); $^{13}$C-NMR (100 MHz, CDCl$_3$) δ 162.2, 151.1, 146.4, 144.9, 139.0, 138.7, 138.4, 130.1, 127.6, 126.9, 126.3, 125.2, 124.2, 115.6, 114.5, 50.4, 50.3, 50.0, 49.6, 10.6. HRMS [M+H]$^+$ (ESI-TOF) calcd for C$_{16}$H$_{14}$F$_3$N$_4$O 335.1120, found 335.1120. HPLC: t$_R$=4.51 min, 96.0%.

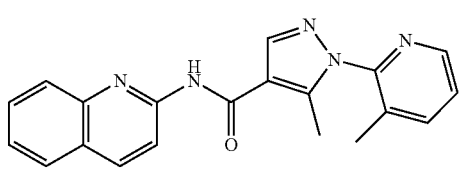 [SMILES: Cc1cccnc1-n1ncc(C(=O)Nc2ccc3ccccc3n2)c1C]

5-methyl-1-(3-methylpyridin-2-yl)-N-(quinolin-2-yl)-1H-pyrazole-4-carboxamide (145)

White solid. Yield: 24%, 25 mg. $^1$H-NMR (400 MHz, CDCl$_3$) δ 8.55 (s, 1H), 8.53 (s, 1H), 8.47-8.46 (d, J=4.0 Hz, 1H), 8.21-8.19 (d, J=8.8 Hz, 1H), 8.01 (s, 1H), 7.85-7.83 (d, J=8.0 Hz, 1H), 7.81-7.79 (d, J=8.0 Hz, 1H), 7.77-7.75 (d, J=8.0 Hz, 1H), 7.70-7.66 (t, J=8.0 Hz, 1H), 7.47-7.43 (t, J=8.0 Hz, 1H), 7.39-7.36 (m, 1H), 2.58 (s, 3H), 2.20 (s, 3H); $^{13}$C-NMR (100 MHz, CDCl$_3$) δ 162.1, 151.1, 150.0, 146.7, 144.7, 140.6, 138.5, 131.0, 130.0, 127.6, 127.3, 126.3, 125.1, 124.8, 114.9, 114.5, 17.2, 11.4. HRMS [M+H]$^+$ (ESI-TOF) calcd for C$_{20}$H$_{18}$N$_5$O 344.1511, found 344.1507. HPLC: t$_R$=3.73 min, 99.6%.

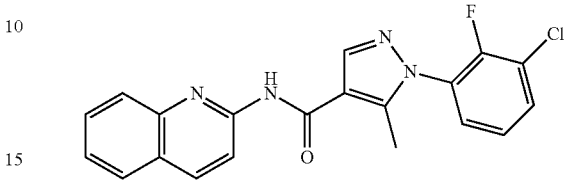

1-(3-chloro-2-fluorophenyl)-5-methyl-N-(quinolin-2-yl)-1H-pyrazole-4-carboxamide (146)

White solid. Yield: 56%, 60 mg. $^1$H-NMR (400 MHz, CDCl$_3$) δ 8.70 (s, 1H), 8.54-8.52 (d, J=8.4 Hz, 1H), 8.22-8.20 (d, J=8.8 Hz, 1H), 8.14 (s, 1H), 7.84-7.82 (d, J=8.8 Hz, 1H), 7.81-7.79 (d, J=8.0 Hz, 1H), 7.69-7.65 (t, J=7.2 Hz, 1H), 7.58-7.54 (t, J=7.2 Hz, 1H), 7.48-7.44 (t, J=7.2 Hz, 1H), 7.41-7.37 (t, J=7.2 Hz, 1H), 7.28-7.24 (t, J=8.0 Hz, 1H), 2.58 (s, 3H); $^{13}$C-NMR (100 MHz, CDCl$_3$) δ 161.8, 154.2, 151.6, 151.1, 146.5, 145.6, 139.5, 138.6, 131.8, 130.1, 127.6, 127.3, 127.2, 126.3, 125.2, 124.9, 124.8, 122.7, 115.4, 114.5, 11.3. HRMS [M+H]$^+$ (ESI-TOF) calcd for C$_{20}$H$_{15}$ClFN$_4$O 381.0918, found 381.0928. HPLC: t$_R$=10.21 min, 99.8%.

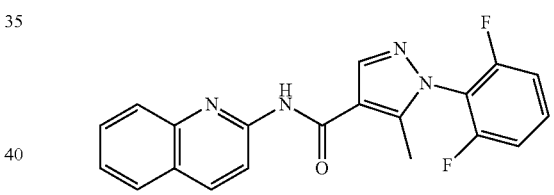

1-(2,6-difluorophenyl)-5-methyl-N-(quinolin-2-yl)-1H-pyrazole-4-carboxamide (147)

Yellow foam. Yield: 64%, 70 mg. $^1$H-NMR (400 MHz, CDCl$_3$) δ 8.91 (s, 1H), 8.53-8.51 (d, J=9.6 Hz, 1H), 8.18 (s, 1H), 8.18-8.16 (d, J=8.8 Hz, 1H), 7.82-7.80 (d, J=8.4 Hz, 1H), 7.77-7.75 (d, J=8.0 Hz, 1H), 7.65-7.61 (t, J=7.2 Hz, 1H), 7.48-7.40 (m, 2H), 7.11-7.07 (t, J=8.0 Hz, 1H), 2.53 (s, 3H); $^{13}$C-NMR (100 MHz, CDCl$_3$) δ 161.9, 159.6, 157.1, 157.0, 151.2, 146.4, 139.9, 138.6, 131.6, 131.5, 131.4, 130.0, 127.6, 127.1, 126.3, 125.1, 115.2, 114.6, 112.5, 112.3, 10.9. HRMS [M+H]$^+$ (ESI-TOF) calcd for C$_{20}$H$_{15}$F$_2$N$_4$O 365.1214, found 365.1210. HPLC: t$_R$=7.08 min, 99.5%.

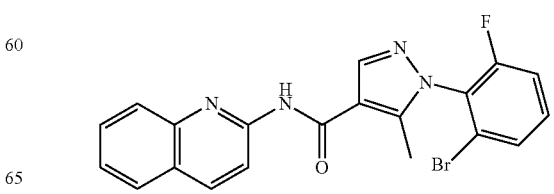

1-(2-bromo-6-fluorophenyl)-5-methyl-N-(quinolin-2-yl)-1H-pyrazole-4-carboxamide (148)

White solid. Yield: 69%, 87 mg. $^1$H-NMR (400 MHz, CDCl$_3$) δ 8.89 (s, 1H), 8.55-8.53 (d, J=8.8 Hz, 1H), 8.20-8.18 (t, J=4.8 Hz, 2H), 7.83-7.81 (d, J=8.0 Hz, 1H), 7.78-7.76 (d, J=8.8 Hz, 1H), 7.67-7.63 (t, J=8.0 Hz, 1H), 7.54-7.52 (d, J=8.0 Hz, 1H), 7.45-7.41 (t, J=8.0 Hz, 1H), 7.40-7.35 (m, 1H), 7.25-7.21 (t, J=8.0 Hz, 1H), 2.50 (s, 3H); $^{13}$C-NMR (100 MHz, CDCl$_3$) δ 161.9, 160.2, 157.6, 151.2, 146.5, 145.9, 139.7, 138.6, 132.3, 132.2, 130.1, 128.9, 127.6, 127.1, 126.5, 126.3, 125.1, 123.9, 115.9, 115.8, 115.1, 114.6, 10.9. HRMS [M+H]$^+$ (ESI-TOF) calcd for C$_{20}$H$_{15}$BrFN$_4$O 425.0413, found 425.0416. HPLC: $t_R$=9.03 min, 99.9%.

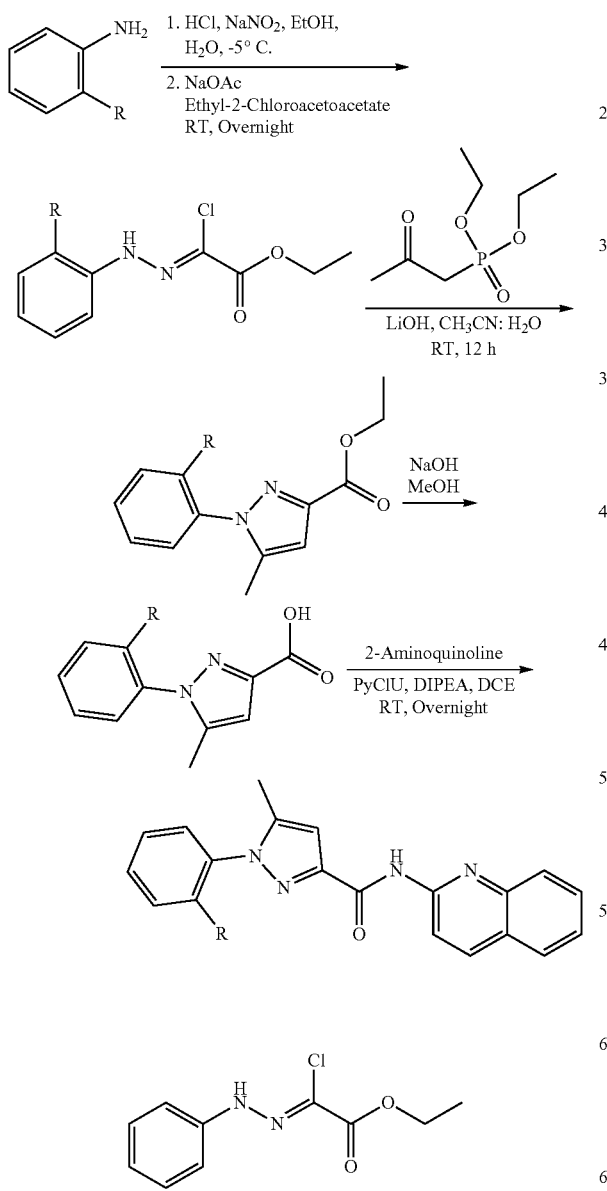

Scheme 5. Synthesis of Pyrazole-based Wnt/β-catenin signaling inhibitors.

(Z)-ethyl 2-chloro-2-(2-phenylhydrazono)acetate

Yellow solid. Yield: 95%. $^1$H-NMR (400 MHz, CDCl$_3$) δ 8.40 (s, 1H), 7.35-7.31 (t, J=8.0 Hz, 2H), 7.24-7.22 (d, J=8.0 Hz, 2H), 7.06-7.02 (t, J=8.0 Hz, 1H), 4.41-4.36 (q, J=7.2 Hz, 2H), 1.42-1.38 (t, J=7.2 Hz, 3H); $^{13}$C-NMR (100 MHz, CDCl$_3$) δ 159.7, 141.6, 129.4, 123.1, 115.9, 114.5, 62.8, 14.2.

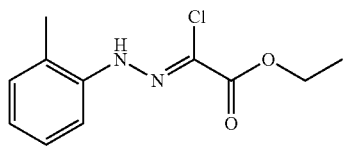 [SMILES: CCOC(=O)/C(Cl)=N/Nc1ccccc1C]

(Z)-ethyl 2-chloro-2-(2-(o-tolyl)hydrazono)acetate

Yellow solid. Yield: 88%. $^1$H-NMR (400 MHz, CDCl$_3$) δ 8.27 (s, 1H), 7.56-7.54 (d, J=8.0 Hz, 1H), 7.26-7.22 (t, J=8.0 Hz, 1H), 7.26-7.22 (t, J=8.0 Hz, 1H), 7.15-7.13 (d, J=8.0 Hz, 1H), 4.43-4.37 (q, J=7.2 Hz, 2H), 2.31 (s, 3H), 1.43-1.39 (t, J=7.2 Hz, 3H); $^{13}$C-NMR (100 MHz, CDCl$_3$) δ 159.7, 139.4, 130.7, 127.4, 122.8, 122.3, 116.8, 114.5, 62.8, 16.7, 14.2.

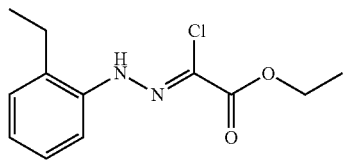 [SMILES: CCOC(=O)/C(Cl)=N/Nc1ccccc1CC]

(Z)-ethyl 2-chloro-2-(2-(2-ethylphenyl)hydrazono)acetate

Yellow solid. Yield: 90%. $^1$H-NMR (400 MHz, CDCl$_3$) δ 8.39 (s, 1H), 7.58-7.56 (d, J=8.0 Hz, 1H), 7.26-7.22 (t, J=8.0 Hz, 1H), 7.17-7.15 (d, J=8.0 Hz, 1H), 7.03-6.99 (t, J=8.0 Hz, 1H), 4.42-4.37 (q, J=7.2 Hz, 2H), 2.68-2.62 (q, J=8.0 Hz, 2H), 1.43-1.39 (t, J=7.2 Hz, 3H), 1.32-1.28 (t, J=8.0 Hz, 3H); $^{13}$C-NMR (100 MHz, CDCl$_3$) δ 159.7, 138.8, 128.7, 128.3, 127.4, 123.1, 116.6, 114.9, 62.7, 23.6, 14.2, 13.4.

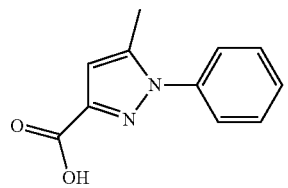

5-methyl-1-phenyl-1H-pyrazole-3-carboxylic acid

Yellow solid. Yield: 85% for two steps. $^1$H-NMR (400 MHz, CDCl$_3$) δ 7.51-7.47 m, 5H), 6.79 (s, 1H), 2.34 (s, 3H); $^{13}$C-NMR (100 MHz, CDCl$_3$) δ166.3, 142.8, 141.0, 138.9, 129.2, 128.8, 125.3, 109.6, 12.4.

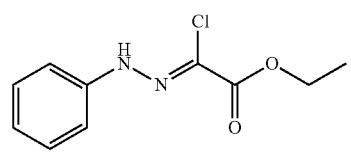

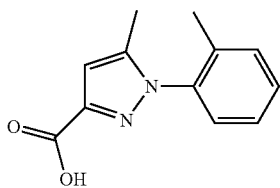 [SMILES: Cc1ccccc1-n1nc(C(=O)O)cc1C]

5-methyl-1-(o-tolyl)-1H-pyrazole-3-carboxylic acid

White solid. Yield: 80% for two steps. $^1$H-NMR (400 MHz, CDCl$_3$) δ 7.41-7.38 (t, J=6.8 Hz, 1H), 7.34-7.32 (d, J=8.4 Hz, 1H), 7.30-7.28 (d, J=8.4 Hz, 1H), 7.26-7.22 (t, J=6.8 Hz, 1H), 6.79 (s, 1H), 2.13 (s, 3H), 2.04 (s, 3H); $^{13}$C-NMR (100 MHz, CDCl$_3$) δ 166.1, 142.7, 141.9, 137.7, 135.8, 131.0, 129.9, 127.5, 126.6, 108.2, 17.1, 11.4.

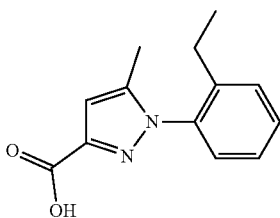 [SMILES: CCc1ccccc1-n1nc(C(=O)O)cc1C]

1-(2-ethylphenyl)-5-methyl-1H-pyrazole-3-carboxylic acid

Yellow solid. Yield: 70% for two steps. $^1$H-NMR (400 MHz, CDCl$_3$) δ 7.47-7.43 (t, J=6.8 Hz, 1H), 7.40-7.38 (d, J=6.8. Hz, 1H), 7.33-7.29 (d, J=6.8 Hz, 1H), 7.22-7.02 (d, J=7.6 Hz, 1H), 6.79 (s, 1H), 2.38-2.33 (q, J=7.2 Hz, 2H), 2.14 (s, 3H), 1.10-1.06 (t, J=7.2 Hz, 3H); $^{13}$C-NMR (100 MHz, CDCl$_3$) δ 165.8, 142.6, 142.1, 141.6, 137.1, 130.1, 129.4, 127.6, 126.6, 108.2, 23.8, 14.3, 11.5.

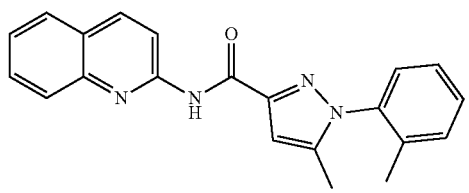 [SMILES: Cc1ccccc1-n1nc(C(=O)Nc2ccc3ccccc3n2)cc1C]

5-methyl-1-phenyl-N-(quinolin-2-yl)-1H-pyrazole-3-carboxamide (149)

White solid. Yield: 71%, 70 mg. $^1$H-NMR (400 MHz, CDCl$_3$) δ 9.65 (s, 1H), 8.62-8.60 (d, J=9.6 Hz, 1H), 8.21-8.18 (d, J=9.6 Hz, 1H), 7.86-7.84 (d, J=8.4 Hz, 1H), 7.79-7.77 (d, J=8.8 Hz, 1H), 7.67-7.63 (t, J=7.2 Hz, 1H), 7.56-7.41 (m, 6H), 6.86 (s, 1H), 2.39 (s, 3H); $^{13}$C-NMR (100 MHz, CDCl$_3$) δ 160.6, 150.9, 146.8, 146.1, 141.4, 139.1, 138.4, 129.8, 129.2, 128.6, 127.5, 127.4, 126.3, 125.0, 124.9, 114.4, 107.8, 12.6. HRMS [M+H]$^+$ (ESI-TOF) calcd for C$_{20}$H$_{17}$N$_4$O 329.1402, found 329.1406. HPLC: t$_R$=20.42 min, 99.9%.

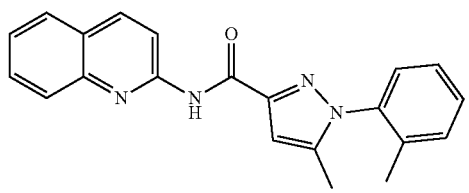 [SMILES: Cc1ccccc1-n1nc(C(=O)Nc2ccc3ccccc3n2)cc1C]

5-methyl-N-(quinolin-2-yl)-1-(o-tolyl)-1H-pyrazole-3-carboxamide (150)

White solid. Yield: 68%, 70 mg. $^1$H-NMR (400 MHz, CDCl$_3$) δ 9.63 (s, 1H), 8.61-8.59 (d, J=9.6 Hz, 1H), 8.19-8.17 (d, J=9.6 Hz, 1H), 7.82-7.80 (d, J=8.8 Hz, 1H), 7.78-7.76 (d, J=8.0 Hz, 1H), 7.65-7.61 (t, J=7.2 Hz, 1H), 7.45-7.28 (m, 4H), 7.28-7.26 (d, J=7.2 Hz, 1H), 6.86 (s, 1H), 2.16 (s, 3H), 2.08 (s, 3H); $^{13}$C-NMR (100 MHz, CDCl$_3$) δ 160.7, 150.9, 146.9, 146.1, 142.2, 138.3, 137.8, 135.9, 131.2, 129.8, 129.7, 127.5, 127.4, 127.4, 126.8, 126.2, 124.9, 114.3, 106.3, 17.2, 11.5. HRMS [M+H]$^+$ (ESI-TOF) calcd for C$_{21}$H$_{19}$N$_4$O 343.1559, found 343.1558. HPLC: t$_R$=8.54 min, 99.9%.

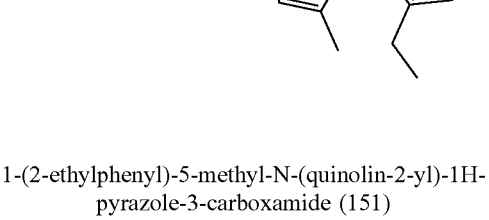

1-(2-ethylphenyl)-5-methyl-N-(quinolin-2-yl)-1H-pyrazole-3-carboxamide (151)

Yellow solid. Yield: 66%, 70 mg. $^1$H-NMR (400 MHz, CDCl$_3$) δ 9.63 (s, 1H), 8.62-8.60 (d, J=8.8 Hz, 1H), 8.19-8.17 (d, J=8.8 Hz, 1H), 7.8-7.80 (d, J=8.8 Hz, 1H), 7.77-7.75 (d, J=8.0 Hz, 1H), 7.64-7.60 (t, J=7.2 Hz, 1H), 7.50-7.39 (m, 3H), 7.37-7.33 (t, J=7.6 Hz, 1H), 7.25-7.23 (d, J=8.0 Hz, 1H), 6.86 (s, 1H), 2.44-2.40 (t, J=8.0 Hz, 2H), 2.15 (s, 3H), 1.13-1.09 (d, J=8.0 Hz, 3H); $^{13}$C-NMR (100 MHz, CDCl$_3$) δ 160.7, 150.9, 146.9, 146.0, 142.4, 141.7, 138.3, 137.3, 130.1, 129.8, 129.6, 127.6, 127.5, 126.7, 126.2, 124.9, 114.3, 106.3, 23.9, 14.5, 11.6. HRMS [M+H]$^+$ (ESI-TOF) calcd for C$_{22}$H$_{21}$N$_4$O 357.1715, found 357.1717. HPLC: t$_R$=11.11 min, 99.7%.

Scheme 6. Synthesis of pyrazoline-based Wnt/β-catenin signaling inhibitors with fused cycloalkyl rings.

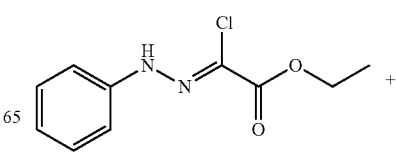

-continued

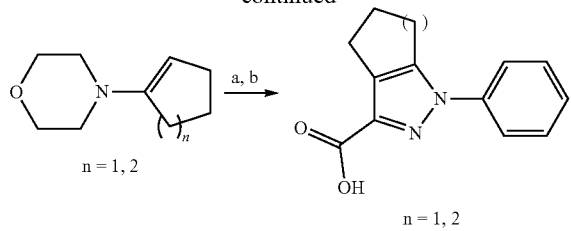

n = 1, 2

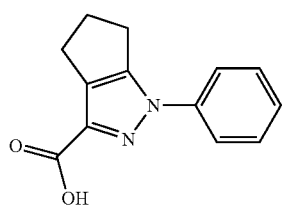 [SMILES: O=C(O)c1nn(-c2ccccc2)c2c1CCC2]

1-phenyl-1,4,5,6-tetrahydrocyclopenta[c]pyrazole-3-carboxylic acid

Brown solid. Yield: 78% for two steps. $^1$H-NMR (400 MHz, DMSO-d$_6$) δ 12.57 (s, 1H), 7.54-7.52 (d, J=8.0 Hz, 2H), 7.37-7.33 (t, J=8.0 Hz, 2H), 7.21-7.17 (t, J=8.0 Hz, 1H), 2.89-2.85 (t, J=7.2 Hz, 2H), 2.57-2.53 (t, J=7.2 Hz, 2H), 2.42-2.34 (m, 2H); $^{13}$C-NMR (100 MHz, DMSO-d$_6$) δ 168.3, 155.2, 144.4, 143.3, 136.7, 134.6, 131.9, 124.5, 35.3, 30.9, 28.4.

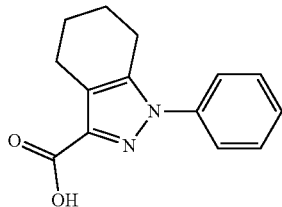 [SMILES: O=C(O)c1nn(-c2ccccc2)c2c1CCCC2]

1-phenyl-4,5,6,7-tetrahydro-1H-indazole-3-carboxylic acid

Brown solid. Yield: 65% for two steps. $^1$H-NMR (400 MHz, DMSO-d$_6$) δ 12.67 (s, 1H), 7.59-7.54 (m, 4H), 7.46-7.42 (t, J=7.2 Hz, 1H), 2.70 (m, 4H), 1.72 (m, 4H); $^{13}$C-NMR (100 MHz, DMSO-d$_6$) δ 169.0, 146.1, 145.3, 144.2, 134.5, 132.9, 128.6, 125.3, 28.0, 27.3, 27.2, 26.7.

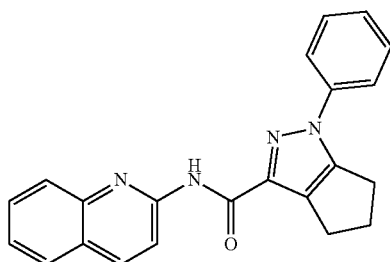

1-phenyl-N-(quinolin-2-yl)-1,4,5,6-tetrahydrocyclopenta[c]pyrazole-3-carboxamide (152)

White solid. Yield: 63%, 66 mg. $^1$H-NMR (400 MHz, CDCl$_3$) δ 9.62 (s, 1H), 8.63-8.51 (d, J=9.6 Hz, 1H), 8.19-8.17 (d, J=8.8 Hz, 1H), 7.90-7.88 (d, J=8.4 Hz, 1H), 7.79-7.77 (d, J=8.0 Hz, 1H), 7.75-7.7.73 (d, J=8.0 Hz, 1H), 7.69-7.65 (t, J=8.0 Hz, 1H), 7.50-7.42 (m, 3H), 7.34-7.30 (t, J=8.0 Hz, 1H), 3.05-3.01 (t, J=7.2 Hz, 2H), 2.98-2.94 (t, J=7.2 Hz, 2H), 2.71-2.66 (m, 2H); $^{13}$C-NMR (100 MHz, CDCl$_3$) δ 160.9, 151.0, 150.9, 146.8, 139.9, 139.7, 138.4, 131.5, 129.9, 129.4, 127.5, 127.4, 126.8, 126.3, 124.9, 119.5, 114.3, 31.0, 26.8, 23.5. HRMS [M+H]$^+$ (ESI-TOF) calcd for C$_{22}$H$_{19}$N$_4$O 355.1559, found 355.1564. HPLC: t$_R$=13.14 min, 99.8%.

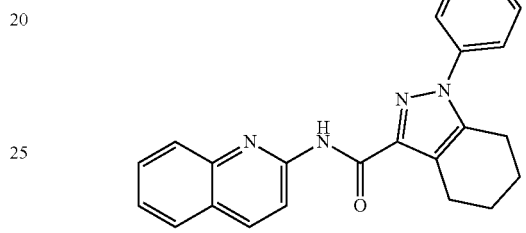

1-phenyl-N-(quinolin-2-yl)-4,5,6,7-tetrahydro-1H-indazole-3-carboxamide (153)

White solid. Yield: 65%, 70 mg. $^1$H-NMR (400 MHz, CDCl$_3$) δ 9.69 (s, 1H), 8.63-8.61 (d, J=8.8 Hz, 1H), 8.18-8.16 (d, J=8.8 Hz, 1H), 7.87-7.85 (d, J=8.8 Hz, 1H), 7.77-7.75 (d, J=8.0 Hz, 1H), 7.66-7.64 (d, J=8.0 Hz, 1H), 7.67-7.63 (t, J=8.0 Hz, 1H), 7.57-7.55 (d, J=8.0 Hz, 2H), 7.52-7.48 (t, J=8.0 Hz, 2H), 7.43-7.40 (m, 2H), 2.97 (m, 2H), 2.73 (m, 2H), 1.82 (m, 4H); $^{13}$C-NMR (100 MHz, CDCl$_3$) δ 161.6, 151.1, 146.9, 142.4, 140.9, 139.2, 138.3, 129.8, 129.2, 127.7, 127.5, 127.4, 126.2, 124.8, 123.5, 120.6, 114.3, 23.8, 22.6, 22.4, 21.6. HRMS [M+H]$^+$ (ESI-TOF) calcd for C$_{23}$H$_{21}$N$_4$O 369.1715, found 369.1717. HPLC: t$_R$=14.85 min, 99.9%.

Scheme 7. Synthesis of substituted pyrazoline-based Wnt/β-catenin signaling inhibitors.

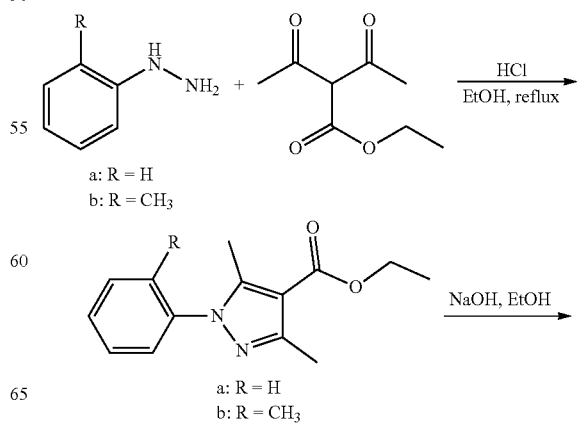

a: R = H
b: R = CH$_3$ a: R = H
b: R = CH$_3$

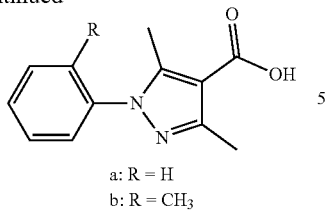

a: R = H
b: R = CH₃

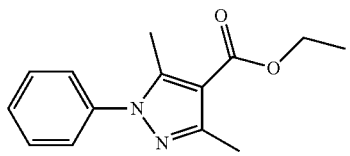 [SMILES: CCOC(=O)c1c(C)nn(-c2ccccc2)c1C]

Ethyl
3,5-dimethyl-1-phenyl-1H-pyrazole-4-carboxylate

Orange solid. Yield: 35%. ¹H-NMR (400 MHz, CDCl₃) δ 7.25-7.21 (t, J=8.0 Hz, 2H), 7.18-7.13 (m, 3H), 4.11-4.05 (q, J=7.2 Hz, 2H), 2.27 (s, 3H), 2.25 (s, 3H), 1.15-1.11 (t, J=7.2 Hz, 3H); ¹³C-NMR (100 MHz, CDCl₃) δ 164.4, 151.2, 144.3, 138.6, 128.9, 128.6, 128.2, 125.4, 121.6, 110.6, 59.5, 14.2, 14.1, 12.4.

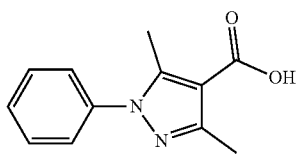 [SMILES: Cc1nn(-c2ccccc2)c(C)c1C(=O)O]

3,5-dimethyl-1-phenyl-1H-pyrazole-4-carboxylic acid

Off-white solid. Yield: 98%. ¹H-NMR (400 MHz, CDCl₃) δ 7.52-7.48 (t, J=8.0 Hz, 2H), 7.46-7.41 (m, 3H), 2.56 (s, 3H), 2.55 (s, 3H); ¹³C-NMR (100 MHz, CDCl₃) δ 170.2, 152.4, 145.7, 138.6, 129.2, 128.6, 125.7, 110.0, 14.3, 12.7.

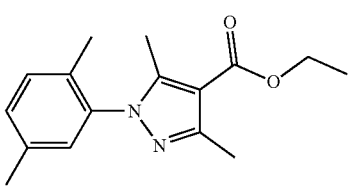 [SMILES: CCOC(=O)c1c(C)nn(-c2cc(C)ccc2C)c1C]

Ethyl 1-(2,5-dimethylphenyl)-3,5-dimethyl-1H-pyrazole-4-carboxylate

White solid. Yield: 1 g. ¹H-NMR (400 MHz, CDCl₃) δ 7.21-7.16 (m, 2H), 7.01 (s, 1H), 4.35-4.29 (q, J=7.2 Hz, 2H), 2.49 (s, 3H), 2.34 (s, 3H), 2.30 (s, 3H), 1.98 (s, 3H), 1.40-4.36 (t, J=7.2 Hz, 3H); ¹³C-NMR (100 MHz, CDCl₃) δ 164.7, 151.2, 145.3, 137.4, 136.6, 132.6, 130.7, 130.3, 128.2, 110.8, 59.6, 20.7, 16.7, 14.4, 14.3, 11.8.

1-(2,5-dimethylphenyl)-3,5-dimethyl-1H-pyrazole-4-carboxylic acid

Yellow solid. Yield: 98%. ¹H-NMR (400 MHz, DMSO-d₆) δ 7.29-7.27 (d, J=8.0 Hz, 1H), 7.25-7.23 (d, J=8.0 Hz, 1H), 7.09 (s, 1H), 2.35 (s, 3H), 2.31 (s, 3H), 2.21 (s, 3H), 1.90 (s, 3H); ¹³C-NMR (100 MHz, DMSO-d₆) δ 170.6, 155.1, 149.7, 142.5, 141.4, 137.3, 135.8, 135.3, 133.2, 114.8, 25.4, 21.5, 19.2, 16.7.

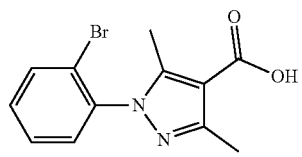 [SMILES: Cc1nn(-c2ccccc2Br)c(C)c1C(=O)O]

1-(2-bromophenyl)-3,5-dimethyl-1H-pyrazole-4-carboxylic acid

Yellow oil. Yield: 40%. ¹H-NMR (400 MHz, DMSO-d₆) δ 12.42 (s, 1H), 7.87-7.85 (d, J=8.0 Hz, 1H), 7.60-7.49 (m, 3H), 2.36 (s, 3H), 2.24 (s, 3H); ¹³C-NMR (100 MHz, DMSO-d₆) δ 170.3, 155.5, 150.4, 142.7, 138.4, 136.8, 135.3, 134.1, 126.7, 115.1, 19.2, 16.

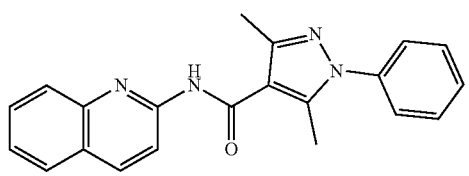 [SMILES: Cc1nn(-c2ccccc2)c(C)c1C(=O)Nc1ccc2ccccc2n1]

3,5-dimethyl-1-phenyl-N-(quinolin-2-yl)-1H-pyrazole-4-carboxamide (154)

White foam. Yield: 68%, 70 mg. ¹H-NMR (400 MHz, CDCl₃) δ 8.70 (br, 1H), 8.53-8.50 (d, J=8.8 Hz, 1H), 8.20-8.18 (d, J=8.8 Hz, 1H), 7.83-7.81 (d, J=8.8 Hz, 1H), 7.78-7.76 (d, J=8.8 Hz, 1H), 7.66-7.62 (t, J=8.0 Hz, 1H), 7.50-7.37 (m, 6H), 2.65 (s, 3H), 2.56 (s, 3H); ¹³C-NMR (100 MHz, CDCl₃) δ 163.4, 151.3, 147.8, 146.6, 142.8, 138.5, 129.9, 129.2, 128.6, 127.6, 127.2, 126.3, 125.6, 125.1, 114.8, 114.6, 14.2, 12.5. HRMS [M+H]⁺ (ESI-TOF) calcd for C₂₁H₁₉N₄O 343.1559, found 343.1556. HPLC: $t_R$=7.96 min, 99.8%.

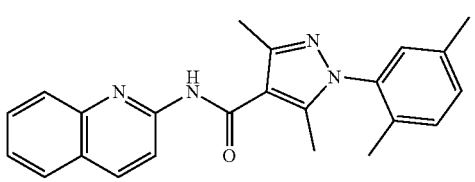 [SMILES: Cc1ccc(C)c(-n2nc(C)c(C(=O)Nc3ccc4ccccc4n3)c2C)c1]

1-(2,5-dimethylphenyl)-3,5-dimethyl-N-(quinolin-2-yl)-1H-pyrazole-4-carboxamide (155)

Yellow solid. Yield: 64%, 71 mg. $^1$H-NMR (400 MHz, CDCl$_3$) δ 8.44-8.42 (d, J=8.8 Hz, 1H), 8.39 (s, 1H), 8.11-8.09 (d, J=8.8 Hz, 1H), 7.75-7.73 (d, J=8.8 Hz, 1H), 7.70-7.68 (d, J=8.8 Hz, 1H), 7.58-7.54 (t, J=8.0 Hz, 1H), 7.36-7.32 (t, J=7.2 Hz, 1H), 7.13-7.09 (m, 2H), 6.90 (s, 1H), 2.58 (s, 3H), 2.29 (s, 3H), 2.25 (s, 3H), 1.91 (s, 3H); $^{13}$C-NMR (100 MHz, CDCl$_3$) δ 163.3, 151.3, 147.5, 146.8, 143.8, 138.4, 137.2, 136.7, 132.5, 130.8, 130.4, 129.9, 128.1, 127.6, 127.3, 126.3, 125.0, 114.6, 113.3, 20.7, 16.7, 14.4, 11.8. HRMS [M+H]$^+$ (ESI-TOF) calcd for C$_{23}$H$_{22}$N$_4$O 371.1872, found 371.1871. HPLC: $t_R$=9.03 min, 99.9%.

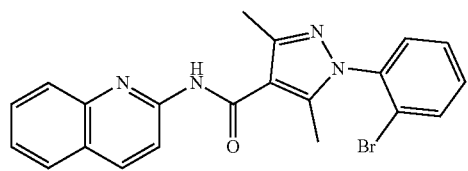 [SMILES: Cc1nn(-c2ccccc2Br)c(C)c1C(=O)Nc1ccc2ccccc2n1]

1-(2-bromophenyl)-3,5-dimethyl-N-(quinolin-2-yl)-1H-pyrazole-4-carboxamide (156)

White foam. Yield: 61%, 77 mg. $^1$H-NMR (400 MHz, CDCl$_3$) δ 8.52-8.50 (d, J=8.8 Hz, 1H), 8.47 (br, 1H), 8.20-8.18 (d, J=9.6 Hz, 1H), 7.84-7.82 (d, J=8.8 Hz, 1H), 7.79-7.77 (d, J=8.0 Hz, 1H), 7.73-7.71 (d, J=8.0 Hz, 1H), 7.67-7.63 (t, J=7.2 Hz, 1H), 7.47-7.42 (m, 2H), 7.38-7.34 (m, 2H), 2.67 (s, 3H), 2.43 (s, 3H); $^{13}$C-NMR (100 MHz, CDCl$_3$) δ 163.1, 151.2, 148.2, 146.7, 144.4, 138.5, 137.8, 133.5, 131.2, 129.9, 129.8, 128.5, 127.6, 127.3, 126.3, 125.1, 122.4, 114.6, 113.9, 14.4, 11.9. HRMS [M+H]$^+$ (ESI-TOF) calcd for C$_{21}$H$_{18}$BrN$_4$O 421.0664, found 421.0670. HPLC: $t_R$=4.89 min, 99.0%.

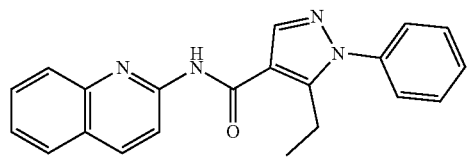 [SMILES: CCc1c(C(=O)Nc2ccc3ccccc3n2)cnn1-c1ccccc1]

5-ethyl-1-phenyl-N-(quinolin-2-yl)-1H-pyrazole-4-carboxamide (157)

White solid. Yield: 66%, 68 mg. $^1$H-NMR (400 MHz, CDCl$_3$) δ 8.66 (s, 1H), 8.55-8.53 (d, J=9.6 Hz, 1H), 8.20-8.18 (d, J=9.6 Hz, 1H), 8.06 (s, 1H), 7.85-7.83 (d, J=8.4 Hz, 1H), 7.80-7.78 (d, J=8.0 Hz, 1H), 7.69-7.65 (t, J=8.0 Hz, 1H), 7.54-7.43 (m, 6H), 3.09-3.04 (q, J=8.0 Hz, 2H), 1.25-1.21 (t, J=8.0 Hz, 3H); $^{13}$C-NMR (100 MHz, CDCl$_3$) δ 161.8, 151.2, 149.6, 146.7, 138.8, 138.5, 138.5, 130.0, 129.3, 129.1, 127.6, 127.2, 126.3, 125.9, 125.1, 114.5, 18.7, 13.7. HRMS [M+H]$^+$ (ESI-TOF) calcd for C$_{21}$H$_{19}$N$_4$O 343.1559, found 343.1558. HPLC: $t_R$=3.63 min, 95.0%.

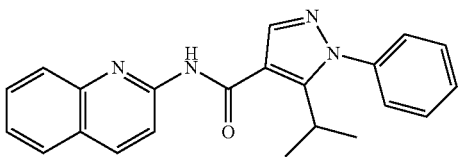 [SMILES: CC(C)c1c(C(=O)Nc2ccc3ccccc3n2)cnn1-c1ccccc1]

5-isopropyl-1-phenyl-N-(quinolin-2-yl)-1H-pyrazole-4-carboxamide (158)

White solid. Yield: 56%, 60 mg. $^1$H-NMR (400 MHz, CDCl$_3$) δ 8.83 (s, 1H), 8.55-8.53 (d, J=8.4 Hz, 1H), 8.19-8.17 (d, J=8.8 Hz, 1H), 8.00 (s, 1H), 7.83-7.81 (d, J=8.8 Hz, 1H), 7.79-7.77 (d, J=8.0 Hz, 1H), 7.66-7.62 (t, J=8.0 Hz, 1H), 7.51-7.49 (m, 3H), 7.45-7.41 (t, J=8.0 Hz, 1H), 7.39-7.37 (d, J=7.2 Hz, 2H), 3.35-3.31 (m, 1H), 1.42-1.40 (d, J=7.2 Hz, 6H); $^{13}$C-NMR (100 MHz, CDCl$_3$) δ 162.1, 152.6, 151.4, 146.7, 139.4, 138.5, 129.9, 129.3, 129.2, 127.6, 127.2, 126.6, 126.3, 125.0, 114.8, 114.5, 26.5, 20.5. HRMS [M+H]$^+$ (ESI-TOF) calcd for C$_{22}$H$_{20}$N$_4$O 357.1715, found 357.1719. HPLC: $t_R$=12.86 min, 99.9%.

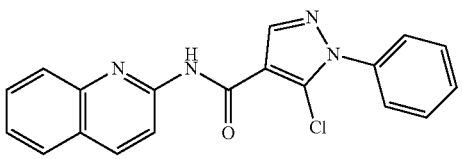 [SMILES: O=C(Nc1ccc2ccccc2n1)c1cnn(-c2ccccc2)c1Cl]

5-chloro-1-phenyl-N-(quinolin-2-yl)-1H-pyrazole-4-carboxamide (159)

White solid. Yield: 55%, 57 mg. $^1$H-NMR (400 MHz, CDCl$_3$) δ 8.93 (s, 1H), 8.53 (s, 1H), 8.27 (s, 1H), 8.22-8.20 (d, J=8.0 Hz, 1H), 7.86-7.84 (d, J=8.0 Hz, 1H), 7.80-7.78 (d, J=8.0 Hz, 1H), 7.68-7.64 (t, J=8.0 Hz, 1H), 7.55-7.45 (m, 5H); $^{13}$C-NMR (100 MHz, CDCl$_3$) δ 159.5, 150.8, 141.6, 139.9, 138.7, 138.6, 130.0, 129.6, 129.4, 129.2, 127.4, 126.5, 126.1, 125.3, 119.5, 115.3, 114.6. HRMS [M+H]$^+$ (ESI-TOF) calcd for C$_{19}$H$_{14}$ClN$_4$O 349.0856, found 349.0652. HPLC: $t_R$=13.58 min, 99.0%.

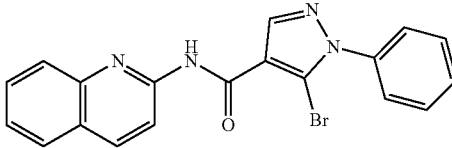

5-bromo-1-phenyl-N-(quinolin-2-yl)-1H-pyrazole-4-carboxamide (160)

White solid. Yield: 60%, 70 mg. $^1$H-NMR (400 MHz, CDCl$_3$) δ 8.94 (s, 1H), 8.56-8.54 (d, J=8.0 Hz, 1H), 8.29 (s, 1H), 8.22-8.20 (d, J=8.0 Hz, 1H), 7.87-7.85 (d, J=8.4 Hz, 1H), 7.81-7.79 (d, J=8.0 Hz, 1H), 7.70-7.66 (t, J=8.0 Hz, 1H), 7.54 (m, 5H), 7.48-7.44 (d, J=8.0 Hz, 1H); $^{13}$C-NMR (100 MHz, CDCl$_3$) δ 161.0, 150.8, 142.1, 138.7, 138.2, 130.0, 129.5, 129.2, 127.6, 127.4, 126.5, 126.2, 125.3, 119.6, 117.9, 114.8, 114.6. HRMS [M+H]$^+$ (ESI-TOF) calcd for C$_{19}$H$_{14}$BrN$_4$O 393.0351, found 393.0355. HPLC: t$_R$=13.12 min, 99.2%.

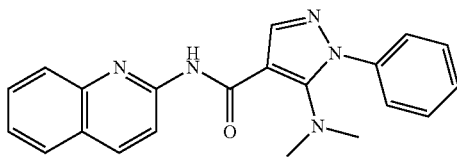

5-(dimethylamino)-1-phenyl-N-(quinolin-2-yl)-1H-pyrazole-4-carboxamide (161)

White solid. Yield: 80%, 86 mg. $^1$H-NMR (400 MHz, CDCl$_3$) δ 9.81 (s, 1H), 8.59-8.57 (d, J=8.8 Hz, 1H), 8.19-8.17 (d, J=8.8 Hz, 1H), 8.15 (s, 1H), 7.86-7.84 (d, J=8.0 Hz, 1H), 7.79-7.77 (d, J=8.8 Hz, 1H), 7.67-7.63 (t, J=8.0 Hz, 1H), 7.55-7.46 (m, 5H), 7.45-7.41 (t, J=8.0 Hz, 1H), 2.84 (s, 6H); $^{13}$C-NMR (100 MHz, CDCl$_3$) δ 161.1, 151.4, 150.5, 146.8, 141.2, 139.7, 138.3, 129.8, 129.3, 129.1, 127.5, 127.4, 126.3, 125.7, 124.8, 114.7, 109.5, 43.1. HRMS [M+H]$^+$ (ESI-TOF) calcd for C$_{21}$H$_{20}$N$_5$O 358.1668, found 358.1666. HPLC: t$_R$=12.40 min, 97.8%.

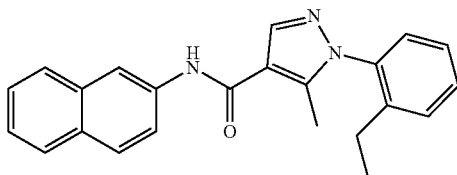

1-(2-ethylphenyl)-5-methyl-N-(naphthalen-2-yl)-1H-pyrazole-4-carboxamide (162)

$^1$H-NMR (400 MHz, CDCl$_3$) δ 8.29 (s, 1H), 8.19 (s, 1H), 8.06 (s, 1H), 7.78-7.76 (m, 3H), 7.58-7.56 (d, J=8.0 Hz, 1H), 7.46-7.38 (m, 4H), 7.31-7.27 (t, J=8.0 Hz, 1H), 7.17-7.15 (d, J=8.0 Hz, 1H), 2.42 (s, 3H), 2.38-2.32 (q, J=8.0 Hz, 2H), 1.10-1.06 (t, J=8.0 Hz, 3H); $^{13}$C-NMR (100 MHz, CDCl$_3$) δ 162.3, 144.2, 141.8, 137.9, 136.9, 135.6, 133.9, 130.6, 130.1, 129.5, 128.6, 127.7, 127.5, 126.7, 126.4, 124.9, 120.4, 117.0, 114.9, 23.9, 14.4, 11.4. HRMS [M+H]$^+$ (ESI-TOF) calcd for C$_{23}$H$_{22}$N$_3$O 356.1763, found 356.1766. HPLC: t$_R$=12.83 min, 98.0%.

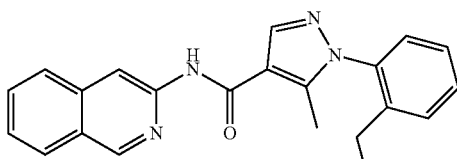

1-(2-ethylphenyl)-N-(isoquinolin-3-yl)-5-methyl-1H-pyrazole-4-carboxamide (163)

$^1$H-NMR (400 MHz, CDCl$_3$) δ 8.98 (s, 1H), 8.70 (s, 1H), 8.65 (s, 1H), 8.08 (s, 1H), 7.88-7.7.86 (d, J=8.8 Hz, 1H), 7.83-7.81 (d, J=8.8 Hz, 1H), 7.64-7.60 (t, J=8.0 Hz, 1H), 7.47-7.43 (m, 2H), 7.40-7.38 (d, J=8.0 Hz, 1H), 7.33-7.29 (t, J=7.2 Hz, 1H), 7.21-7.19 (d, J=8.4 Hz, 1H), 2.47 (s, 3H), 2.39-2.34 (q, J=7.2 Hz, 2H), 1.10-1.06 (t, J=7.2 Hz, 3H); $^{13}$C-NMR (100 MHz, CDCl$_3$) δ 161.9, 151.1, 146.5, 144.2, 141.8, 138.0, 136.9, 130.8, 130.0, 129.5, 127.7, 126.8, 126.7, 126.4, 125.7, 114.6, 107.9, 23.9, 14.4, 11.5. HRMS [M+H]$^+$ (ESI-TOF) calcd for C$_{22}$H$_{21}$N$_4$O 357.1715, found 357.1709. HPLC: t$_R$=10.40 min, 99.9%.

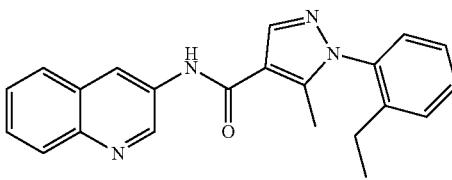

1-(2-ethylphenyl)-5-methyl-N-(quinolin-3-yl)-1H-pyrazole-4-carboxamide (164)

$^1$H-NMR (400 MHz, CDCl$_3$) δ 8.88 (s, 1H), 8.78 (s, 1H), 8.69 (s, 1H), 8.13 (s, 1H), 8.02-8.00 (d, J=8.8 Hz, 1H), 7.76-7.74 (d, J=8.0 Hz, 1H), 7.61-7.57 (t, J=8.0 Hz, 1H), 7.52-7.48 (t, J=8.0 Hz, 1H), 7.44-7.40 (t, J=8.0 Hz, 1H), 7.38-7.36 (d, J=8.0 Hz, 1H), 7.30-7.26 (t, J=8.0 Hz, 1H), 7.18-7.16 (d, J=8.0 Hz, 1H), 2.42 (s, 3H), 2.36-2.30 (d, J=8.0 Hz, 2H), 1.08-1.04 (t, J=8.0 Hz, 3H); $^{13}$C-NMR (100 MHz, CDCl$_3$) δ 162.6, 144.9, 144.6, 144.5, 141.7, 138.1, 136.8, 131.9, 130.1, 129.5, 128.8, 128.2, 127.7, 127.2, 126.7, 124.4, 114.4, 23.8, 14.4, 11.4. HRMS [M+H]$^+$ (ESI-TOF) calcd for C$_{22}$H$_{21}$N$_4$O 357.1715, found 357.1710. HPLC: t$_R$=7.81 min, 99.4%.

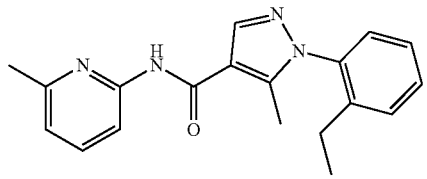 [SMILES: CCc1ccccc1-n1ncc(C(=O)Nc2cccc(C)n2)c1C]

1-(2-ethylphenyl)-5-methyl-N-(6-methylpyridin-2-yl)-1H-pyrazole-4-carboxamide (165)

$^1$H-NMR (400 MHz, CDCl$_3$) δ 8.52 (s, 1H), 8.12-8.10 (d, J=8.0 Hz, 1H), 8.00 (s, 1H), 7.60-7.56 (t, J=8.0 Hz, 1H), 7.43-7.39 (t, J=8.0 Hz, 1H), 7.37-7.35 (d, J=8.0 Hz, 1H), 7.30-7.26 (t, J=8.0 Hz, 1H), 7.17-7.15 (d, J=8.0 Hz, 1H), 6.87-6.85 (d, J=8.0 Hz, 1H), 2.42 (s, 3H), 2.39 (s, 3H), 2.35-2.29 (q, J=8.0 Hz, 2H), 1.06-1.02 (t, J=8.0 Hz, 3H); $^{13}$C-NMR (100 MHz, CDCl$_3$) δ 161.9, 156.7, 150.9, 144.3, 141.7, 138.6, 138.1, 136.9, 130.0, 129.5, 127.7, 126.6, 119.0, 114.5, 110.9, 23.9, 23.8, 14.4, 11.4. HRMS [M+H]$^+$ (ESI-TOF) calcd for C$_{19}$H$_{21}$N$_4$O 321.1715, found 321.1712. HPLC: t$_R$=5.18 min, 99.0%.

HPLC Conditions for foregoing compounds in Example 2. Method A: 45% Acetonitrile/55% H$_2$O (0.1% TFA), 1 mL/min.

Example 3: YW1149 as a Candidate Compound to Suppress Glucose Production in Hepatocytes The assay provided herein is a dual-luciferase assay to measure Wnt/β-catenin pathway activation using a TCF/LEF responsive reporter construct similar to that described previously (Thorne et al., 2010). In this assay, HEK293 cells were transiently transfected with firefly luciferase plasmid containing the latter construct and constitutively active *renilla* luciferase expression plasmids as control. Lithium chloride (LiCl), which has been previously established as an activator of Wnt/β-catenin pathway through its direct and indirect effects on GSK3β, was used for pathway activation. The inhibition of Wnt/β-catenin pathway by a compound can be determined after its incubation with the cells for 24 hours. This assay has been validated with different Wnt pathway inhibitors/activators (data not shown) and by analyzing the protein and gene expression of pathway components via immunoblotting and RT-PCR.

As shown in FIG. 1, YW1149 is a more potent inhibitor of the Wnt/β-catenin pathway ($IC_{50}$=74 nM) as compared to pyrvinium ($IC_{50}$=273 nM).

In light of this evidence, a class of triazole-based inhibitors were synthesized and tested, as described herein. This new scaffold contains four key structural features: (1) the permanent charge, which is a major reason for the low bioavailability of pyrvinium (Smith et al., 1976), has been removed by replacing the methylquinoline moiety with a quinolone moiety; (2) the alkenyl linker that causes the poor aqueous solubility and poor stability of pyrvinium, was replaced by an amide linker. The amide bond is more stable under physiological conditions; moreover, the NH and carbonyl groups can form additional H-bonding interactions to amino acid residues critical for their inhibitory activities; (3) the well-documented chemically unstable 2,5-dimethylpyrrole moiety (Zhu et al., 2013) has been replaced by a triazole ring; and (4) the right end phenyl group was replaced by an o-methoxy-phenyl group. These efforts have yielded the identification of one novel pyrvinium analog YW1149, which inhibits Wnt signaling activity with significantly improved potency ($IC_{50}$=74 nM) compared to pyrvinium ($IC_{50}$=273 nM), using the cellular luciferase gene reporter assay described above. Moreover, this new inhibitor reduces glucose production in primary hepatocytes, and is nontoxic even at higher concentrations in vivo, and shows improved PK profile comparing to pyrvinium.

Example 4: Pharmacological Validation of Wnt/β-Catenin Pathway Inhibition as a Strategy to Treat Type 2 Diabetes Reduced Wnt/β-catenin signaling activity may confer a reduced risk of type 2 diabetes. The potential of Wnt/β-catenin signaling inhibition by small molecules as a strategy to treat type 2 diabetes was explored. Without being limited to any one theory of the invention, the working hypothesis is that the compounds of the invention can work through inhibition of hepatic Wnt/β-catenin pathway to reduce glucose production and treat type 2 diabetes.

With the transgenic mice overexpressing the Wnt pathway classical effector Tcf7l2, global upregulation of Wnt signaling has been suggested to confer an increased risk of metabolic dysregulation (Bailey et al., 2015; Savic et al., 2011). In contrast, as demonstrated in Tcf7l2+/− mice, global downregulation of the pathway leads to the resistance to high fat diet-induced metabolic disorders (Savic et al., 2011; Yang et al., 2012). The hepatic Wnt signaling likely plays a critical role in the effect on metabolic homeostasis. Hepatic deletion of either β-catenin or Tcf7l2 reduces hepatic glucose production in adult liver-specific knockout mice which display significantly improved metabolic homeostasis when maintained on a high-fat diet (Boj et al., 2012; Liu et al., 2011). Thus, downregulation of Wnt/β-catenin pathway may serve as a strategy to treat metabolic disorders including type 2 diabetes.

Figure 2A:
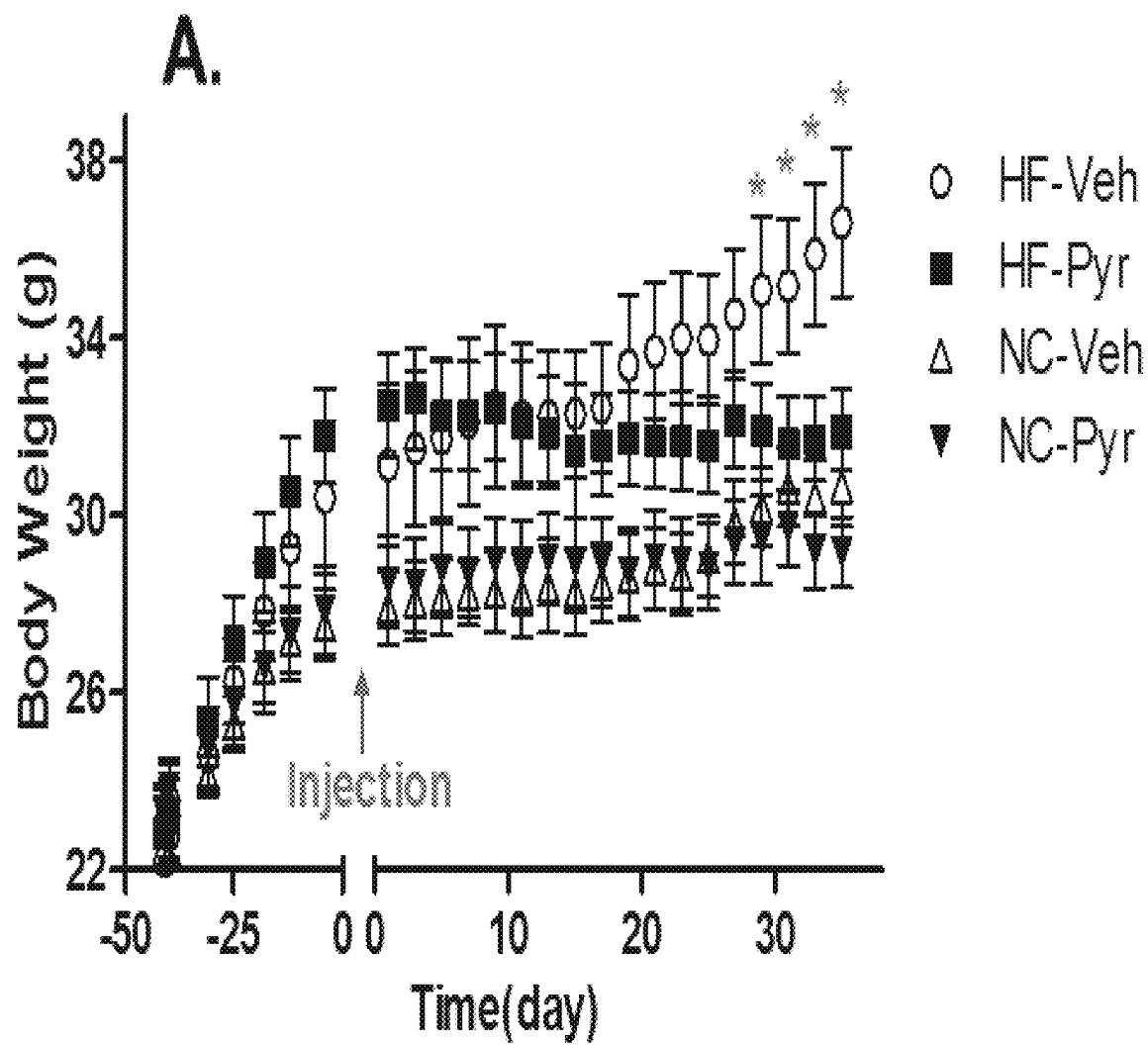
FIGS. 2A and 2B illustrate the effects of pyrvinium treatment on body weight gain and glucose tolerance in mice. C57BL/6 mice (n=6/group) were put either on high-fat (HF) or normal chow (NC) diet. Seven weeks after the start of the HF diet, the mice received either pyrvinium (Pyr) (initial 0.2 mg/kg/2 days and increased to 0.5 mg/kg/2 days from day 20) or vehicle (Veh) by I.P. for 5 weeks. Body weight monitoring during the study is shown in FIG. 2A. Intraperitoneal glucose tolerance test (GTT) is shown in FIG. 2B. GTT was conducted at the end of the study. *$P<0.05$ compared to the other 3 groups.
Figure 2B:
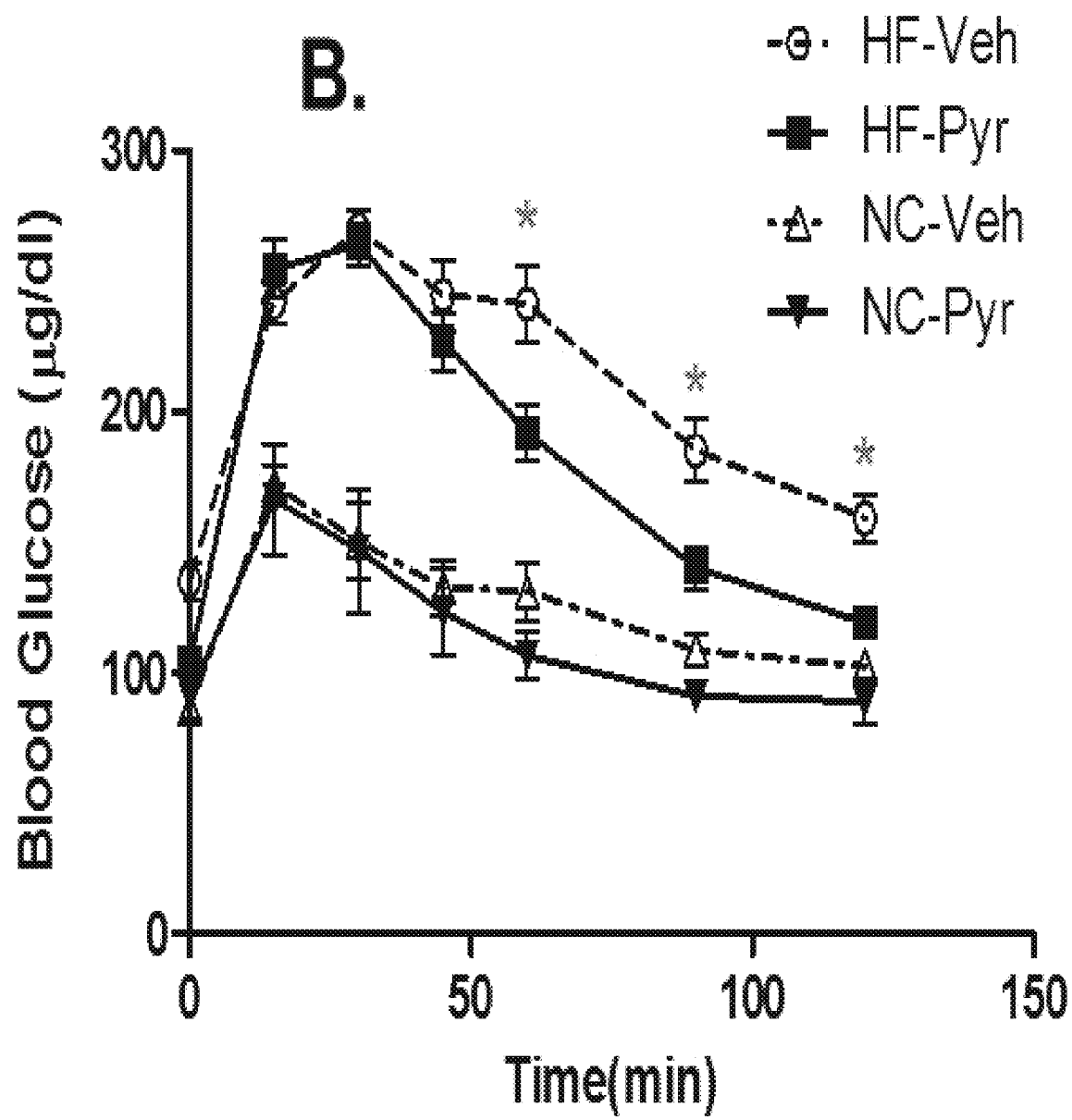
Figure 3:
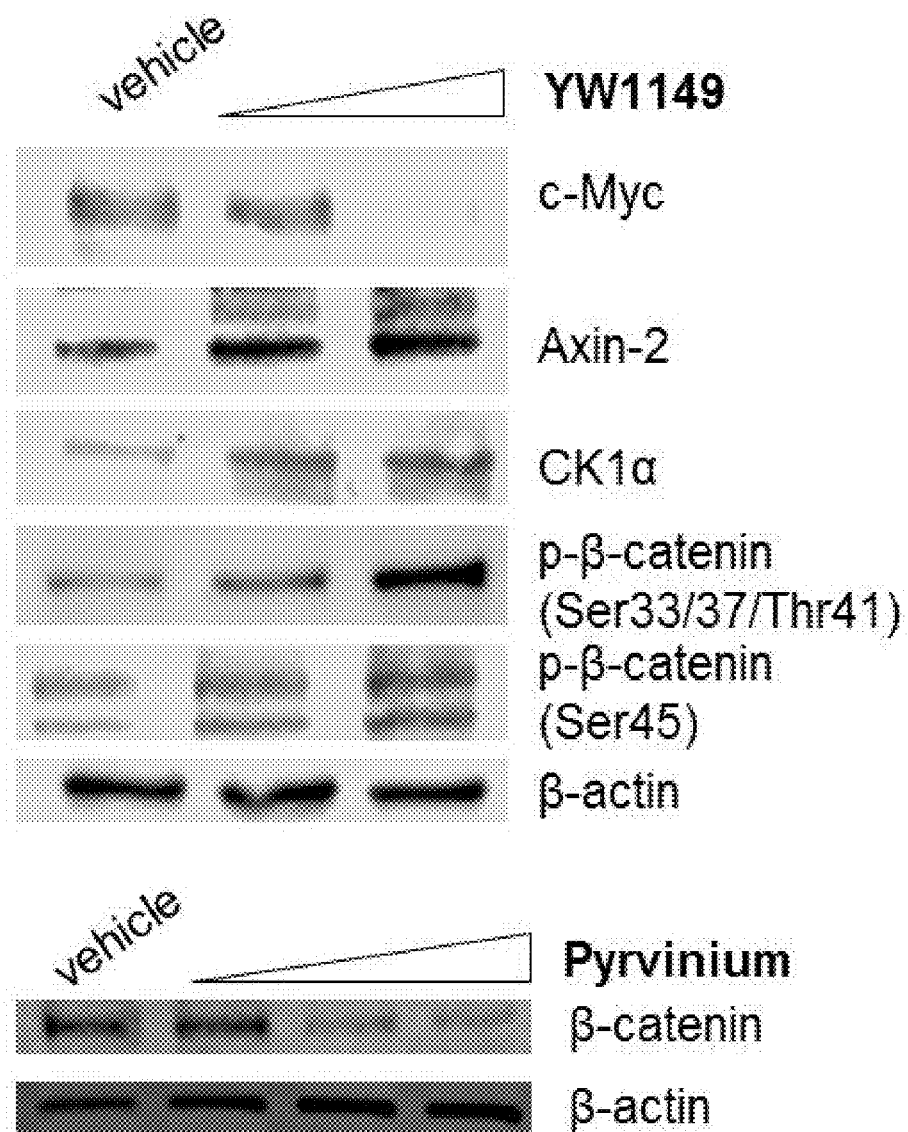
FIG. 3 illustrates the effect of treatment of YW1149 or pyrvinium on the expression of Wnt pathway proteins. HepG2 cells were treated by YW1149 (vehicle, 0.1, 1 μM). HEK293 cells treated by pyrvinium (vehicle, 0.1, 1, 10 μM).

In the foregoing studies, intraperitoneal pyrvinium injection was able to decrease weight gain in mice fed with a high fat diet (FIG. 2). Glucose tolerance was also improved in the mice. Pyrvinium and YW1149 treatment in HepG2 cells showed results consistent with inhibition of the Wnt pathway—attenuation of β-catenin and the target gene c-Myc, as well as increased Axin protein expression (FIG. 3). In addition, both compounds could significantly suppress glucose production and the expression of glucose 6-phosphatase (G6P), a key gluconeogenic enzyme (Boj et al., 2012; Yang et al., 2012), and increase phosphorylation of AMPK, a key kinase involved in energy metabolism (Shu et al., 2007), in hepatic HepG2 cells (FIG. 4). While overt toxicity was not observed by 0.5 mg/kg/3 days of pyrvinium in the mice, a single dose of 2 mg/kg of pyrvinium has caused mouse death. This narrow therapeutic window, along with undesirable PK properties of pyrvinium, allows the research to focus towards YW1149 and additional analogs that are more potent Wnt pathway inhibitors but possess less toxicity.

Example 5: Pharmacokinetic Properties and Toxicity of YW1149

Pyrvinium has poor bioavailability (Smith et al., 1976) and little evidence is available for pyrvinium analogs when administered orally, which is an essential consideration in antidiabetic drug development. The objective is to characterize the absorption, distribution, metabolism and excretion (ADME) properties and toxicity of the compounds of the invention.

Figure 5A:
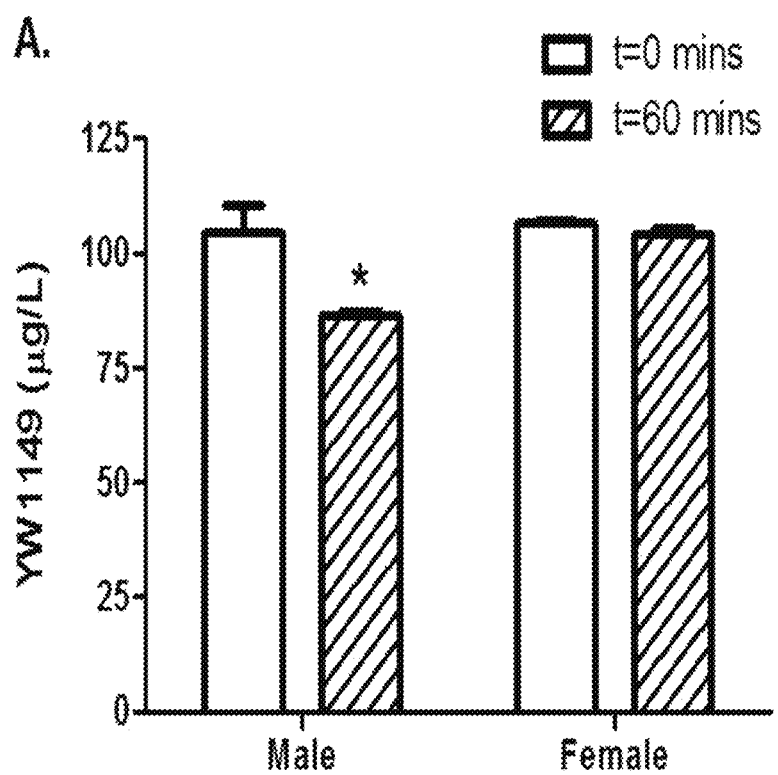
FIGS. 5A and 5B illustrate the the metabolic stability of YW1149. S9 fraction from mouse liver tissues (FIG. 5A) and mouse plasma samples (FIG. 5B) were mixed with YW1149 and incubated at 37 degrees, respectively. *$P<0.05$ as compared to time 0.
Figure 5B:
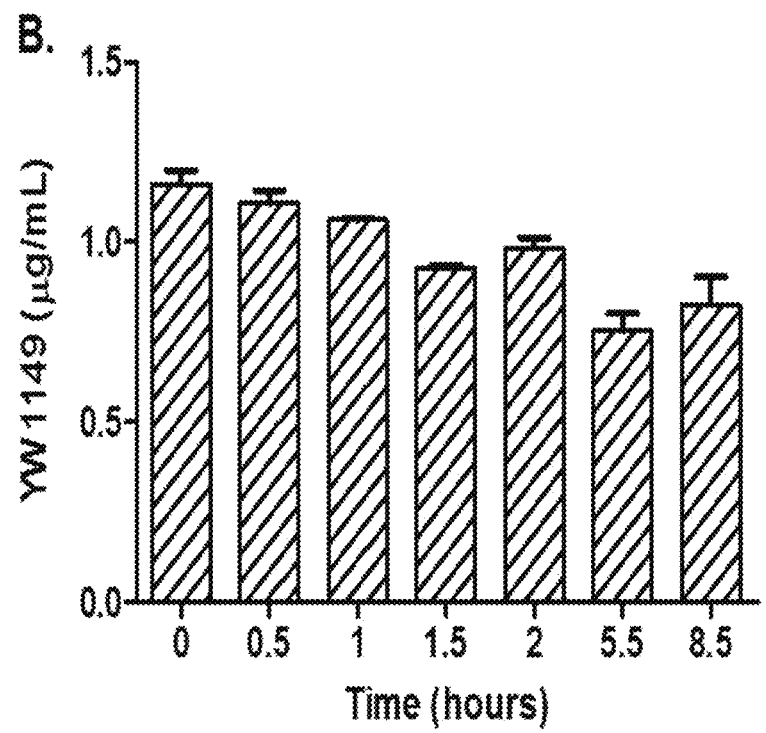

Permeability studies were performed with pyrvinium and the compound YW2013, using Madin-Darby Canine Kidney (MDCK) epithelial cell monolayer formed on transwell cell culture plates. There was significant apical-to-basolateral and basolateral-to-apical flux for YW2013 while pyrvinium was detected below the limit of detection (data not shown). This suggested that the compounds of the invention could have improved cellular permeability and bioavailability. The metabolic stability of these compounds was then estimated using YW1149 as a prototypical compound, with in vitro substrate depletion in mouse liver tissue S9 fraction as previously described (Jones and Houston, 2004). Only minor metabolism was observed after one hour, suggesting that this compound might be metabolically stable (FIG. 5A). More so, YW1149 was stable in plasma for up to eight hours (FIG. 5B), which suggests that biotransformation, if any, would occur in the tissues.

Figure 6A:
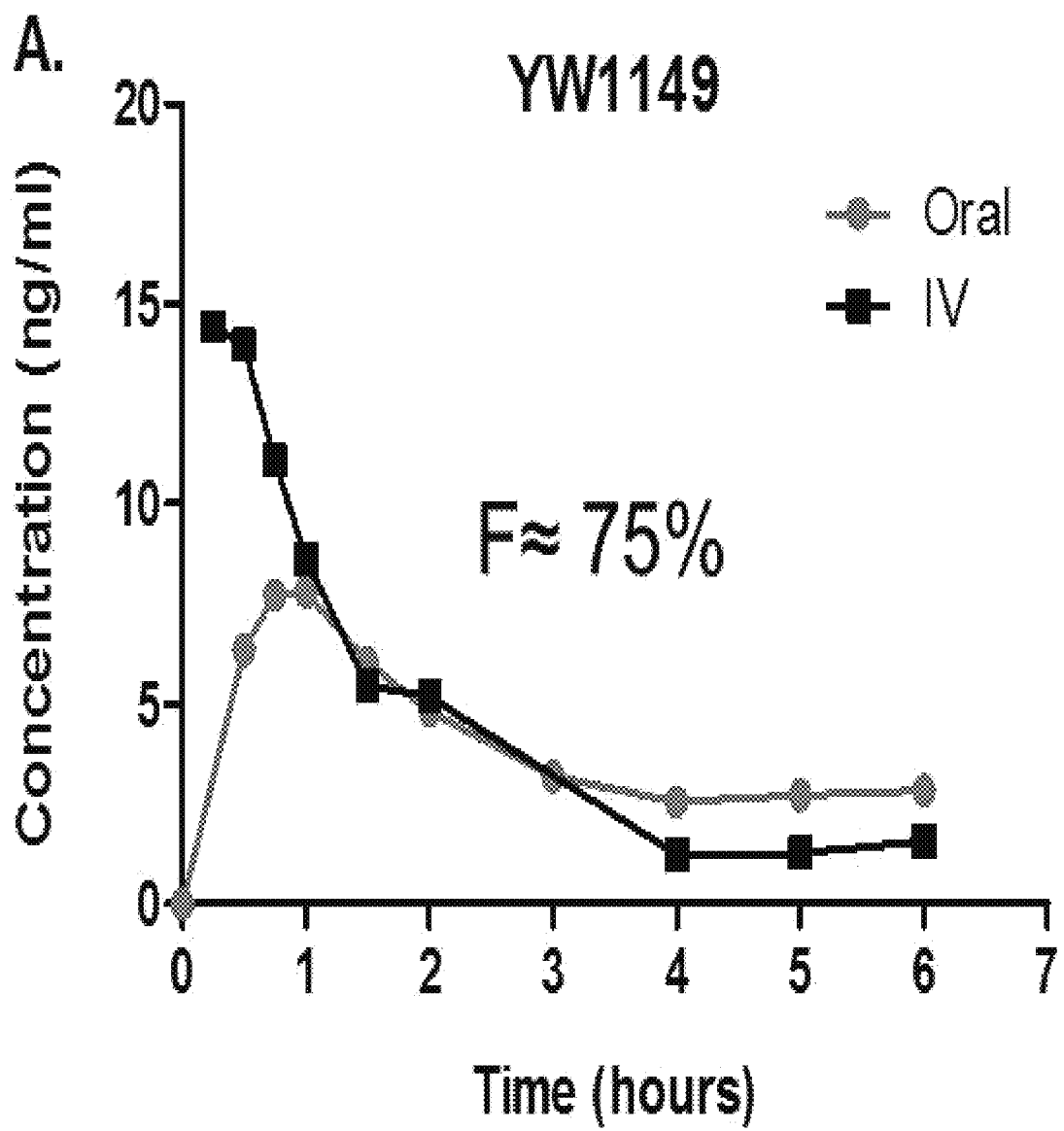
FIGS. 6A and 6B illustrate a pharmacokinetic study for YW1149 and pyrvinium in mice. Single intravenous (IV, tail vein) and oral administration of YW1149 (10 mg/kg) (FIG. 6A) and pyrvinium pamoate (2 mg/kg) (FIG. 6B) were dosed in 12-week old C57BL/6 mice, respectively. The mice that received IV pyrvinium died after thirty minutes. Representative data from each group is shown.
Figure 6B:
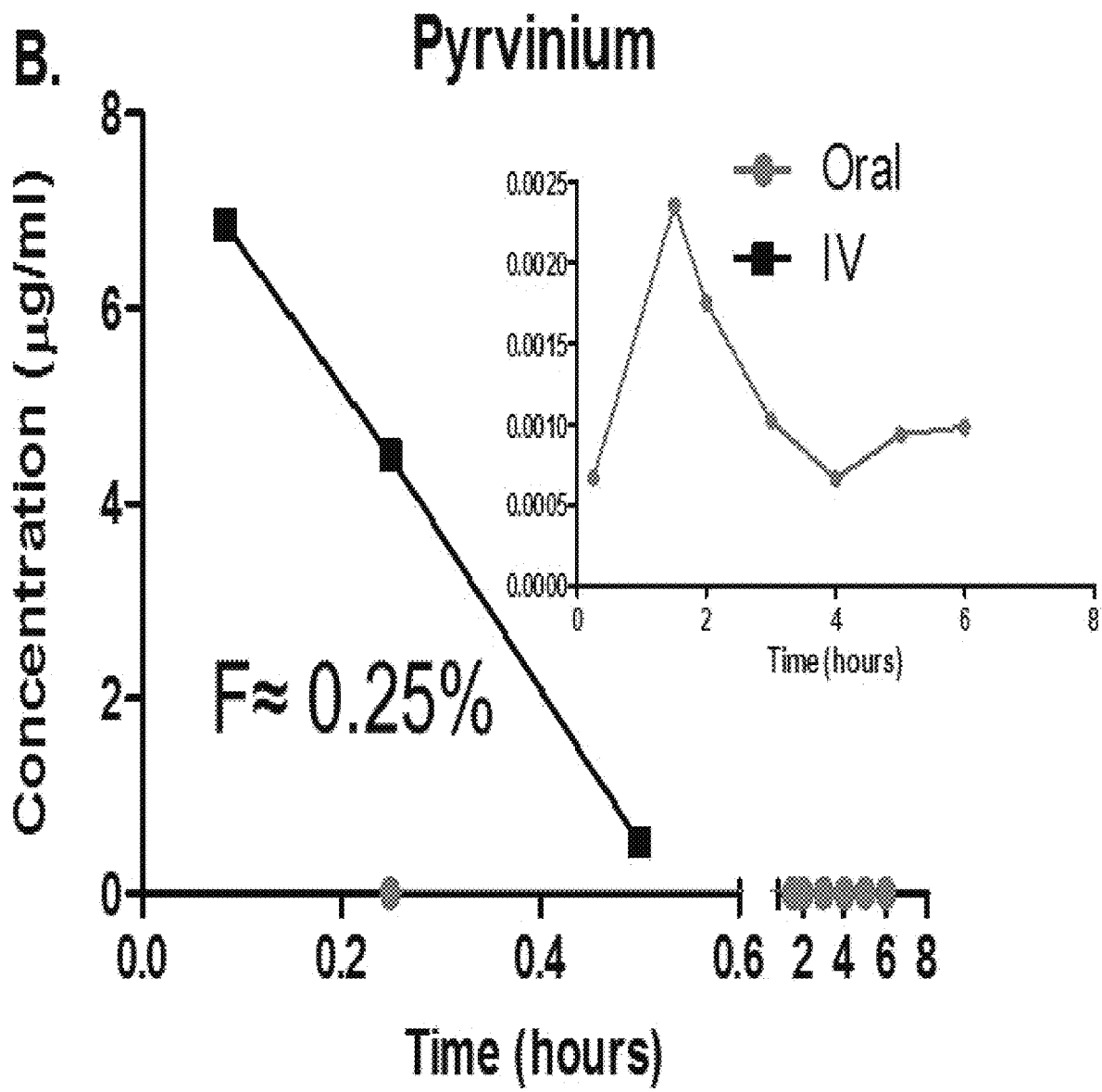

A pilot pharmacokinetic study was followed up for both YW1149 and pyrvinium (FIG. 6). Single intravenous and oral administration of pyrvinium pamoate (2 mg/kg) and YW1149 (10 mg/kg) was initiated in 12-week old C57BL/6 mice respectively. Blood samples were collected at multiple time points. The mouse intravenously administered with pyrvinium pamoate died after thirty minutes so blood collection was discontinued. Ultra-performance liquid chromatography system with a triple quadruple detector (UPLC/TQD) was used for compound quantitation. It was found that pyrvinium exhibited little or no absorption. The intravenous half-life of this drug was about six minutes while oral half-life extended to about one hour as calculated using Phoenix Winnolin non-compartmental analysis function. Intravenous YW1149 showed a half-life of one hour. The bioavailability (F) of YW1149 was 0.75, which was much higher than that of pyrvinium (0.0025).

Figure 7A:
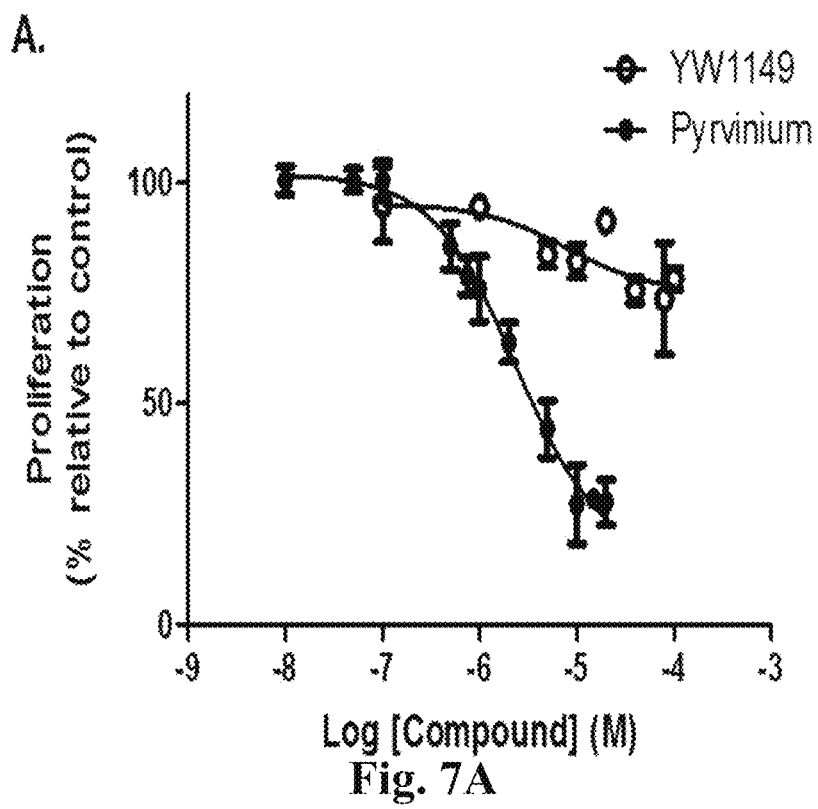
FIGS. 7A and 7B illustrate a comparison of cytotoxicity and mouse toxicity between YW1149 and pyrvinium.
Figure 7B:
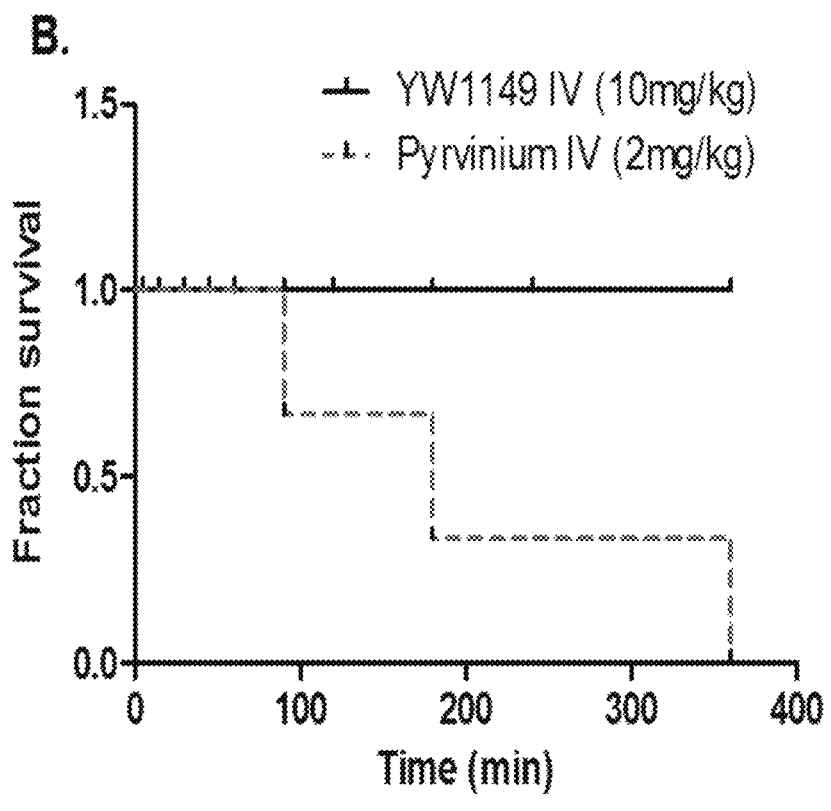

The cytotoxicity of series of a compound of the invention was measured using a colorimetric assay, Cell Counting Kit-8 (Sigma) in HEK293 cells. While YW1149 was a more potent Wnt pathway inhibitor (FIG. 1), it caused less cytotoxicity with an anti-proliferation $IC_{50}$ above 100 μM, as compared to pyrvinium ($IC_{50}$: 2 μM) (FIG. 7A). Consistently, in a preliminary survival study, mice died within 6 hours after a single dose of 2 mg/kg pyrvinium but a dose of 10 mg/kg YW1149 was tolerated well in another group of mice (FIG. 7B).

Example 6: Cancer Cell Proliferation and Growth Inhibition Assays for Compounds of the Invention Compounds of the invention were tested to determine their growth inhibiting activity against a variety of cancer cell lines which are described in FIG. 10.

Cell Culture.

The human colorectal cancer cell lines HT-29, HCT-116, WiDr, SW620, SW480, T84; human lung cancer cell line A549; human breast cancer cell line MCF-7; human hepatocarcinoma HepG2; and human cervical cancer cell line Hela were purchased from ATCC. HT-29 and HCT116 were maintained in McCoy's 5a with 10% FBS, HepG2 were maintained in low glucose DMEM with 20% FBS and the other cells were maintained in high glucose DMEM with 10% FBS.

Cell Proliferation and Growth Inhibition Assay.

HT-29, HCT-116, WiDr, SW620, SW480, T84, A549, MCF-7, HepG2, Hela cells were cultured in respective growth medium. Cells of log phase were used. 3000-5000 cells/well were seeded in 96-well plates with a 100 μL volume. After 24 h, Compounds were dissolved to 50 μM with DMSO, and a 3-fold serial dilution of the compounds from $5\times10^{-5}$ M to $23\times10^{-9}$ M was performed. 2 μL of compound solution was added to 998 μL of growth medium, the mixture was vortexed sufficiently. 100 μL of the mixture was correspondingly added to the 96-well plate. 2 μL DMSO instead of compound solution was used as the 0% inhibitor control. After coincubation for 72 h, the old medium was removed and 100 μL of 10% CCK-8 in culture medium was added. 2 h later the plates were read in the microplate reader (Bio-Rad) at 450 nm. The data was calculated using Graph Pad Prism version 5.0. The $IC_{50}$ were fitted using a nonlinear regression model with a sigmoidal dose response.

Figure 8A:
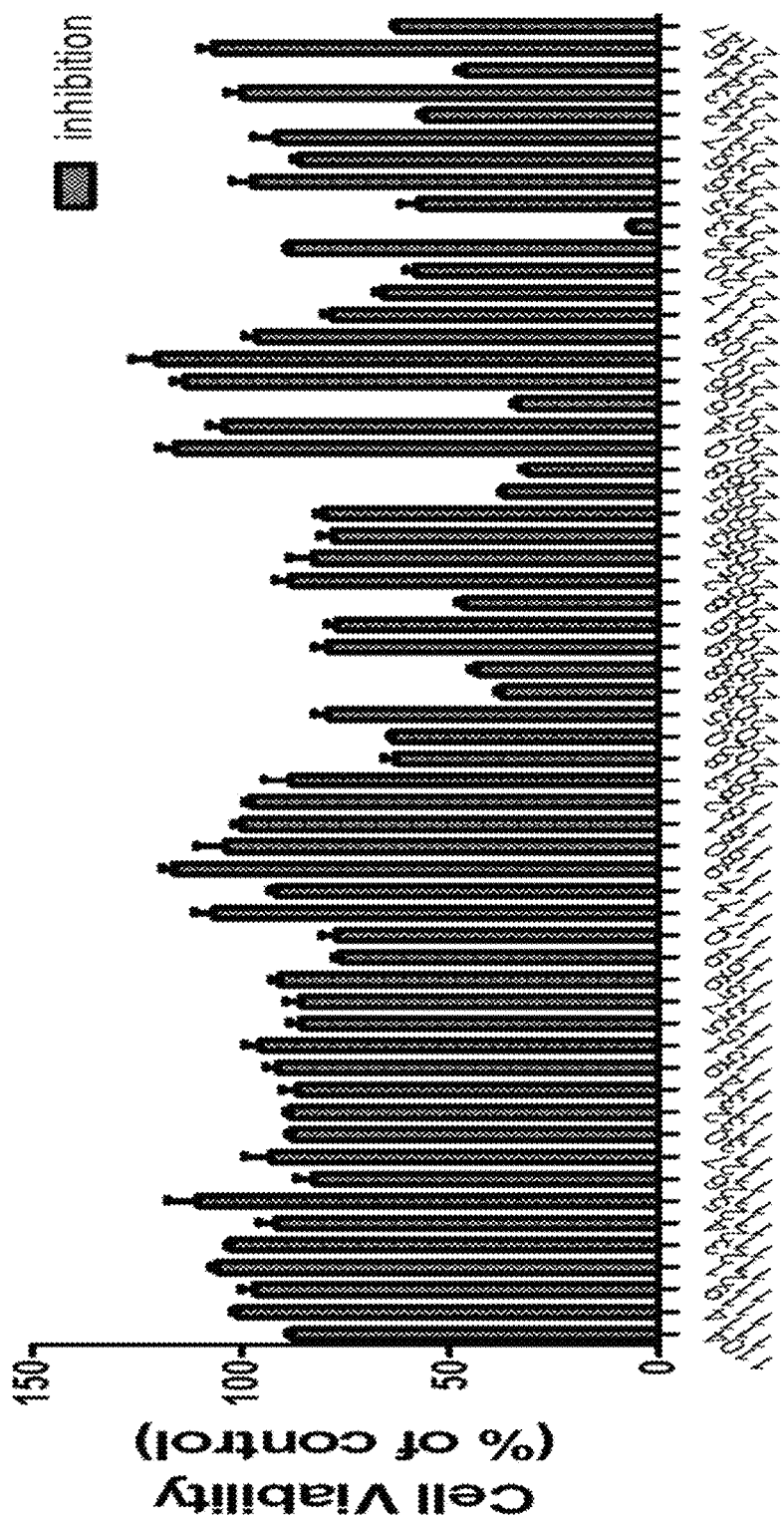
FIGS. 8A and 8B illustrate the effect of certain compounds of the invention on cell proliferation and growth in SW480 cells at 10 µM (FIG. 8A) and 50 µM (FIG. 8B).
Figure 8B:
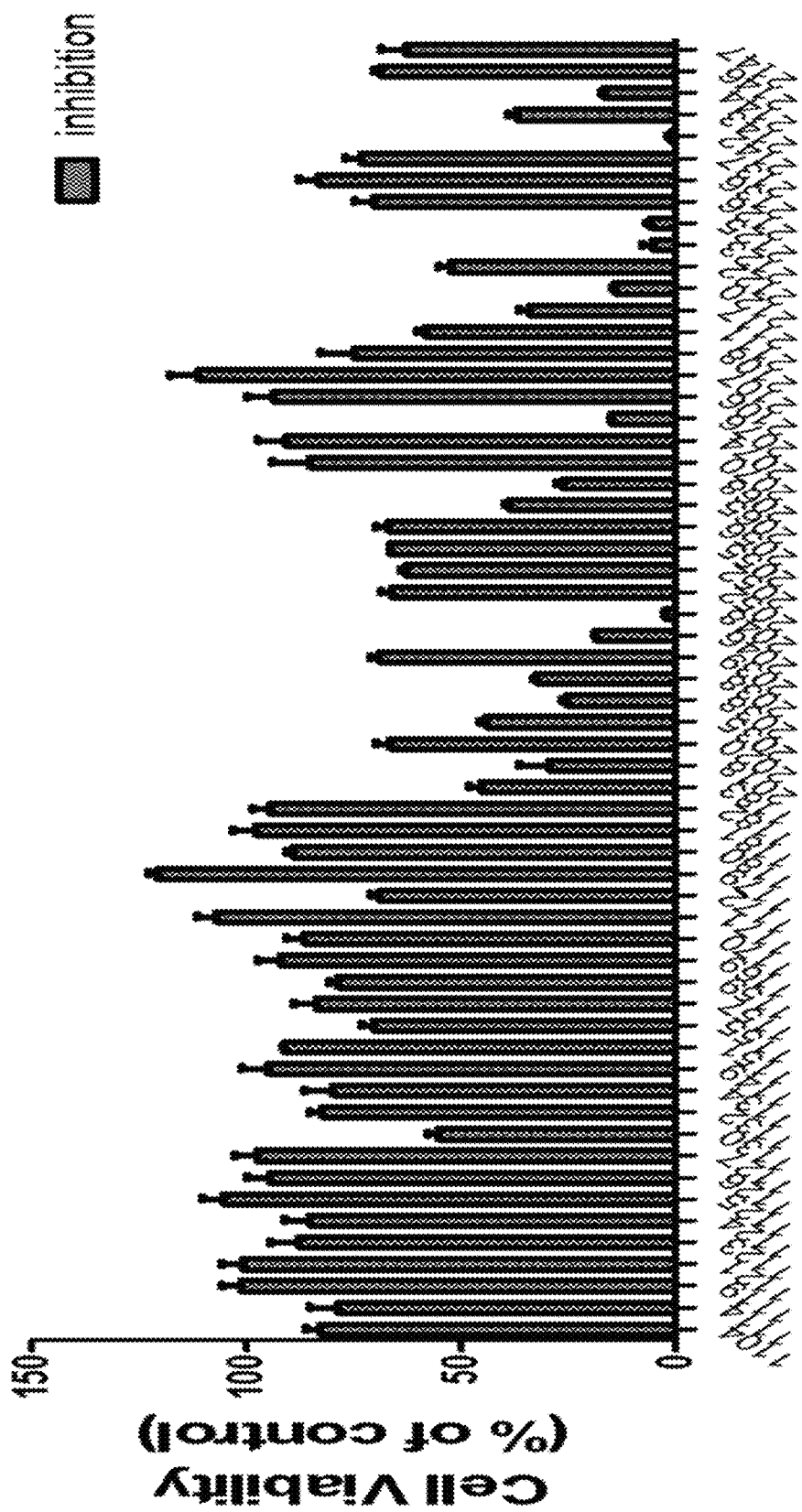

A variety of the compounds of the invention were tested as set forth herein at M (FIG. 8A) and 50 μM (FIG. 8B) for their ability to inhibit the growth of colon cancer cells (i.e., SW480; primary carcinoma). A specific set of compounds displayed micro-molar $IC_{50}$ values as shown in FIG. 9.

Figure 11:
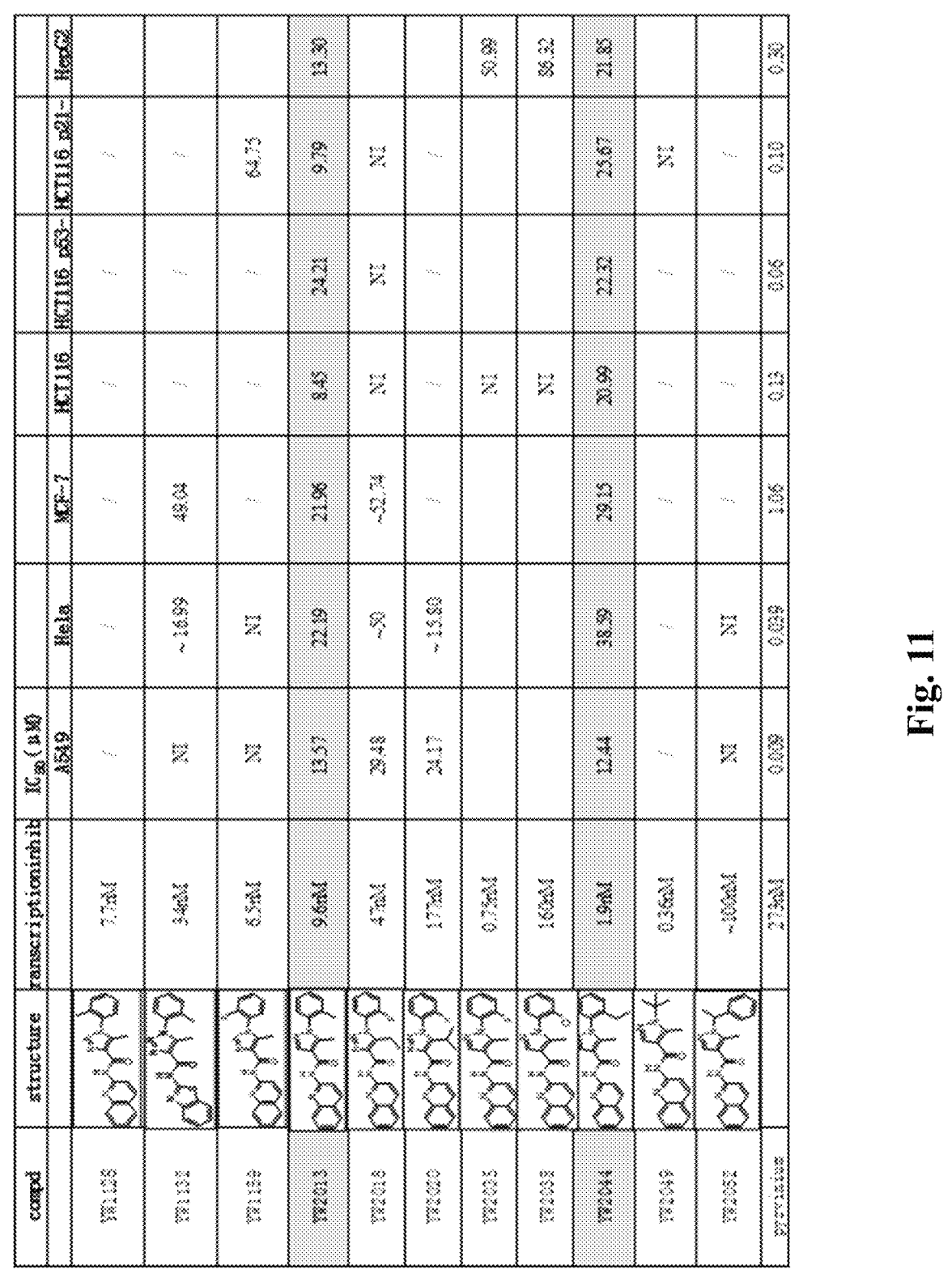
Figures 12, 13:
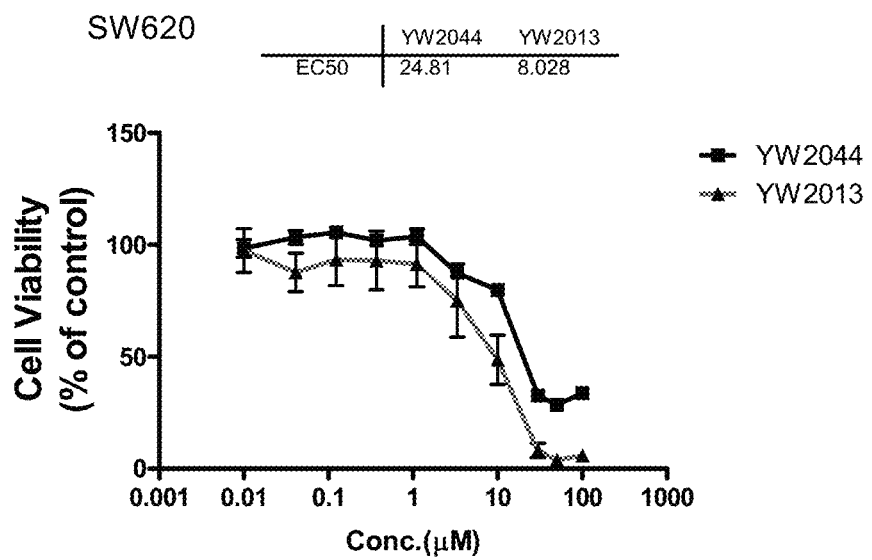
FIG. 12 illustrates the cytotoxic activity of certain compounds of the invention on the micromolar scale in various cancer cell lines.
FIG. 13 illustrates the cytotoxic activity of YW2013 and YW2044 against SW620 cells.
Figure 14:
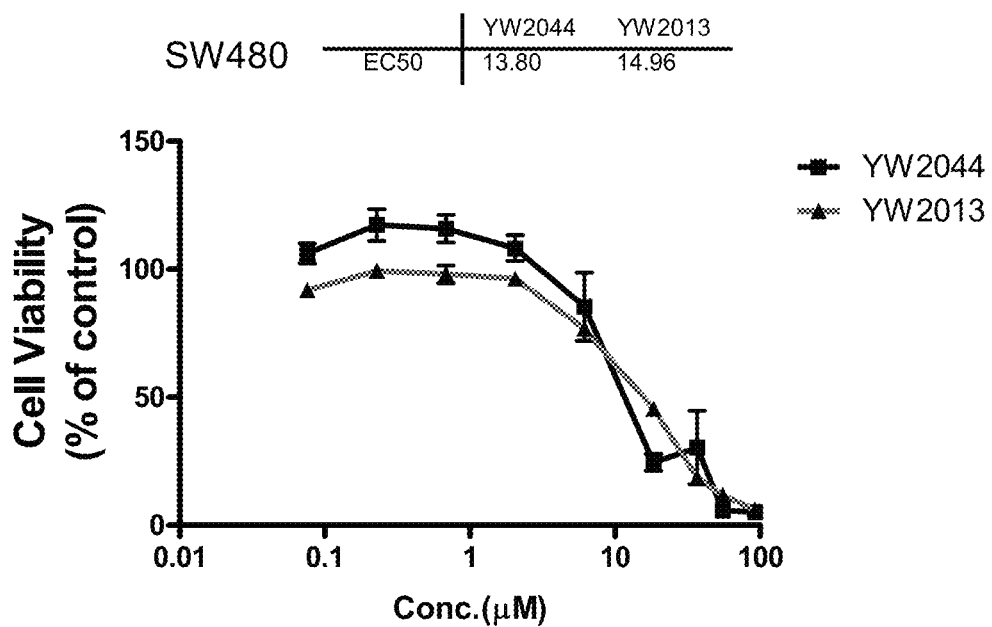
FIG. 14 illustrates the cytotoxic activity of YW2013 and YW2044 against SW480 cells.
Figure 15:
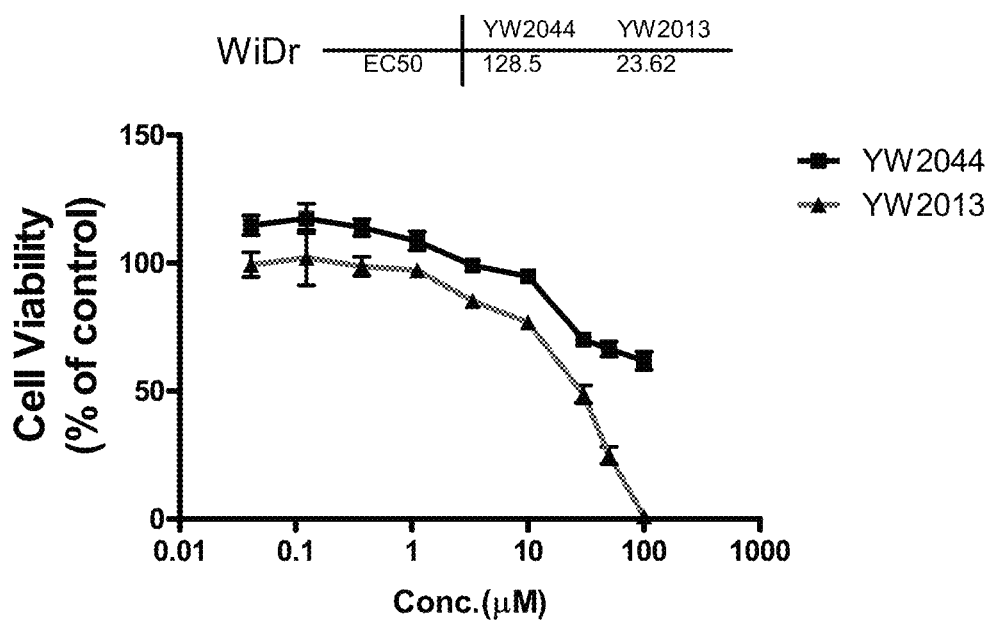
FIG. 15 illustrates the cytotoxic activity of YW2013 and YW2044 against WiDr cells.
Figure 16:
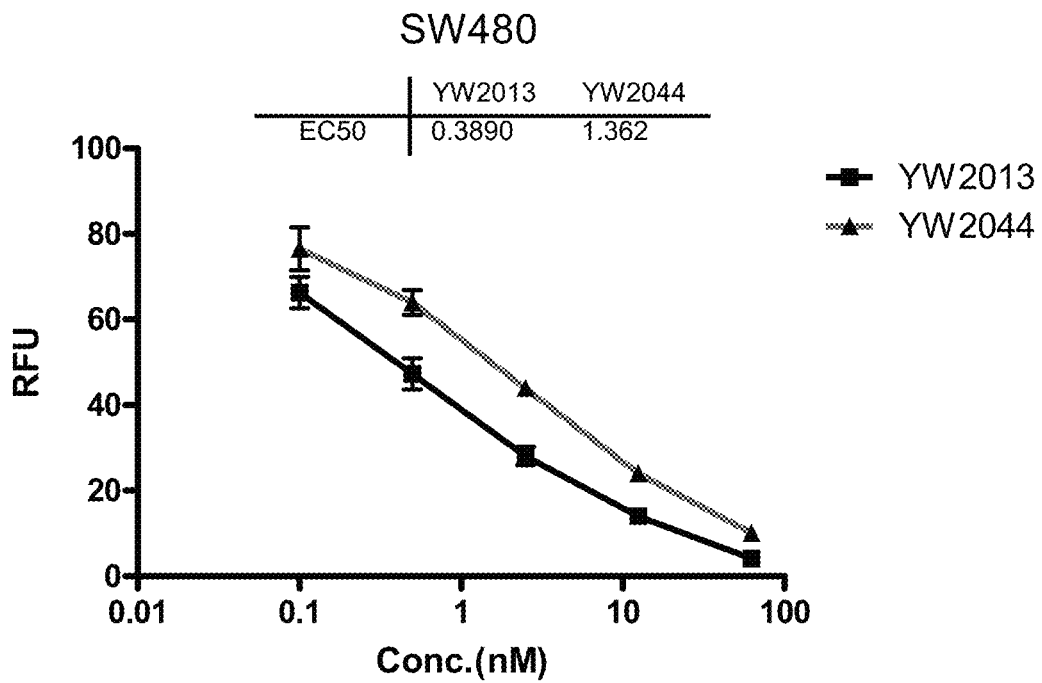
FIG. 16 illustrates the activity of YW2013 and YW2044 as inhibitors of β-catenin signaling in SW480 cells.

As compared to pyrvinium, a number of compounds of the invention displayed cytotoxic activity against A549, Hela, MCF-7, HCT116, HCT116 p53, HCT116 p21−, and HepG2 cells (FIG. 11). As shown in FIG. 11, certain compounds of the invention were also nanomolar inhibitors of transcription. Furthermore, the micromolar growth inhibitory activity of YW1059, YW1061, YW2013, YW1128, YW2035, YW2044, and YW2049 is set forth in FIG. 12 against the WiDr, SW620, HT29, HEK_LTV, and T84 cell lines.

Specific dose response curves, comparing certain compounds of the invention as inhibitors of β-catenin in several cell lines, are shown in FIGS. 13-16 and 18.

Figure 17:
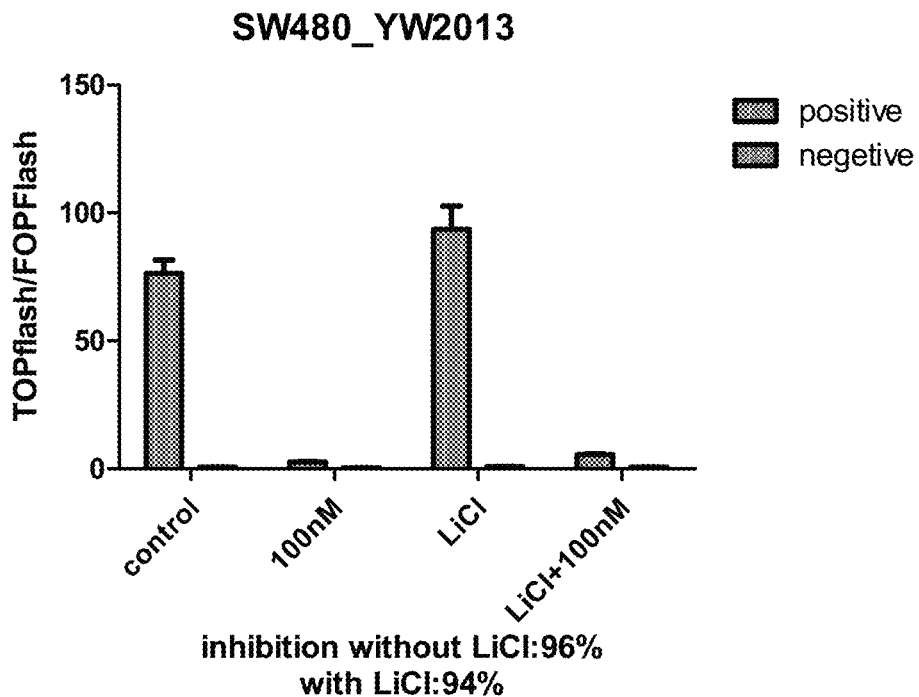
FIG. 17 illustrates the activity of YW2013 as an inhibitor of β-catenin signaling in SW480 cells in a TOPflash/FOP-Flash assay with and without LiCl.
Figure 18:
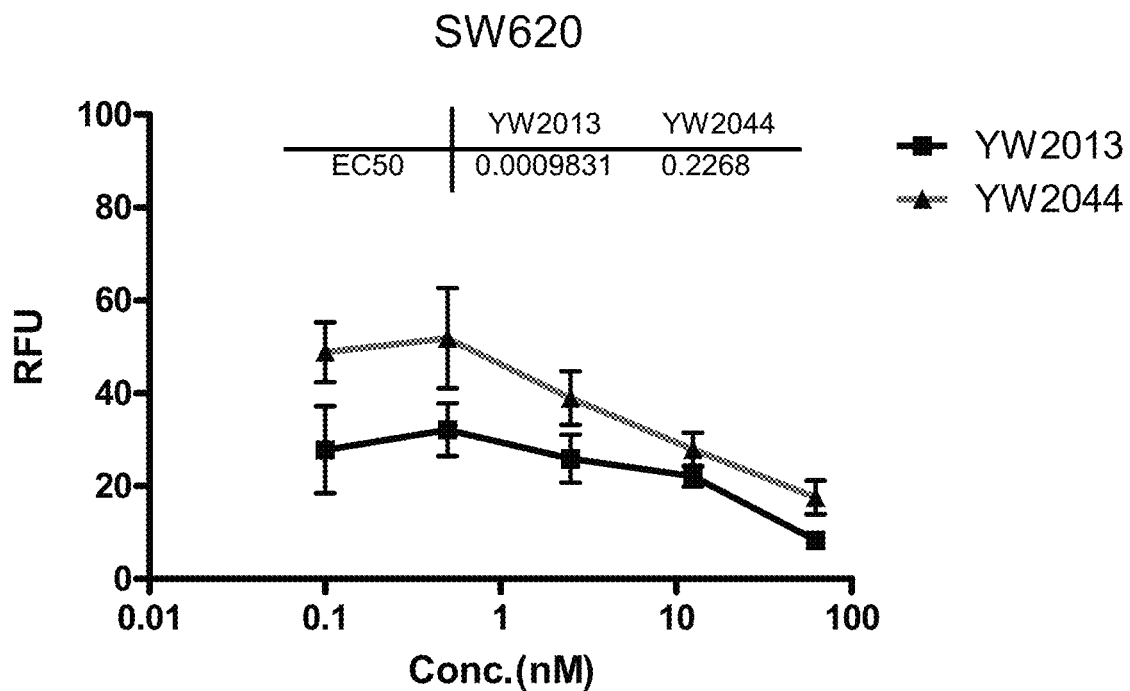
FIG. 18 illustrates the activity of YW2013 and YW2044 as inhibitors of β-catenin signaling in SW620 cells.

With a TOPflash/FOPFlash Assay against SW480 cells, the inhibitory effect of YW2013 against Wnt signaling, with and without LiCl was determined at 100 nM (FIG. 17).

Example 7: Effect of YW2013 and YW2044 on the Expression of the Genes Regulated by Wnt Signaling in Cancer Cells Quantitative Real-Time RT-PCR.

The total RNA extracted from the cells using TRIzol (Invitrogen) and 2 μg was reverse transcribed in a 20-μl volume system (QuantiTect Reverse Transcription Kit (Qiagen)) for quantitative PCR assays. SYBR green quantitative real-time PCR analyses were carried out using gene-specific primers (working concentration at 250 nM) in StepOnePlus real time PCR system (Applied Biosystems, AB), using the housekeeping gene GAPDH as an internal control. The PCR running procedure was as follows: 4 min denaturing at 95° C., followed by 40 cycles of 30 seconds of denaturing at 95° C. and then annealing and extension at 60° C. for 1 min. The primer sequences were as follows: Axin-2 for, 5'-CTCCTTGGAGGCAAGAGC-3' (SEQ ID NO: 1); rev, 5'-GGCCACGCAGCACCGCTG-3' (SEQ ID NO: 2); Cyclin D1 for, 5'-AAGGCGGAGGAGACCTGCGCG-3' (SEQ ID NO: 3); rev, 5'-ATCGTGCGGCATTGCGGC-3' (SEQ ID NO: 4); GAPDH for, 5'-ACCACAGTCCATGCCATCAC-3' (SEQ ID NO: 5); rev, 5'-TCCACCACCCTGTTGCTGT-3' (SEQ ID NO: 6).

Figure 19:
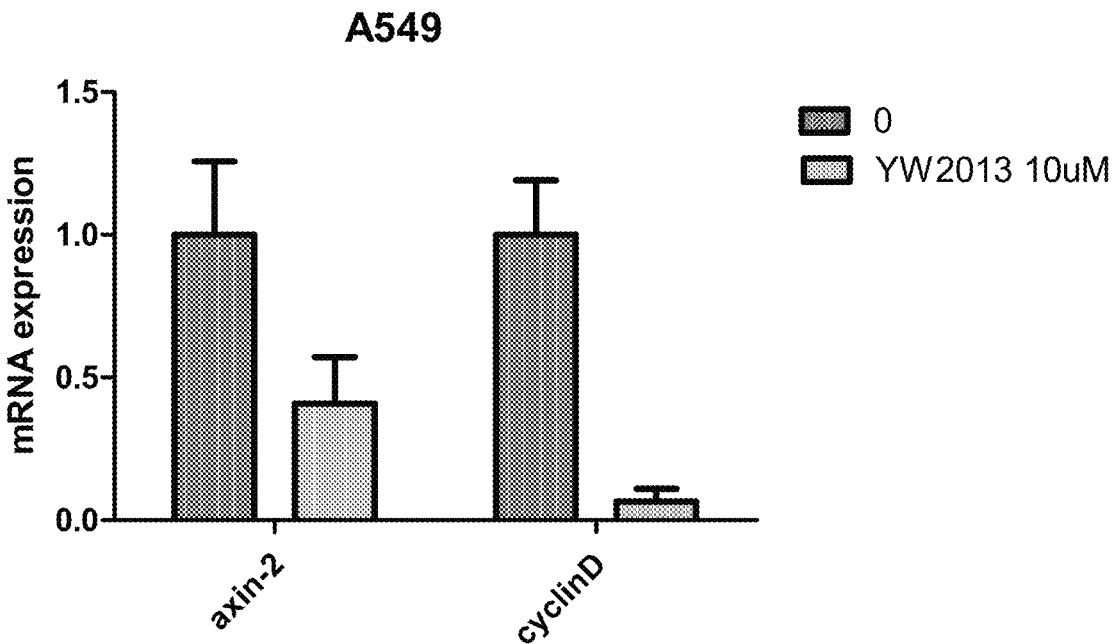
FIG. 19 illustrates the effect of YW2013 on mRNA expression of Wnt regulated genes in A549 cells.
Figure 20:
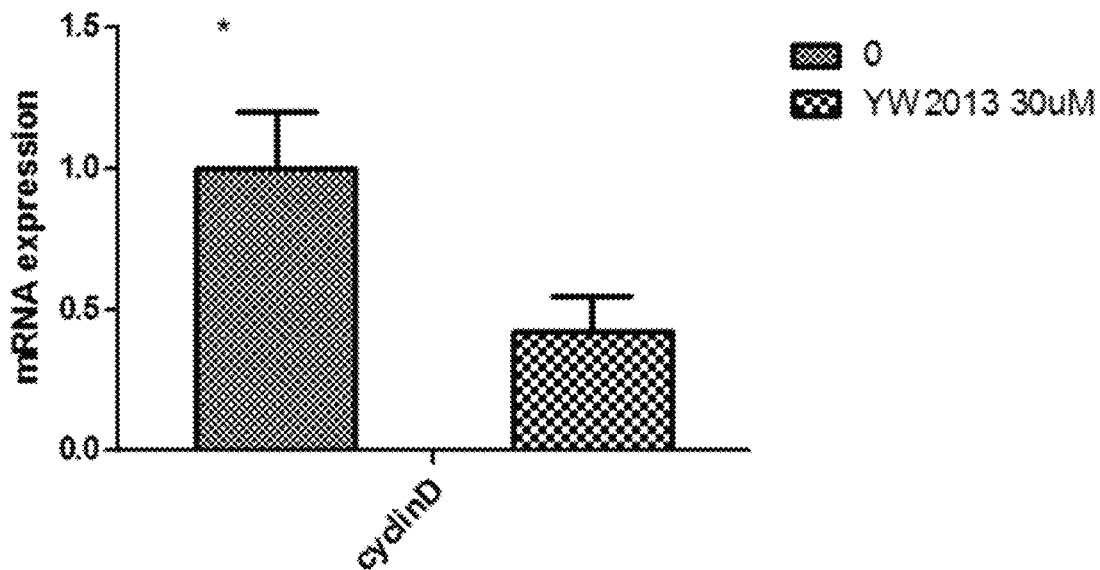
FIG. 20 illustrates the effect of YW2013 on mRNA expression of Wnt regulated genes in SW620 cells.
Figure 21:
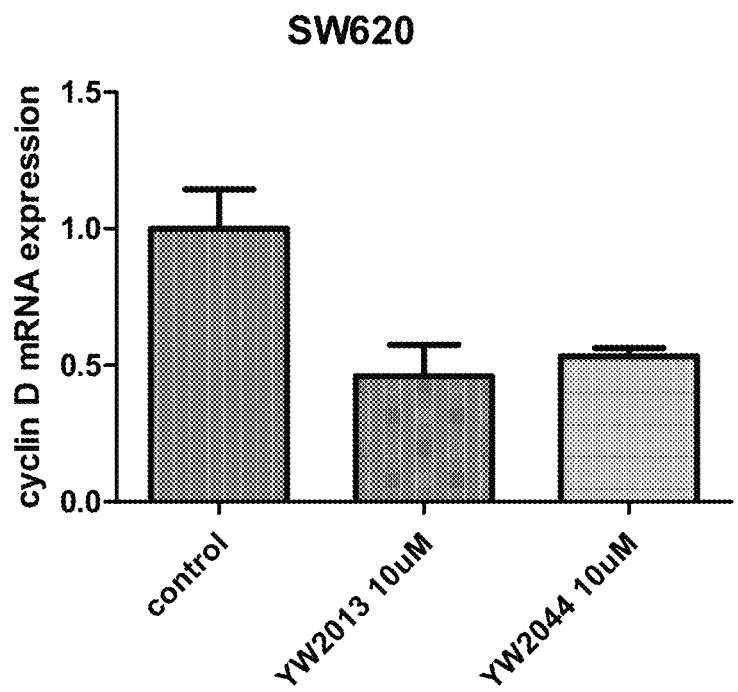
FIG. 21 illustrates the effect of YW2013 and YW2044 on mRNA expression of Wnt regulated genes in SW620 cells.
Figure 22:
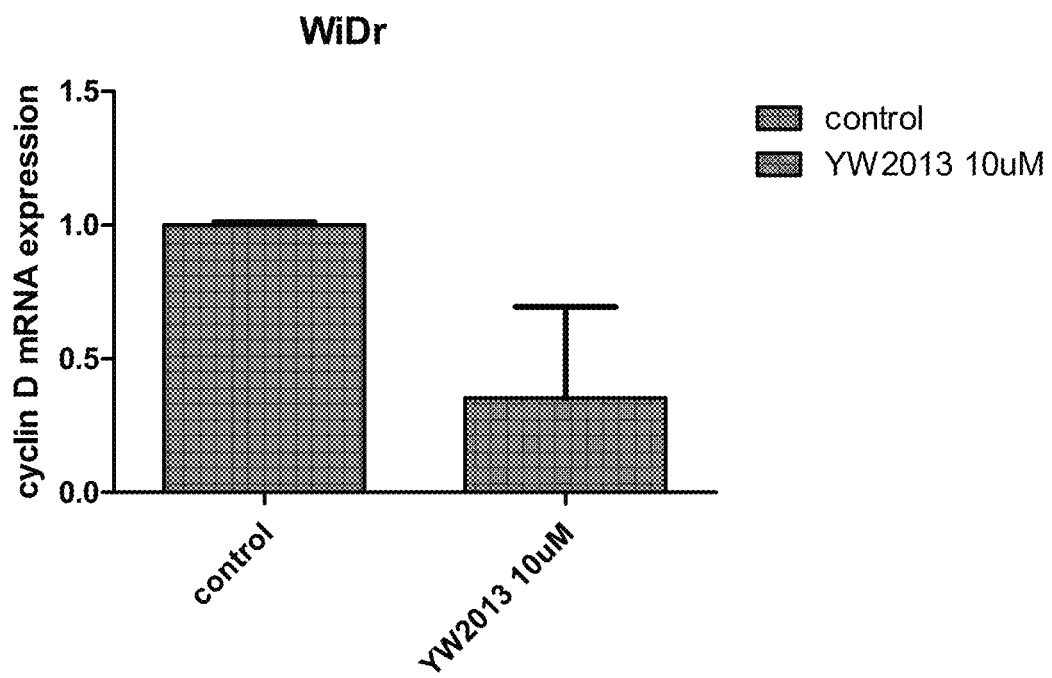
FIG. 22 illustrates the effect of YW2013 on mRNA expression of Wnt regulated genes in WiDr cells.

YW2013 reduced mRNA expression of Wnt regulated genes (Axin-2 and/or cyclin D1) in A549 cells (FIG. 19), SW620 cells (FIGS. 20 and 21), and WiDr cells (FIG. 22). YW2044 was shown to reduce mRNA expression of Wnt regulated genes in SW620 cells (FIG. 21).

Example 8: Effect of YW2013 and YW2123 on the Expression of Wnt Signaling Proteins Using a Western Blot, compounds YW2013 and YW2123 were tested in SW480 cells to determine their effect on the expression of Axin-2, β-catenin, and c-myc.

Western Blot:

$1\times10^6$ Cells of SW480 cells were seeded into 6-well plates overnight. A concentration of 3, 10, 30 μM/L YW2013 and 3, 10 μM/L YW2123 was added after 24 h, medium with 1‰ DMSO was used as the control. Cells were exposed to treatment for 48 h. The dishes was washed twice using precold PBS and 100 μL of RIPA then added. After incubating plates on ice for 15 min, cells were scraped carefully and centrifuged for 10 minutes at 14,000 g at 4° C. immediately. The remaining supernatant and lysates were maintained at −70° C. A Bio-Rad protein assay kit (500-0002) was used to quantitate the cell lysates. The concentration was adjusted to 2 mg/ml. A ratio of 1:1 2× loading buffer was added and the samples were denatured by boiling. Protein samples were separated on 4-15% SDS-polyacrylamide gel (SDS-PAGE) and transferred onto the PVDF membranes (Millipore). Immune complexes were formed by incubation of the proteins with primary antibody β-catenin, c-myc, Axin-2, and GAPDH at 4° C. overnight. A second antibody with horseradish peroxidase (HRP, sigma) conjugated was used then. Blots were developed by enhanced chemiluminescence (Thermo).

Figure 23:
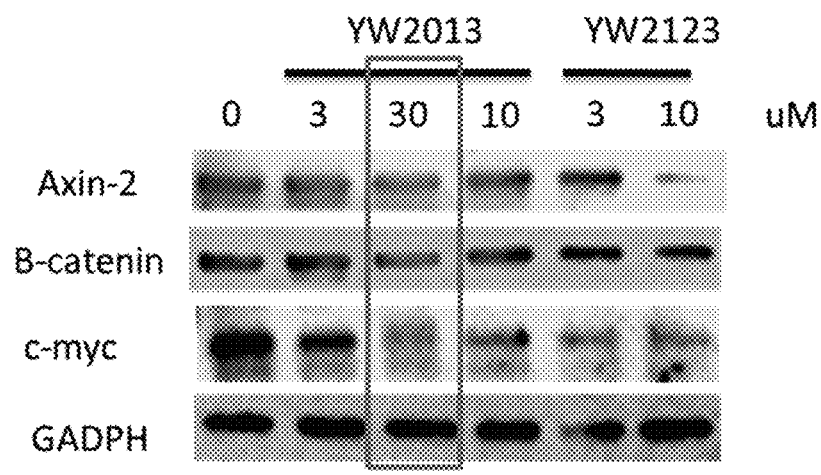
FIG. 23 illustrates the effect of YW2013 and YW2123 on Axin-2, β-catenin, and c-myc protein expression in SW480 cells.

As shown in FIG. 23, at least YW2013 visibly reduced the expression of Axin-2, β-catenin, and c-myc. YW2044 also had a noticeable effect on Axin-2 expression (FIG. 23).

Example 9: Effect of Compounds of the Invention on Cancer Cell Colony Formation

Figure 31:
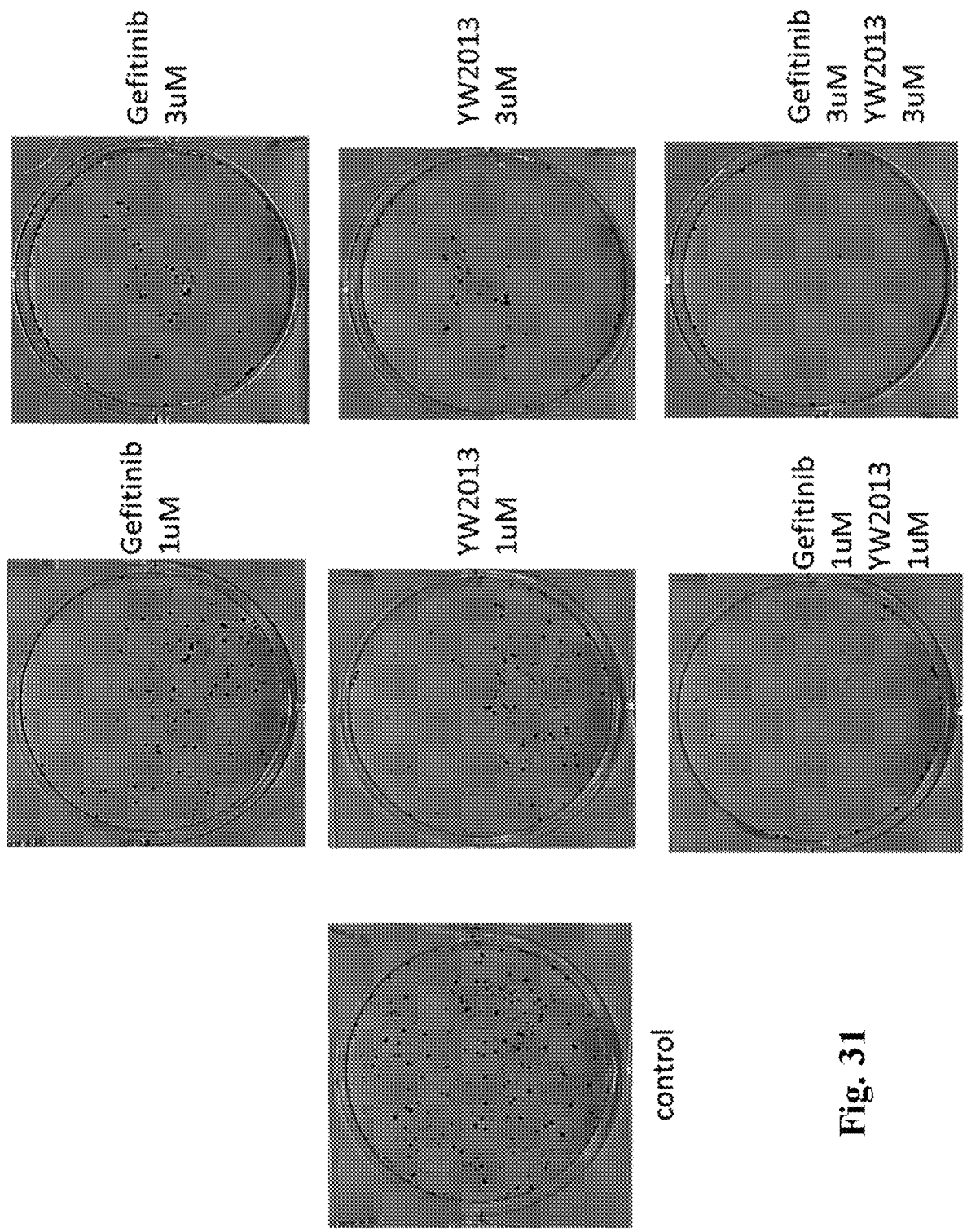
FIG. 31 illustrates the effect of YW2013 in combination with Gefitinib on cell colony formation in SW620 cells.

Certain compounds of the invention were tested to determine their ability to inhibit colony formation in several cancer cell lines (FIGS. 24-26 and 31). Moreover, SW2013 was paired with Gefitinib to determine the effect of a combination therapy on colony formation of SW620 cells (FIG. 31).

Colony Formation Assay.

HT-29 and SW620, SW480 cells were seeded into 6-well dishes with the medium containing 0, 1, 3, 10, 30 μM/L of YW2013 or YW2044, 500 cells/well. After 2 weeks, cells were fixed with 4% paraformaldehyde solution and stained with 0.5% crystal violet for 1 h at room temperature. The images of colonies were captured by microscopy.

Figure 24:
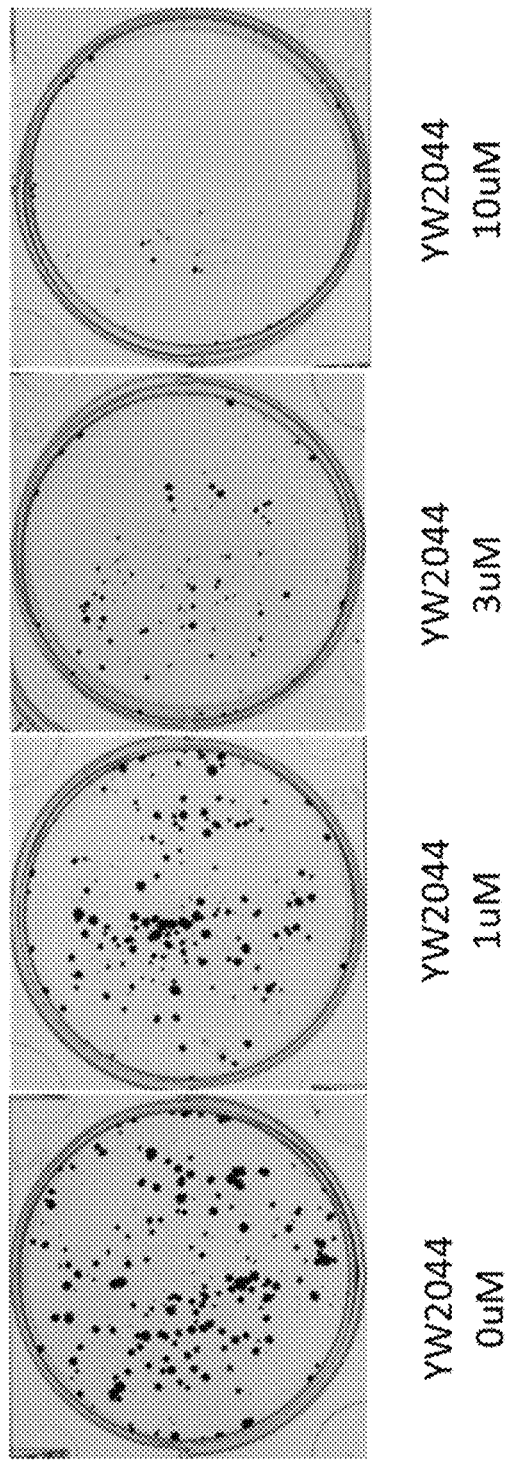
FIG. 24 illustrates the effect of YW2044 on colony formation in HT-29 cells.
Figure 25:
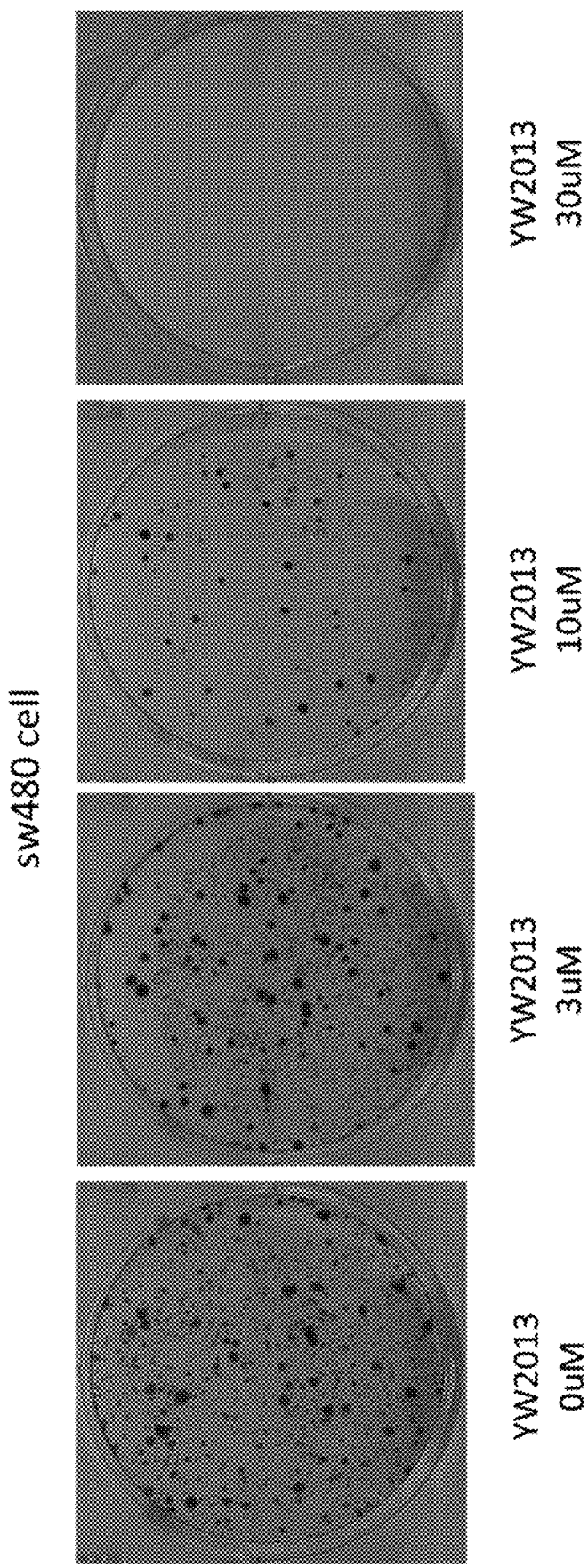
FIG. 25 illustrates the effect of YW2013 on colony formation in SW480 cells.
Figure 26:
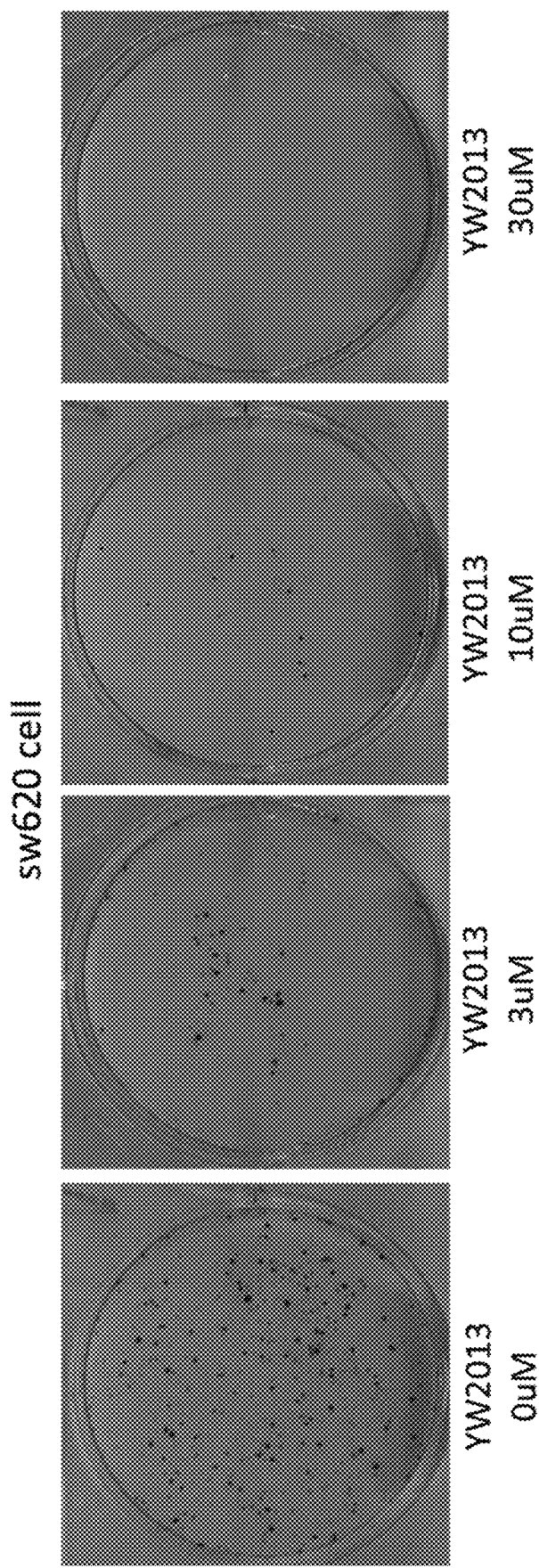
FIG. 26 illustrates the effect of YW2013 on colony formation in SW620 cells.

YW2044 exhibited a dose dependent reduction in colony formation in HT-29 cells (FIG. 24). YW2013 exhibited a dose dependent reduction in colony formation in SW480 cells (FIG. 25) and SW620 cells (FIG. 26). Furthermore, YW2013 exhibited a dose dependent reduction in colony formation that was markedly increased when combined with Gefitinib, demonstrating that Gefitinib and YW2013 may provide synergistic activity against colony formation (FIG. 31).

Example 10: Effect of YW2013 on Cell Cycle in SW620 Cells

Figure 27A:
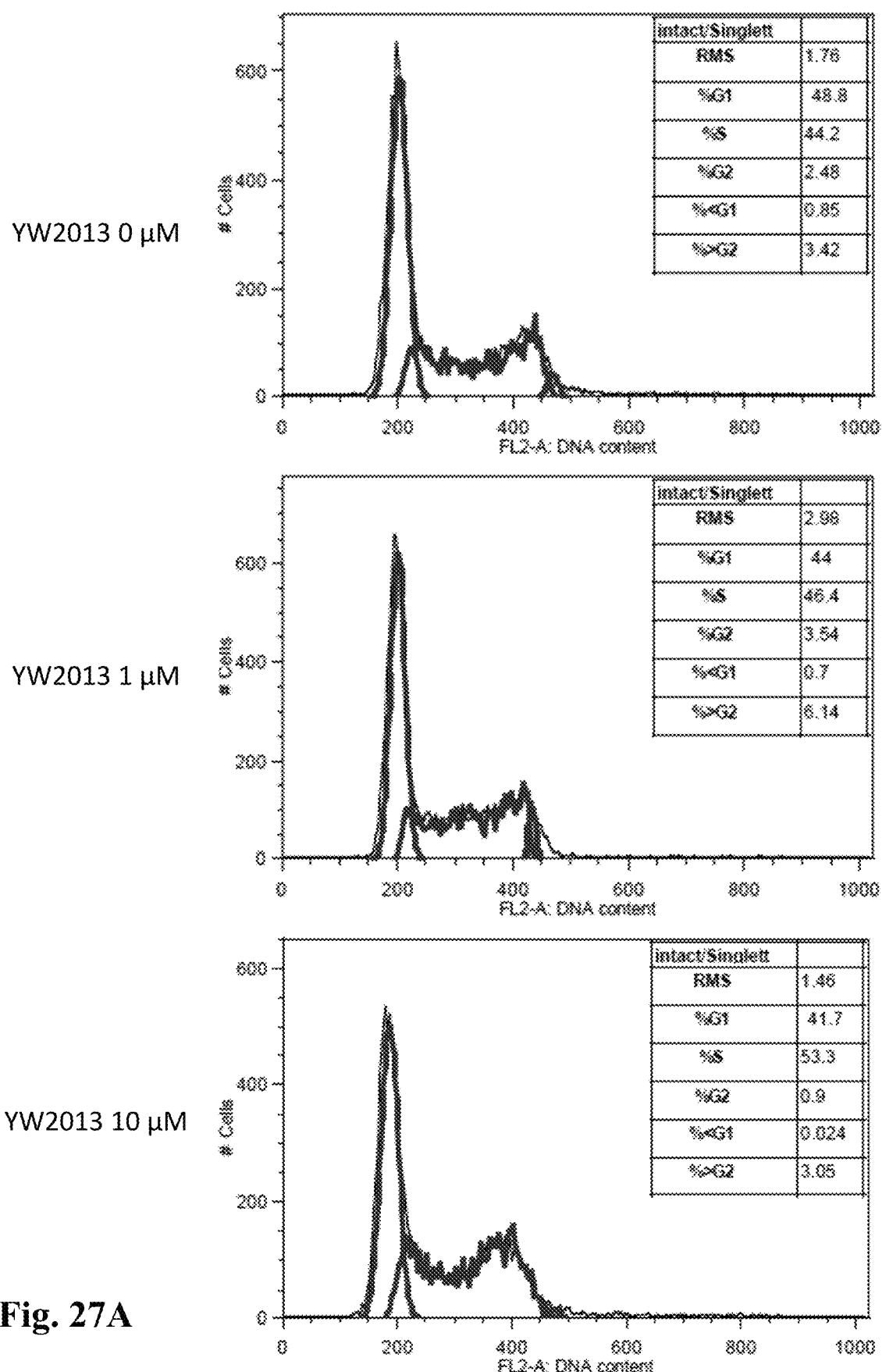
FIGS. 27A and 27B illustrate the effect of YW2013 on cell cycle in SW620 cells that are unsynchronized (FIG. 27A) and synchronized (FIG. 27B).
Figure 27B:
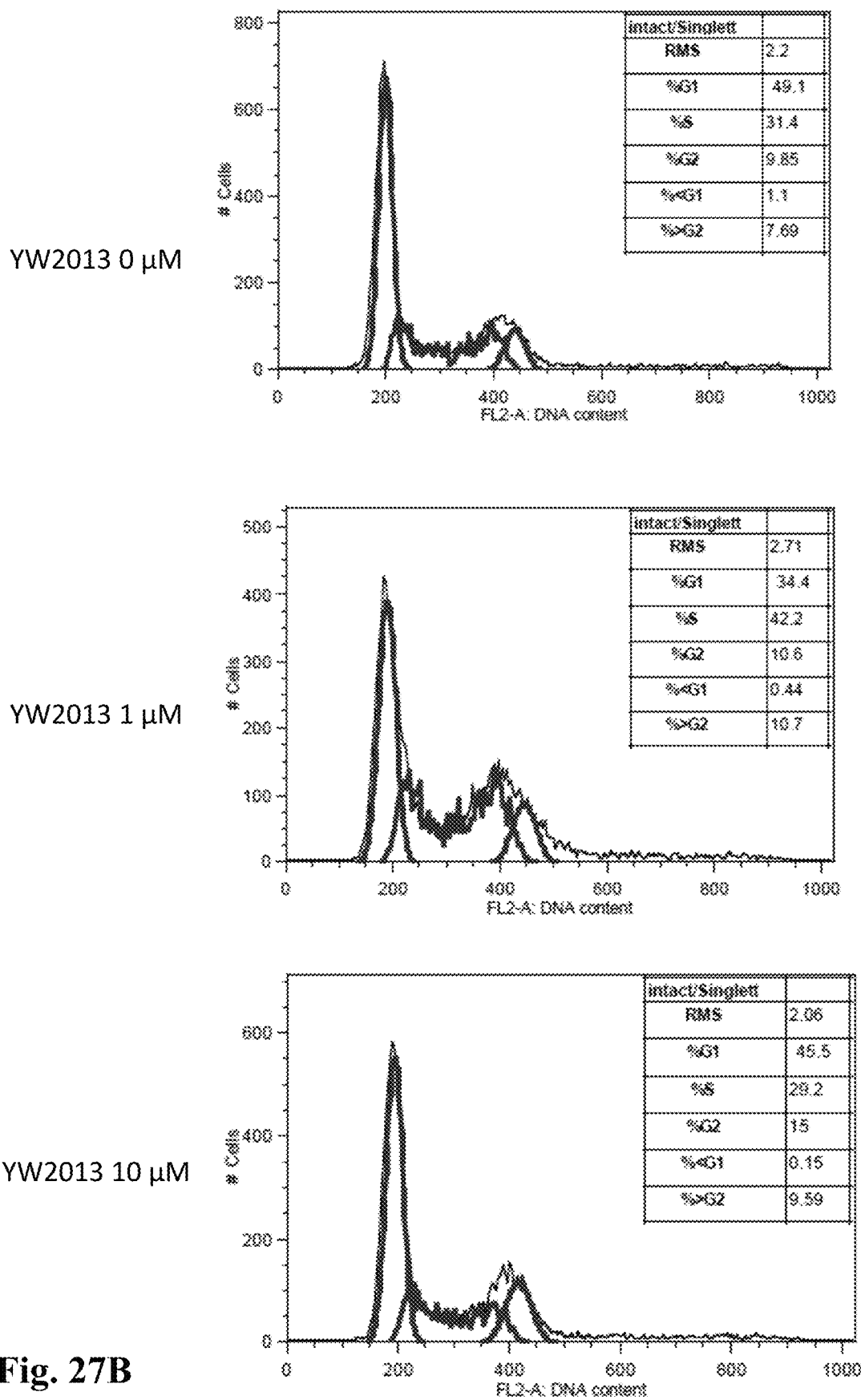

SW620 cells were treated with YW2013 at various concentrations (0, 1, 10 μM) to determine the effect of YW2013 on the SW620 cell cycle in an unsynchronized assay (FIG. 27A) and an assay where cells were treated with FBS free medium for 24 hours up to synchronization before adding YW2013 (FIG. 27B).

Cell Cycle Analysis.

SW620 cells were plated in 6-well plates for 24 h, and the medium was replaced with medium containing 0, 1, 10, μM/L of YW2013. After incubation for 24 h, the cells were harvested by trypsinization and then fixed with 70% 4° C. ethanol. Intracellular DNA was stained with 50 ng/ml propidium iodide in the dark for 30 min at room temperature, and the percentages of different phase of cells were determined by flow cytometry (BD FACScan; BD Biosciences).

Figure 28:
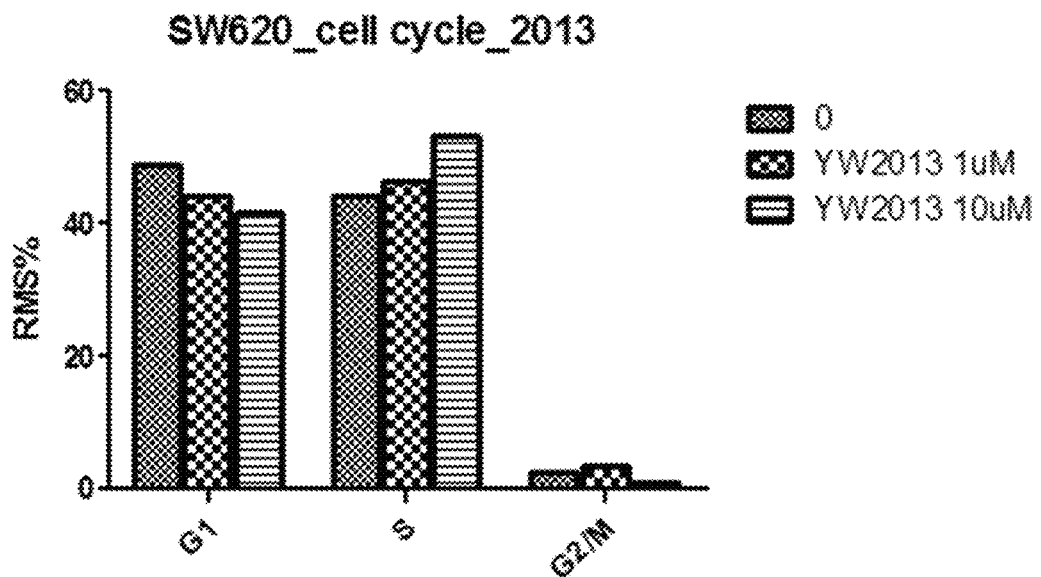
FIG. 28 illustrates the effect of YW2013 on cell cycle in SW620 cells that are unsynchronized.
Figure 29:
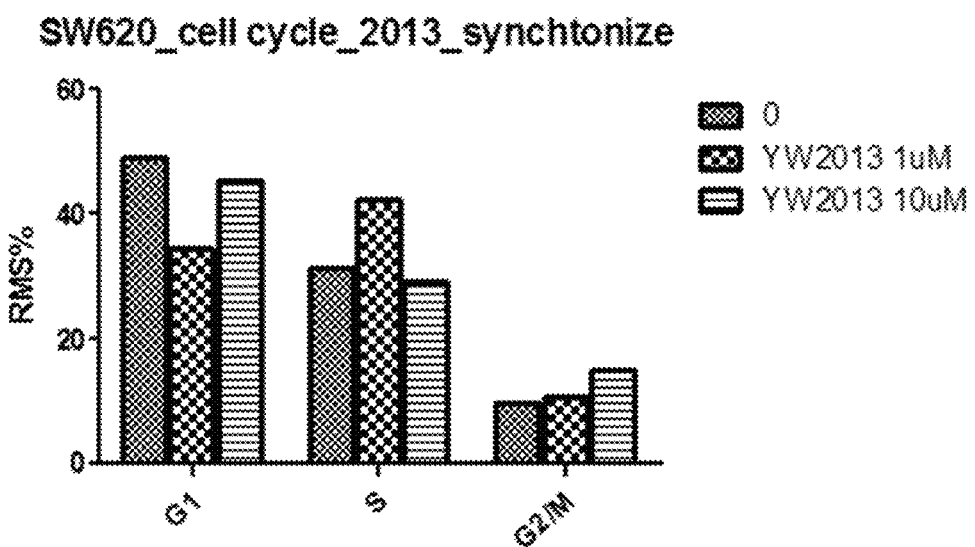
FIG. 29 illustrates the effect of YW2013 on cell cycle in SW620 cells that are synchronized.

The results shown FIGS. 28 and 29 indicate cell cycle arrest in the Gi and S phases for both unsynchronized (FIG. 28) and synchronized (FIG. 29) assays.

Example 11: YW2013 Induced Apoptosis in SW620 Cells

Annexin-V/AAD-7 Double-Staining Assay.

SW620 cells were treated with 0, 3, 10, 30 μM/L of YW2013 for 48 h. Then they were harvested and washed with PBS. Apoptotic cells were determined with an FITC Annexin V Apoptosis Detection Kit according to the manufacturer's protocol. Briefly, the cells were washed and subsequently incubated for 15 min at room temperature in the dark in 100 μL of 1× binding buffer containing 2 μL of Annexin V-FITC and 2 μL of AAD-7. After 30 min, apoptosis was analyzed by BD FACSCanto II Flow Cytometer.

Figure 30:
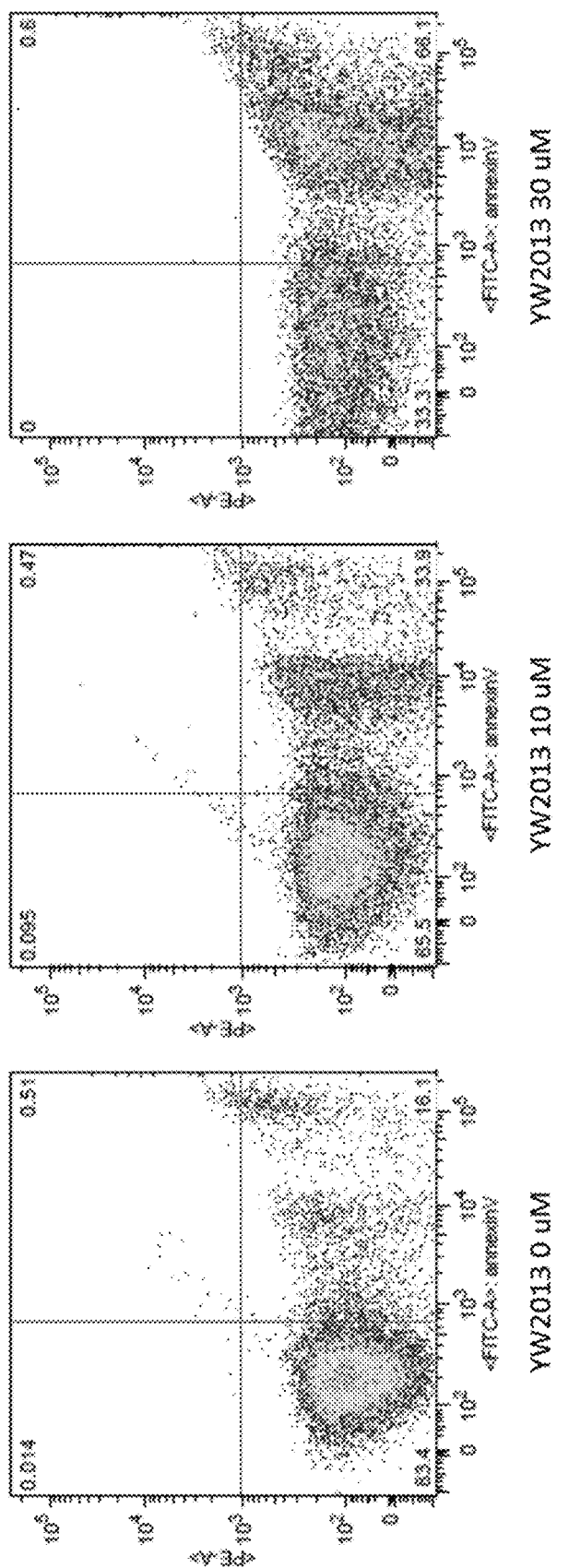
FIG. 30 illustrates the apoptotic effect of YW2013 on SW620 cells.

As shown in FIG. 30, YW2013 induced apoptosis in SW620 cells in a dose dependent manner.

Figure 32:
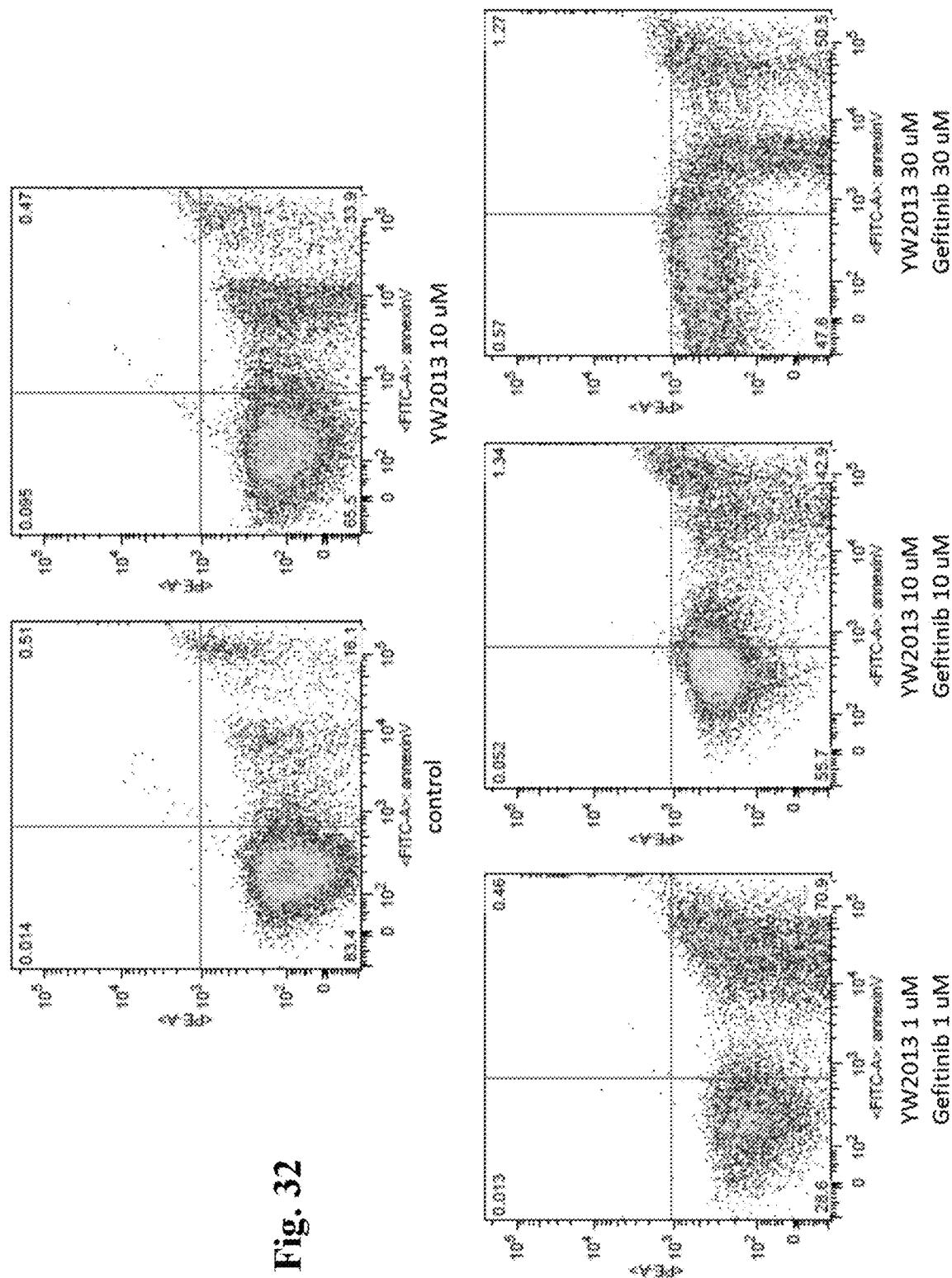
FIG. 32 illustrates the apopotic effect of YW2013 in combination with Gefitinib on SW620 cells.

Furthermore, the effect of YW2013 in combination of Gefitinib is shown in FIG. 32 where the two compounds were tested as a combination therapy for SW620 cells. Gefitinib was tested at 1, 10, and 30 μM.

Example 12: Characterization of Wnt/β-Catenin Signaling Inhibitors (e.g., YW1128) Against Non-Alcoholic Fatty Liver Disease and its Sequelae Wnt/β-catenin signalling downregulation appears to fully reverse non-alcoholic fatty liver disease in a mouse model. The Wnt/β-catenin signaling inhibitors disclosed herein may be used in the treatment of non-alcoholic fatty liver disease (NAFLD) and its sequelae non-alcoholic steatohepatitis (NASH). These inhibitors are expected to safely inhibit the Wnt/β-catenin pathway with improved potency, metabolic stability, and bioavailability.

The Wnt/β-catenin signaling pathway has been long recognized to play a pivotal role in cell proliferation, differentiation, and organ development. As an emerging research area, however, the link between Wnt/β-catenin pathway and metabolic diseases has only been appreciated recently. For example, a strong association exists between type 2 diabetes risk and single nucleotide polymorphisms (SNPs) in TCF7L2, a classic effector of Wnt/β-catenin pathway. Similar genetic evidence exists for additional modulators of Wnt signaling pathway such as WNT5B, WNT1B, and LRP6. Follow-up genetic studies have indicated that global downregulation of Wnt/β-catenin signaling activity leads to overall improved metabolic homeostasis in diabetic animal models The metabolic disease NAFLD is the most common form of chronic liver disease and ranges in severity from relatively simple benign steatosis to NASH, which is highly prevalent in type 2 diabetes or obese patients, and is a burgeoning public health problem due to the global diabetes and obesity epidemic. Dietary control and exercise are currently the recommendation to reverse NAFLD/NASH; however, their long-term effectiveness is uncertain because many patients are unable to comply. Thus, an effective pharmacological therapeutic is highly in demand.

Reducing β-catenin expression by antisense oligonucleotides decreases expression of enzymes involved in hepatic fatty acid esterification and ameliorates diet-induced hepatic steatosis and insulin resistance. Indeed, an antisense oligonucleotide against β-catenin could totally reverse diet-induced fatty liver and obesity back to normal, improve glucose tolerance, and reduce fasting glucose levels in the blood of mice.

These results support targeting the Wnt/β-catenin pathway as a strategy to treat NAFLD.

Figure 33A:
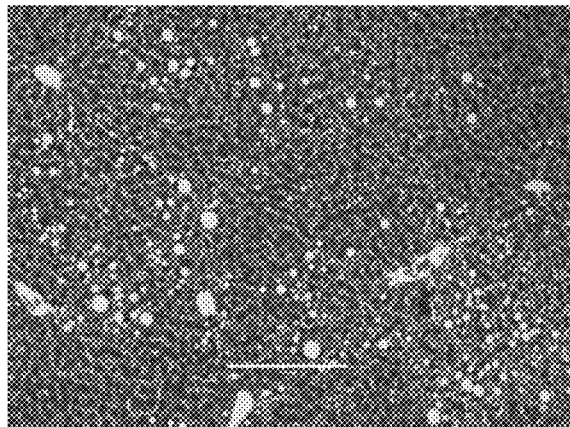
FIGS. 33A to 33D illustrate the effect of Wnt signaling inhibitor YW1128 on hepatic lipid accumulation in mice fed with a high-fat diet.
Figure 33B:
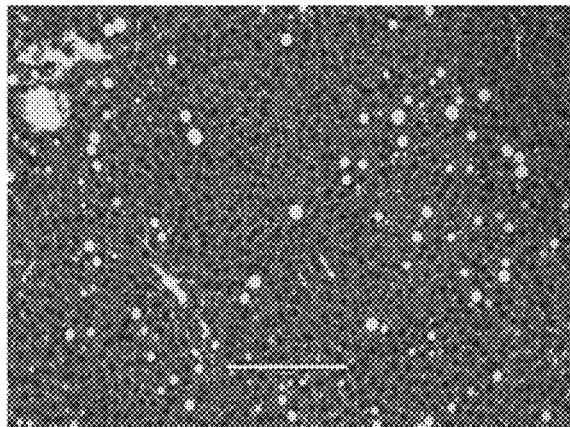
Figure 33C:
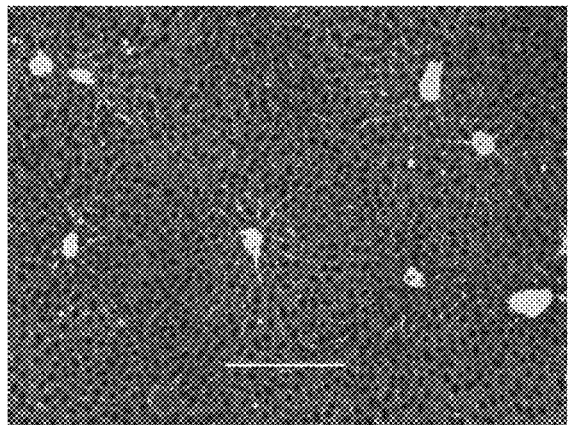
Figure 33D:
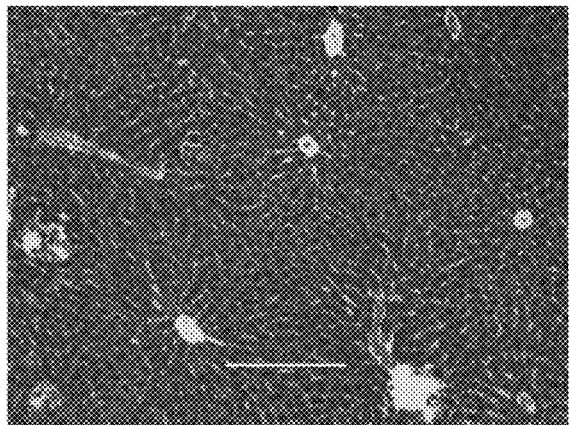

Mice were treated with YW1128 and representative liver histology was observed through H&E staining. C57BL/6 mice were placed on a high-fat diet. Seven weeks later (week 0), the mice received either vehicle or YW1128 by IP injection for 11 weeks. Regarding treatment with YW1128, the mice were initially treated at a dose of 10 mg/kg/2 days, which was increased to 40 mg/kg/2 days from week 8. The mice were then euthanized at the end of 11 weeks. Liver histology for vehicle (FIGS. 33A and 33B) and YW1128 (FIGS. 33C and 33D) was examined by H&E staining.

Figure 34A:
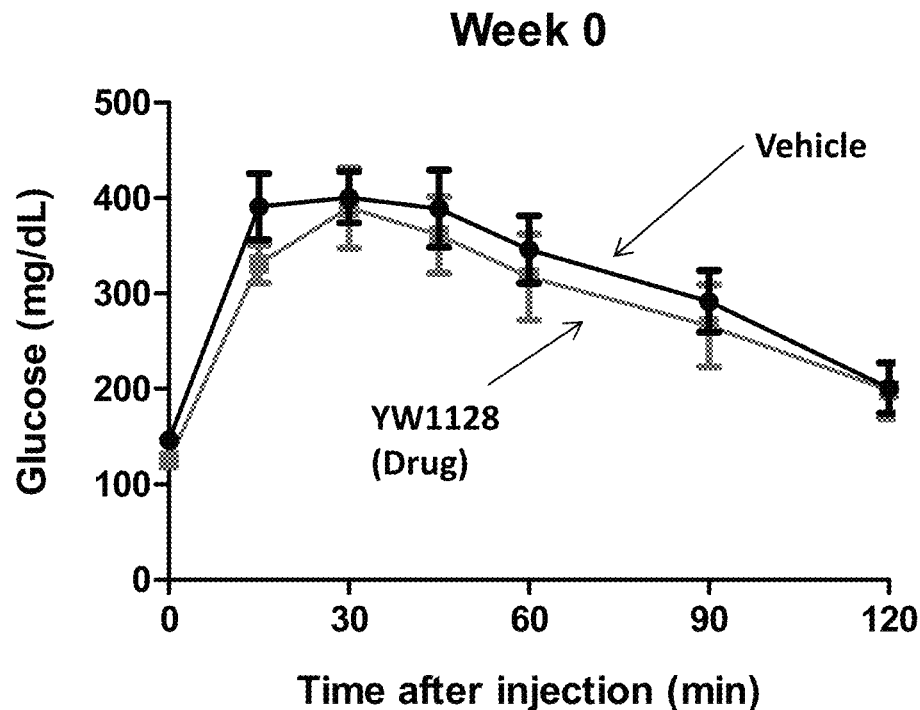
FIGS. 34A and 34B illustrate the effect of Wnt signaling inhibitor YW1128 on glucose tolerance in mice fed with a high-fat diet.
Figure 34B:
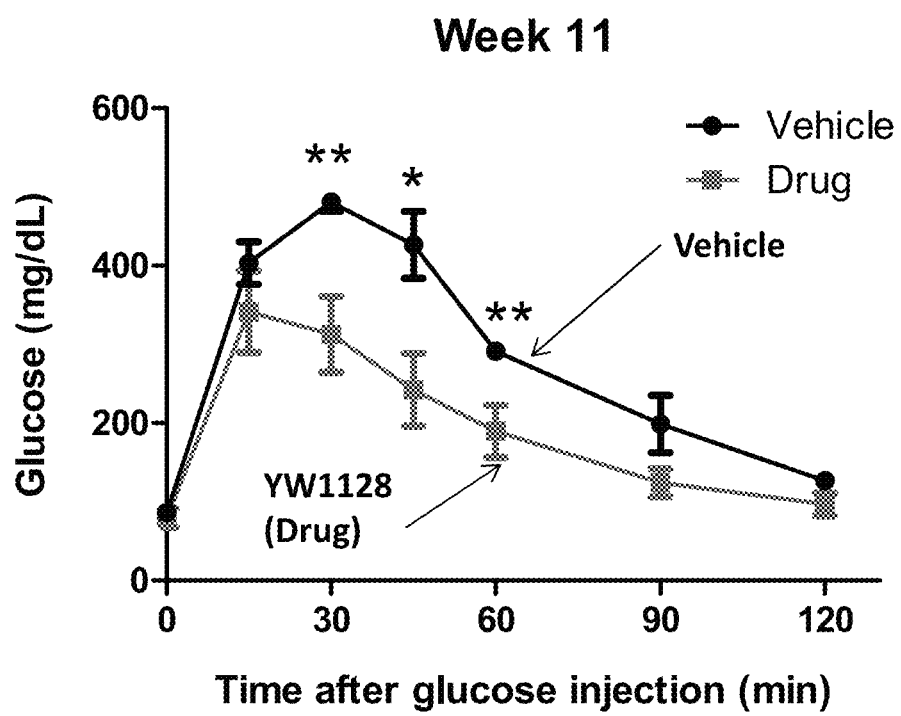

An intraperitoneal glucose tolerance test (IPGTT) was conducted on high-fat diet (HFD) groups at the end of the study. C57BL/6 mice (n=3-4 per group) were put on a high fat diet. Seven weeks later (week 0), the mice received either vehicle or YW1128 by IP injection for 11 weeks. Regarding the treatment with YW1128, the mice were initially treated at a dose of 10 mg/kg/2 days, which was increased to 40 mg/kg/2 days from week 8. The results of this study are set forth in FIGS. 34A and 34B. FIG. 34A describes the glucose levels at up to 120 minutes post-injection at week 0. FIG. 34B describes the glucose levels at up to 120 minutes post-injection at week 11, where *P<0.05 and **P<0.01, compared to the YW1128 group.

Figure 35:
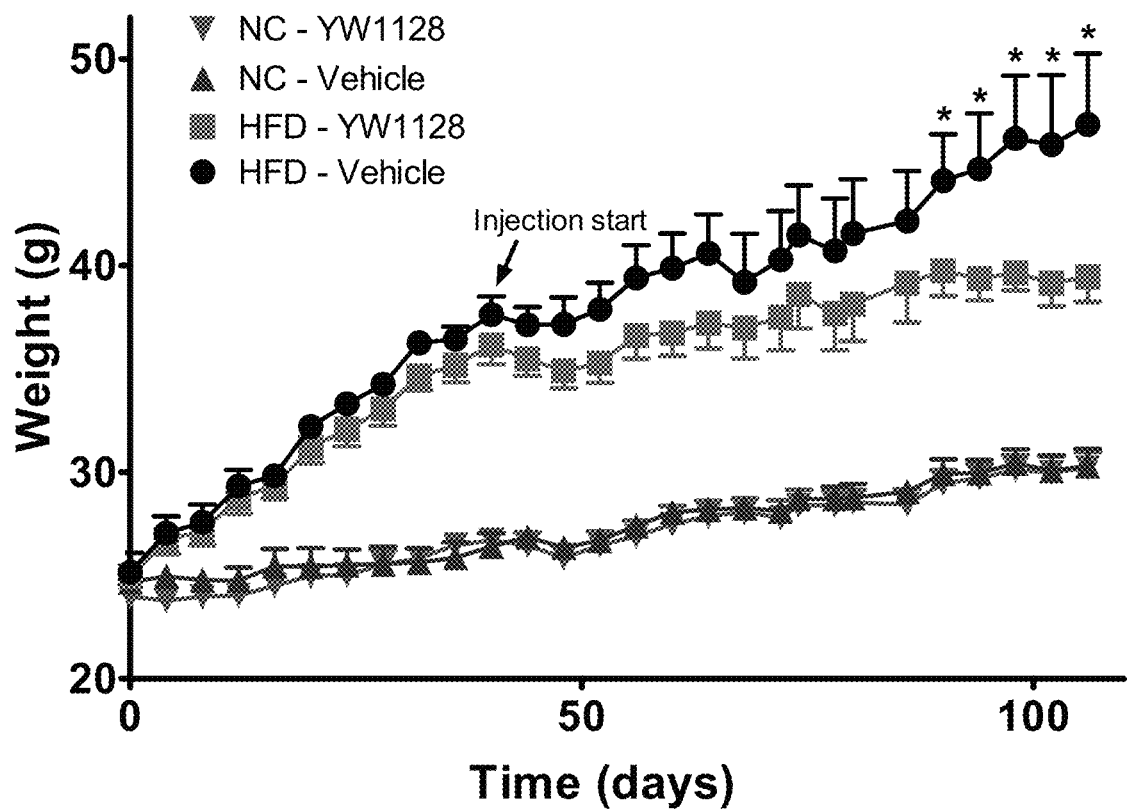
FIG. 35 illustrates the effect of Wnt signalling inhibitor YW1128 on body weight gain in mice fed with a normal chow (NC) diet and mice fed with a high-fat diet (HFD). *P<0.05 for the comparison between HFD-vehicle and the other three groups.

The effect of YW1128 on body weight was also observed in mice having normal diets (NC) and those having high-fat (HF) diets. C57BL/6 mice (n=3-4 per group) were put on either an HF diet or an NC diet. Seven weeks later, the mice received either YW1128 or vehicle by IP injection. Regarding the treatment with YW1128, the mice were treated at a dose of 40 mg/kg/2 days for seven weeks. The results of such study are shown in FIG. 35, where *P<0.05 for the comparison between HF-vehicle and the other three groups.

Given the importance of Wnt/β-catenin signaling in regulation of cell proliferation and differentiation, there are questions regarding long-term inhibition of canonical Wnt signaling in chronic diseases that may result in toxicity, in particular in tissues with high cellular turnover. It has been observed that injection of YW1128 could significantly improve glucose tolerance and decrease body weight gain in the mice fed on high-fat diet (FIGS. 33A to 33D, 34A and 34B, and 35). Furthermore, the mice that received YW1128 did not exhibit any histology of fatty liver disease which was apparent in those received vehicle. In addition, the subchronic treatment of YW1128 did not cause any obvious toxicity in the mice.

Example 13: Effect of YW1128 on a High-Fat Diet (HFD)-Induced Steatosis

Figure 36A:
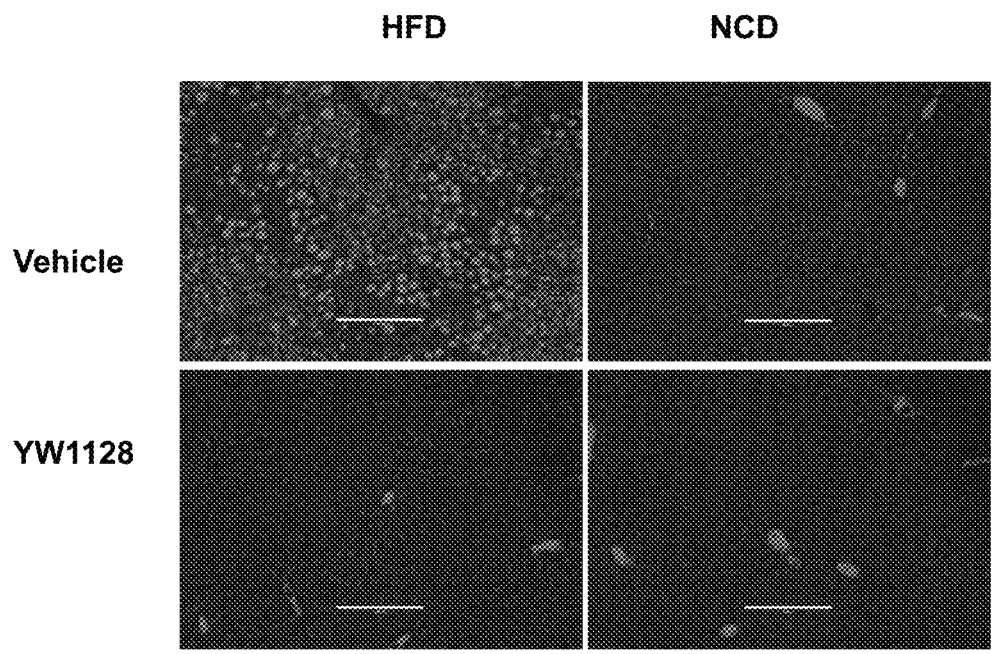
FIGS. 36A to 36D illustrate the effect of YW1128 on a high-fat diet (HFD)-induced steatosis.
Figure 36B:
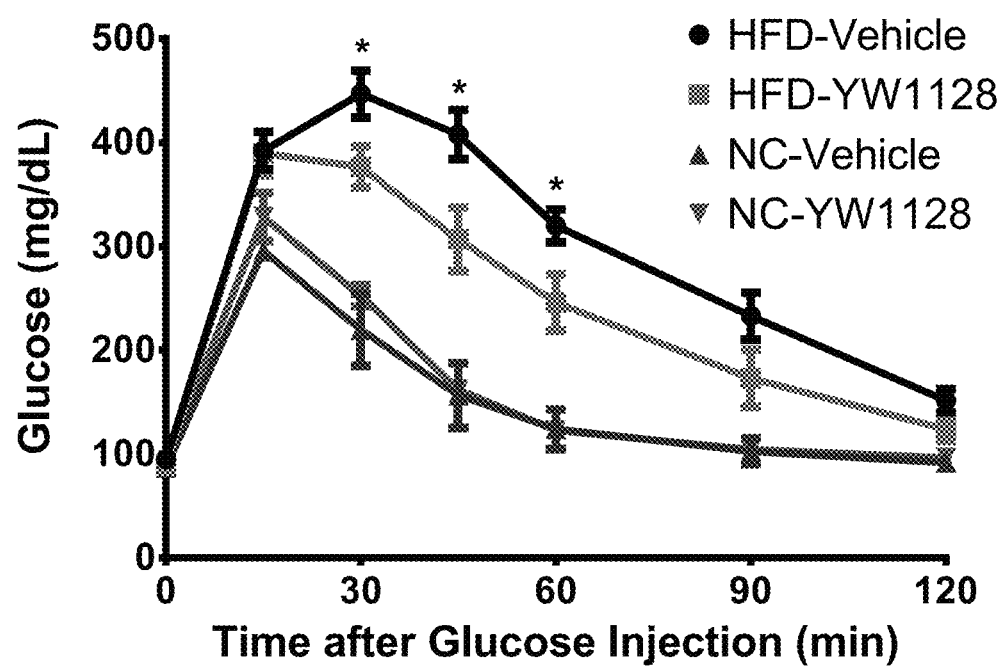
Figure 36C:
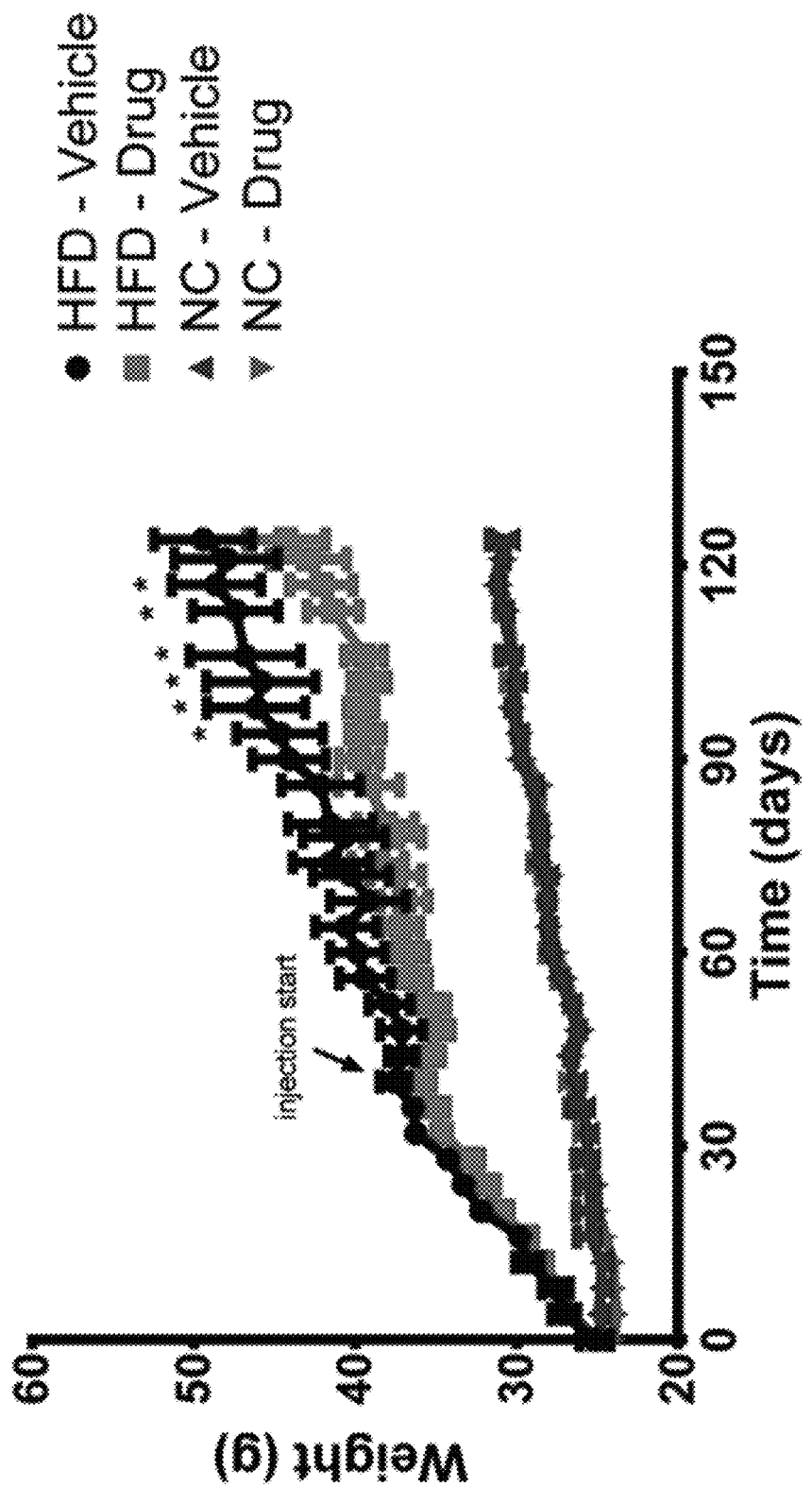
Figure 36D:
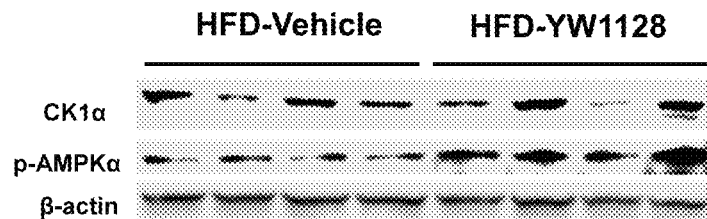

C57BL/6 mice (n=7/group) were put on a Western high-fat diet (HFD) or normal chow diet (NCD). Seven weeks later, the mice received either vehicle or YW1128 by I.P., 40 mg/kg/2 days, for 11 weeks. Representative liver histology was measured by H&E staining (FIG. 36A). An intraperitoneal glucose tolerance test (IPGTT) was conducted at the end of the study (FIG. 36B). Body weight for the mice was monitored during the treatment (FIG. 36C). Increased phosphorylation of AMPKα1 at threonine 172 (T172) (p-AMPKα) in YW1128-treated livers was observed as compared to vehicle-treated livers (FIG. 36D). CK1a did not show any significant change.

Example 14: YW2065 Inhibited SW620 Xenograft Tumor Growth in Nude Mice

Figure 37A:
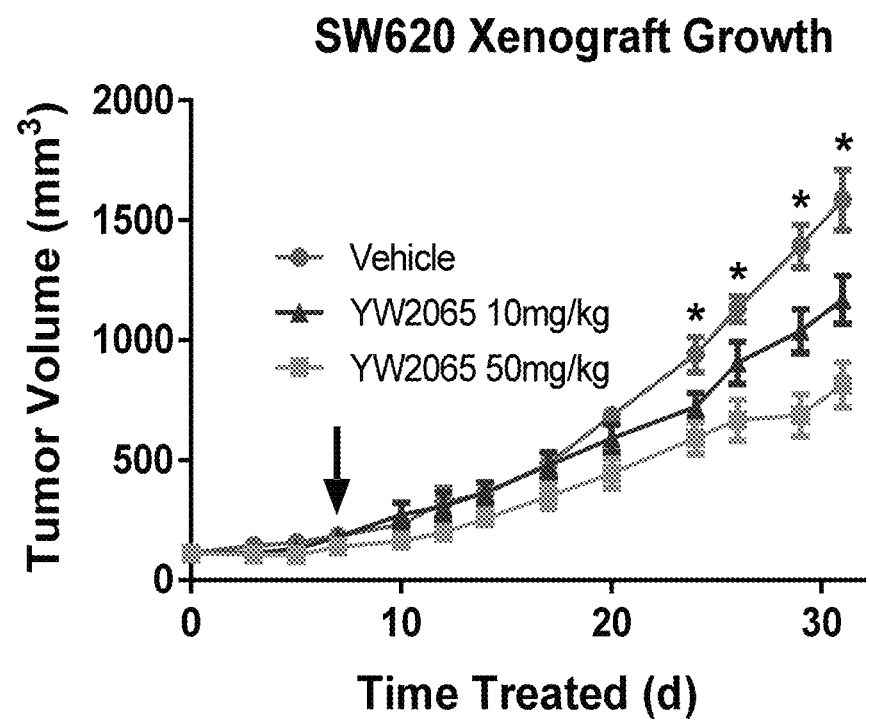
FIGS. 37A to 37C illustrate that YW2065 inhibited SW620 xenograft growth in nude mice.
Figure 37B:
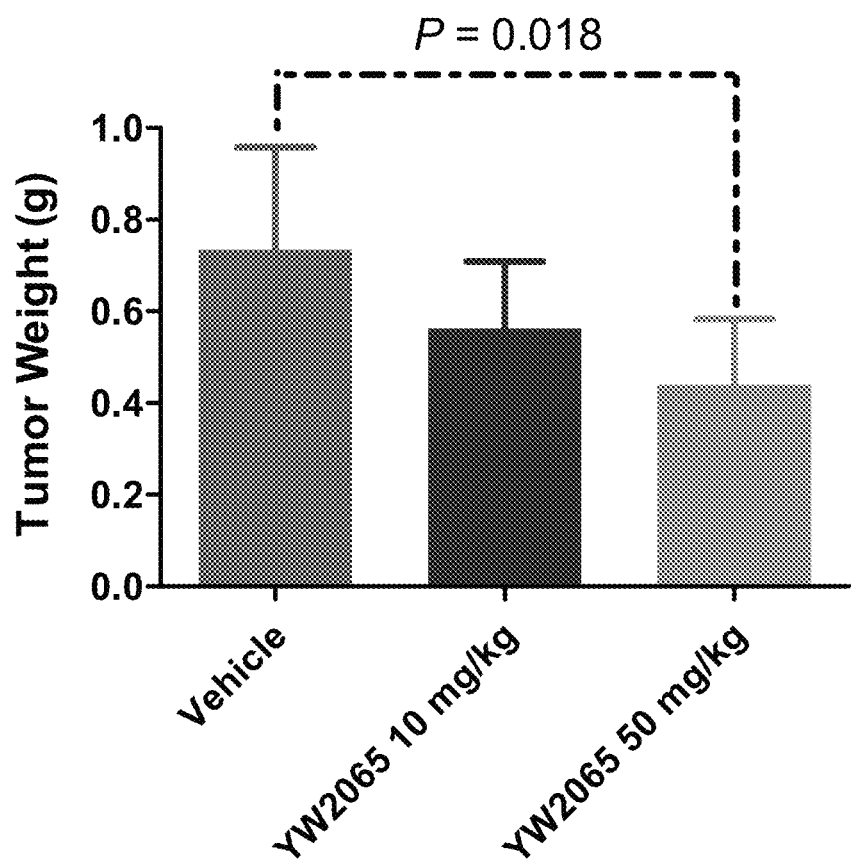
Figure 37C:
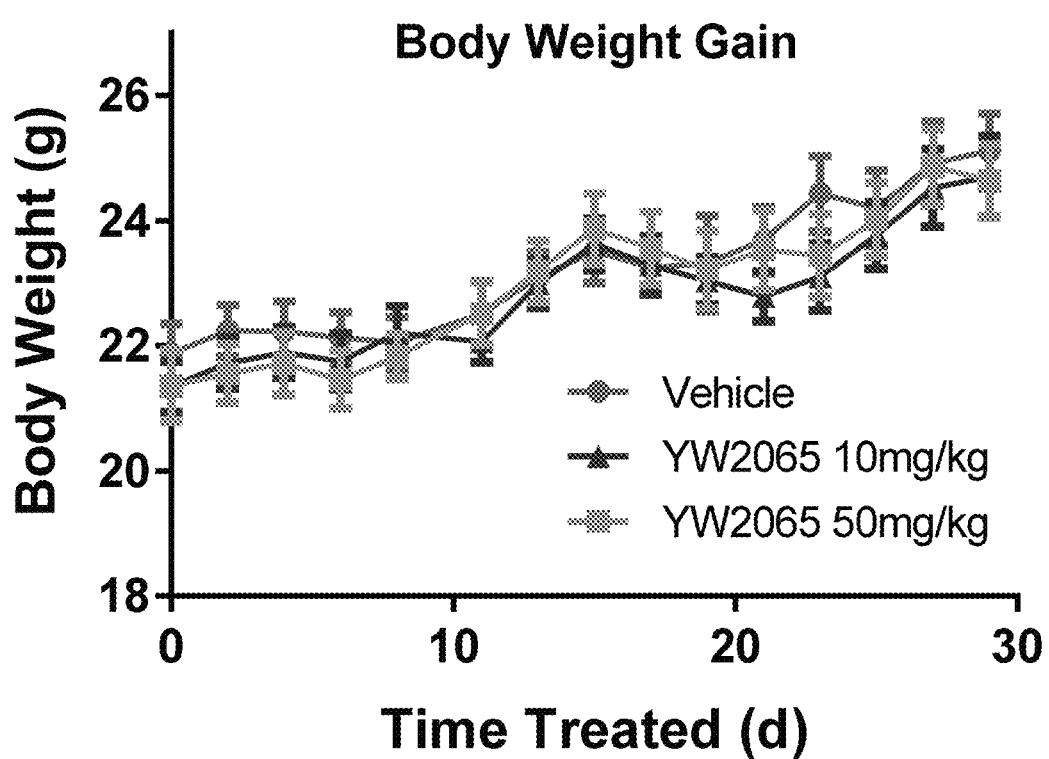

Six-week old nude mice were injected with 2×106 SW620 cells subcutaneously. 10 days after inoculation, mice received an i.p. injection of YW2065 at 10 mg/kg or 50 mg/kg or vehicle each day. The tumor growth (FIG. 37A) was measured every other day. The mice were euthanized at day 32, and tumors were weighed (FIG. 37B). Body weight change was monitored during the study (FIG. 37C). As shown during the study compared to vehicle, YW2065 markedly inhibited tumor growth over a 32 day study.

Figure 38A:
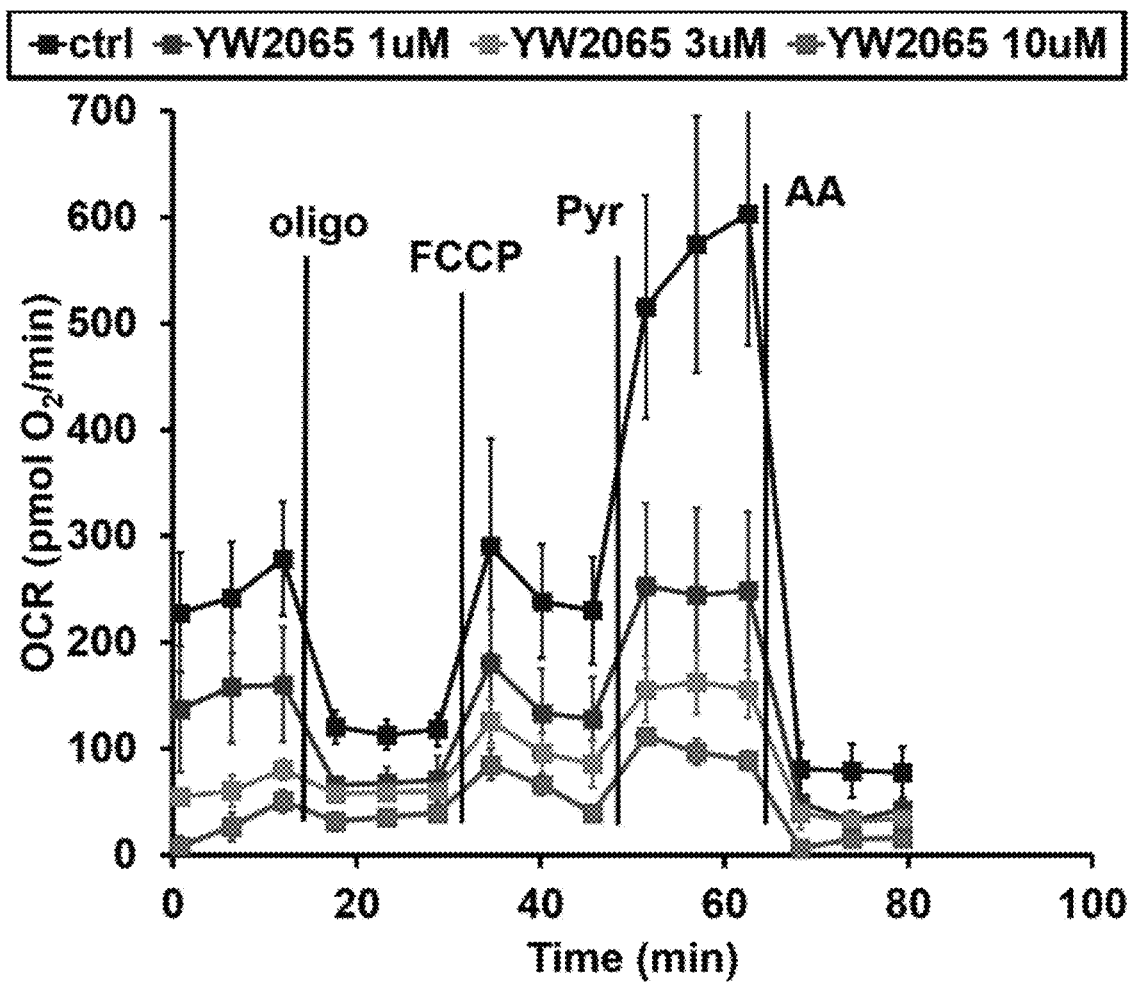
FIGS. 38A to 38D illustrate the effects of YW2065 treatment on mitochondrial function and morphology in SW480 cancer cells.
Figure 38B:
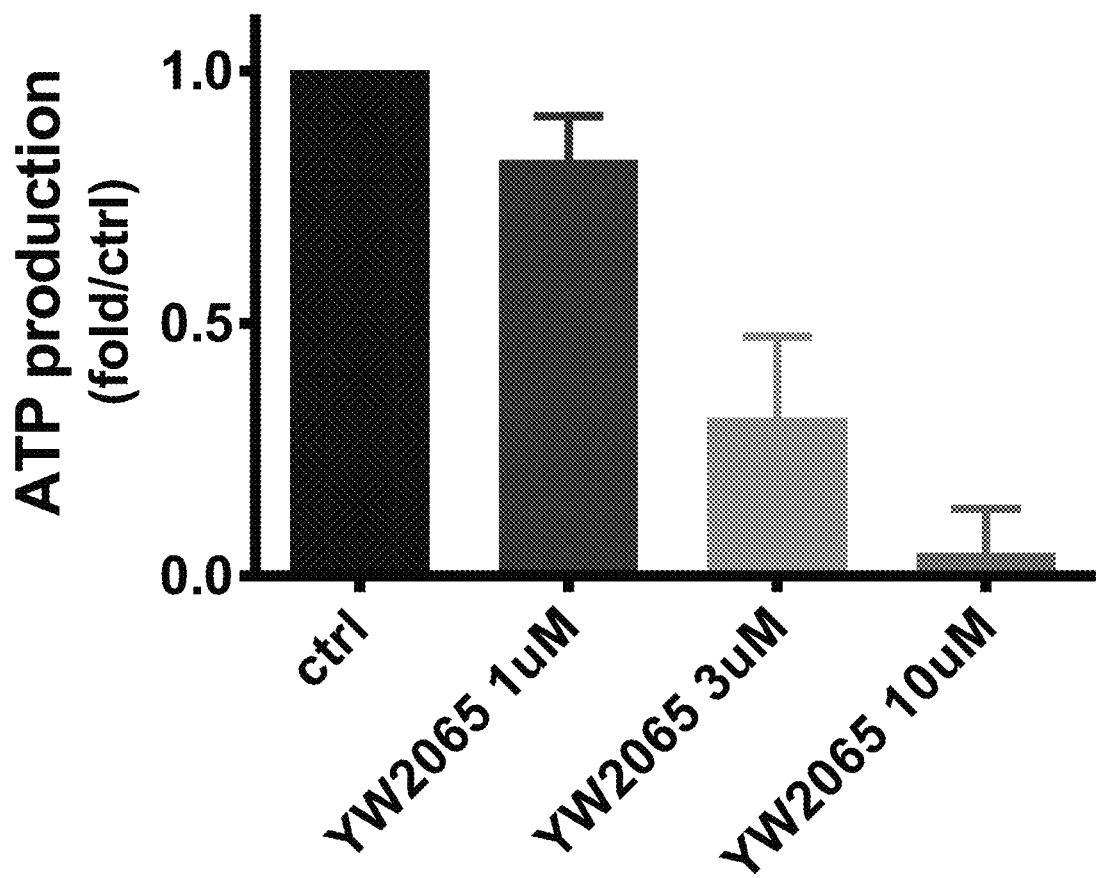
Figure 38C:
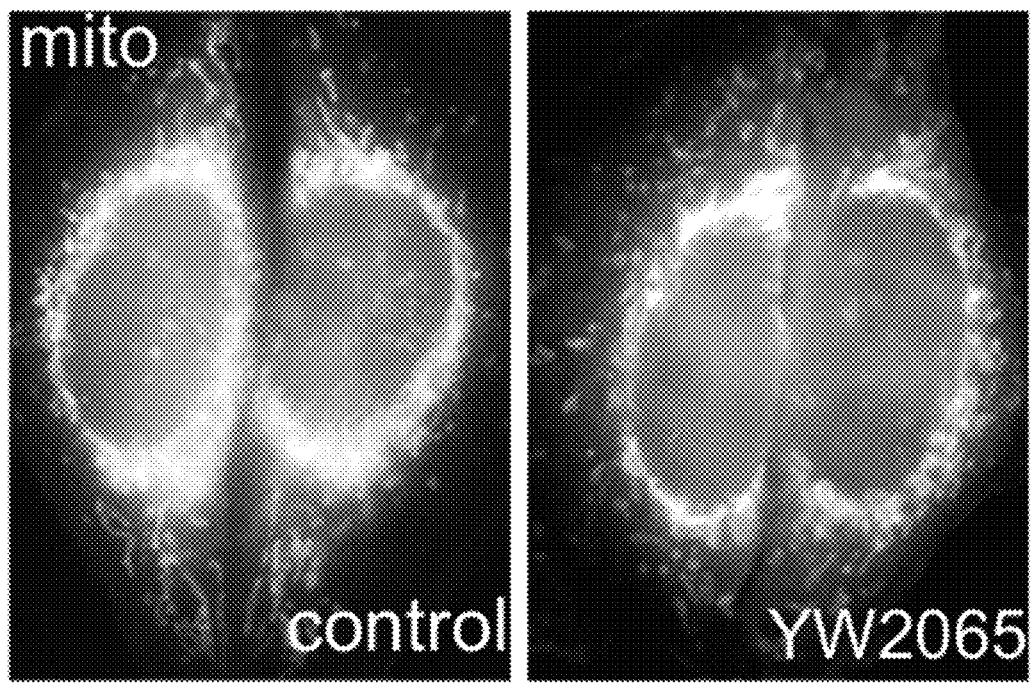
Figure 38D:
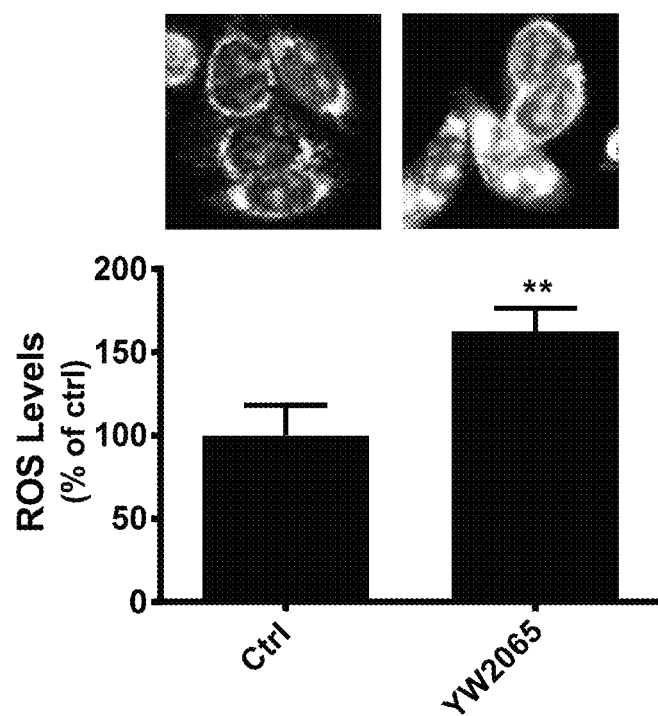

Example 15: Effects of YW2065 Treatment on Mitochondrial Function and Morphology in Colon Cancer Cells Mitochondrial function and morphology was determined in SW480 cells treated with YW2065. YW2065 produced a reduced oxygen consumption rate (OCR) (FIG. 38A) and inhibited ATP production as a function of dosage (FIG. 38B). YW2065 (10 µM) caused short and punctuated mitochondria in SW480 cells after 4 hours of treatment (FIG. 38C). Furthermore, YW2065 increased ROS generation in SW480 cells as evaluated by staining the treated cells with DHE.

A number of patent and non-patent publications are cited herein in order to describe the state of the art to which this invention pertains. The entire disclosure of each of these publications is incorporated by reference herein.

While certain embodiments of the present invention have been described and/or exemplified above, various other embodiments will be apparent to those skilled in the art from the foregoing disclosure. The present invention is, therefore, not limited to the particular embodiments described and/or exemplified, but is capable of considerable variation and modification without departure from the scope and spirit of the appended claims.

Moreover, as used herein, the term "about" means that dimensions, sizes, formulations, parameters, shapes and other quantities and characteristics are not and need not be exact, but may be approximate and/or larger or smaller, as desired, reflecting tolerances, conversion factors, rounding off, measurement error and the like, and other factors known to those of skill in the art. In general, a dimension, size, formulation, parameter, shape or other quantity or characteristic is "about" or "approximate" whether or not expressly stated to be such. It is noted that embodiments of very different sizes, shapes and dimensions may employ the described arrangements.

Furthermore, the transitional terms "comprising", "consisting essentially of" and "consisting of", when used in the appended claims, in original and amended form, define the claim scope with respect to what unrecited additional claim elements or steps, if any, are excluded from the scope of the claim(s). The term "comprising" is intended to be inclusive or open-ended and does not exclude any additional, unrecited element, method, step or material. The term "consisting of" excludes any element, step or material other than those specified in the claim and, in the latter instance, impurities ordinary associated with the specified material(s). The term "consisting essentially of" limits the scope of a claim to the specified elements, steps or material(s) and those that do not materially affect the basic and novel characteristic(s) of the claimed invention. All compounds, compositions, formulations, and methods described herein that embody the present invention can, in alternate embodiments, be more specifically defined by any of the transitional terms "comprising," "consisting essentially of," and "consisting of."

REFERENCES

1. Bailey, K. A., Savic, D., Zielinski, M., Park, S. Y., Wang, L. J., Witkowski, P., Brady, M., Hara, M., Bell, G. I., and Nobrega, M. A. (2015). Evidence of non-pancreatic beta cell-dependent roles of Tcf7l2 in the regulation of glucose metabolism in mice. Hum Mol Genet 24, 1646-1654.
2. Boj, S. F., van Es, J. H., Huch, M., Li, V. S., Jose, A., Hatzis, P., Mokry, M., Haegebarth, A., van den Born, M., Chambon, P., et al. (2012). Diabetes risk gene and Wnt effector Tcf7l2/TCF4 controls hepatic response to perinatal and adult metabolic demand. Cell 151, 1595-1607.
3. Bordonaro, M. (2009). Role of Wnt signaling in the development of type 2 diabetes. Vitam Horm 80, 563-581.
4. Caricasole, A., Copani, A., Caruso, A., Caraci, F., Iacovelli, L., Sortino, M. A., Terstappen, G. C., and Nicoletti, F. (2003). The Wnt pathway, cell-cycle activation and beta-amyloid: novel therapeutic strategies in Alzheimer's disease? Trends Pharmacol Sci 24, 233-238.
5. Cauchi, S., El Achhab, Y., Choquet, H., Dina, C., Krempler, F., Weitgasser, R., Nejjari, C., Patsch, W., Chikri, M., Meyre, D., et al. (2007). TCF7L2 is reproducibly associated with type 2 diabetes in various ethnic groups: a global meta-analysis. J Mol Med (Berl) 85, 777-782.
6. Chang, H. W., Lee, Y. S., Nam, H. Y., Han, M. W., Kim, H. J., Moon, S. Y., Jeon, H., Park, J. J., Carey, T. E., Chang, S. E., et al. (2013). Knockdown of beta-catenin controls both apoptotic and autophagic cell death through LKB1/AMPK signaling in head and neck squamous cell carcinoma cell lines. Cell Signal 25, 839-847.
7. Christodoulides, C., Scarda, A., Granzotto, M., Milan, G., Dalla Nora, E., Keogh, J., De Pergola, G., Stirling, H., Pannacciulli, N., Sethi, J. K., et al. (2006). WNT10B mutations in human obesity. Diabetologia 49, 678-684.
8. Clevers, H. (2006). Wnt/beta-catenin signaling in development and disease. Cell 127, 469-480.
9. Cselenyi, C. S., Jemigan, K. K., Tahinci, E., Thorne, C. A., Lee, L. A., and Lee, E. (2008). LRP6 transduces a canonical Wnt signal independently of Axin degradation by inhibiting GSK3's phosphorylation of beta-catenin. Proceedings of the National Academy of Sciences of the United States of America 105, 8032-8037.
10. Elbein, S. C., Chu, W. S., Das, S. K., Yao-Borengasser, A., Hasstedt, S. J., Wang, H., Rasouli, N., and Kern, P. A. (2007). Transcription factor 7-like 2 polymorphisms and type 2 diabetes, glucose homeostasis traits and gene expression in US participants of European and African descent. Diabetologia 50, 1621-1630.
11. Florez, J. C., Jablonski, K. A., Bayley, N., Pollin, T. I., de Bakker, P. I., Shuldiner, A. R., Knowler, W. C., Nathan, D. M., and Altshuler, D. (2006). TCF7L2 polymorphisms and progression to diabetes in the Diabetes Prevention Program. The New England journal of medicine 355, 241-250.
12. Freland, L., and Beaulieu, J. M. (2012). Inhibition of GSK3 by lithium, from single molecules to signaling networks. Front Mol Neurosci 5, 14.
13. Grant, S. F., Thorleifsson, G., Reynisdottir, I., Benediktsson, R., Manolescu, A., Sainz, J., Helgason, A., Stefansson, H., Emilsson, V., Helgadottir, A., et al. (2006). Variant of transcription factor 7-like 2 (TCF7L2) gene confers risk of type 2 diabetes. Nature genetics 38, 320-323.
14. Gwak, J., Hwang, S. G., Park, H. S., Choi, S. R., Park, S. H., Kim, H., Ha, N. C., Bae, S. J., Han, J. K., Kim, D. E., et al. (2012). Small molecule-based disruption of the Axin/beta-catenin protein complex regulates mesenchymal stem cell differentiation. Cell Res 22, 237-247.
15. Hao, J., Ao, A., Zhou, L., Murphy, C. K., Frist, A. Y., Keel, J. J., Thorne, C. A., Kim, K., Lee, E., and Hong, C. C. (2013). Selective small molecule targeting beta-catenin function discovered by in vivo chemical genetic screen. Cell Rep 4, 898-904.
16. He, L., Sabet, A., Djedjos, S., Miller, R., Sun, X., Hussain, M. A., Radovick, S., and Wondisford, F. E. (2009). Metformin and insulin suppress hepatic gluconeogenesis through phosphorylation of CREB binding protein. Cell 137, 635-646.
17. Henderson, W. R., Jr., Chi, E. Y., Ye, X., Nguyen, C., Tien, Y. T., Zhou, B., Borok, Z., Knight, D. A., and Kahn, M. (2010). Inhibition of Wnt/beta-catenin/CREB binding protein (CBP) signaling reverses pulmonary fibrosis. Proc Natl Acad Sci USA 107, 14309-14314.
18. Huang, S. M., Mishina, Y. M., Liu, S., Cheung, A., Stegmeier, F., Michaud, G. A., Charlat, O., Wiellette, E., Zhang, Y., Wiessner, S., et al. (2009). Tankyrase inhibition stabilizes axin and antagonizes Wnt signalling. Nature 461, 614-620.
19. Jin, T. (2008). The WNT signalling pathway and diabetes mellitus. Diabetologia 51, 1771-1780.
20. Jones, H. M., and Houston, J. B. (2004). Substrate depletion approach for determining in vitro metabolic clearance: time dependencies in hepatocyte and microsomal incubations. Drug Metab Dispos 32, 973-982.
21. Kanazawa, A., Tsukada, S., Sekine, A., Tsunoda, T., Takahashi, A., Kashiwagi, A., Tanaka, Y., Babazono, T., Matsuda, M., Kaku, K., et al. (2004). Association of the gene encoding wingless-type mammary tumor virus integration-site family member 5B (WNT5B) with type 2 diabetes. American journal of human genetics 75, 832-843.
22. Katsu, T., Ujike, H., Nakano, T., Tanaka, Y., Nomura, A., Nakata, K., Takaki, M., Sakai, A., Uchida, N., Imamura, T., et al. (2003). The human frizzled-3 (FZD3) gene on chromosome 8p21, a receptor gene for Wnt ligands, is associated with the susceptibility to schizophrenia. Neurosci Lett 353, 53-56.
23. Kimelman, D., and Xu, W. (2006). beta-catenin destruction complex: insights and questions from a structural perspective. Oncogene 25, 7482-7491.
24. Kinzler, K. W., and Vogelstein, B. (1996). Lessons from hereditary colorectal cancer. Cell 87, 159-170.
25. Kozlovsky, N., Belmaker, R. H., and Agam, G. (2002). GSK-3 and the neurodevelopmental hypothesis of schizophrenia. Eur Neuropsychopharmacol 12, 13-25.
26. Lenth, R. V. Java Applets for Power and Sample Size [Computer software], the website being located at www.statuiowa.edu/~rlenth/Power.
27. Lepourcelet, M., Chen, Y. N. P., France, D. S., Wang, H. S., Crews, P., Petersen, F., Bruseo, C., Wood, A. W., and Shivdasani, R. A. (2004). Small-molecule antagonists of the oncogenic Tcf/beta-catenin protein complex. Cancer Cell 5, 91-102.
28. Li, Q., Guo, D., Dong, Z., Zhang, W., Zhang, L., Huang, S. M., Polli, J. E., and Shu, Y. (2013). Ondansetron can enhance cisplatin-induced nephrotoxicity via inhibition of multiple toxin and extrusion proteins (MATEs). Toxicol Appl Pharmacol 273, 100-109.
29. Li, Q., Peng, X., Yang, H., Wang, H., and Shu, Y. (2011). Deficiency of multidrug and toxin extrusion 1 enhances renal accumulation of paraquat and deteriorates kidney injury in mice. Mol Pharm 8, 2476-2483.
30. Liang, H., Chen, Q., Coles, A. H., Anderson, S. J., Pihan, G., Bradley, A., Gerstein, R., Jurecic, R., and Jones, S. N. (2003). Wnt5a inhibits B cell proliferation and functions as a tumor suppressor in hematopoietic tissue. Cancer Cell 4, 349-360.
31. Liu, C., Li, Y., Semenov, M., Han, C., Baeg, G. H., Tan, Y., Zhang, Z., Lin, X., and He, X. (2002). Control of beta-catenin phosphorylation/degradation by a dual-kinase mechanism. Cell 108, 837-847.
32. Liu, H., Fergusson, M. M., Wu, J. J., Rovira, II, Liu, J., Gavrilova, O., Lu, T., Bao, J., Han, D., Sack, M. N., et al. (2011). Wnt signaling regulates hepatic metabolism. Sci Signal 4, ra6.
33. Lu, D., Choi, M. Y., Yu, J., Castro, J. E., Kipps, T. J., and Carson, D. A. (2011). Salinomycin inhibits Wnt signaling and selectively induces apoptosis in chronic lymphocytic leukemia cells. Proc Natl Acad Sci USA 108, 13253-13257.

34. Luo, J., Chen, J., Deng, Z. L., Luo, X., Song, W. X., Sharff, K. A., Tang, N., Haydon, R. C., Luu, H. H., and He, T. C. (2007). Wnt signaling and human diseases: what are the therapeutic implications? Lab Invest 87, 97-103.
35. Lyssenko, V., Lupi, R., Marchetti, P., Del Guerra, S., Orho-Melander, M., Almgren, P., Sjogren, M., Ling, C., Eriksson, K. F., Lethagen, A. L., et al. (2007). Mechanisms by which common variants in the TCF7L2 gene increase risk of type 2 diabetes. The Journal of clinical investigation 117, 2155-2163.
36. Miyaoka, T., Seno, H., and Ishino, H. (1999). Increased expression of Wnt-1 in schizophrenic brains. Schizophr Res 38, 1-6.
37. Mudher, A., and Lovestone, S. (2002). Alzheimer's disease-do tauists and baptists finally shake hands? Trends Neurosci 25, 22-26.
38. Niemann, S., Zhao, C., Pascu, F., Stahl, U., Aulepp, U., Niswander, L., Weber, J. L., and Muller, U. (2004). Homozygous WNT3 mutation causes tetra-amelia in a large consanguineous family. Am J Hum Genet 74, 558-563.
39. Oh, D. Y., and Olefsky, J. M. (2010). Medicine. Wnt fans the flames in obesity. Science 329, 397-398.
40. Oh, K. J., Park, J., Lee, S. Y., Hwang, I., Kim, J. B., Park, T. S., Lee, H. J., and Koo, S. H. (2011). Atypical antipsychotic drugs perturb AMPK-dependent regulation of hepatic lipid metabolism. Am J Physiol Endocrinol Metab 300, E624-632.
41. Ohishi, K., Toume, K., Arai, M. A., Koyano, T., Kowithayakom, T., Mizoguchi, T., Itoh, M., and Ishibashi, M. (2015). 9-Hydroxycanthin-6-one, a beta-Carboline Alkaloid from *Eurycoma longifolia*, Is the First Wnt Signal Inhibitor through Activation of Glycogen Synthase Kinase 3beta without Depending on Casein Kinase 1alpha. J Nat Prod.
42. Pai, R., Tamawski, A. S., and Tran, T. (2004). Deoxycholic acid activates beta-catenin signaling pathway and increases colon cell cancer growth and invasiveness. Mol Biol Cell 15, 2156-2163.
43. Park, H. Y., Toume, K., Arai, M. A., Sadhu, S. K., Ahmed, F., and Ishibashi, M. (2014). Calotropin: A Cardenolide from *Calotropis gigantea* that Inhibits Wnt Signaling by Increasing Casein Kinase 1 alpha in Colon Cancer Cells. Chembiochem 15, 872-878.
44. Piao, S., Lee, S. H., Kim, H., Yum, S., Stamos, J. L., Xu, Y., Lee, S. J., Lee, J., Oh, S., Han, J. K., et al. (2008). Direct inhibition of GSK3beta by the phosphorylated cytoplasmic domain of LRP6 in Wnt/beta-catenin signaling. PloS one 3, e4046.
45. Pokhodylo, N. T., Matiychuk, V. S., and Obushak, M. D. (2010). Synthesis of 1-(R-Phenyl)-5-(R-Methyl)-1H-1,2,3-triazole-4-carboxylic Acids by One-Pot Tandem Reaction. Synthetic Communications 40, 1932-1938.
46. Rodova, M., Islam, M. R., Maser, R. L., and Calvet, J. P. (2002). The polycystic kidney disease-1 promoter is a target of the beta-catenin/T-cell factor pathway. J Biol Chem 277, 29577-29583.
47. Sadot, E., Conacci-Sorrell, M., Zhurinsky, J., Shnizer, D., Lando, Z., Zharhary, D., Kam, Z., Ben-Ze'ev, A., and Geiger, B. (2002). Regulation of S33/S37 phosphorylated beta-catenin in normal and transformed cells. Journal of cell science 115, 2771-2780.
48. Savic, D., Ye, H., Aneas, I., Park, S. Y., Bell, G. I., and Nobrega, M. A. (2011). Alterations in TCF7L2 expression define its role as a key regulator of glucose metabolism. Genome Res.
49. Saxena, R., Gianniny, L., Burtt, N. P., Lyssenko, V., Giuducci, C., Sjogren, M., Florez, J. C., Almgren, P., Isomaa, B., Orho-Melander, M., et al. (2006). Common single nucleotide polymorphisms in TCF7L2 are reproducibly associated with type 2 diabetes and reduce the insulin response to glucose in nondiabetic individuals. Diabetes 55, 2890-2895.
50. Schinner, S. (2009). Wnt-signalling and the metabolic syndrome. Horm Metab Res 41, 159-163.
51. Scriven, E. F. V., and Turnbull, K. (1988). Azides—Their Preparation and Synthetic Uses. Chemical Reviews 88, 297-368.
52. Shu, Y., Sheardown, S. A., Brown, C., Owen, R. P., Zhang, S., Castro, R. A., Ianculescu, A. G., Yue, L., Lo, J. C., Burchard, E. G., et al. (2007). Effect of genetic variation in the organic cation transporter 1 (OCT1) on metformin action. The Journal of clinical investigation 117, 1422-1431.
53. Singh, R., De Aguiar, R. B., Naik, S., Mani, S., Ostadsharif, K., Wencker, D., Sotoudeh, M., Malekzadeh, R., Sherwin, R. S., and Mani, A. (2013). LRP6 enhances glucose metabolism by promoting TCF7L2-dependent insulin receptor expression and IGF receptor stabilization in humans. Cell Metab 17, 197-209.
54. Smith, T. C., Kinkel, A. W., Gryczko, C. M., and Goulet, J. R. (1976). Absorption of pyrvinium pamoate. Clin Pharmacol Ther 19, 802-806.
55. Taelman, V. F., Dobrowolski, R., Plouhinec, J. L., Fuentealba, L. C., Vorwald, P. P., Gumper, I., Sabatini, D. D., and De Robertis, E. M. (2010). Wnt signaling requires sequestration of glycogen synthase kinase 3 inside multivesicular endosomes. Cell 143, 1136-1148.
56. Thome, C. A., Hanson, A. J., Schneider, J., Tahinci, E., Orton, D., Cselenyi, C. S., Jemigan, K. K., Meyers, K. C., Hang, B. I., Waterson, A. G., et al. (2010). Small-molecule inhibition of Wnt signaling through activation of casein kinase 1 alpha. Nature Chemical Biology 6, 829-836.
57. Toume, K., Kamiya, K., Arai, M. A., Mori, N., Sadhu, S. K., Ahmed, F., and Ishibashi, M. (2013). Xylogranin B: a potent Wnt signal inhibitory limonoid from *Xylocarpus granatum*. Org Lett 15, 6106-6109.
58. van Breemen, R. B., and Li, Y. (2005). Caco-2 cell permeability assays to measure drug absorption. Expert Opin Drug Metab Toxicol 1, 175-185.
59. Venerando, A., Girardi, C., Ruzzene, M., and Pinna, L. A. (2013). Pyrvinium pamoate does not activate protein kinase CK1, but promotes Akt/PKB down-regulation and GSK3 activation. Biochem J 452, 131-137.
60. Vivian, D., and Polli, J. E. (2014). Synthesis and in vitro evaluation of bile acid prodrugs of floxuridine to target the liver. International journal of pharmaceutics 475, 597-604.
61. Wu, G., Huang, H., Garcia Abreu, J., and He, X. (2009). Inhibition of GSK3 phosphorylation of beta-catenin via phosphorylated PPPSPXS motifs of Wnt coreceptor LRP6. PloS one 4, e4926.
62. Yang, H., Li, Q., Lee, J. H., and Shu, Y. (2012). Reduction in Tcf7l2 expression decreases diabetic susceptibility in mice. Int J Biol Sci 8, 791-801.
63. Zheng, Y., Zhang, W., Pendleton, E., Leng, S., Wu, J., Chen, R., and Sun, X. J. (2009). Improved insulin sensitivity by calorie restriction is associated with reduction of ERK and p70S6K activities in the liver of obese Zucker rats. J Endocrinol 203, 337-347.
64. Zhu, W., Groh, M., Haupenthal, J., and Hartmann, R. W. (2013). A detective story in drug discovery: elucidation of a screening artifact reveals polymeric carboxylic acids as potent inhibitors of RNA polymerase. Chemistry 19, 8397-8400.

What is claimed is:

1. A method of treating or preventing a disease alleviated by inhibiting Wnt/β-catenin signaling in a patient in need of said treatment or prevention, the method comprising administering a therapeutically effective amount of one or more compounds having the formula:

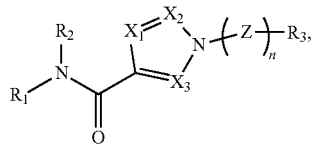

(I)

wherein $R_1$ and $R_2$ each can independently represent a substituent selected from the group consisting of H and substituted or unsubstituted alkyl, alkenyl, alkynyl, cycloalkyl, aryl, heterocycle, heteroaryl, alkoxy, carboxy, carbalkoxy, and carboxamido;

$R_3$ represents a substituent selected from the group consisting of substituted or unsubstituted alkyl, alkenyl, alkynyl, cycloalkyl, aryl, heterocycle, and heteroaryl;

n represents an integer of 0 to 2, Z represents one or more substituted or unsubstituted alkyl substituents when n is 1 or 2;

$X_1$ represents N or $CR_4$;
$X_2$ represents N or $CR_5$;
$X_3$ represents N or $CR_6$;

$R_4$, $R_5$, and $R_6$ each can independently represent a substituent selected from the group consisting of H, OH, $NO_2$, CN, halo, and substituted or unsubstituted alkyl, alkylcarbonyl, alkenyl, alkynyl, cycloalkyl, aryl, heterocycle, heteroaryl, amino, alkoxy, carboxy, carbalkoxy, carboxamido, sulfonyl, sulfonamido, sulfinyl, monoalkylaminosulfinyl, dialkylaminosulfinyl, monoalkylaminosulfonyl, dialkylaminosulfonyl, alkylsulfonylamino, hydroxysulfonyloxy, alkoxysulfonyloxy, alkylsulfonyloxy, hydroxysulfonyl, alkoxysulfonyl, alkylsulfonylalkyl, monoalkylaminosulfonylalkyl, dialkylaminosulfonylalkyl, monoalkylaminosulfinylalkyl, and dialkylaminosulfinylalkyl;

wherein when both are present, $R_4$ and $R_5$ can be taken together to form a substituted or unsubstituted m-membered cycloalkyl or heterocycle, wherein m represents an integer of 5 to 7;

or the pharmaceutically acceptable salts of said one or more compounds;

with the proviso that:
when $X_1$ and $X_2$ represent $CR_4$ and $CR_5$, respectively, then $R_3$ is substituted aryl; and
compounds wherein $R_1$ and $R_2$ each are H and substituted aryl, $R_3$ is substituted aryl, n is 0, $X_1$ is N, $X_2$ is N, $X_3$ is $CR_6$, and $R_6$ is alkyl, are excluded.

2. The method of claim 1, wherein the one or more compounds are selected from the group consisting of:

2,5-Dimethyl-N-(pyridin-2-yl)-1-(p-tolyl)-1H-pyrrole-3-carboxamide,
2,5-Dimethyl-N-(pyrazin-2-yl)-1-(p-tolyl)-1H-pyrrole-3-carboxamide,
2,5-Dimethyl-N-(4-phenylthiazol-2-yl)-1-(p-tolyl)-1H-pyrrole-3-carboxamide,
N-Benzyl-2,5-dimethyl-1-(p-tolyl)-1H-pyrrole-3-carboxamide,
5-Methyl-N-(pyridin-2-yl)-1-(p-tolyl)-1H-1,2,3-triazole-4-carboxamide,
5-Methyl-N-(6-methylpyridin-2-yl)-1-(p-tolyl)-1H-1,2,3-triazole-4-carboxamide,
5-Methyl-N-(pyridin-2-ylmethyl)-1-(p-tolyl)-1H-1,2,3-triazole-4-carboxamide,
5-Methyl-N-(2-methyl-4-oxo-4H-chromen-7-yl)-1-(p-tolyl)-1H-1,2,3-triazole-4-carboxamide,
5-Methyl-N-(3-methylisoxazol-5-yl)-1-(p-tolyl)-1H-1,2,3-triazole-4-carboxamide,
N-(4,5-diphenylthiazol-2-yl)-5-methyl-1-(p-tolyl)-1H-1,2,3-triazole-4-carboxamide,
5-Methyl-N-(1-methyl-1H-benzo[d]imidazol-2-yl)-1-(p-tolyl)-1H-1,2,3-triazole-4-carboxamide,
5-Methyl-N-(quinolin-2-yl)-1-(p-tolyl)-1H-1,2,3-triazole-4-carboxamide,
5-Methyl-N-(quinolin-2-yl)-1-(o-tolyl)-1H-1,2,3-triazole-4-carboxamide,
5-Methyl-N-(naphthalen-2-yl)-1-(o-tolyl)-1H-1,2,3-triazole-4-carboxamide,
N-(benzo[d]thiazol-2-yl)-5-methyl-1-(o-tolyl)-1H-1,2,3-triazole-4-carboxamide,
5-Methyl-N-(4-phenylthiazol-2-yl)-1-(o-tolyl)-1H-1,2,3-triazole-4-carboxamide,
1-(2,3-Dimethylphenyl)-5-methyl-N-(quinolin-2-yl)-1H-1,2,3-triazole-4-carboxamide,
1-(2,4-Dimethylphenyl)-5-methyl-N-(quinolin-2-yl)-1H-1,2,3-triazole-4-carboxamide,
1-(3-Chlorophenyl)-5-methyl-N-(quinolin-2-yl)-1H-1,2,3-triazole-4-carboxamide,
1-(2-Fluorophenyl)-5-methyl-N-(quinolin-2-yl)-1H-1,2,3-triazole-4-carboxamide,
1-(2-Bromophenyl)-5-methyl-N-(quinolin-2-yl)-1H-1,2,3-triazole-4-carboxamide,
1-(2-Cyanophenyl)-5-methyl-N-(quinolin-2-yl)-1H-1,2,3-triazole-4-carboxamide,
1-(2-Methoxyphenyl)-5-methyl-N-(quinolin-2-yl)-1H-1,2,3-triazole-4-carboxamide,
1-(4-Fluoro-2-nitrophenyl)-5-methyl-N-(quinolin-2-yl)-1H-1,2,3-triazole-4-carboxamide,
1-(2-Acetylphenyl)-5-methyl-N-(quinolin-2-yl)-1H-1,2,3-triazole-4-carboxamide,
1-(2-Carbamoylphenyl)-5-methyl-N-(quinolin-2-yl)-1H-1,2,3-triazole-4-carboxamide,
1-([1,1'-biphenyl]-2-yl)-5-methyl-N-(quinolin-2-yl)-1H-1,2,3-triazole-4-carboxamide,
5-Methyl-1-(2-morpholinophenyl)-N-(quinolin-2-yl)-1H-1,2,3-triazole-4-carboxamide,
5-Methyl-1-(naphthalen-1-yl)-N-(quinolin-2-yl)-1H-1,2,3-triazole-4-carboxamide,
1-(2-fluorophenyl)-5-isopropyl-N-(quinolin-2-yl)-1H-1,2,3-triazole-4-carboxamide,
5-Ethyl-1-(2-fluorophenyl)-N-(quinolin-2-yl)-1H-1,2,3-triazole-4-carboxamide,
5-Methyl-N-(quinolin-2-yl)-1-(o-tolyl)-1H-pyrazole-4-carboxamide,
1-(2-Fluorophenyl)-5-methyl-N-(quinolin-2-yl)-1H-pyrazole-4-carboxamide,
1-(2-Bromophenyl)-5-methyl-N-(quinolin-2-yl)-1H-pyrazole-4-carboxamide,
2,5-Dimethyl-N-(quinolin-2-yl)-1-(o-tolyl)-1H-imidazole-4-carboxamide,
1-(2-Fluorophenyl)-2,5-dimethyl-N-(quinolin-2-yl)-1H-imidazole-4-carboxamide,
1-(2-Bromophenyl)-2,5-dimethyl-N-(quinolin-2-yl)-1H-imidazole-4-carboxamide,
2,5-Dimethyl-1-phenyl-N-(quinolin-2-yl)-1H-imidazole-4-carboxamide,
1-(2-Chlorophenyl)-5-methyl-N-(quinolin-2-yl)-1H-pyrazole-4-carboxamide
1-(2-Ethylphenyl)-5-methyl-N-(quinolin-2-yl)-1H-pyrazole-4-carboxamide,
1-(2,6-dimethylphenyl)-5-methyl-N-(quinolin-2-yl)-1H-pyrazole-4-carboxamide, 1-(Tert-butyl)-5-methyl-N-(quinolin-2-yl)-1H-pyrazole-4-carboxamide,
1-(2,5-dimethylphenyl)-5-methyl-N-(quinolin-2-yl)-1H-pyrazole-4-carboxamide,
1-(2,4-difluorophenyl)-5-methyl-N-(quinolin-2-yl)-1H-pyrazole-4-carboxamide,
5-methyl-1-phenyl-N-(quinolin-2-yl)-1H-pyrazole-4-carboxamide,
1-cyclohexyl-5-methyl-N-(quinolin-2-yl)-1H-pyrazole-4-carboxamide,
5-methyl-1-(1-phenylethyl)-N-(quinolin-2-yl)-1H-pyrazole-4-carboxamide,
5-methyl-N-(quinolin-2-yl)-1-(2,2,2-trifluoroethyl)-1H-pyrazole-4-carboxamide,
5-methyl-1-(3-methylpyridin-2-yl)-N-(quinolin-2-yl)-1H-pyrazole-4-carboxamide,
1-(3-chloro-2-fluorophenyl)-5-methyl-N-(quinolin-2-yl)-1H-pyrazole-4-carboxamide,
1-(2,6-difluorophenyl)-5-methyl-N-(quinolin-2-yl)-1H-pyrazole-4-carboxamide,
1-(2-bromo-6-fluorophenyl)-5-methyl-N-(quinolin-2-yl)-1H-pyrazole-4-carboxamide,
5-methyl-1-phenyl-N-(quinolin-2-yl)-1H-pyrazole-3-carboxamide,
5-methyl-N-(quinolin-2-yl)-1-(o-tolyl)-1H-pyrazole-3-carboxamide,
1-(2-ethylphenyl)-5-methyl-N-(quinolin-2-yl)-1H-pyrazole-3-carboxamide,
1-phenyl-N-(quinolin-2-yl)-1,4,5,6-tetrahydrocyclopenta[c]pyrazole-3-carboxamide,
1-phenyl-N-(quinolin-2-yl)-4,5,6,7-tetrahydro-1H-indazole-3-carboxamide,
3,5-dimethyl-1-phenyl-N-(quinolin-2-yl)-1H-pyrazole-4-carboxamide,
1-(2,5-dimethylphenyl)-3,5-dimethyl-N-(quinolin-2-yl)-1H-pyrazole-4-carboxamide,
1-(2-bromophenyl)-3,5-dimethyl-N-(quinolin-2-yl)-1H-pyrazole-4-carboxamide,
5-ethyl-1-phenyl-N-(quinolin-2-yl)-1H-pyrazole-4-carboxamide,
5-isopropyl-1-phenyl-N-(quinolin-2-yl)-1H-pyrazole-4-carboxamide,
5-chloro-1-phenyl-N-(quinolin-2-yl)-1H-pyrazole-4-carboxamide,
5-bromo-1-phenyl-N-(quinolin-2-yl)-1H-pyrazole-4-carboxamide,
5-(dimethylamino)-1-phenyl-N-(quinolin-2-yl)-1H-pyrazole-4-carboxamide,
1-(2-ethylphenyl)-5-methyl-N-(naphthalen-2-yl)-1H-pyrazole-4-carboxamide,
1-(2-ethylphenyl)-N-(isoquinolin-3-yl)-5-methyl-1H-pyrazole-4-carboxamide,
1-(2-ethylphenyl)-5-methyl-N-(quinolin-3-yl)-1H-pyrazole-4-carboxamide,
1-(2-ethylphenyl)-5-methyl-N-(6-methylpyridin-2-yl)-1H-pyrazole-4-carboxamide,
N-(6-bromoquinolin-2-yl)-5-methyl-1-(o-tolyl)-1H-1,2,3-triazole-4-carboxamide,
5-methyl-N-(6-(morpholinomethyl)quinolin-2-yl)-1-(o-tolyl)-1H-1,2,3-triazole-4-carboxamide,
5-methyl-N-(6-((4-methylpiperazin-1-yl)methyl)quinolin-2-yl)-1-(o-tolyl)-1H-1,2,3-triazole-4-carboxamide,
5-methyl-N-(6-(pyrrolidin-1-ylmethyl)quinolin-2-yl)-1-(o-tolyl)-1H-1,2,3-triazole-4-carboxamide,
N-(6-((diethylamino)methyl)quinolin-2-yl)-5-methyl-1-(o-tolyl)-1H-1,2,3-triazole-4-carboxamide,
5-methyl-N-(6-(piperidin-1-ylmethyl)quinolin-2-yl)-1-(o-tolyl)-1H-1,2,3-triazole-4-carboxamide,
tert-butyl 4-((2-(5-methyl-1-(o-tolyl)-1H-1,2,3-triazole-4-carboxamido)quinolin-6-yl)methyl)piperazine-1-carboxylate,
N-(6-(((dimethylamino)methyl)quinolin-2-yl)-5-methyl-1-(o-tolyl)-1H-1,2,3-triazole-4-carboxamide,
5-methyl-N-(6-(thiomorpholinomethyl)quinolin-2-yl)-1-(o-tolyl)-1H-1,2,3-triazole-4-carboxamide,
5-methyl-N-(6-((4-morpholinopiperidin-1-yl)methyl)quinolin-2-yl)-1-(o-tolyl)-1H-1,2,3-triazole-4-carboxamide, and
5-methyl-N-(6-((4-(4-methylpiperazin-1-yl)piperidin-1-yl)methyl)quinolin-2-yl)-1-(o-tolyl)-1H-1,2,3-triazole-4-carboxamide,
and the pharmaceutically acceptable salts thereof.

3. The method of claim 1, wherein the one or more compounds are of the formula:

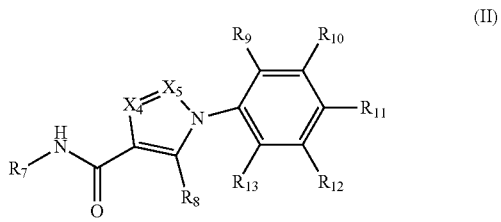

(II)

wherein $R_7$ represents a substituent selected from the group consisting of H and substituted or unsubstituted alkyl, alkenyl, alkynyl, cycloalkyl, aryl, heterocycle, heteroaryl, alkoxy, carboxy, carbalkoxy, and carboxamido;

$R_8$ represents a substituent selected from the group consisting of H, OH, $NO_2$, CN, halo, and substituted or unsubstituted alkyl, alkenyl, alkynyl, aryl, amino, and alkoxy;

$R_9$, $R_{10}$, $R_{11}$, $R_{12}$, and $R_{13}$ each can independently represent a substituent selected from the group consisting of H, OH, $NO_2$, CN, halo, and substituted or unsubstituted alkyl, alkylcarbonyl, alkenyl, alkynyl, cycloalkyl, aryl, heterocycle, heteroaryl, amino, alkoxy, carboxy, carbalkoxy, carboxamido, sulfonyl, sulfonamido, sulfinyl, monoalkylaminosulfinyl, dialkylaminosulfinyl, monoalkylaminosulfonyl, dialkylaminosulfonyl, alkylsulfonylamino, hydroxysulfonyloxy, alkoxysulfonyloxy, alkylsulfonyloxy, hydroxysulfonyl, alkoxysulfonyl, alkylsulfonylalkyl, monoalkylaminosulfonylalkyl, dialkylaminosulfonylalkyl, monoalkylaminosulfinylalkyl, and dialkylaminosulfinylalkyl, with the proviso $R_{11}$ is not H when $R_9$, $R_{10}$, $R_{12}$, and $R_{13}$ each is independently H;

$X_4$ represents N or $CR_{14}$;
$X_5$ represents N or $CR_{15}$;
$R_{14}$ and $R_{15}$ each can independently represent a substituent selected from the group consisting of H, OH, $NO_2$, CN, halo, and substituted or unsubstituted alkyl, alkylcarbonyl, alkenyl, alkynyl, cycloalkyl, aryl, heterocycle, heteroaryl, amino, alkoxy, carboxy, carbalkoxy, carboxamido, sulfonyl, sulfonamido, sulfinyl, monoalkylaminosulfinyl, dialkylaminosulfinyl, monoalkylaminosulfonyl, dialkylaminosulfonyl, alkylsulfonylamino, hydroxysulfonyloxy, alkoxysulfonyloxy, alkylsulfonyloxy, hydroxysulfonyl, alkoxysulfonyl, alkylsulfonylalkyl, monoalkylaminosulfonylalkyl, dialkylaminosulfonylalkyl, monoalkylaminosulfinylalkyl, and dialkylaminosulfinylalkyl;

wherein if $X_4$ and $X_5$ are $CR_{14}$ and $CR_{15}$, respectively, then $R_{14}$ and $R_{15}$ can be taken together to form a substituted or unsubstituted m-membered cycloalkyl or heterocycle, wherein m is an integer of 5 to 7;

or the pharmaceutically acceptable salts of said one or more compounds;

with the proviso that:

when $X_4$ and $X_5$ are $CR_{14}$ and $CR_{15}$ respectively, then at least one of $R_9$, $R_{10}$, $R_{11}$, $R_{12}$, and $R_{13}$ is not H;

when $X_4$ is N and $X_5$ is N, then $R_7$ is not substituted aryl; and compounds wherein $R_7$ is substituted heteroaryl; $R_8$ is alkyl; $R_9$, $R_{10}$, $R_{12}$, and $R_{13}$ are each H; $R_{11}$ is halo; $X_4$ is N; and $X_5$ is N are excluded.

4. The method of claim 3, wherein the one or more compounds are selected from the group consisting of:

2,5-Dimethyl-N-(pyridin-2-yl)-1-(p-tolyl)-1H-pyrrole-3-carboxamide,
2,5-Dimethyl-N-(pyrazin-2-yl)-1-(p-tolyl)-1H-pyrrole-3-carboxamide,
2,5-Dimethyl-N-(4-phenylthiazol-2-yl)-1-(p-tolyl)-1H-pyrrole-3-carboxamide,
N-Benzyl-2,5-dimethyl-1-(p-tolyl)-1H-pyrrole-3-carboxamide,
5-Methyl-N-(pyridin-2-yl)-1-(p-tolyl)-1H-1,2,3-triazole-4-carboxamide,
5-Methyl-N-(6-methylpyridin-2-yl)-1-(p-tolyl)-1H-1,2,3-triazole-4-carboxamide,
5-Methyl-N-(pyridin-2-ylmethyl)-1-(p-tolyl)-1H-1,2,3-triazole-4-carboxamide,
5-Methyl-N-(2-methyl-4-oxo-4H-chromen-7-yl)-1-(p-tolyl)-1H-1,2,3-triazole-4-carboxamide,
5-Methyl-N-(3-methylisoxazol-5-yl)-1-(p-tolyl)-1H-1,2,3-triazole-4-carboxamide,
N-(4,5-diphenylthiazol-2-yl)-5-methyl-1-(p-tolyl)-1H-1,2,3-triazole-4-carboxamide,
5-Methyl-N-(1-methyl-1H-benzo[d]imidazol-2-yl)-1-(p-tolyl)-1H-1,2,3-triazole-4-carboxamide,
5-Methyl-N-(quinolin-2-yl)-1-(p-tolyl)-1H-1,2,3-triazole-4-carboxamide,
5-Methyl-N-(quinolin-2-yl)-1-(o-tolyl)-1H-1,2,3-triazole-4-carboxamide,
5-Methyl-N-(naphthalen-2-yl)-1-(o-tolyl)-1H-1,2,3-triazole-4-carboxamide,
N-(benzo[d]thiazol-2-yl)-5-methyl-1-(o-tolyl)-1H-1,2,3-triazole-4-carboxamide,
5-Methyl-N-(4-phenylthiazol-2-yl)-1-(o-tolyl)-1H-1,2,3-triazole-4-carboxamide,
1-(2,3-Dimethylphenyl)-5-methyl-N-(quinolin-2-yl)-1H-1,2,3-triazole-4-carboxamide,
1-(2,4-Dimethylphenyl)-5-methyl-N-(quinolin-2-yl)-1H-1,2,3-triazole-4-carboxamide,
1-(3-Chlorophenyl)-5-methyl-N-(quinolin-2-yl)-1H-1,2,3-triazole-4-carboxamide,
1-(2-Fluorophenyl)-5-methyl-N-(quinolin-2-yl)-1H-1,2,3-triazole-4-carboxamide,
1-(2-Bromophenyl)-5-methyl-N-(quinolin-2-yl)-1H-1,2,3-triazole-4-carboxamide,
1-(2-Cyanophenyl)-5-methyl-N-(quinolin-2-yl)-1H-1,2,3-triazole-4-carboxamide,
1-(2-Methoxyphenyl)-5-methyl-N-(quinolin-2-yl)-1H-1,2,3-triazole-4-carboxamide,
1-(4-Fluoro-2-nitrophenyl)-5-methyl-N-(quinolin-2-yl)-1H-1,2,3-triazole-4-carboxamide,
1-(2-Acetylphenyl)-5-methyl-N-(quinolin-2-yl)-1H-1,2,3-triazole-4-carboxamide,
1-(2-Carbamoylphenyl)-5-methyl-N-(quinolin-2-yl)-1H-1,2,3-triazole-4-carboxamide,
1-([1,1'-biphenyl]-2-yl)-5-methyl-N-(quinolin-2-yl)-1H-1,2,3-triazole-4-carboxamide,
5-Methyl-1-(2-morpholinophenyl)-N-(quinolin-2-yl)-1H-1,2,3-triazole-4-carboxamide,
5-Methyl-1-(naphthalen-1-yl)-N-(quinolin-2-yl)-1H-1,2,3-triazole-4-carboxamide,
1-(2-fluorophenyl)-5-isopropyl-N-(quinolin-2-yl)-1H-1,2,3-triazole-4-carboxamide,
5-Ethyl-1-(2-fluorophenyl)-N-(quinolin-2-yl)-1H-1,2,3-triazole-4-carboxamide,
5-Methyl-N-(quinolin-2-yl)-1-(o-tolyl)-1H-pyrazole-4-carboxamide,
1-(2-Fluorophenyl)-5-methyl-N-(quinolin-2-yl)-1H-pyrazole-4-carboxamide,
1-(2-Bromophenyl)-5-methyl-N-(quinolin-2-yl)-1H-pyrazole-4-carboxamide,
2,5-Dimethyl-N-(quinolin-2-yl)-1-(o-tolyl)-1H-imidazole-4-carboxamide,
1-(2-Fluorophenyl)-2,5-dimethyl-N-(quinolin-2-yl)-1H-imidazole-4-carboxamide,
1-(2-Bromophenyl)-2,5-dimethyl-N-(quinolin-2-yl)-1H-imidazole-4-carboxamide,
2,5-Dimethyl-1-phenyl-N-(quinolin-2-yl)-1H-imidazole-4-carboxamide,
1-(2-Chlorophenyl)-5-methyl-N-(quinolin-2-yl)-1H-pyrazole-4-carboxamide,
1-(2-Ethylphenyl)-5-methyl-N-(quinolin-2-yl)-1H-pyrazole-4-carboxamide,
1-(2,6-dimethylphenyl)-5-methyl-N-(quinolin-2-yl)-1H-pyrazole-4-carboxamide,
1-(2,5-dimethylphenyl)-5-methyl-N-(quinolin-2-yl)-1H-pyrazole-4-carboxamide,
1-(2,4-difluorophenyl)-5-methyl-N-(quinolin-2-yl)-1H-pyrazole-4-carboxamide,
5-methyl-1-phenyl-N-(quinolin-2-yl)-1H-pyrazole-4-carboxamide,
5-methyl-1-(3-methylpyridin-2-yl)-N-(quinolin-2-yl)-1H-pyrazole-4-carboxamide,
1-(3-chloro-2-fluorophenyl)-5-methyl-N-(quinolin-2-yl)-1H-pyrazole-4-carboxamide,
1-(2,6-difluorophenyl)-5-methyl-N-(quinolin-2-yl)-1H-pyrazole-4-carboxamide,
1-(2-bromo-6-fluorophenyl)-5-methyl-N-(quinolin-2-yl)-1H-pyrazole-4-carboxamide,
3,5-dimethyl-1-phenyl-N-(quinolin-2-yl)-1H-pyrazole-4-carboxamide,
1-(2,5-dimethylphenyl)-3,5-dimethyl-N-(quinolin-2-yl)-1H-pyrazole-4-carboxamide,
1-(2-bromophenyl)-3,5-dimethyl-N-(quinolin-2-yl)-1H-pyrazole-4-carboxamide,
5-ethyl-1-phenyl-N-(quinolin-2-yl)-1H-pyrazole-4-carboxamide,
5-isopropyl-1-phenyl-N-(quinolin-2-yl)-1H-pyrazole-4-carboxamide,
5-chloro-1-phenyl-N-(quinolin-2-yl)-1H-pyrazole-4-carboxamide,
5-bromo-1-phenyl-N-(quinolin-2-yl)-1H-pyrazole-4-carboxamide,
5-(dimethylamino)-1-phenyl-N-(quinolin-2-yl)-1H-pyrazole-4-carboxamide,
1-(2-ethylphenyl)-5-methyl-N-(naphthalen-2-yl)-1H-pyrazole-4-carboxamide, 1-(2-ethylphenyl)-N-(isoquinolin-3-yl)-5-methyl-1H-pyrazole-4-carboxamide,
1-(2-ethylphenyl)-5-methyl-N-(quinolin-3-yl)-1H-pyrazole-4-carboxamide,
1-(2-ethylphenyl)-5-methyl-N-(6-methylpyridin-2-yl)-1H-pyrazole-4-carboxamide,
N-(6-bromoquinolin-2-yl)-5-methyl-1-(o-tolyl)-1H-1,2,3-triazole-4-carboxamide,
5-methyl-N-(6-(morpholinomethyl)quinolin-2-yl)-1-(o-tolyl)-1H-1,2,3-triazole-4-carboxamide,
5-methyl-N-(6-((4-methylpiperazin-1-yl)methyl)quinolin-2-yl)-1-(o-tolyl)-1H-1,2,3-triazole-4-carboxamide,
5-methyl-N-(6-(pyrrolidin-1-ylmethyl)quinolin-2-yl)-1-(o-tolyl)-1H-1,2,3-triazole-4-carboxamide,
N-(6-((diethylamino)methyl)quinolin-2-yl)-5-methyl-1-(o-tolyl)-1H-1,2,3-triazole-4-carboxamide,
5-methyl-N-(6-(piperidin-1-ylmethyl)quinolin-2-yl)-1-(o-tolyl)-1H-1,2,3-triazole-4-carboxamide,
tert-butyl 4-((2-(5-methyl-1-(o-tolyl)-1H-1,2,3-triazole-4-carboxamido)quinolin-6-yl)methyl)piperazine-1-carboxylate,
N-(6-((dimethylamino)methyl)quinolin-2-yl)-5-methyl-1-(o-tolyl)-1H-1,2,3-triazole-4-carboxamide,
5-methyl-N-(6-(thiomorpholinomethyl)quinolin-2-yl)-1-(o-tolyl)-1H-1,2,3-triazole-4-carboxamide,
5-methyl-N-(6-((4-morpholinopiperidin-1-yl)methyl)quinolin-2-yl)-1-(o-tolyl)-1H-1,2,3-triazole-4-carboxamide, and
5-methyl-N-(6-((4-(4-methylpiperazin-1-yl)piperidin-1-yl)methyl)quinolin-2-yl)-1-(o-tolyl)-1H-1,2,3-triazole-4-carboxamide,
and the pharmaceutically acceptable salts thereof.

5. The method of claim 1, wherein the one or more compounds are selected from the group consisting of N-(benzo[d]thiazol-2-yl)-5-methyl-1-(o-tolyl)-1H-1,2,3-triazole-4-carboxamide, 2,5-Dimethyl-N-(4-phenylthiazol-2-yl)-1-(p-tolyl)-1H-pyrrole-3-carboxamide, 5-Methyl-N-(naphthalen-2-yl)-1-(o-tolyl)-1H-1,2,3-triazole-4-carboxamide, 5-Methyl-N-(6-methylpyridin-2-yl)-1-(p-tolyl)-1H-1,2,3-triazole-4-carboxamide, 5-Methyl-N-(quinolin-2-yl)-1-(o-tolyl)-1H-1,2,3-triazole-4-carboxamide, 1-(2-Fluorophenyl)-5-methyl-N-(quinolin-2-yl)-1H-1,2,3-triazole-4-carboxamide, 1-(2-Bromophenyl)-5-methyl-N-(quinolin-2-yl)-1H-1,2,3-triazole-4-carboxamide, 1-(2-Methoxyphenyl)-5-methyl-N-(quinolin-2-yl)-1H-1,2,3-triazole-4-carboxamide, 1-(3-Chlorophenyl)-5-methyl-N-(quinolin-2-yl)-1H-1,2,3-triazole-4-carboxamide, 1-(2,3-Dimethylphenyl)-5-methyl-N-(quinolin-2-yl)-1H-1,2,3-triazole-4-carboxamide, 1-(2-Cyanophenyl)-5-methyl-N-(quinolin-2-yl)-1H-1,2,3-triazole-4-carboxamide, 1-(2-Acetylphenyl)-5-methyl-N-(quinolin-2-yl)-1H-1,2,3-triazole-4-carboxamide, 1-(2,4-Dimethylphenyl)-5-methyl-N-(quinolin-2-yl)-1H-1,2,3-triazole-4-carboxamide, 5-Methyl-N-(quinolin-2-yl)-1-(o-tolyl)-1H-pyrazole-4-carboxamide, 5-Ethyl-1-(2-fluorophenyl)-N-(quinolin-2-yl)-1H-1,2,3-triazole-4-carboxamide, 1-(2-fluorophenyl)-5-isopropyl-N-(quinolin-2-yl)-1H-1,2,3-triazole-4-carboxamide, N-(benzo[d]thiazol-2-yl)-5-methyl-1-(o-tolyl)-1H-1,2,3-triazole-4-carboxamide, 1-(2-Fluorophenyl)-5-methyl-N-(quinolin-2-yl)-1H-pyrazole-4-carboxamide, 1-(2-Chlorophenyl)-5-methyl-N-(quinolin-2-yl)-1H-pyrazole-4-carboxamide, 1-(2-Ethylphenyl)-5-methyl-N-(quinolin-2-yl)-1H-pyrazole-4-carboxamide, 1-(Tert-butyl)-5-methyl-N-(quinolin-2-yl)-1H-pyrazole-4-carboxamide, and 5-methyl-1-(1-phenylethyl)-N-(quinolin-2-yl)-1H-pyrazole-4-carboxamide, and the pharmaceutically acceptable salts thereof.

6. The method of claim 3, wherein the one or more compounds comprise 1-(2-Methoxyphenyl)-5-methyl-N-(quinolin-2-yl)-1H-1,2,3-triazole-4-carboxamide, 5-Methyl-N-(quinolin-2-yl)-1-(o-tolyl)-1H-pyrazole-4-carboxamide, 1-(2-Ethylphenyl)-5-methyl-N-(quinolin-2-yl)-1H-pyrazole-4-carboxamide, 1-(2-Bromophenyl)-5-methyl-N-(quinolin-2-yl)-1H-pyrazole-4-carboxamide, or a pharmaceutically acceptable salt thereof.

7. The method of claim 1, wherein the disease is cancer or a metabolic disease.

8. The method of claim 1, wherein the disease is selected from the group consisting of type 2 diabetes, obesity, hyperlipidemia, fatty liver disease, adrenocortical cancer, hepatocellular cancer, hepatoblastoma, malignant melanoma, ovarian cancer, Wilm's tumor, Barrett's esophageal cancer, prostate cancer, pancreatic cancer, bladder cancer, breast cancer, gastric cancer, head & neck cancer, lung cancer, mesothelioma, cervical cancer, uterine cancer, myeloid leukemia cancer, lymphoid leukemia cancer, pilometricoma cancer, medulloblastoma cancer, glioblastoma, and familial adenomatous polyposis.

9. The method of claim 1, wherein the disease is type 2 diabetes.

10. The method of claim 1, wherein the disease is colon cancer.

11. A compound of the formula:

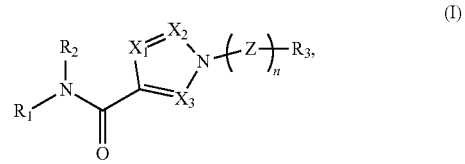

(I)

wherein $R_1$ and $R_2$ each can independently represent a substituent selected from the group consisting of H and substituted or unsubstituted alkyl, alkenyl, alkynyl, cycloalkyl, aryl, heterocycle, heteroaryl, alkoxy, carboxy, carbalkoxy, and carboxamido;
$R_3$ represents a substituent selected from the group consisting of substituted or unsubstituted alkyl, alkenyl, alkynyl, cycloalkyl, aryl, heterocycle, and heteroaryl;
n represents an integer of 0 to 2, Z represents one or more substituted or unsubstituted alkyl substituents when n is 1 or 2;
$X_1$ represents N or $CR_4$;
$X_2$ represents N or $CR_5$;
$X_3$ represents N or $CR_6$; $R_4$, $R_5$, and $R_6$ each can independently represent a substituent selected from the group consisting of H, OH, $NO_2$, CN, halo, and substituted or unsubstituted alkyl, alkylcarbonyl, alkenyl, alkynyl, cycloalkyl, aryl, heterocycle, heteroaryl, amino, alkoxy, carboxy, carbalkoxy, carboxamido, sulfonyl, sulfonamido, sulfinyl, monoalkylaminosulfinyl, dialkylaminosulfinyl, monoalkylaminosulfonyl, dialkylaminosulfonyl, alkylsulfonylamino, hydroxysulfonyloxy, alkoxysulfonyloxy, alkylsulfonyloxy, hydroxysulfonyl, alkoxysulfonyl, alkylsulfonylalkyl, monoalkylaminosulfonylalkyl, dialkylaminosulfonylalkyl, monoalkylaminosulfinylalkyl, and dialkylaminosulfinylalkyl;
wherein when both are present, $R_4$ and $R_5$ can be taken together to form a substituted or unsubstituted m-membered cycloalkyl or heterocycle, wherein m represents an integer of 5 to 7;

or the pharmaceutically acceptable salts of said one or more compounds;
with the proviso that:
when $X_1$ and $X_2$ represent $CR_4$ and $CR_5$, respectively, then $R_3$ is substituted aryl; and
compounds wherein $R_1$ and $R_2$ each are H and substituted aryl, $R_3$ is substituted aryl, n is 0, $X_1$ is N, $X_2$ is N, $X_3$ is $CR_6$, and $R_6$ is alkyl, are excluded.

12. The compound of claim 11, wherein the compound is selected from the group consisting of:
2,5-Dimethyl-N-(pyridin-2-yl)-1-(p-tolyl)-1H-pyrrole-3-carboxamide,
2,5-Dimethyl-N-(pyrazin-2-yl)-1-(p-tolyl)-1H-pyrrole-3-carboxamide,
2,5-Dimethyl-N-(4-phenylthiazol-2-yl)-1-(p-tolyl)-1H-pyrrole-3-carboxamide,
N-Benzyl-2,5-dimethyl-1-(p-tolyl)-1H-pyrrole-3-carboxamide,
5-Methyl-N-(pyridin-2-yl)-1-(p-tolyl)-1H-1,2,3-triazole-4-carboxamide,
5-Methyl-N-(6-methylpyridin-2-yl)-1-(p-tolyl)-1H-1,2,3-triazole-4-carboxamide,
5-Methyl-N-(pyridin-2-ylmethyl)-1-(p-tolyl)-1H-1,2,3-triazole-4-carboxamide,
5-Methyl-N-(2-methyl-4-oxo-4H-chromen-7-yl)-1-(p-tolyl)-1H-1,2,3-triazole-4-carboxamide,
5-Methyl-N-(3-methylisoxazol-5-yl)-1-(p-tolyl)-1H-1,2,3-triazole-4-carboxamide,
N-(4,5-diphenylthiazol-2-yl)-5-methyl-1-(p-tolyl)-1H-1,2,3-triazole-4-carboxamide,
5-Methyl-N-(1-methyl-1H-benzo[d]imidazol-2-yl)-1-(p-tolyl)-1H-1,2,3-triazole-4-carboxamide,
5-Methyl-N-(quinolin-2-yl)-1-(p-tolyl)-1H-1,2,3-triazole-4-carboxamide,
5-Methyl-N-(quinolin-2-yl)-1-(o-tolyl)-1H-1,2,3-triazole-4-carboxamide,
5-Methyl-N-(naphthalen-2-yl)-1-(o-tolyl)-1H-1,2,3-triazole-4-carboxamide,
N-(benzo[d]thiazol-2-yl)-5-methyl-1-(o-tolyl)-1H-1,2,3-triazole-4-carboxamide,
5-Methyl-N-(4-phenylthiazol-2-yl)-1-(o-tolyl)-1H-1,2,3-triazole-4-carboxamide,
1-(2,3-Dimethylphenyl)-5-methyl-N-(quinolin-2-yl)-1H-1,2,3-triazole-4-carboxamide,
1-(2,4-Dimethylphenyl)-5-methyl-N-(quinolin-2-yl)-1H-1,2,3-triazole-4-carboxamide,
1-(3-Chlorophenyl)-5-methyl-N-(quinolin-2-yl)-1H-1,2,3-triazole-4-carboxamide,
1-(2-Fluorophenyl)-5-methyl-N-(quinolin-2-yl)-1H-1,2,3-triazole-4-carboxamide,
1-(2-Bromophenyl)-5-methyl-N-(quinolin-2-yl)-1H-1,2,3-triazole-4-carboxamide,
1-(2-Cyanophenyl)-5-methyl-N-(quinolin-2-yl)-1H-1,2,3-triazole-4-carboxamide,
1-(2-Methoxyphenyl)-5-methyl-N-(quinolin-2-yl)-1H-1,2,3-triazole-4-carboxamide,
1-(4-Fluoro-2-nitrophenyl)-5-methyl-N-(quinolin-2-yl)-1H-1,2,3-triazole-4-carboxamide,
1-(2-Acetylphenyl)-5-methyl-N-(quinolin-2-yl)-1H-1,2,3-triazole-4-carboxamide,
1-(2-Carbamoylphenyl)-5-methyl-N-(quinolin-2-yl)-1H-1,2,3-triazole-4-carboxamide,
1-([1,1'-biphenyl]-2-yl)-5-methyl-N-(quinolin-2-yl)-1H-1,2,3-triazole-4-carboxamide,
5-Methyl-1-(2-morpholinophenyl)-N-(quinolin-2-yl)-1H-1,2,3-triazole-4-carboxamide,
5-Methyl-1-(naphthalen-1-yl)-N-(quinolin-2-yl)-1H-1,2,3-triazole-4-carboxamide,
1-(2-fluorophenyl)-5-isopropyl-N-(quinolin-2-yl)-1H-1,2,3-triazole-4-carboxamide,
5-Ethyl-1-(2-fluorophenyl)-N-(quinolin-2-yl)-1H-1,2,3-triazole-4-carboxamide,
5-Methyl-N-(quinolin-2-yl)-1-(o-tolyl)-1H-pyrazole-4-carboxamide,
1-(2-Fluorophenyl)-5-methyl-N-(quinolin-2-yl)-1H-pyrazole-4-carboxamide,
1-(2-Bromophenyl)-5-methyl-N-(quinolin-2-yl)-1H-pyrazole-4-carboxamide,
2,5-Dimethyl-N-(quinolin-2-yl)-1-(o-tolyl)-1H-imidazole-4-carboxamide,
1-(2-Fluorophenyl)-2,5-dimethyl-N-(quinolin-2-yl)-1H-imidazole-4-carboxamide,
1-(2-Bromophenyl)-2,5-dimethyl-N-(quinolin-2-yl)-1H-imidazole-4-carboxamide,
2,5-Dimethyl-1-phenyl-N-(quinolin-2-yl)-1H-imidazole-4-carboxamide,
1-(2-Chlorophenyl)-5-methyl-N-(quinolin-2-yl)-1H-pyrazole-4-carboxamide
1-(2-Ethylphenyl)-5-methyl-N-(quinolin-2-yl)-1H-pyrazole-4-carboxamide,
1-(2,6-dimethylphenyl)-5-methyl-N-(quinolin-2-yl)-1H-pyrazole-4-carboxamide,
1-(Tert-butyl)-5-methyl-N-(quinolin-2-yl)-1H-pyrazole-4-carboxamide,
1-(2,5-dimethylphenyl)-5-methyl-N-(quinolin-2-yl)-1H-pyrazole-4-carboxamide,
1-(2,4-difluorophenyl)-5-methyl-N-(quinolin-2-yl)-1H-pyrazole-4-carboxamide,
5-methyl-1-phenyl-N-(quinolin-2-yl)-1H-pyrazole-4-carboxamide,
1-cyclohexyl-5-methyl-N-(quinolin-2-yl)-1H-pyrazole-4-carboxamide,
5-methyl-1-(1-phenylethyl)-N-(quinolin-2-yl)-1H-pyrazole-4-carboxamide,
5-methyl-N-(quinolin-2-yl)-1-(2,2,2-trifluoroethyl)-1H-pyrazole-4-carboxamide,
5-methyl-1-(3-methylpyridin-2-yl)-N-(quinolin-2-yl)-1H-pyrazole-4-carboxamide,
1-(3-chloro-2-fluorophenyl)-5-methyl-N-(quinolin-2-yl)-1H-pyrazole-4-carboxamide,
1-(2,6-difluorophenyl)-5-methyl-N-(quinolin-2-yl)-1H-pyrazole-4-carboxamide,
1-(2-bromo-6-fluorophenyl)-5-methyl-N-(quinolin-2-yl)-1H-pyrazole-4-carboxamide,
5-methyl-1-phenyl-N-(quinolin-2-yl)-1H-pyrazole-3-carboxamide,
5-methyl-N-(quinolin-2-yl)-1-(o-tolyl)-1H-pyrazole-3-carboxamide,
1-(2-ethylphenyl)-5-methyl-N-(quinolin-2-yl)-1H-pyrazole-3-carboxamide,
1-phenyl-N-(quinolin-2-yl)-1,4,5,6-tetrahydrocyclopenta[c]pyrazole-3-carboxamide,
1-phenyl-N-(quinolin-2-yl)-4,5,6,7-tetrahydro-1H-indazole-3-carboxamide,
3,5-dimethyl-1-phenyl-N-(quinolin-2-yl)-1H-pyrazole-4-carboxamide,
1-(2,5-dimethylphenyl)-3,5-dimethyl-N-(quinolin-2-yl)-1H-pyrazole-4-carboxamide,
1-(2-bromophenyl)-3,5-dimethyl-N-(quinolin-2-yl)-1H-pyrazole-4-carboxamide,
5-ethyl-1-phenyl-N-(quinolin-2-yl)-1H-pyrazole-4-carboxamide, 5-isopropyl-1-phenyl-N-(quinolin-2-yl)-1H-pyrazole-4-carboxamide,
5-chloro-1-phenyl-N-(quinolin-2-yl)-1H-pyrazole-4-carboxamide,
5-bromo-1-phenyl-N-(quinolin-2-yl)-1H-pyrazole-4-carboxamide,
5-(dimethylamino)-1-phenyl-N-(quinolin-2-yl)-1H-pyrazole-4-carboxamide,
1-(2-ethylphenyl)-5-methyl-N-(naphthalen-2-yl)-1H-pyrazole-4-carboxamide,
1-(2-ethylphenyl)-N-(isoquinolin-3-yl)-5-methyl-1H-pyrazole-4-carboxamide,
1-(2-ethylphenyl)-5-methyl-N-(quinolin-3-yl)-1H-pyrazole-4-carboxamide,
1-(2-ethylphenyl)-5-methyl-N-(6-methylpyridin-2-yl)-1H-pyrazole-4-carboxamide,
N-(6-bromoquinolin-2-yl)-5-methyl-1-(o-tolyl)-1H-1,2,3-triazole-4-carboxamide,
5-methyl-N-(6-(morpholinomethyl)quinolin-2-yl)-1-(o-tolyl)-1H-1,2,3-triazole-4-carboxamide,
5-methyl-N-(6-((4-methylpiperazin-1-yl)methyl)quinolin-2-yl)-1-(o-tolyl)-1H-1,2,3-triazole-4-carboxamide,
5-methyl-N-(6-(pyrrolidin-1-ylmethyl)quinolin-2-yl)-1-(o-tolyl)-1H-1,2,3-triazole-4-carboxamide,
N-(6-((diethylamino)methyl)quinolin-2-yl)-5-methyl-1-(o-tolyl)-1H-1,2,3-triazole-4-carboxamide,
5-methyl-N-(6-(piperidin-1-ylmethyl)quinolin-2-yl)-1-(o-tolyl)-1H-1,2,3-triazole-4-carboxamide,
tert-butyl 4-((2-(5-methyl-1-(o-tolyl)-1H-1,2,3-triazole-4-carboxamido)quinolin-6-yl)methyl)piperazine-1-carboxylate,
N-(6-((dimethylamino)methyl)quinolin-2-yl)-5-methyl-1-(o-tolyl)-1H-1,2,3-triazole-4-carboxamide,
5-methyl-N-(6-(thiomorpholinomethyl)quinolin-2-yl)-1-(o-tolyl)-1H-1,2,3-triazole-4-carboxamide,
5-methyl-N-(6-((4-morpholinopiperidin-1-yl)methyl)quinolin-2-yl)-1-(o-tolyl)-1H-1,2,3-triazole-4-carboxamide, and
5-methyl-N-(6-((4-(4-methylpiperazin-1-yl)piperidin-1-yl)methyl)quinolin-2-yl)-1-(o-tolyl)-1H-1,2,3-triazole-4-carboxamide, and the pharmaceutically acceptable salts of said compound.

13. The compound of claim 11, comprising the formula:

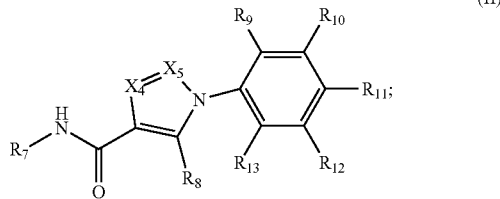

(II)

wherein $R_7$ represents a substituent selected from the group consisting of H and substituted or unsubstituted alkyl, alkenyl, alkynyl, cycloalkyl, aryl, heterocycle, heteroaryl, alkoxy, carboxy, carbalkoxy, and carboxamido;
$R_8$ represents a substituent selected from the group consisting of H, OH, $NO_2$, CN, halo, and substituted or unsubstituted alkyl, alkenyl, alkynyl, aryl, amino, and alkoxy;
$R_9$, $R_{10}$, $R_{11}$, $R_{12}$, and $R_{13}$ each can independently represent a substituent selected from the group consisting of H, OH, $NO_2$, CN, halo, and substituted or unsubstituted alkyl, alkylcarbonyl, alkenyl, alkynyl, cycloalkyl, aryl, heterocycle, heteroaryl, amino, alkoxy, carboxy, carbalkoxy, carboxamido, sulfonyl, sulfonamido, sulfinyl, monoalkylaminosulfinyl, dialkylaminosulfinyl, monoalkylaminosulfonyl, dialkylaminosulfonyl, alkylsulfonylamino, hydroxysulfonyloxy, alkoxysulfonyloxy, alkylsulfonyloxy, hydroxysulfonyl, alkoxysulfonyl, alkylsulfonylalkyl, monoalkylaminosulfonylalkyl, dialkylaminosulfonylalkyl, monoalkylaminosulfinylalkyl, and dialkylaminosulfinylalkyl, with the proviso $R_{11}$ is not H when $R_9$, $R_{10}$, $R_{12}$, and $R_{13}$ each is independently H;
$X_4$ represents N or $CR_{14}$;
$X_5$ represents N or $CR_{15}$; $R_{14}$ and $R_{15}$ each can independently represent a substituent selected from the group consisting of H, OH, $NO_2$, CN, halo, and substituted or unsubstituted alkyl, alkylcarbonyl, alkenyl, alkynyl, cycloalkyl, aryl, heterocycle, heteroaryl, amino, alkoxy, carboxy, carbalkoxy, carboxamido, sulfonyl, sulfonamido, sulfinyl, monoalkylaminosulfinyl, dialkylaminosulfinyl, monoalkylaminosulfonyl, dialkylaminosulfonyl, alkylsulfonylamino, hydroxysulfonyloxy, alkoxysulfonyloxy, alkylsulfonyloxy, hydroxysulfonyl, alkoxysulfonyl, alkylsulfonylalkyl, monoalkylaminosulfonylalkyl, dialkylaminosulfonylalkyl, monoalkylaminosulfinylalkyl, and dialkylaminosulfinylalkyl;
wherein if $X_4$ and $X_5$ are $CR_{14}$ and $CR_{15}$, respectively, then $R_{14}$ and $R_{15}$ can be taken together to form a substituted or unsubstituted m-membered cycloalkyl or heterocycle, wherein m is an integer of 5 to 7;
or the pharmaceutically acceptable salts of said one or more compounds;
with the proviso that:
when $X_4$ and $X_5$ are $CR_{14}$ and $CR_{15}$, respectively, then at least one of $R_9$, $R_{10}$, $R_{11}$, $R_{12}$, and $R_{13}$ is not H;
when $X_4$ is N and $X_5$ is N, then $R_7$ is not substituted aryl; and
compounds wherein $R_7$ is substituted heteroaryl; $R_8$ is alkyl; $R_9$, $R_{10}$, $R_{12}$, and $R_{13}$ are each H; $R_{11}$ is halo; $X_4$ is N; and $X_5$ is N are excluded.

14. The compound of claim 13, wherein the compound is selected from the group consisting of:
2,5-Dimethyl-N-(pyridin-2-yl)-1-(p-tolyl)-1H-pyrrole-3-carboxamide,
2,5-Dimethyl-N-(pyrazin-2-yl)-1-(p-tolyl)-1H-pyrrole-3-carboxamide,
2,5-Dimethyl-N-(4-phenylthiazol-2-yl)-1-(p-tolyl)-1H-pyrrole-3-carboxamide,
N-Benzyl-2,5-dimethyl-1-(p-tolyl)-1H-pyrrole-3-carboxamide,
5-Methyl-N-(pyridin-2-yl)-1-(p-tolyl)-1H-1,2,3-triazole-4-carboxamide,
5-Methyl-N-(6-methylpyridin-2-yl)-1-(p-tolyl)-1H-1,2,3-triazole-4-carboxamide,
5-Methyl-N-(pyridin-2-ylmethyl)-1-(p-tolyl)-1H-1,2,3-triazole-4-carboxamide,
5-Methyl-N-(2-methyl-4-oxo-4H-chromen-7-yl)-1-(p-tolyl)-1H-1,2,3-triazole-4-carboxamide,
5-Methyl-N-(3-methylisoxazol-5-yl)-1-(p-tolyl)-1H-1,2,3-triazole-4-carboxamide,
N-(4,5-diphenylthiazol-2-yl)-5-methyl-1-(p-tolyl)-1H-1,2,3-triazole-4-carboxamide,
5-Methyl-N-(1-methyl-1H-benzo[d]imidazol-2-yl)-1-(p-tolyl)-1H-1,2,3-triazole-4-carboxamide,
5-Methyl-N-(quinolin-2-yl)-1-(p-tolyl)-1H-1,2,3-triazole-4-carboxamide, 5-Methyl-N-(quinolin-2-yl)-1-(o-tolyl)-1H-1,2,3-triazole-4-carboxamide,
5-Methyl-N-(naphthalen-2-yl)-1-(o-tolyl)-1H-1,2,3-triazole-4-carboxamide,
N-(benzo[d]thiazol-2-yl)-5-methyl-1-(o-tolyl)-1H-1,2,3-triazole-4-carboxamide,
5-Methyl-N-(4-phenylthiazol-2-yl)-1-(o-tolyl)-1H-1,2,3-triazole-4-carboxamide,
1-(2,3-Dimethylphenyl)-5-methyl-N-(quinolin-2-yl)-1H-1,2,3-triazole-4-carboxamide,
1-(2,4-Dimethylphenyl)-5-methyl-N-(quinolin-2-yl)-1H-1,2,3-triazole-4-carboxamide,
1-(3-Chlorophenyl)-5-methyl-N-(quinolin-2-yl)-1H-1,2,3-triazole-4-carboxamide,
1-(2-Fluorophenyl)-5-methyl-N-(quinolin-2-yl)-1H-1,2,3-triazole-4-carboxamide,
1-(2-Bromophenyl)-5-methyl-N-(quinolin-2-yl)-1H-1,2,3-triazole-4-carboxamide,
1-(2-Cyanophenyl)-5-methyl-N-(quinolin-2-yl)-1H-1,2,3-triazole-4-carboxamide,
1-(2-Methoxyphenyl)-5-methyl-N-(quinolin-2-yl)-1H-1,2,3-triazole-4-carboxamide,
1-(4-Fluoro-2-nitrophenyl)-5-methyl-N-(quinolin-2-yl)-1H-1,2,3-triazole-4-carboxamide,
1-(2-Acetylphenyl)-5-methyl-N-(quinolin-2-yl)-1H-1,2,3-triazole-4-carboxamide,
1-(2-Carbamoylphenyl)-5-methyl-N-(quinolin-2-yl)-1H-1,2,3-triazole-4-carboxamide,
1-([1,1'-biphenyl]-2-yl)-5-methyl-N-(quinolin-2-yl)-1H-1,2,3-triazole-4-carboxamide,
5-Methyl-1-(2-morpholinophenyl)-N-(quinolin-2-yl)-1H-1,2,3-triazole-4-carboxamide,
5-Methyl-1-(naphthalen-1-yl)-N-(quinolin-2-yl)-1H-1,2,3-triazole-4-carboxamide,
1-(2-fluorophenyl)-5-isopropyl-N-(quinolin-2-yl)-1H-1,2,3-triazole-4-carboxamide,
5-Ethyl-1-(2-fluorophenyl)-N-(quinolin-2-yl)-1H-1,2,3-triazole-4-carboxamide,
5-Methyl-N-(quinolin-2-yl)-1-(o-tolyl)-1H-pyrazole-4-carboxamide,
1-(2-Fluorophenyl)-5-methyl-N-(quinolin-2-yl)-1H-pyrazole-4-carboxamide,
1-(2-Bromophenyl)-5-methyl-N-(quinolin-2-yl)-1H-pyrazole-4-carboxamide,
2,5-Dimethyl-N-(quinolin-2-yl)-1-(o-tolyl)-1H-imidazole-4-carboxamide,
1-(2-Fluorophenyl)-2,5-dimethyl-N-(quinolin-2-yl)-1H-imidazole-4-carboxamide,
1-(2-Bromophenyl)-2,5-dimethyl-N-(quinolin-2-yl)-1H-imidazole-4-carboxamide,
2,5-Dimethyl-1-phenyl-N-(quinolin-2-yl)-1H-imidazole-4-carboxamide,
1-(2-Chlorophenyl)-5-methyl-N-(quinolin-2-yl)-1H-pyrazole-4-carboxamide,
1-(2-Ethylphenyl)-5-methyl-N-(quinolin-2-yl)-1H-pyrazole-4-carboxamide,
1-(2,6-dimethylphenyl)-5-methyl-N-(quinolin-2-yl)-1H-pyrazole-4-carboxamide,
1-(2,5-dimethylphenyl)-5-methyl-N-(quinolin-2-yl)-1H-pyrazole-4-carboxamide,
1-(2,4-difluorophenyl)-5-methyl-N-(quinolin-2-yl)-1H-pyrazole-4-carboxamide,
5-methyl-1-phenyl-N-(quinolin-2-yl)-1H-pyrazole-4-carboxamide,
5-methyl-1-(3-methylpyridin-2-yl)-N-(quinolin-2-yl)-1H-pyrazole-4-carboxamide,
1-(3-chloro-2-fluorophenyl)-5-methyl-N-(quinolin-2-yl)-1H-pyrazole-4-carboxamide,
1-(2,6-difluorophenyl)-5-methyl-N-(quinolin-2-yl)-1H-pyrazole-4-carboxamide,
1-(2-bromo-6-fluorophenyl)-5-methyl-N-(quinolin-2-yl)-1H-pyrazole-4-carboxamide,
3,5-dimethyl-1-phenyl-N-(quinolin-2-yl)-1H-pyrazole-4-carboxamide,
1-(2,5-dimethylphenyl)-3,5-dimethyl-N-(quinolin-2-yl)-1H-pyrazole-4-carboxamide,
1-(2-bromophenyl)-3,5-dimethyl-N-(quinolin-2-yl)-1H-pyrazole-4-carboxamide,
5-ethyl-1-phenyl-N-(quinolin-2-yl)-1H-pyrazole-4-carboxamide,
5-isopropyl-1-phenyl-N-(quinolin-2-yl)-1H-pyrazole-4-carboxamide,
5-chloro-1-phenyl-N-(quinolin-2-yl)-1H-pyrazole-4-carboxamide,
5-bromo-1-phenyl-N-(quinolin-2-yl)-1H-pyrazole-4-carboxamide,
5-(dimethylamino)-1-phenyl-N-(quinolin-2-yl)-1H-pyrazole-4-carboxamide,
1-(2-ethylphenyl)-5-methyl-N-(naphthalen-2-yl)-1H-pyrazole-4-carboxamide,
1-(2-ethylphenyl)-N-(isoquinolin-3-yl)-5-methyl-1H-pyrazole-4-carboxamide,
1-(2-ethylphenyl)-5-methyl-N-(quinolin-3-yl)-1H-pyrazole-4-carboxamide,
1-(2-ethylphenyl)-5-methyl-N-(6-methylpyridin-2-yl)-1H-pyrazole-4-carboxamide,
N-(6-bromoquinolin-2-yl)-5-methyl-1-(o-tolyl)-1H-1,2,3-triazole-4-carboxamide,
5-methyl-N-(6-(morpholinomethyl)quinolin-2-yl)-1-(o-tolyl)-1H-1,2,3-triazole-4-carboxamide,
5-methyl-N-(6-((4-methylpiperazin-1-yl)methyl)quinolin-2-yl)-1-(o-tolyl)-1H-1,2,3-triazole-4-carboxamide,
5-methyl-N-(6-(pyrrolidin-1-ylmethyl)quinolin-2-yl)-1-(o-tolyl)-1H-1,2,3-triazole-4-carboxamide,
N-(6-((diethylamino)methyl)quinolin-2-yl)-5-methyl-1-(o-tolyl)-1H-1,2,3-triazole-4-carboxamide,
5-methyl-N-(6-(piperidin-1-ylmethyl)quinolin-2-yl)-1-(o-tolyl)-1H-1,2,3-triazole-4-carboxamide,
tert-butyl 4-((2-(5-methyl-1-(o-tolyl)-1H-1,2,3-triazole-4-carboxamido)quinolin-6-yl)methyl)piperazine-1-carboxylate,
N-(6-((dimethylamino)methyl)quinolin-2-yl)-5-methyl-1-(o-tolyl)-1H-1,2,3-triazole-4-carboxamide,
5-methyl-N-(6-(thiomorpholinomethyl)quinolin-2-yl)-1-(o-tolyl)-1H-1,2,3-triazole-4-carboxamide,
5-methyl-N-(6-((4-morpholinopiperidin-1-yl)methyl)quinolin-2-yl)-1-(o-tolyl)-1H-1,2,3-triazole-4-carboxamide, and
5-methyl-N-(6-((4-(4-methylpiperazin-1-yl)piperidin-1-yl)methyl)quinolin-2-yl)-1-(o-tolyl)-1H-1,2,3-triazole-4-carboxamide, and the pharmaceutically acceptable salts of said compound.

15. The compound of claim 11, wherein the compound is selected from the group consisting of N-(benzo[d]thiazol-2-yl)-5-methyl-1-(o-tolyl)-1H-1,2,3-triazole-4-carboxamide, 2,5-Dimethyl-N-(4-phenylthiazol-2-yl)-1-(p-tolyl)-1H-pyrrole-3-carboxamide, 5-Methyl-N-(naphthalen-2-yl)-1-(o-tolyl)-1H-1,2,3-triazole-4-carboxamide, 5-Methyl-N-(6-methylpyridin-2-yl)-1-(p-tolyl)-1H-1,2,3-triazole-4-carboxamide, 5-Methyl-N-(quinolin-2-yl)-1-(o-tolyl)-1H-1,2,3-triazole-4-carboxamide, 1-(2-Fluorophenyl)-5-methyl-N-(quinolin-2-yl)-1H-1,2,3-triazole-4-carboxamide, 1-(2-Bromophenyl)-5-methyl-N-(quinolin-2-yl)-1H-1,2,3-triazole-4- carboxamide, 1-(2-Methoxyphenyl)-5-methyl-N-(quinolin-2-yl)-1H-1,2,3-triazole-4-carboxamide, 1-(3-Chlorophenyl)-5-methyl-N-(quinolin-2-yl)-1H-1,2,3-triazole-4-carboxamide, 1-(2,3-Dimethylphenyl)-5-methyl-N-(quinolin-2-yl)-1H-1,2,3-triazole-4-carboxamide, 1-(2-Cyanophenyl)-5-methyl-N-(quinolin-2-yl)-1H-1,2,3-triazole-4-carboxamide, 1-(2-Acetylphenyl)-5-methyl-N-(quinolin-2-yl)-1H-1,2,3-triazole-4-carboxamide, 1-(2,4-Dimethylphenyl)-5-methyl-N-(quinolin-2-yl)-1H-1,2,3-triazole-4-carboxamide, 5-Methyl-N-(quinolin-2-yl)-1-(o-tolyl)-1H-pyrazole-4-carboxamide, 5-Ethyl-1-(2-fluorophenyl)-N-(quinolin-2-yl)-1H-1,2,3-triazole-4-carboxamide, 1-(2-fluorophenyl)-5-isopropyl-N-(quinolin-2-yl)-1H-1,2,3-triazole-4-carboxamide, N-(benzo[d]thiazol-2-yl)-5-methyl-1-(o-tolyl)-1H-1,2,3-triazole-4-carboxamide, 1-(2-Fluorophenyl)-5-methyl-N-(quinolin-2-yl)-1H-pyrazole-4-carboxamide, 1-(2-Chlorophenyl)-5-methyl-N-(quinolin-2-yl)-1H-pyrazole-4-carboxamide, 1-(2-Ethylphenyl)-5-methyl-N-(quinolin-2-yl)-1H-pyrazole-4-carboxamide, 1-(Tert-butyl)-5-methyl-N-(quinolin-2-yl)-1H-pyrazole-4-carboxamide, and 5-methyl-1-(1-phenylethyl)-N-(quinolin-2-yl)-1H-pyrazole-4-carboxamide, and the pharmaceutically acceptable salts of said compound.

16. The compound of claim 13, wherein the compound is selected from the group consisting of 1-(2-Methoxyphenyl)-5-methyl-N-(quinolin-2-yl)-1H-1,2,3-triazole-4-carboxamide, 5-Methyl-N-(quinolin-2-yl)-1-(o-tolyl)-1H-pyrazole-4-carboxamide, 1-(2-Bromophenyl)-5-methyl-N-(quinolin-2-yl)-1H-pyrazole-4-carboxamide, and 1-(2-Ethylphenyl)-5-methyl-N-(quinolin-2-yl)-1H-pyrazole-4-carboxamide, and the pharmaceutically acceptable salts of said compound.

17. The compound of claim 13, wherein the compound is 1-(2-Methoxyphenyl)-5-methyl-N-(quinolin-2-yl)-1H-1,2,3-triazole-4-carboxamide, or 5-Methyl-N-(quinolin-2-yl)-1-(o-tolyl)-1H-1,2,3-triazole-4-carboxamide, or a pharmaceutically acceptable salt thereof.

18. The method of claim 1, wherein the disease comprises alcoholic fatty liver disease (ALD) or a non-alcoholic fatty liver disease (NAFLD).

19. The method of claim 1, wherein the disease is selected from the group consisting of simple fatty liver (steatosis), non-alcoholic steatohepatitis (NASH), and cirrhosis.

20. The method of claim 1, wherein the disease is non-alcoholic steatohepatitis (NASH).

21. The method of claim 2, wherein the one or more compounds are selected from the group consisting of:
2,5-Dimethyl-N-(pyridin-2-yl)-1-(p-tolyl)-1H-pyrrole-3-carboxamide,
2,5-Dimethyl-N-(pyrazin-2-yl)-1-(p-tolyl)-1H-pyrrole-3-carboxamide,
2,5-Dimethyl-N-(4-phenylthiazol-2-yl)-1-(p-tolyl)-1H-pyrrole-3-carboxamide,
N-Benzyl-2,5-dimethyl-1-(p-tolyl)-1H-pyrrole-3-carboxamide,
and the pharmaceutically acceptable salts thereof.

22. The method of claim 2, wherein the one or more compounds are selected from the group consisting of:
5-Methyl-N-(pyridin-2-yl)-1-(p-tolyl)-1H-1,2,3-triazole-4-carboxamide,
5-Methyl-N-(6-methylpyridin-2-yl)-1-(p-tolyl)-1H-1,2,3-triazole-4-carboxamide,
5-Methyl-N-(pyridin-2-ylmethyl)-1-(p-tolyl)-1H-1,2,3-triazole-4-carboxamide,
5-Methyl-N-(2-methyl-4-oxo-4H-chromen-7-yl)-1-(p-tolyl)-1H-1,2,3-triazole-4-carboxamide,
5-Methyl-N-(3-methylisoxazol-5-yl)-1-(p-tolyl)-1H-1,2,3-triazole-4-carboxamide,
N-(4,5-diphenylthiazol-2-yl)-5-methyl-1-(p-tolyl)-1H-1,2,3-triazole-4-carboxamide,
5-Methyl-N-(1-methyl-1H-benzo[d]imidazol-2-yl)-1-(p-tolyl)-1H-1,2,3-triazole-4-carboxamide,
5-Methyl-N-(quinolin-2-yl)-1-(p-tolyl)-1H-1,2,3-triazole-4-carboxamide,
5-Methyl-N-(quinolin-2-yl)-1-(o-tolyl)-1H-1,2,3-triazole-4-carboxamide,
5-Methyl-N-(naphthalen-2-yl)-1-(o-tolyl)-1H-1,2,3-triazole-4-carboxamide,
N-(benzo[d]thiazol-2-yl)-5-methyl-1-(o-tolyl)-1H-1,2,3-triazole-4-carboxamide,
5-Methyl-N-(4-phenylthiazol-2-yl)-1-(o-tolyl)-1H-1,2,3-triazole-4-carboxamide,
1-(2,3-Dimethylphenyl)-5-methyl-N-(quinolin-2-yl)-1H-1,2,3-triazole-4-carboxamide,
1-(2,4-Dimethylphenyl)-5-methyl-N-(quinolin-2-yl)-1H-1,2,3-triazole-4-carboxamide,
1-(3-Chlorophenyl)-5-methyl-N-(quinolin-2-yl)-1H-1,2,3-triazole-4-carboxamide,
1-(2-Fluorophenyl)-5-methyl-N-(quinolin-2-yl)-1H-1,2,3-triazole-4-carboxamide,
1-(2-Bromophenyl)-5-methyl-N-(quinolin-2-yl)-1H-1,2,3-triazole-4-carboxamide,
1-(2-Cyanophenyl)-5-methyl-N-(quinolin-2-yl)-1H-1,2,3-triazole-4-carboxamide,
1-(2-Methoxyphenyl)-5-methyl-N-(quinolin-2-yl)-1H-1,2,3-triazole-4-carboxamide,
1-(4-Fluoro-2-nitrophenyl)-5-methyl-N-(quinolin-2-yl)-1H-1,2,3-triazole-4-carboxamide,
1-(2-Acetylphenyl)-5-methyl-N-(quinolin-2-yl)-1H-1,2,3-triazole-4-carboxamide,
1-(2-Carbamoylphenyl)-5-methyl-N-(quinolin-2-yl)-1H-1,2,3-triazole-4-carboxamide,
1-([1,1'-biphenyl]-2-yl)-5-methyl-N-(quinolin-2-yl)-1H-1,2,3-triazole-4-carboxamide,
5-Methyl-1-(2-morpholinophenyl)-N-(quinolin-2-yl)-1H-1,2,3-triazole-4-carboxamide,
5-Methyl-1-(naphthalen-1-yl)-N-(quinolin-2-yl)-1H-1,2,3-triazole-4-carboxamide,
1-(2-fluorophenyl)-5-isopropyl-N-(quinolin-2-yl)-1H-1,2,3-triazole-4-carboxamide,
5-Ethyl-1-(2-fluorophenyl)-N-(quinolin-2-yl)-1H-1,2,3-triazole-4-carboxamide,
N-(6-bromoquinolin-2-yl)-5-methyl-1-(o-tolyl)-1H-1,2,3-triazole-4-carboxamide,
5-methyl-N-(6-(morpholinomethyl)quinolin-2-yl)-1-(o-tolyl)-1H-1,2,3-triazole-4-carboxamide,
5-methyl-N-(6-((4-methylpiperazin-1-yl)methyl)quinolin-2-yl)-1-(o-tolyl)-1H-1,2,3-triazole-4-carboxamide,
5-methyl-N-(6-(pyrrolidin-1-ylmethyl)quinolin-2-yl)-1-(o-tolyl)-1H-1,2,3-triazole-4-carboxamide,
N-(6-((diethylamino)methyl)quinolin-2-yl)-5-methyl-1-(o-tolyl)-1H-1,2,3-triazole-4-carboxamide,
5-methyl-N-(6-(piperidin-1-ylmethyl)quinolin-2-yl)-1-(o-tolyl)-1H-1,2,3-triazole-4-carboxamide,
tert-butyl 4-((2-(5-methyl-1-(o-tolyl)-1H-1,2,3-triazole-4-carboxamido)quinolin-6-yl)methyl)piperazine-1-carboxylate,
N-(6-((dimethylamino)methyl)quinolin-2-yl)-5-methyl-1-(o-tolyl)-1H-1,2,3-triazole-4-carboxamide,
5-methyl-N-(6-(thiomorpholinomethyl)quinolin-2-yl)-1-(o-tolyl)-1H-1,2,3-triazole-4-carboxamide,
5-methyl-N-(6-((4-morpholinopiperidin-1-yl)methyl)quinolin-2-yl)-1-(o-tolyl)-1H-1,2,3-triazole-4-carboxamide, and 5-methyl-N-(6-((4-(4-methylpiperazin-1-yl)piperidin-1-yl)methyl)quinolin-2-yl)-1-(o-tolyl)-1H-1,2,3-triazole-4-carboxamide, and the pharmaceutically acceptable salts thereof.

23. The method of claim 2, wherein the one or more compounds are selected from the group consisting of:

5-Methyl-N-(quinolin-2-yl)-1-(o-tolyl)-1H-pyrazole-4-carboxamide, 1-(2-Fluorophenyl)-5-methyl-N-(quinolin-2-yl)-1H-pyrazole-4-carboxamide, 1-(2-Bromophenyl)-5-methyl-N-(quinolin-2-yl)-1H-pyrazole-4-carboxamide, 1-(2-Chlorophenyl)-5-methyl-N-(quinolin-2-yl)-1H-pyrazole-4-carboxamide 1-(2-Ethylphenyl)-5-methyl-N-(quinolin-2-yl)-1H-pyrazole-4-carboxamide, 1-(2,6-dimethylphenyl)-5-methyl-N-(quinolin-2-yl)-1H-pyrazole-4-carboxamide, 1-(Tert-butyl)-5-methyl-N-(quinolin-2-yl)-1H-pyrazole-4-carboxamide, 1-(2,5-dimethylphenyl)-5-methyl-N-(quinolin-2-yl)-1H-pyrazole-4-carboxamide, 1-(2,4-difluorophenyl)-5-methyl-N-(quinolin-2-yl)-1H-pyrazole-4-carboxamide, 5-methyl-1-phenyl-N-(quinolin-2-yl)-1H-pyrazole-4-carboxamide, 1-cyclohexyl-5-methyl-N-(quinolin-2-yl)-1H-pyrazole-4-carboxamide, 5-methyl-1-(1-phenylethyl)-N-(quinolin-2-yl)-1H-pyrazole-4-carboxamide, 5-methyl-N-(quinolin-2-yl)-1-(2,2,2-trifluoroethyl)-1H-pyrazole-4-carboxamide, 5-methyl-1-(3-methylpyridin-2-yl)-N-(quinolin-2-yl)-1H-pyrazole-4-carboxamide, 1-(3-chloro-2-fluorophenyl)-5-methyl-N-(quinolin-2-yl)-1H-pyrazole-4-carboxamide, 1-(2,6-difluorophenyl)-5-methyl-N-(quinolin-2-yl)-1H-pyrazole-4-carboxamide, 1-(2-bromo-6-fluorophenyl)-5-methyl-N-(quinolin-2-yl)-1H-pyrazole-4-carboxamide, 5-methyl-1-phenyl-N-(quinolin-2-yl)-1H-pyrazole-3-carboxamide, 5-methyl-N-(quinolin-2-yl)-1-(o-tolyl)-1H-pyrazole-3-carboxamide, 1-(2-ethylphenyl)-5-methyl-N-(quinolin-2-yl)-1H-pyrazole-3-carboxamide, 1-phenyl-N-(quinolin-2-yl)-1,4,5,6-tetrahydrocyclopenta[c]pyrazole-3-carboxamide, 1-phenyl-N-(quinolin-2-yl)-4,5,6,7-tetrahydro-1H-indazole-3-carboxamide, 3,5-dimethyl-1-phenyl-N-(quinolin-2-yl)-1H-pyrazole-4-carboxamide, 1-(2,5-dimethylphenyl)-3,5-dimethyl-N-(quinolin-2-yl)-1H-pyrazole-4-carboxamide, 1-(2-bromophenyl)-3,5-dimethyl-N-(quinolin-2-yl)-1H-pyrazole-4-carboxamide, 5-ethyl-1-phenyl-N-(quinolin-2-yl)-1H-pyrazole-4-carboxamide, 5-isopropyl-1-phenyl-N-(quinolin-2-yl)-1H-pyrazole-4-carboxamide, 5-chloro-1-phenyl-N-(quinolin-2-yl)-1H-pyrazole-4-carboxamide, 5-bromo-1-phenyl-N-(quinolin-2-yl)-1H-pyrazole-4-carboxamide, 5-(dimethylamino)-1-phenyl-N-(quinolin-2-yl)-1H-pyrazole-4-carboxamide, 1-(2-ethylphenyl)-5-methyl-N-(naphthalen-2-yl)-1H-pyrazole-4-carboxamide, 1-(2-ethylphenyl)-N-(isoquinolin-3-yl)-5-methyl-1H-pyrazole-4-carboxamide, 1-(2-ethylphenyl)-5-methyl-N-(quinolin-3-yl)-1H-pyrazole-4-carboxamide, 1-(2-ethylphenyl)-5-methyl-N-(6-methylpyridin-2-yl)-1H-pyrazole-4-carboxamide, and the pharmaceutically acceptable salts thereof.

24. The method of claim 2, wherein the one or more compounds are selected from the group consisting of:

2,5-Dimethyl-N-(quinolin-2-yl)-1-(o-tolyl)-1H-imidazole-4-carboxamide, 1-(2-Fluorophenyl)-2,5-dimethyl-N-(quinolin-2-yl)-1H-imidazole-4-carboxamide, 1-(2-Bromophenyl)-2,5-dimethyl-N-(quinolin-2-yl)-1H-imidazole-4-carboxamide, 2,5-Dimethyl-1-phenyl-N-(quinolin-2-yl)-1H-imidazole-4-carboxamide, and the pharmaceutically acceptable salts thereof.

25. The compound of claim 12, wherein the compound is selected from the group consisting of:

2,5-Dimethyl-N-(pyridin-2-yl)-1-(p-tolyl)-1H-pyrrole-3-carboxamide, 2,5-Dimethyl-N-(pyrazin-2-yl)-1-(p-tolyl)-1H-pyrrole-3-carboxamide, 2,5-Dimethyl-N-(4-phenylthiazol-2-yl)-1-(p-tolyl)-1H-pyrrole-3-carboxamide, N-Benzyl-2,5-dimethyl-1-(p-tolyl)-1H-pyrrole-3-carboxamide, and the pharmaceutically acceptable salts thereof.

26. The compound of claim 12, wherein the compound is selected from the group consisting of:

5-Methyl-N-(pyridin-2-yl)-1-(p-tolyl)-1H-1,2,3-triazole-4-carboxamide,

5-Methyl-N-(6-methylpyridin-2-yl)-1-(p-tolyl)-1H-1,2,3-triazole-4-carboxamide,

5-Methyl-N-(pyridin-2-ylmethyl)-1-(p-tolyl)-1H-1,2,3-triazole-4-carboxamide,

5-Methyl-N-(2-methyl-4-oxo-4H-chromen-7-yl)-1-(p-tolyl)-1H-1,2,3-triazole-4-carboxamide, 5-Methyl-N-(3-methylisoxazol-5-yl)-1-(p-tolyl)-1H-1,2,3-triazole-4-carboxamide, N-(4,5-diphenylthiazol-2-yl)-5-methyl-1-(p-tolyl)-1H-1,2,3-triazole-4-carboxamide, 5-Methyl-N-(1-methyl-1H-benzo[d]imidazol-2-yl)-1-(p-tolyl)-1H-1,2,3-triazole-4-carboxamide, 5-Methyl-N-(quinolin-2-yl)-1-(p-tolyl)-1H-1,2,3-triazole-4-carboxamide, 5-Methyl-N-(quinolin-2-yl)-1-(o-tolyl)-1H-1,2,3-triazole-4-carboxamide, 5-Methyl-N-(naphthalen-2-yl)-1-(o-tolyl)-1H-1,2,3-triazole-4-carboxamide, N-(benzo[d]thiazol-2-yl)-5-methyl-1-(o-tolyl)-1H-1,2,3-triazole-4-carboxamide, 5-Methyl-N-(4-phenylthiazol-2-yl)-1-(o-tolyl)-1H-1,2,3-triazole-4-carboxamide, 1-(2,3-Dimethylphenyl)-5-methyl-N-(quinolin-2-yl)-1H-1,2,3-triazole-4-carboxamide, 1-(2,4-Dimethylphenyl)-5-methyl-N-(quinolin-2-yl)-1H-1,2,3-triazole-4-carboxamide, 1-(3-Chlorophenyl)-5-methyl-N-(quinolin-2-yl)-1H-1,2,3-triazole-4-carboxamide, 1-(2-Fluorophenyl)-5-methyl-N-(quinolin-2-yl)-1H-1,2,3-triazole-4-carboxamide, 1-(2-Bromophenyl)-5-methyl-N-(quinolin-2-yl)-1H-1,2,3-triazole-4-carboxamide, 1-(2-Cyanophenyl)-5-methyl-N-(quinolin-2-yl)-1H-1,2,3-triazole-4-carboxamide,
1-(2-Methoxyphenyl)-5-methyl-N-(quinolin-2-yl)-1H-1,2,3-triazole-4-carboxamide,
1-(4-Fluoro-2-nitrophenyl)-5-methyl-N-(quinolin-2-yl)-1H-1,2,3-triazole-4-carboxamide,
1-(2-Acetylphenyl)-5-methyl-N-(quinolin-2-yl)-1H-1,2,3-triazole-4-carboxamide,
1-(2-Carbamoylphenyl)-5-methyl-N-(quinolin-2-yl)-1H-1,2,3-triazole-4-carboxamide,
1-([1,1'-biphenyl]-2-yl)-5-methyl-N-(quinolin-2-yl)-1H-1,2,3-triazole-4-carboxamide,
5-Methyl-1-(2-morpholinophenyl)-N-(quinolin-2-yl)-1H-1,2,3-triazole-4-carboxamide,
5-Methyl-1-(naphthalen-1-yl)-N-(quinolin-2-yl)-1H-1,2,3-triazole-4-carboxamide,
1-(2-fluorophenyl)-5-isopropyl-N-(quinolin-2-yl)-1H-1,2,3-triazole-4-carboxamide,
5-Ethyl-1-(2-fluorophenyl)-N-(quinolin-2-yl)-1H-1,2,3-triazole-4-carboxamide,
N-(6-bromoquinolin-2-yl)-5-methyl-1-(o-tolyl)-1H-1,2,3-triazole-4-carboxamide,
5-methyl-N-(6-(morpholinomethyl)quinolin-2-yl)-1-(o-tolyl)-1H-1,2,3-triazole-4-carboxamide,
5-methyl-N-(6-((4-methylpiperazin-1-yl)methyl)quinolin-2-yl)-1-(o-tolyl)-1H-1,2,3-triazole-4-carboxamide,
5-methyl-N-(6-(pyrrolidin-1-ylmethyl)quinolin-2-yl)-1-(o-tolyl)-1H-1,2,3-triazole-4-carboxamide,
N-(6-((diethylamino)methyl)quinolin-2-yl)-5-methyl-1-(o-tolyl)-1H-1,2,3-triazole-4-carboxamide,
5-methyl-N-(6-(piperidin-1-ylmethyl)quinolin-2-yl)-1-(o-tolyl)-1H-1,2,3-triazole-4-carboxamide,
tert-butyl 4-((2-(5-methyl-1-(o-tolyl)-1H-1,2,3-triazole-4-carboxamido)quinolin-6-yl)methyl)piperazine-1-carboxylate,
N-(6-((dimethylamino)methyl)quinolin-2-yl)-5-methyl-1-(o-tolyl)-1H-1,2,3-triazole-4-carboxamide,
5-methyl-N-(6-(thiomorpholinomethyl)quinolin-2-yl)-1-(o-tolyl)-1H-1,2,3-triazole-4-carboxamide,
5-methyl-N-(6-((4-morpholinopiperidin-1-yl)methyl)quinolin-2-yl)-1-(o-tolyl)-1H-1,2,3-triazole-4-carboxamide, and
5-methyl-N-(6-((4-(4-methylpiperazin-1-yl)piperidin-1-yl)methyl)quinolin-2-yl)-1-(o-tolyl)-1H-1,2,3-triazole-4-carboxamide,
and the pharmaceutically acceptable salts thereof.

27. The compound of claim 12, wherein the compound is selected from the group consisting of:
5-Methyl-N-(quinolin-2-yl)-1-(o-tolyl)-1H-pyrazole-4-carboxamide,
1-(2-Fluorophenyl)-5-methyl-N-(quinolin-2-yl)-1H-pyrazole-4-carboxamide,
1-(2-Bromophenyl)-5-methyl-N-(quinolin-2-yl)-1H-pyrazole-4-carboxamide,
1-(2-Chlorophenyl)-5-methyl-N-(quinolin-2-yl)-1H-pyrazole-4-carboxamide
1-(2-Ethylphenyl)-5-methyl-N-(quinolin-2-yl)-1H-pyrazole-4-carboxamide,
1-(2,6-dimethylphenyl)-5-methyl-N-(quinolin-2-yl)-1H-pyrazole-4-carboxamide,
1-(Tert-butyl)-5-methyl-N-(quinolin-2-yl)-1H-pyrazole-4-carboxamide,
1-(2,5-dimethylphenyl)-5-methyl-N-(quinolin-2-yl)-1H-pyrazole-4-carboxamide,
1-(2,4-difluorophenyl)-5-methyl-N-(quinolin-2-yl)-1H-pyrazole-4-carboxamide,
5-methyl-1-phenyl-N-(quinolin-2-yl)-1H-pyrazole-4-carboxamide,
1-cyclohexyl-5-methyl-N-(quinolin-2-yl)-1H-pyrazole-4-carboxamide,
5-methyl-1-(1-phenylethyl)-N-(quinolin-2-yl)-1H-pyrazole-4-carboxamide,
5-methyl-N-(quinolin-2-yl)-1-(2,2,2-trifluoroethyl)-1H-pyrazole-4-carboxamide,
5-methyl-1-(3-methylpyridin-2-yl)-N-(quinolin-2-yl)-1H-pyrazole-4-carboxamide,
1-(3-chloro-2-fluorophenyl)-5-methyl-N-(quinolin-2-yl)-1H-pyrazole-4-carboxamide,
1-(2,6-difluorophenyl)-5-methyl-N-(quinolin-2-yl)-1H-pyrazole-4-carboxamide,
1-(2-bromo-6-fluorophenyl)-5-methyl-N-(quinolin-2-yl)-1H-pyrazole-4-carboxamide,
5-methyl-1-phenyl-N-(quinolin-2-yl)-1H-pyrazole-3-carboxamide,
5-methyl-N-(quinolin-2-yl)-1-(o-tolyl)-1H-pyrazole-3-carboxamide,
1-(2-ethylphenyl)-5-methyl-N-(quinolin-2-yl)-1H-pyrazole-3-carboxamide,
1-phenyl-N-(quinolin-2-yl)-1,4,5,6-tetrahydrocyclopenta[c]pyrazole-3-carboxamide,
1-phenyl-N-(quinolin-2-yl)-4,5,6,7-tetrahydro-1H-indazole-3-carboxamide,
3,5-dimethyl-1-phenyl-N-(quinolin-2-yl)-1H-pyrazole-4-carboxamide,
1-(2,5-dimethylphenyl)-3,5-dimethyl-N-(quinolin-2-yl)-1H-pyrazole-4-carboxamide,
1-(2-bromophenyl)-3,5-dimethyl-N-(quinolin-2-yl)-1H-pyrazole-4-carboxamide,
5-ethyl-1-phenyl-N-(quinolin-2-yl)-1H-pyrazole-4-carboxamide,
5-isopropyl-1-phenyl-N-(quinolin-2-yl)-1H-pyrazole-4-carboxamide,
5-chloro-1-phenyl-N-(quinolin-2-yl)-1H-pyrazole-4-carboxamide,
5-bromo-1-phenyl-N-(quinolin-2-yl)-1H-pyrazole-4-carboxamide,
5-(dimethylamino)-1-phenyl-N-(quinolin-2-yl)-1H-pyrazole-4-carboxamide,
1-(2-ethylphenyl)-5-methyl-N-(naphthalen-2-yl)-1H-pyrazole-4-carboxamide,
1-(2-ethylphenyl)-N-(isoquinolin-3-yl)-5-methyl-1H-pyrazole-4-carboxamide,
1-(2-ethylphenyl)-5-methyl-N-(quinolin-3-yl)-1H-pyrazole-4-carboxamide,
1-(2-ethylphenyl)-5-methyl-N-(6-methylpyridin-2-yl)-1H-pyrazole-4-carboxamide,
and the pharmaceutically acceptable salts thereof.

28. The compound of claim 12, wherein the compound is selected from the group consisting of:
2,5-Dimethyl-N-(quinolin-2-yl)-1-(o-tolyl)-1H-imidazole-4-carboxamide,
1-(2-Fluorophenyl)-2,5-dimethyl-N-(quinolin-2-yl)-1H-imidazole-4-carboxamide,
1-(2-Bromophenyl)-2,5-dimethyl-N-(quinolin-2-yl)-1H-imidazole-4-carboxamide,
2,5-Dimethyl-1-phenyl-N-(quinolin-2-yl)-1H-imidazole-4-carboxamide,
and the pharmaceutically acceptable salts thereof.

* * * * *

SEQUENCE LISTING

```
<160> NUMBER OF SEQ ID NOS: 6

<210> SEQ ID NO 1
<211> LENGTH: 18
<212> TYPE: DNA
<213> ORGANISM: Artificial Sequence
<220> FEATURE:
<223> OTHER INFORMATION: Synthetic sequence (primer)

<400> SEQUENCE: 1
ctccttggag gcaagagc                                                 18

<210> SEQ ID NO 2
<211> LENGTH: 18
<212> TYPE: DNA
<213> ORGANISM: Artificial Sequence
<220> FEATURE:
<223> OTHER INFORMATION: Synthetic sequence (primer)

<400> SEQUENCE: 2
ggccacgcag caccgctg                                                 18

<210> SEQ ID NO 3
<211> LENGTH: 21
<212> TYPE: DNA
<213> ORGANISM: Artificial Sequence
<220> FEATURE:
<223> OTHER INFORMATION: Synthetic sequence (primer)

<400> SEQUENCE: 3
aaggcggagg agacctgcgc g                                             21

<210> SEQ ID NO 4
<211> LENGTH: 18
<212> TYPE: DNA
<213> ORGANISM: Artificial Sequence
<220> FEATURE:
<223> OTHER INFORMATION: Synthetic sequence (primer)

<400> SEQUENCE: 4
atcgtgcggc attgcggc                                                 18

<210> SEQ ID NO 5
<211> LENGTH: 20
<212> TYPE: DNA
<213> ORGANISM: Artificial Sequence
<220> FEATURE:
<223> OTHER INFORMATION: Synthetic sequence (primer)

<400> SEQUENCE: 5
accacagtcc atgccatcac                                               20

<210> SEQ ID NO 6
<211> LENGTH: 19
<212> TYPE: DNA
<213> ORGANISM: Artificial Sequence
<220> FEATURE:
<223> OTHER INFORMATION: Synthetic sequence (primer)

<400> SEQUENCE: 6
tccaccaccc tgttgctgt                                                19
```